(12) United States Patent
Fukuzaki

(10) Patent No.: US 9,287,515 B2
(45) Date of Patent: Mar. 15, 2016

(54) COMPOSITIONS COMPRISING ORGANIC AND ORGANOMETALLIC COMPOUNDS, AND THEIR APPLICATIONS IN ORGANIC ELECTROLUMINESCENCE, LIGHT EMISSION, DISPLAY, AND ILLUMINATION DEVICES

(75) Inventor: Eiji Fukuzaki, Kanagawa (JP)

(73) Assignee: UDC Ireland, Dublin (IE)

(*) Notice: Subject to any disclaimer, the term of this patent is extended or adjusted under 35 U.S.C. 154(b) by 0 days.

(21) Appl. No.: 13/393,186

(22) PCT Filed: Aug. 30, 2010

(86) PCT No.: PCT/JP2010/064755
§ 371 (c)(1),
(2), (4) Date: Feb. 28, 2012

(87) PCT Pub. No.: WO2011/025018
PCT Pub. Date: Mar. 3, 2011

(65) Prior Publication Data
US 2012/0153272 A1    Jun. 21, 2012

(30) Foreign Application Priority Data

Aug. 31, 2009 (JP) .................................. 2009-201153
Sep. 28, 2009 (JP) .................................. 2009-223456
Mar. 29, 2010 (JP) .................................. 2010-076449

(51) Int. Cl.
| | | |
|---|---|---|
| H01L 51/54 | (2006.01) | |
| C09K 11/06 | (2006.01) | |
| H01L 51/00 | (2006.01) | |
| C07D 487/04 | (2006.01) | |
| H05B 33/10 | (2006.01) | |
| H01L 51/50 | (2006.01) | |

(52) U.S. Cl.
CPC .......... *H01L 51/0094* (2013.01); *C07D 487/04* (2013.01); *C09K 11/06* (2013.01); *H01L 51/0072* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0067* (2013.01); *H01L 51/0085* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 6,835,469 B2* | 12/2004 | Kwong | ................ C07D 215/04 313/504 |
| 2003/0189216 A1 | 10/2003 | Kamatani et al. | |
| 2004/0214038 A1 | 10/2004 | Kwong et al. | |
| 2005/0037236 A1 | 2/2005 | Kamatani et al. | |
| 2005/0084710 A1 | 4/2005 | Kishino et al. | |
| 2005/0164030 A1 | 7/2005 | Knowles et al. | |
| 2006/0063037 A1 | 3/2006 | Kim et al. | |
| 2006/0127696 A1 | 6/2006 | Stossel et al. | |
| 2008/0220265 A1 | 9/2008 | Xia et al. | |
| 2008/0261076 A1 | 10/2008 | Kwong et al. | |
| 2008/0297033 A1 | 12/2008 | Knowles et al. | |
| 2008/0299414 A1 | 12/2008 | Watanabe et al. | |
| 2009/0072721 A1 | 3/2009 | Kishino et al. | |
| 2009/0108737 A1 | 4/2009 | Kwong et al. | |
| 2009/0124805 A1 | 5/2009 | Alleyne | |
| 2009/0179555 A1 | 7/2009 | Kim et al. | |
| 2009/0184631 A1 | 7/2009 | Kim et al. | |
| 2009/0295276 A1 | 12/2009 | Asari et al. | |
| 2009/0302742 A1 | 12/2009 | Komori et al. | |
| 2009/0315454 A1 | 12/2009 | Igarashi | |
| 2010/0148161 A1 | 6/2010 | Kai et al. | |
| 2010/0148162 A1 | 6/2010 | Komori et al. | |
| 2010/0187977 A1 | 7/2010 | Kai et al. | |
| 2011/0037062 A1 | 2/2011 | Fukumatsu et al. | |

FOREIGN PATENT DOCUMENTS

| | | | |
|---|---|---|---|
| JP | 11-162650 A | 6/1999 | |
| JP | 11-176578 A | 7/1999 | |
| JP | 2004-204234 A | 7/2004 | |
| JP | 2005-100957 A | 4/2005 | |
| JP | 2005-536565 A | 12/2005 | |
| JP | 2007-522126 A | 8/2007 | |
| JP | 2007-308376 A | 11/2007 | |
| JP | 2008-513441 A | 5/2008 | |
| JP | 2008-137994 A | 6/2008 | |
| JP | 2008-297382 A | 12/2008 | |
| JP | 2009-173630 A | 8/2009 | |

(Continued)

OTHER PUBLICATIONS

Written Opinion (PCT/ISA/237) of the International Searching Authority, issued in corresponding International Application No. PCT/JP2010/064755 on Sep. 21, 2010.

(Continued)

Primary Examiner — Andrew K Bohaty
(74) Attorney, Agent, or Firm — Riverside Law LLP

(57) ABSTRACT

An object of the present invention is to provide an organic electroluminescence device having excellent light emission efficiency and durability, in particular, durability when driving at a high temperature. Provided is an organic electroluminescence device including on a substrate a pair of electrodes, and at least one layer of an organic layer including a light emitting layer containing a light emitting material disposed between the electrodes, wherein the light emitting layer includes at least each one of specific indolocarbazole derivatives and specific condensed ring metal complexes.

12 Claims, 1 Drawing Sheet

(56) References Cited

FOREIGN PATENT DOCUMENTS

| | | |
|---|---|---|
| JP | 2009-185017 A | 8/2009 |
| JP | 2009-224593 A | 10/2009 |
| WO | 03/077609 A1 | 9/2003 |
| WO | 2007/063754 A1 | 6/2007 |
| WO | 2007/063796 A1 | 6/2007 |
| WO | 2008/056746 A1 | 5/2008 |
| WO | 2008/109824 A2 | 9/2008 |
| WO | 2008/146839 A1 | 12/2008 |
| WO | 2008/149691 A1 | 12/2008 |
| WO | 2009/073245 A1 | 6/2009 |
| WO | 2009/073246 A1 | 6/2009 |
| WO | 2009/116377 A1 | 9/2009 |

OTHER PUBLICATIONS

International Search Report (PCT/ISA/210) issued by the International Searching Authority in corresponding International Application No. PCT/JP2010/064755 on Sep. 21, 2010.

Japanese Office Action, issued by the Japanese Patent Office in corresponding Japanese Application No. 2009-223456 on Nov. 25, 2009.

* cited by examiner

COMPOSITIONS COMPRISING ORGANIC AND ORGANOMETALLIC COMPOUNDS, AND THEIR APPLICATIONS IN ORGANIC ELECTROLUMINESCENCE, LIGHT EMISSION, DISPLAY, AND ILLUMINATION DEVICES

TECHNICAL FIELD

The present invention relates to a luminescence device that may convert electric energy into light to emit light, and particularly, to an organic electroluminescence device (referred to as a luminescence device, an EL device or device).

BACKGROUND ART

Organic electroluminescence (EL) devices are capable of obtaining a light emission with high luminance intensity at low voltage, and thus, have gained attention as a promising display device. An important characteristic value of the organic electroluminescence device is electric power consumption. The electric power consumption is expressed as the product of voltage and electric current, and the lower the voltage is required to obtain a desired brightness and the smaller value the electric current becomes, the lower the power consumption of the device may be made.

As one attempt to lower the value of electric current that flows through the device, a luminescence device utilizing light emission from an ortho-metalated iridium complex (Ir(ppy)$_3$: tris-ortho-metalated complex of Iridium(III) with 2-phenylpyridine) has been reported (see, for example, Patent Documents 1 to 3). The phosphorescent luminescence device described therein is greatly enhanced in the external quantum efficiency as compared with singlet luminescence devices of the related art, and thus, succeeded in lowering the value of electric current.

As described above, although the iridium complex is used as a light emission material for implementing light emission efficiency, the solubility is generally poor, and thus, there was a case where the service life of the device was shortened due to aggregation or association of the complex. In particular, when the complex has a condensed ring structure such as a quinoline ring and an isoquinoline ring in the ligand, it is considered that the degree of freedom of molecular motion is decreased, and thus, the complex is easily aggregated. In order to suppress aggregation or association of the complex, an attempt to increase the solubility has been made by introducing, for example, a specific substituent (Patent Documents 4 and 5), but the effects thereof were not sufficient.

Meanwhile, devices using a compound which has an indolocarbazole structure as a host material for the purpose of improving light emission efficiency and durability of a phosphorescent luminescence device (Patent Documents 6 and 7) have been reported, but more improvements are demanded from the viewpoint of durability and light emission efficiency.

Further, since indolocarbazole also has an extended p-conjugated plane, and has a small degree of freedom of molecular motion, it is considered that association and aggregation is easily generated.

In addition, in the manufacture of an organic electroluminescence device, a method for forming a thin film which is an organic layer disposed between a pair of electrodes includes a deposition method such as vacuum deposition, and a wet method such as a spin coating method, a printing method and an inkjet method.

Among them, if a wet method is used, it is also possible to use polymeric organic compounds, for which it is difficult to form a film in dry processes such as vapor deposition, and when a wet method is used in a flexible display and the like, the method is appropriate from the viewpoint of durability such as flex resistance, film strength and the like, and when the device is manufactured to have a large area, the method is particularly preferable.

However, organic electroluminescence devices obtained by a wet method were problematic in that the devices have low light emission efficiency or device durability.

RELATED ART

Patent Document

Patent Document 1: US Patent Application Publication No. 2008/0297033

Patent Document 2: Japanese Patent Application Laid-Open No. 2008-297382

Patent Document 3: Japanese Patent Application Laid-Open No. 2008-137994

Patent Document 4: International Publication No. WO08/109,824

Patent Document 5: International Publication No. WO09/073,245

Patent Document 6: International Publication No. WO07/063,796

Patent Document 7: International Publication No. WO07/063,754

DISCLOSURE OF INVENTION

Problems to be Solved by the Invention

An object of the present invention is to provide an organic electroluminescence device having excellent light emission efficiency and durability (in particular, durability when driving at a high temperature).

Means for Solving the Problems

The above object is solved by the following means.

[1] An organic electroluminescence device, comprising on a substrate:

a pair of electrodes; and at least one layer of an organic layer including a light emitting layer containing a light emitting material disposed between the electrodes, wherein the light emitting layer contains at least each one of a compound represented by the following Formula (3) and a compound represented by the following Formula (D-1):

$$Z^3 \!-\! (Y^3)_{n^3} \tag{3}$$

wherein $Z^3$ represents benzene, pyridine, triazine, pyrimidine, biphenyl, phenylpyridine, bipyridine, a silicon atom or a carbon atom, and may be further substituted by at least one group selected from an alkyl group, an aryl group, a silyl group, a cyano group, a fluorine atom and a combination thereof;

$Y^3$ represents a group represented by the following Formula (3a-1) or (3a-2); and $n^3$ represents an integer of 1 to 4:

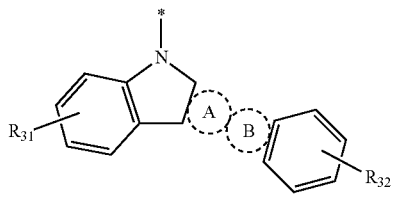
(3a-1)

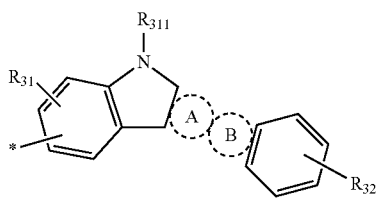
(3a-2)

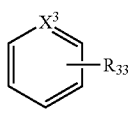
(3b)

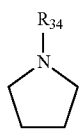
(3c)

in Formulas (3a-1) and (3a-2), the ring A represents an aromatic ring or a heterocyclic ring, represented by Formula (3b), which is condensed with an adjacent ring;

the ring B represents a heterocyclic ring represented by Formula (3c), which is condensed with an adjacent ring;

$X^3$ represents C—R" in which R" represents a hydrogen atom or a substituent, or a nitrogen atom;

each of $R_{34}$ and $R_{311}$ independently represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom;

$R_{33}$ represents a hydrogen atom;

each of $R_{31}$ and $R_{32}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group, if possible; and

* represents a bond for linking to $Z^3$:

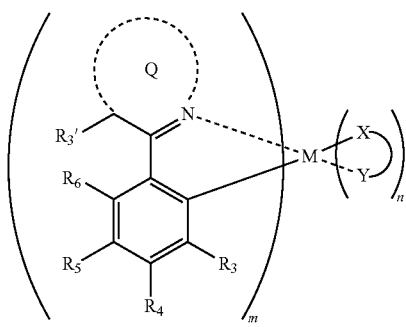
(D-1)

in Formula (D-1), M represents iridium;

each of $R_3$ to $R_6$ independently represents a hydrogen atom, an alkyl group or an aryl group;

$R_3'$ represents a hydrogen atom, an alkyl group or an aryl group;

the ring Q represents a pyridine ring, a quinoline ring or an isoquinoline ring, which is coordinated to iridium, and may be further substituted by an alkyl group or an aryl group;

$R_5$ represents an aryl group or a heteroaryl group when the ring Q is a pyridine ring, and the aryl group or the heteroaryl group may be further substituted by an alkyl group;

$R_3'$ and $R_6$ may be linked to each other by a linking group selected from —$CR_2$—$CR_2$—, —CR=CR—, —$CR_2$—, —O—, —NR—, —O—$CR_2$—, —NR—$CR_2$— and —N=CR— to form a ring;

each R independently represents a hydrogen atom, an alkyl group, an alkenyl group, an alkynyl group, an aryl group or a heteroaryl group, and may further have a substituent selected from a halogen atom, —R', —OR', —N(R)$_2$, —SR', —C(O)R', —C(O)OR', —C(O)$_N$(R')$_2$, —CN, —NO$_2$, —SO$_2$, —SOR', —SO$_2$R' and —SO$_3$R';

each R' independently represents a hydrogen atom, an alkyl group, a perhaloalkyl group, an alkenyl group, an alkynyl group, an aryl group or a heteroaryl group;

(X—Y) represents a ligand represented by any one of the following Formula (1-1), (1-4) or (1-15);

m represents an integer of 1 to 3; and n represents an integer of 0 to 2, provided that m+n is 3:

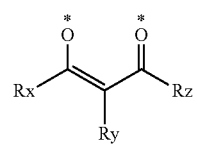
(I-1)

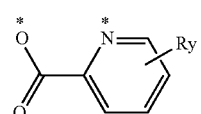
(I-4)

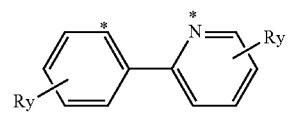
(I-15)

in Formulas (1-1), (1-4) and (1-15), each of Rx, Ry and Rz independently represents a hydrogen atom, an alkyl group, a perfluoroalkyl group, a halogen atom or an aryl group.

[2] The organic electroluminescence device as described in [1] above, wherein the compound represented by Formula (3) is represented by the following Formula (1):

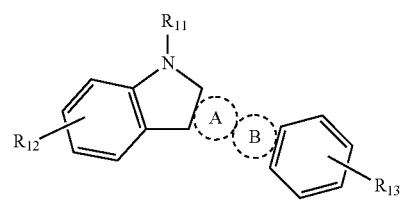
(1)

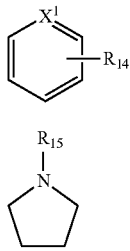

(1a)

(1b)

wherein the ring A represents an aromatic ring or a heterocyclic ring, represented by Formula (1a), which is condensed with an adjacent ring;

the ring B represents a heterocyclic ring represented by Formula (1b), which is condensed with an adjacent ring;

$X^1$ represents C—R'' in which R'' represents a hydrogen atom or a substituent, or a nitrogen atom;

each of $R_{11}$ and $R_{15}$ independently represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom;

$R_{14}$ represents a hydrogen atom; and each of $R_{12}$ and $R_{13}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group.

[3] The organic electroluminescence device as described in [2] above, wherein the compound represented by Formula (1) is represented by the following Formula (15):

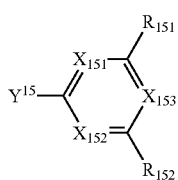

(15)

wherein $X_{151}$ to $X_{153}$ represent a nitrogen atom or C—$R_{153}$;

$R_{153}$ represents a hydrogen atom, a methyl group, an isobutyl group, a t-butyl group, a neopentyl group, a phenyl group, a naphthyl group, a cyano group or a fluorine atom;

each of $R_{151}$ and $R_{152}$ independently represents a hydrogen atom, a methyl group, an isobutyl group, a t-butyl group, a neopentyl group, a phenyl group, a naphthyl group, a cyano group or a fluorine atom; and $Y^{15}$ represents a group represented by any one of the following Formulas (15a) to (15c):

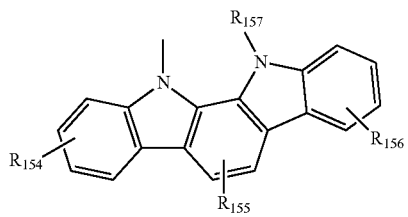

(15a)

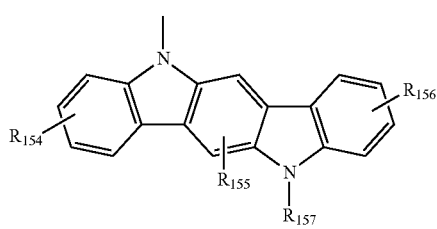

(15b)

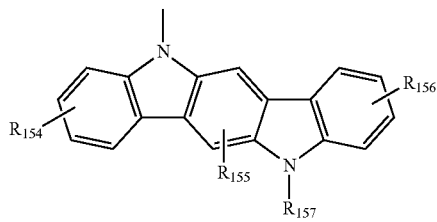

(15c)

wherein $R_{155}$ represents a hydrogen atom;

each of $R_{154}$ and $R_{156}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and $R_{157}$ represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom.

[4] The organic electroluminescence device as described in [3] above, wherein the compound represented by Formula (15) is represented by the following Formula (16):

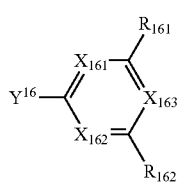

(16)

wherein $X_{161}$ to $X_{163}$ represent a nitrogen atom or C—H, and each of $R_{161}$ and $R_{162}$ independently represents a hydrogen atom, a methyl group, an isobutyl group, a t-butyl group, a neopentyl group, a phenyl group, a naphthyl group, a cyano group or a fluorine atom; and $Y^{16}$ represents a group represented by any one of the Formulas (15a) to (15c).

[5] The organic electroluminescence device as described in [4] above,
wherein the compound represented by Formula (16) is represented by the following Formula (17):

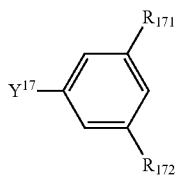
(17)

wherein each of $R_{171}$ and $R_{172}$ independently represents a hydrogen atom, a methyl group, an isobutyl group, a t-butyl group, a neopentyl group, a phenyl group, a naphthyl group, a cyano group or a fluorine atom; and $Y^{17}$ represents a group represented by any one of the Formulas (15a) to (15c).

[6] The organic electroluminescence device as described in [4] above,
wherein the compound represented by Formula (16) is represented by the following Formula (18):

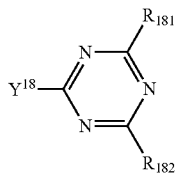
(18)

wherein each of $R_{181}$ and $R_{182}$ independently represents a hydrogen atom, a methyl group, an isobutyl group, a t-butyl group, a neopentyl group, a phenyl group, a naphthyl group, a cyano group or a fluorine atom; and $Y^{18}$ represents a group represented by any one of the Formulas (15a) to (15c).

[7] The organic electroluminescence device as described in [1] above,
wherein the compound represented by Formula (3) is represented by the following Formula (5):

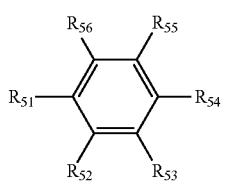
(5)

wherein each of $R_{51}$ to $R_{56}$ independently represents a hydrogen atom, a methyl group, an isobutyl group, a t-butyl group, a neopentyl group, a phenyl group, a naphthyl group, a cyano group, a fluorine atom or a group represented by any one of the following Formula (10), (10-2) or (10-3), provided that each of at least two of $R_{51}$ to $R_{56}$ is independently a group represented by any one of the following Formula (10), (10-2) or (10-3):

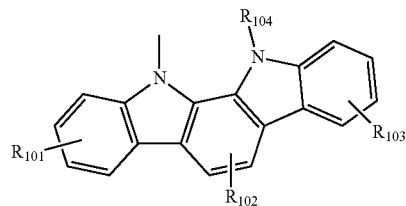
(10)

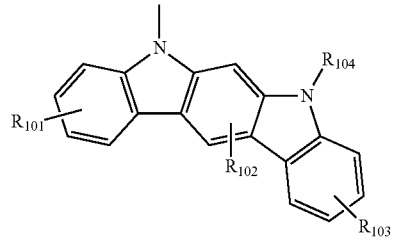
(10-2)

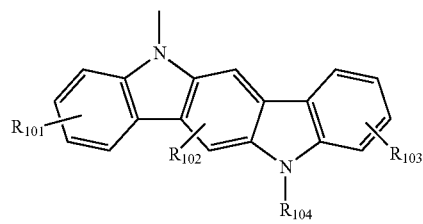
(10-3)

wherein $R_{102}$ represents a hydrogen atom;
each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and $R_{104}$ represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom.

[8] The organic electroluminescence device as described in [1] above,
wherein the compound represented by Formula (3) is represented by the following Formula (6):

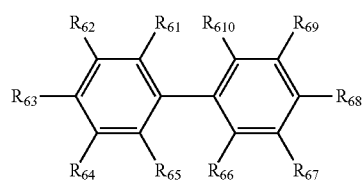
(6)

wherein each of $R_{61}$ to $R_{610}$ independently represents a hydrogen atom, a methyl group, an isobutyl group, a t-butyl group, a neopentyl group, a phenyl group, a naphthyl group, a cyano group, a fluorine atom or a group represented by any one of the following Formula (10), (10-2) or (10-3), provided that each of at least two of $R_{61}$ to $R_{610}$ is independently a group represented by any one of the following Formula (10), (10-2) or (10-3):

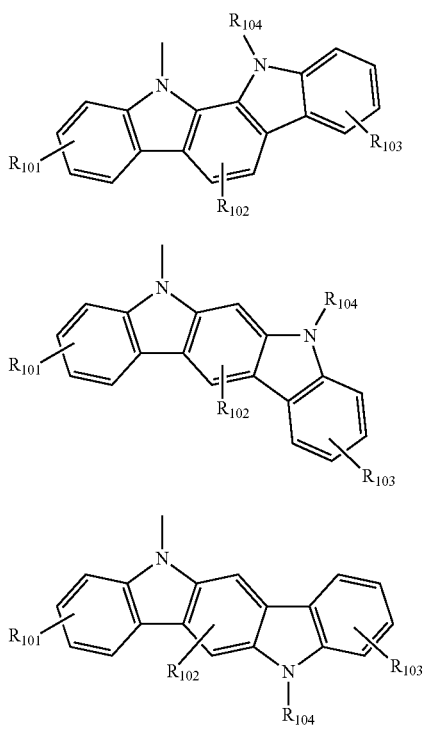

(10)

(10-2)

(10-3)

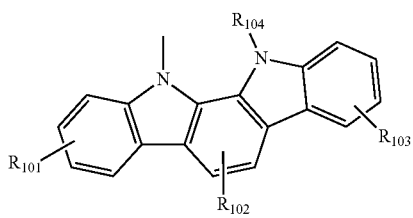

(10)

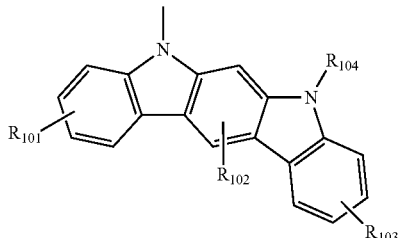

(10-2)

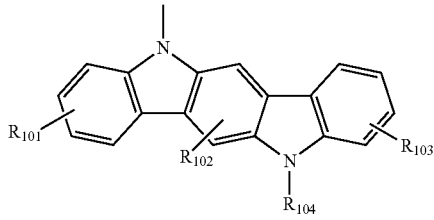

(10-3)

wherein $R_{102}$ represents a hydrogen atom;

each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and $R_{104}$ represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom.

[9] The organic electroluminescence device as described in [8] above, wherein the compound represented by Formula (6) is represented by the following Formula (7):

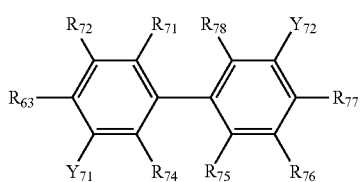

(7)

wherein each of $R_{71}$ to $R_{78}$ independently represents a hydrogen atom, a methyl group, an isobutyl group, a t-butyl group, a neopentyl group, a phenyl group, a naphthyl group, a cyano group, a fluorine atom or a group represented by any one of the following Formula (10), (10-2) or (10-3); and each of $Y_{71}$ and $Y_{72}$ is independently a group represented by any one of the following Formula (10), (10-2) or (10-3):

wherein $R_{102}$ represents a hydrogen atom;

each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and $R_{104}$ represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom.

[10] The organic electroluminescence device as described in [8] above, wherein the compound represented by Formula (6) is represented by the following Formula (8):

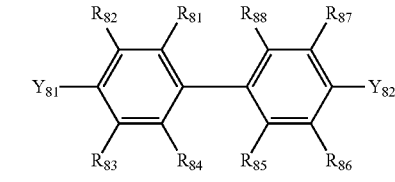

(8)

wherein each of $R_{81}$ to $R_{88}$ independently represents a hydrogen atom, a methyl group, an isobutyl group, a t-butyl group, a neopentyl group, a phenyl group, a naphthyl group, a cyano group, a fluorine atom or a group represented by any one of the following Formula (10), (10-2) or (10-3); and each of $Y_{81}$ and $Y_{82}$ is independently a group represented by any one of the following Formula (10), (10-2) or (10-3):

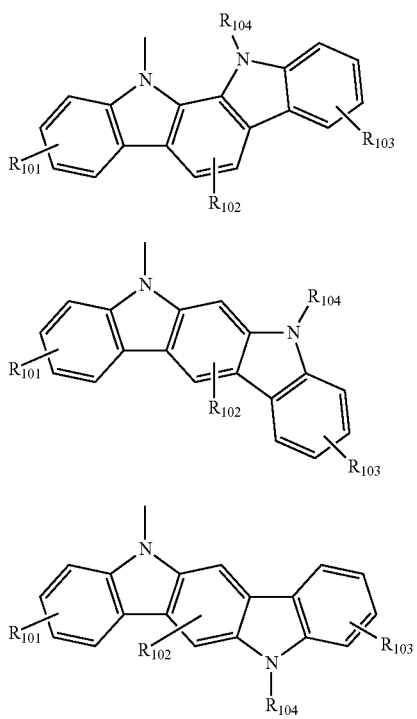

wherein $R_{102}$ represents a hydrogen atom;

each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and $R_{104}$ represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom.

[11] The organic electroluminescence device as described in [1] above, wherein the compound represented by Formula (3) is represented by the following Formula (9):

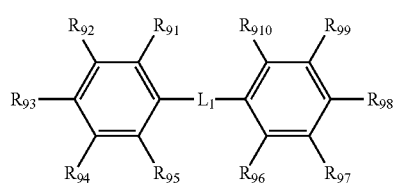

wherein each of $R_{91}$ to $R_{910}$ independently represents a hydrogen atom, a methyl group, an isobutyl group, a t-butyl group, a neopentyl group, a phenyl group, a naphthyl group, a cyano group, a fluorine atom or a group represented by any one of the following Formula (10), (10-2) or (10-3), provided that each of at least two of $R_{91}$ to $R_{910}$ is independently a group represented by any one of the following Formula (10), (10-2) or (10-3); and $L_1$ represents a silicon atom or a carbon atom, and the silicon atom or the carbon atom may be further substituted by at least one group selected from an alkyl group and an aryl group:

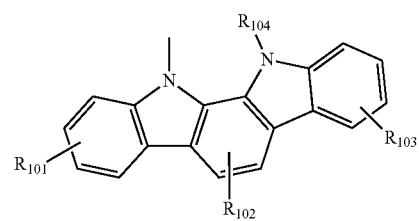

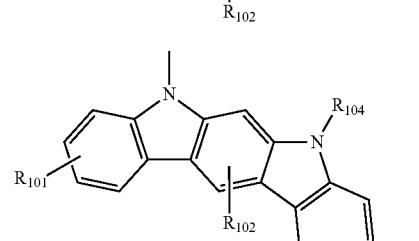

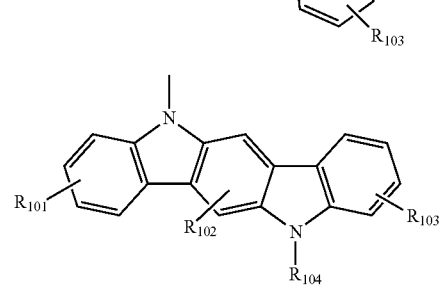

wherein $R_{102}$ represents a hydrogen atom;

each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and $R_{104}$ represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom.

[12] The organic electroluminescence device as described in [1] above, wherein the compound represented by Formula (3) is represented by the following Formula (11):

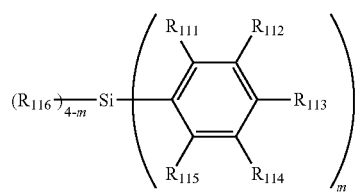

wherein each of $R_{111}$ to $R_{116}$ independently represents a hydrogen atom, a methyl group, an isobutyl group, a t-butyl group, a neopentyl group, a phenyl group, a naphthyl group, a cyano group, a fluorine atom or a group represented by any one of the following Formula (10), (10-2) or (10-3), provided that at least one of $R_{111}$ to $R_{115}$ is a group represented by any one of the following Formula (10), (10-2) or (10-3); and
m represents an integer of 1 to 4:

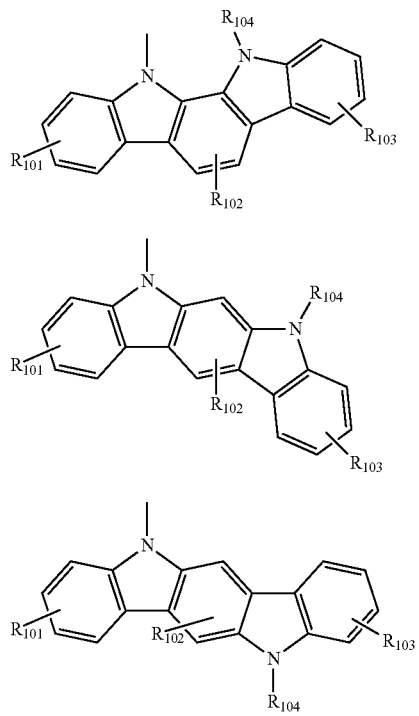

wherein $R_{102}$ represents a hydrogen atom;
each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and
$R_{104}$ represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom.

[13] The organic electroluminescence device as described in [1] above,
wherein the compound represented by Formula (3) is represented by the following Formula (12):

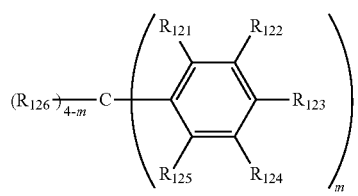

wherein each of $R_{121}$ to $R_{126}$ independently represents a hydrogen atom, a methyl group, an isobutyl group, a t-butyl group, a neopentyl group, a phenyl group, a naphthyl group, a cyano group, a fluorine atom or a group represented by any one of the following Formula (10), (10-2) or (10-3), provided that at least one of $R_{121}$ to $R_{125}$ is independently a group represented by any one of the following Formula (10), (10-2) or (10-3); and
m represents an integer of 1 to 4:

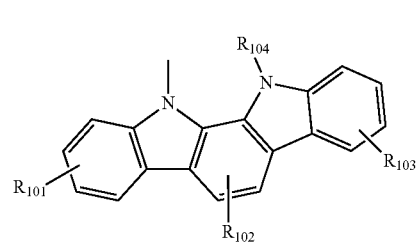

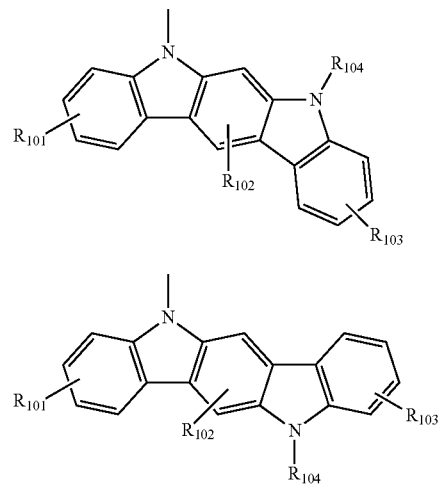

wherein $R_{102}$ represents a hydrogen atom;
each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and
$R_{104}$ represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom.

[14] The organic electroluminescence device as described in [1] above,
wherein the compound represented by Formula (3) is represented by the following Formula (13):

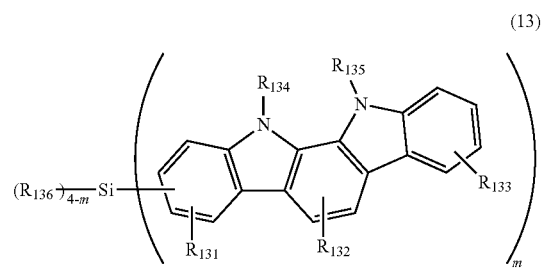

wherein $R_{132}$ represents a hydrogen atom;

each of $R_{131}$ and $R_{133}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group;

each of $R_{134}$ and $R_{135}$ independently represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom;

$R_{136}$ represents a hydrogen atom, a methyl group, an isobutyl group, a t-butyl group, a neopentyl group, a phenyl group, a naphthyl group, a cyano group or a fluorine atom;

m represents an integer of 1 to 4; and a silicon linking group is substituted to a carbon atom as one of $R_{131}$.

[15] The organic electroluminescence device as described in [1] above, wherein the compound represented by Formula (3) is represented by the following Formula (14):

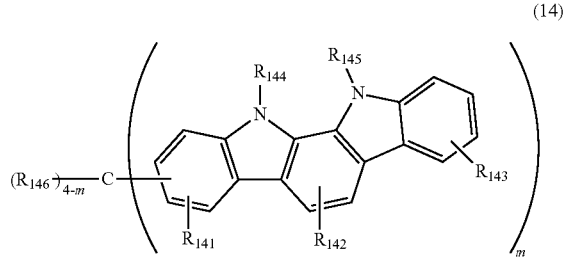

(14)

wherein $R_{142}$ represents a hydrogen atom;

each of $R_{141}$ and $R_{143}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group;

each of $R_{144}$ and $R_{145}$ independently represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom;

a carbon linking group is substituted to a carbon atom as one of $R_{141}$;

$R_{146}$ represents a hydrogen atom, a methyl group, an isobutyl group, a t-butyl group, a neopentyl group, a phenyl group, a naphthyl group, a cyano group or a fluorine atom; and m represents an integer of 1 to 4.

[16] The organic electroluminescence device as described in any one of [1] to [15] above, wherein the compound represented by Formula (D-1) is a compound represented by the following Formula (D-2):

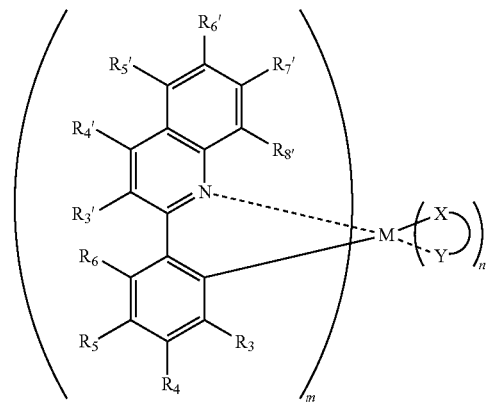

(D-2)

in Formula (D-2), M represents iridium;

each of $R_3$ to $R_6$ independently represents a hydrogen atom, an alkyl group or an aryl group;

$R_3'$ to $R_8'$ represent a hydrogen atom, an alkyl group or an aryl group;

$R_3'$ and $R_6$ may be linked to each other by a linking group selected from —$CR_2$—$CR_2$—, —CR=CR—, —$CR_2$—, —O—, —NR—, —O—$CR_2$—, —NR—$CR_2$— and —N=CR— to form a ring;

each R independently represents a hydrogen atom, an alkyl group, an alkenyl group, an alkynyl group, an aryl group or a heteroaryl group, and may further have a substituent selected from a halogen atom, —R', —OR', —N(R')$_2$, —SR', —C(O)R', —C(O)OR', —C(O)$_N$(R')$_2$, —CN, —NO$_2$, —SO$_2$, —SOR', —SO$_2$R' and —SO$_3$R';

each R' independently represents a hydrogen atom, an alkyl group, a perhaloalkyl group, an alkenyl group, an alkynyl group, an aryl group or a heteroaryl group;

(X—Y) represents a ligand represented by any one of Formula (1-1), (1-4) or (1-15);

m represents an integer of 1 to 3; and n represents an integer of 0 to 2, provided that m+n is 3.

[17] The organic electroluminescence device as described in any one of [1] to [15] above, wherein the compound represented by Formula (D-1) is a compound represented by the following Formula (D-3):

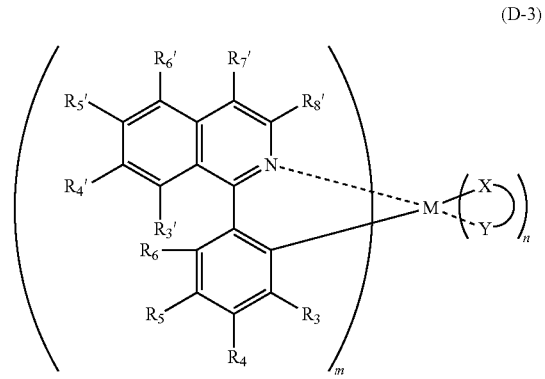

(D-3)

in Formula (D-3), M represents iridium;

each of $R_3$ to $R_6$ independently represents a hydrogen atom, an alkyl group or an aryl group;

each of $R_3'$ to $R_8'$ independently represents a hydrogen atom, an alkyl group or an aryl group;

$R_3'$ and $R_6$ may be linked to each other by a linking group selected from —CR$_2$—CR$_2$—, —CR═CR—, —CR$_2$—, —O—, —NR—, —O—CR$_2$—, —NR—CR$_2$— and —N═CR— to form a ring;

each R independently represents a hydrogen atom, an alkyl group, an alkenyl group, an alkynyl group, an aryl group or a heteroaryl group, and may further have a substituent selected from a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' and —SO$_3$R';

each R' independently represents a hydrogen atom, an alkyl group, a perhaloalkyl group, an alkenyl group, an alkynyl group, an aryl group or a heteroaryl group;

(X—Y) represents a ligand represented by any one of Formula (1-1), (1-4) or (1-15);

m represents an integer of 1 to 3; and n represents an integer of 0 to 2, provided that m+n is 3.

[18] The organic electroluminescence device as described in any one of [1] to [15] above, wherein the compound represented by Formula (D-1) is a compound represented by the following Formula (D-4):

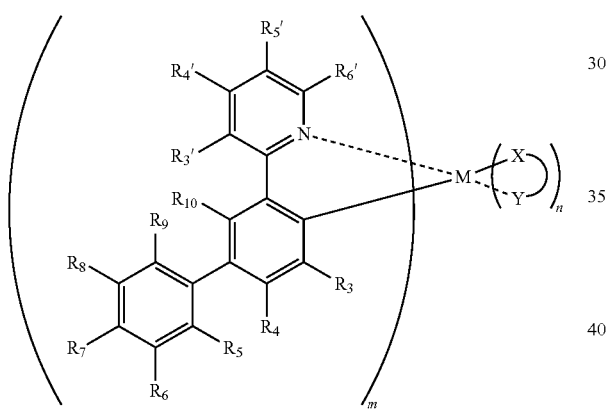

(D-4)

in Formula (D-4), M represents iridium;

each of $R_3$ to $R_{10}$ independently represents a hydrogen atom, an alkyl group or an aryl group;

each of $R_3'$ to $R_6'$ independently represents a hydrogen atom, an alkyl group or an aryl group;

$R_3'$ and $R_{10}$ may be linked to each other by a linking group selected from —CR$_2$—CR$_2$—, —CR═CR—, —CR$_2$—, —O—, —NR—, —O—CR$_2$—, —NR—CR$_2$— and —N═CR— to form a ring;

each R independently represents a hydrogen atom, an alkyl group, an alkenyl group, an alkynyl group, an aryl group or a heteroaryl group, and may further have a substituent selected from a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' and —SO$_3$R';

each R' independently represents a hydrogen atom, an alkyl group, a perhaloalkyl group, an alkenyl group, an alkynyl group, an aryl group or a heteroaryl group;

(X—Y) represents a ligand represented by any one of Formula (1-1), (1-4) or (1-15);

m represents an integer of 1 to 3; and n represents an integer of 0 to 2, provided that m+n is 3.

[19] The organic electroluminescence device as described in any one of [1] to [18] above, wherein the light emitting layer containing at least each one of the compound represented by Formula (3) and the compound represented by Formula (D-1) is formed by a wet process.

[20] A composition, comprising:

at least each one of a compound represented by the following Formula (3) and a compound represented by the following Formula (D-1):

(3)

wherein $Z^3$ represents benzene, pyridine, triazine, pyrimidine, biphenyl, phenylpyridine, bipyridine, a silicon atom or a carbon atom, and may be further substituted by at least one group selected from an alkyl group, an aryl group, a silyl group, a cyano group, a fluorine atom and a combination thereof;

$Y^3$ represents a group represented by the following Formula (3a-1) or (3a-2); and $n^3$ represents an integer of 1 to 4:

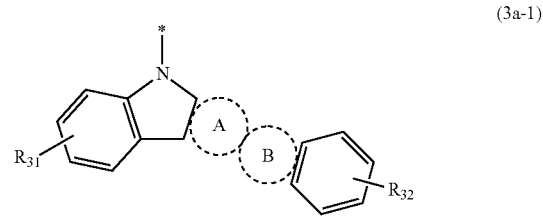

(3a-1)

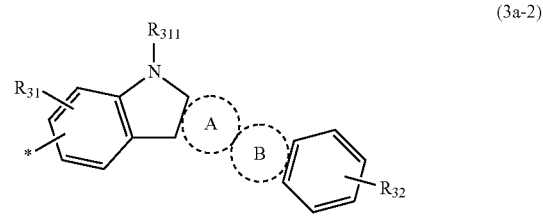

(3a-2)

(3b)

(3c)

in Formulas (3a-1) and (3a-2), the ring A represents an aromatic ring or a heterocyclic ring, represented by Formula (3b), which is condensed with an adjacent ring;

the ring B represents a heterocyclic ring represented by Formula (3c), which is condensed with an adjacent ring;

$X^3$ represents C—R″ in which R″ represents a hydrogen atom or a substituent, or a nitrogen atom;

each of $R_{34}$ and $R_{311}$ independently represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom;

$R_{33}$ represents a hydrogen atom;

each of $R_{31}$ and $R_{32}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group, if possible; and

* represents a bond for linking to $Z^3$:

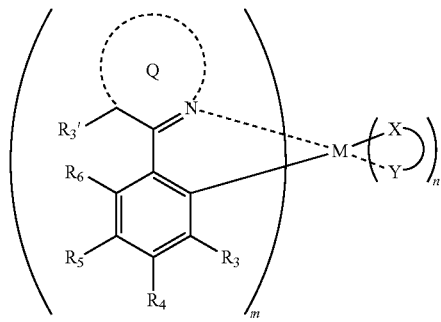

(D-1)

in Formula (D-1), M represents iridium;

each of $R_3$ to $R_6$ independently represents a hydrogen atom, an alkyl group or an aryl group;

$R_3'$ represents a hydrogen atom, an alkyl group or an aryl group;

the ring Q represents a pyridine ring, a quinoline ring or an isoquinoline ring, which is coordinated to iridium, and may be further substituted by an alkyl group or an aryl group;

$R_5$ represents an aryl group or a heteroaryl group when the ring Q is a pyridine ring, and the aryl group or the heteroaryl group may be further substituted by an alkyl group;

$R_3'$ and $R_6$ may be linked to each other by a linking group selected from —$CR_2$—$CR_2$—, —CR═CR—, —$CR_2$—, —O—, —NR—, —O—$CR_2$—, —NR—$CR_2$— and —N═CR— to form a ring;

each R independently represents a hydrogen atom, an alkyl group, an alkenyl group, an alkynyl group, an aryl group or a heteroaryl group, and may further have a substituent selected from a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' and —SO$_3$R';

each R' independently represents a hydrogen atom, an alkyl group, a perhaloalkyl group, an alkenyl group, an alkynyl group, an aryl group or a heteroaryl group;

(X—Y) represents a ligand represented by any one of the following Formula (1-1), (1-4) or (1-15);

m represents an integer of 1 to 3; and n represents an integer of 0 to 2, provided that m+n is 3:

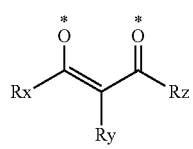

(I-1)

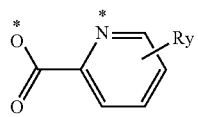

(I-4)

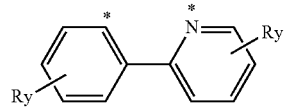

(I-15)

in Formulas (1-1), (1-4) and (1-15), each of Rx, Ry and Rz independently represents a hydrogen atom, an alkyl group, a perfluoroalkyl group, a halogen atom or an aryl group.

[21] A light emitting layer, comprising:

at least each one of a compound represented by the following Formula (3) and a compound represented by the following Formula (D-1):

$$Z^3\text{—}(Y^3)_{n^3} \quad (3)$$

wherein $Z^3$ represents benzene, pyridine, triazine, pyrimidine, biphenyl, phenylpyridine, bipyridine, a silicon atom or a carbon atom, and may be further substituted by at least one group selected from an alkyl group, an aryl group, a silyl group, a cyano group, a fluorine atom and a combination thereof;

$Y^3$ represents a group represented by the following Formula (3a-1) or (3a-2); and $n^3$ represents an integer of 1 to 4:

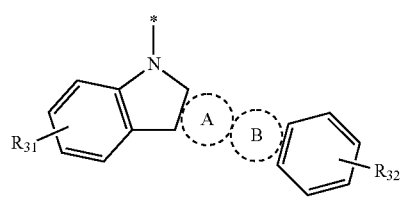

(3a-1)

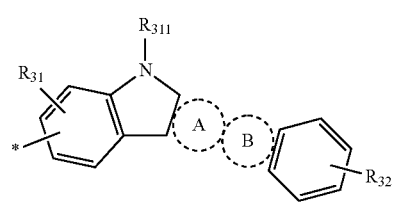

(3a-2)

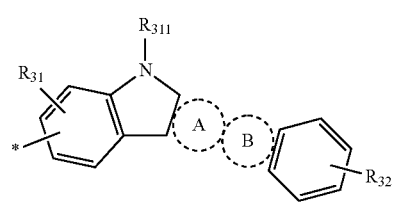

(3b)

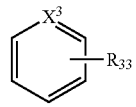

(3c)

in Formulas (3a-1) and (3a-2), the ring A represents an aromatic ring or a heterocyclic ring represented by Formula (3b), which is condensed with an adjacent ring;

the ring B represents a heterocyclic ring represented by Formula (3c), which is condensed with an adjacent ring;

$X^3$ represents C—R" in which R" represents a hydrogen atom or a substituent, or a nitrogen atom;

each of $R_{34}$ and $R_{311}$ independently represents a benzene ring, a naphthalene ring, a pyridine ring, a triazine ring or a pyrimidine ring, and these rings may be further substituted by at least one group selected from a methyl group, an isobutyl group, a t-butyl group, a neopentyl group, a phenyl group, a naphthyl group, a cyano group and a fluorine atom;

$R_{33}$ represents a hydrogen atom;

each of $R_{31}$ and $R_{32}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group, if possible; and

* represents a bond for linking to $Z^3$:

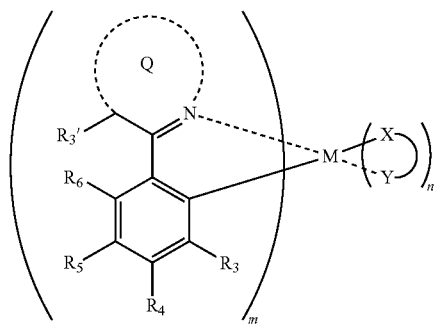

(D-1)

in Formula (D-1), M represents iridium;

each of $R_3$ to $R_6$ independently represents a hydrogen atom, an alkyl group or an aryl group;

$R_3'$ represents a hydrogen atom, an alkyl group or an aryl group;

the ring Q represents a pyridine ring, a quinoline ring or an isoquinoline ring, which is coordinated to iridium, and may be further substituted by an alkyl group or an aryl group;

$R_5$ represents an aryl group or a heteroaryl group when the ring Q is a pyridine ring, and the aryl group or the heteroaryl group may be further substituted by an alkyl group;

$R_3'$ and $R_6$ may be linked to each other by a linking group selected from $-CR_2-CR_2-$, $-CR=CR-$, $-CR_2-$, $-O-$, $-NR-$, $-O-CR_2-$, $-NR-CR_2-$ and $-N=CR-$ to form a ring;

each R independently represents a hydrogen atom, an alkyl group, an alkenyl group, an alkynyl group, an aryl group or a heteroaryl group, and may further have a substituent selected from a halogen atom, $-R'$, $-OR'$, $-N(R')_2$, $-SR'$, $-C(O)R'$, $-C(O)OR'$, $-C(O)N(R')_2$, $-CN$, $-NO_2$, $-SO_2$, $-SOR'$, $-SO_2R'$ and $-SO_3R'$;

each R' independently represents a hydrogen atom, an alkyl group, a perhaloalkyl group, an alkenyl group, an alkynyl group, an aryl group or a heteroaryl group;

(X—Y) represents a ligand represented by any one of the following Formula (1-1), (1-4) or (1-15);

m represents an integer of 1 to 3; and n represents an integer of 0 to 2, provided that m+n is 3:

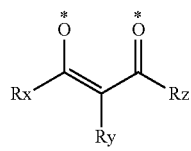

(I-1)

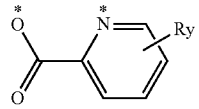

(I-4)

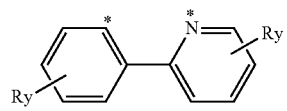

(I-5)

in Formulas (1-1), (1-4) and (1-15), each of Rx, Ry and Rz independently represents a hydrogen atom, an alkyl group, a perfluoroalkyl group, a halogen atom or an aryl group.

[22] A light emission apparatus using the organic electroluminescence device as described in any one of [1] to [19] above.

[23] A display apparatus using the organic electroluminescence device as described in any one of [1] to [19] above.

[24] An illumination apparatus using the organic electroluminescence device as described in any one of [1] to [19] above.

Further, the present invention preferably has the following configuration.

<1>

An organic electroluminescence device, comprising on a substrate:

a pair of electrodes; and at least one layer of an organic layer including a light emitting layer containing a light emitting material disposed between the electrodes, wherein the light emitting layer contains at least each one of a compound represented by the following Formula (7), (8) or (11) and a compound represented by the following Formula (D-4), (D-2) or (D-3):

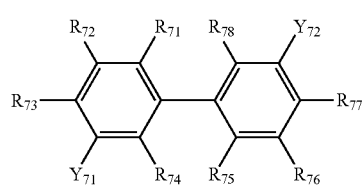

(7)

wherein $R_{71}$ to $R_{78}$ represent a hydrogen atom; and each of $Y_{71}$ and $Y_{72}$ independently represents a group represented by the following Formula (10):

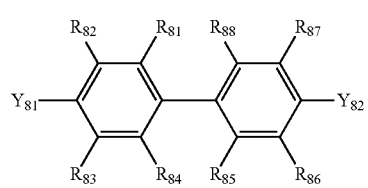

(8)

wherein $R_{81}$ to $R_{88}$ represent a hydrogen atom; and each of $Y_{81}$ and $Y_{82}$ independently represents a group represented by the following Formula (10):

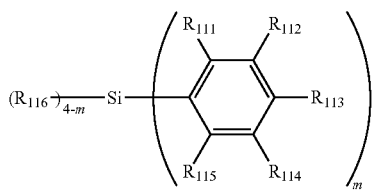

(11)

wherein $R_{113}$ represents a group represented by the following Formula (10);

$R_{111}$, $R_{112}$, $R_{114}$ and $R_{115}$ represent a hydrogen atom;

$R_{116}$ represents a hydrogen atom, an alkyl group or an aromatic hydrocarbon ring group; and m represents 2:

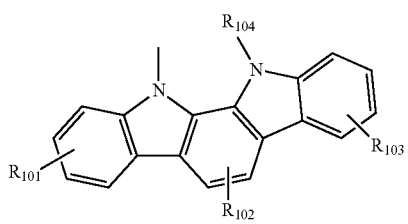

(10)

wherein $R_{101}$ to $R_{103}$ represent a hydrogen atom; and $R_{104}$ represents a benzene ring, a biphenyl ring or a pyridine ring, and these rings may be further substituted with an alkyl group having 1 to 6 carbon atoms, a phenyl group or a pyridyl group:

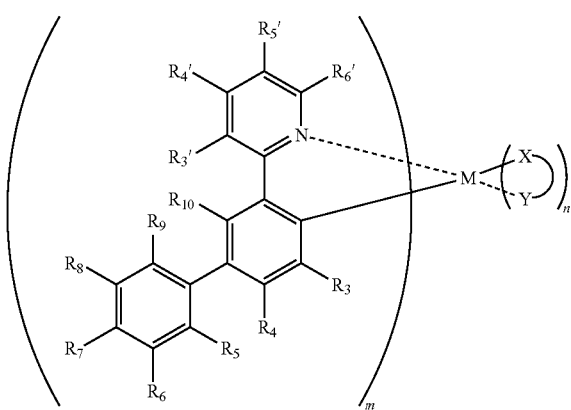

(D-4)

in Formula (D-4), M represents iridium;

each of $R_3$ to $R_{10}$ independently represents a hydrogen atom, an alkyl group or an aryl group;

each of $R_3'$ to $R_6'$ independently represents a hydrogen atom, an alkyl group or an aryl group;

(X—Y) represents a ligand of phenylpyridine, picolinic acid or acetylacetone, and the phenylpyridine may be substituted with an alkyl group;

m represents 1 to 3; and n represents 0 to 2, provided that m+n is 3:

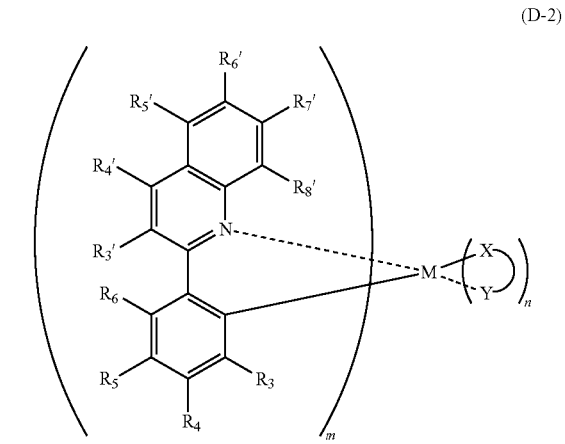

(D-2)

in Formula (D-2), M represents iridium;

each of $R_3$ to $R_6$ independently represents a hydrogen atom, an alkyl group or an aryl group;

each of $R_3'$ to $R_8'$ independently represents a hydrogen atom, an alkyl group or an aryl group;

(X—Y) represents a ligand of phenylpyridine, picolinic acid or acetylacetone, and the phenylpyridine may be substituted with an alkyl group;

m represents 1 to 3; and n represents 0 to 2, provided that m+n is 3:

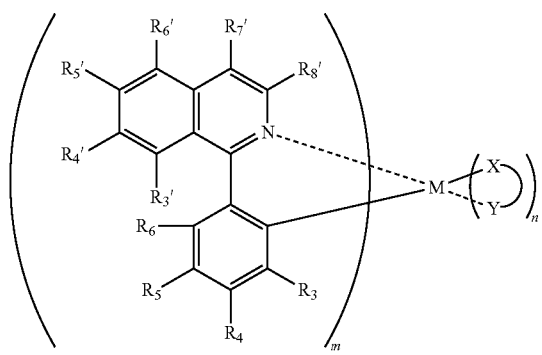

(D-3)

in Formula (D-3), M represents iridium;

each of $R_3$ to $R_6$ independently represents a hydrogen atom, an alkyl group or an aryl group;

each of $R_3'$ to $R_3'$ independently represents a hydrogen atom, an alkyl group or an aryl group;

(X—Y) represents a ligand of phenylpyridine, picolinic acid or acetylacetone, and the phenylpyridine may be substituted with an alkyl group;

m represents 1 to 3; and n represents 0 to 2, provided that m+n is 3.

<2>

The organic electroluminescence device as described in <1>, wherein $R_{104}$ in Formula (10) represents a benzene ring, a biphenyl ring or a pyridine ring.

<3>

The organic electroluminescence device as described in <1>, wherein $R_{104}$ in Formula (10) represents a benzene ring.

<4>

The organic electroluminescence device as described in any one of <1> to <3>, wherein $R_{116}$ in Formula (11) represents an alkyl group or an aromatic hydrocarbon ring group.

<5>

The organic electroluminescence device as described in any one of <1> to <4>, wherein each of, $R_3$ to $R_6$ and $R_3'$ to $R_8'$ in Formula (D-2), $R_3$ to $R_6$ and $R_3'$ to $R_8'$ in Formula (D-3), or $R_3$ to $R_{10}$ and $R_3'$ to $R_6'$ in Formula (D-4) independently represents a hydrogen atom or an alkyl group.

<6>

The organic electroluminescence device as described in any one of <1> to <5>, wherein a light emitting layer containing at least each one of the compound represented by Formula (7), (8) or (11) and the compound represented by Formula (D-4), (D-2) or (D-3) is formed by a wet process.

<7>

A composition, containing:

at least each one of a compound represented by the following Formula (7), (8) or (11) and a compound represented by the following Formula (D-4), (D-2) or (D-3):

(7)

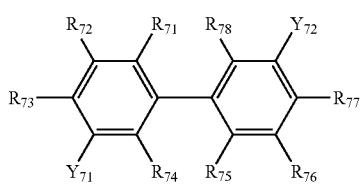

wherein $R_{71}$ to $R_{78}$ represent a hydrogen atom; and each of $Y_{71}$ and $Y_{72}$ independently represents a group represented by the following Formula (10):

(8)

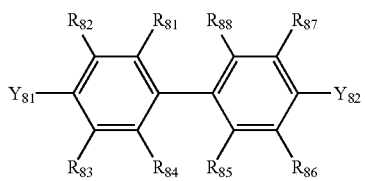

wherein $R_{81}$ to $R_{88}$ represent a hydrogen atom; and each of $Y_{81}$ and $Y_{82}$ independently represents a group represented by the following Formula (10):

(11)

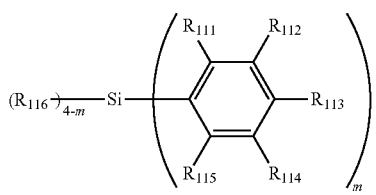

wherein $R_{113}$ represents a group represented by the following Formula (10);

$R_{111}$, $R_{112}$, $R_{114}$ and $R_{115}$ represent a hydrogen atom;

$R_{116}$ represents a hydrogen atom, an alkyl group or an aromatic hydrocarbon ring group; and m represents 2:

(10)

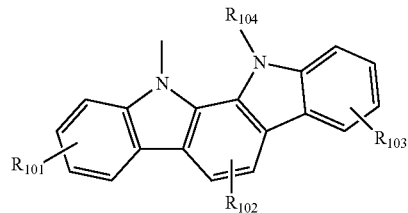

wherein $R_{101}$ to $R_{103}$ represent a hydrogen atom; and $R_{104}$ represents a benzene ring, a biphenyl ring or a pyridine ring, and these rings may be further substituted with an alkyl group having 1 to 6 carbon atoms, a phenyl group or a pyridyl group:

(D-4)

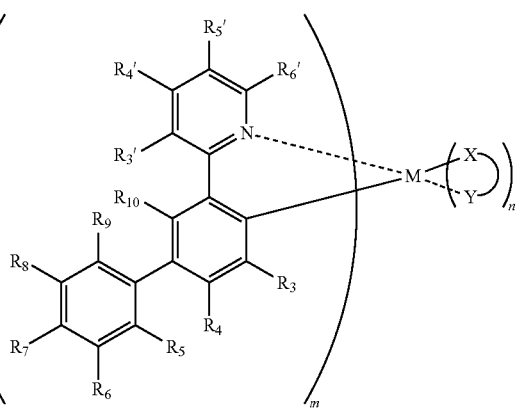

in Formula (D-4), M represents iridium;

each of $R_3$ to $R_{10}$ independently represents a hydrogen atom, an alkyl group or an aryl group;

each of $R_3'$ to $R_6'$ independently represents a hydrogen atom, an alkyl group or an aryl group;

(X—Y) represents a ligand of phenylpyridine, picolinic acid or acetylacetone, and the phenylpyridine may be substituted with an alkyl group;

m represents 1 to 3; and n represents 0 to 2, provided that m+n is 3:

(D-2)

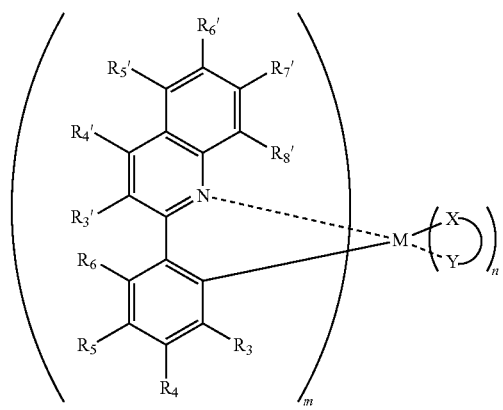

in Formula (D-2), M represents iridium;

each of $R_3$ to $R_6$ independently represents a hydrogen atom, an alkyl group or an aryl group;

each of $R_3'$ to $R_8'$ independently represents a hydrogen atom, an alkyl group or an aryl group;

(X—Y) represents a ligand of phenylpyridine, picolinic acid or acetylacetone, and the phenylpyridine may be substituted with an alkyl group;

m represents 1 to 3; and n represents 0 to 2, provided that m+n is 3:

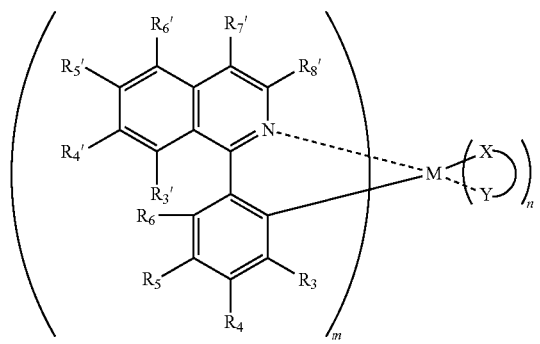

(D-3)

in Formula (D-3), M represents iridium;

each of $R_3$ to $R_6$ independently represents a hydrogen atom, an alkyl group or an aryl group;

each of $R_3'$ to $R_8'$ independently represents a hydrogen atom, an alkyl group or an aryl group;

(X—Y) represents a ligand of phenylpyridine, picolinic acid or acetylacetone, and the phenylpyridine may be substituted with an alkyl group;

m represents 1 to 3; and n represents 0 to 2, provided that m+n is 3.

<8>

A light emitting layer, comprising:

at least each one of a compound represented by the following Formula (7), (8) or (11) and a compound represented by the following Formula (D-4), (D-2) or (D-3):

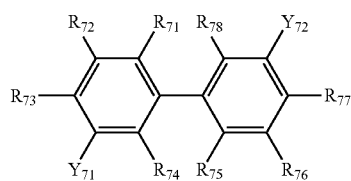

(7)

wherein $R_{71}$ to $R_{78}$ represent a hydrogen atom; and each of $Y_{71}$ and $Y_{72}$ independently represents a group represented by the following Formula (10):

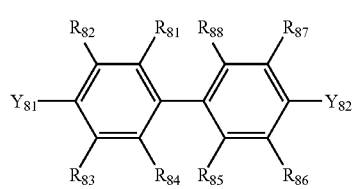

(8)

wherein $R_{81}$ to $R_{88}$ represent a hydrogen atom; and each of $Y_{81}$ and $Y_{82}$ independently represents a group represented by the following Formula (10):

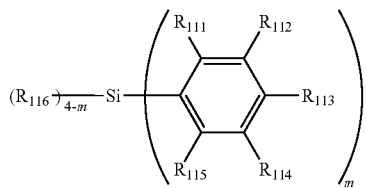

(11)

wherein $R_{113}$ represents a group represented by the following Formula (10);

$R_{111}$, $R_{112}$, $R_{114}$ and $R_{115}$ represent a hydrogen atom;

$R_{116}$ represents a hydrogen atom, an alkyl group or an aromatic hydrocarbon ring group; and m represents 2:

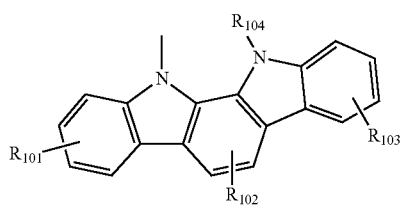

(10)

wherein $R_{101}$ to $R_{103}$ represent a hydrogen atom; and $R_{104}$ represents a benzene ring, a biphenyl ring or a pyridine ring, and these rings may be further substituted with an alkyl group having 1 to 6 carbon atoms, a phenyl group or a pyridyl group:

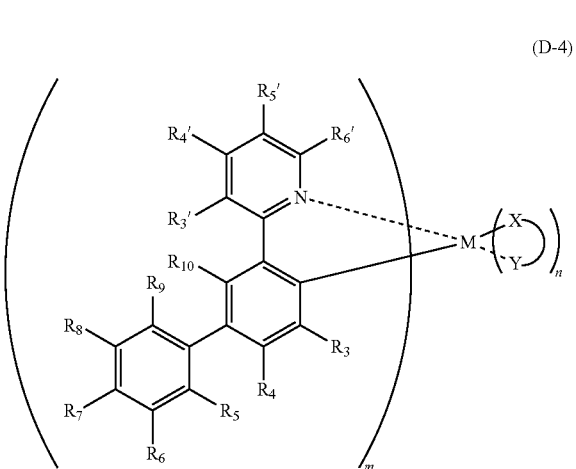

(D-4)

in Formula (D-4), M represents iridium;

each of $R_3$ to $R_{10}$ independently represents a hydrogen atom, an alkyl group or an aryl group;

each of $R_3'$ to $R_6'$ independently represents a hydrogen atom, an alkyl group or an aryl group;

(X—Y) represents a ligand of phenylpyridine, picolinic acid or acetylacetone, and the phenylpyridine may be substituted with an alkyl group;

m represents 1 to 3; and n represents 0 to 2, provided that m+n is 3:

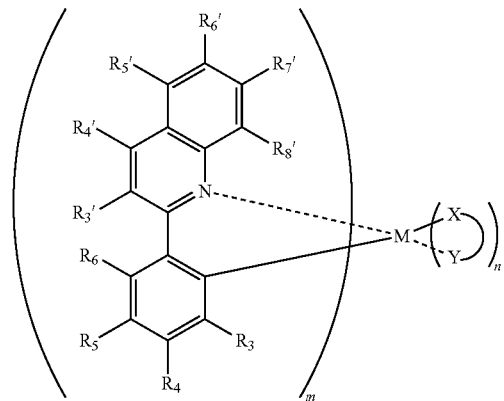
(D-2)

in Formula (D-2), M represents iridium;

each of $R_3$ to $R_6$ independently represents a hydrogen atom, an alkyl group or an aryl group;

$R_3'$ to $R_8'$ represent a hydrogen atom, an alkyl group or an aryl group; (X—Y) represents a ligand of phenylpyridine, picolinic acid or acetylacetone, and the phenylpyridine may be substituted with an alkyl group;

m represents 1 to 3; and n represents 0 to 2, provided that m+n is 3:

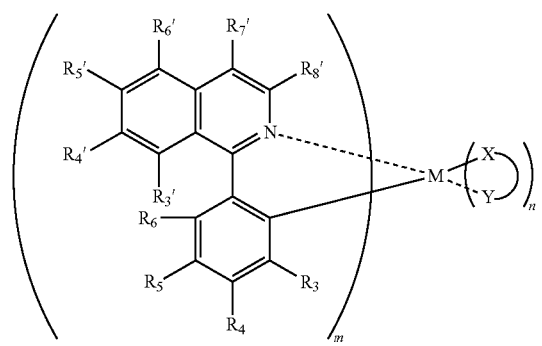
(D-3)

in Formula (D-3), M represents iridium;

each of $R_3$ to $R_6$ independently represents a hydrogen atom, an alkyl group or an aryl group;

each of $R_3'$ to $R_8'$ independently represents a hydrogen atom, an alkyl group or an aryl group;

(X—) represents a ligand of phenylpyridine, picolinic acid or acetylacetone, and the phenylpyridine may be substituted with an alkyl group;

m represents 1 to 3; and n represents 0 to 2, provided that m+n is 3.

<9>

A light emission apparatus using the organic electroluminescence device as described in any one of <1> to <6>.

<10>

A display apparatus using the organic electroluminescence device as described in any one of <1> to <6>.

<11>

An illumination apparatus using the organic electroluminescence device as described in any one of <1> to <6>.

Effects of the Invention

According to the present invention, it is possible to provide an organic electroluminescence device having excellent light emission efficiency and durability (in particular, durability when driving at a high temperature).

EMBODIMENTS FOR CARRYING OUT THE INVENTION

Figure 1:
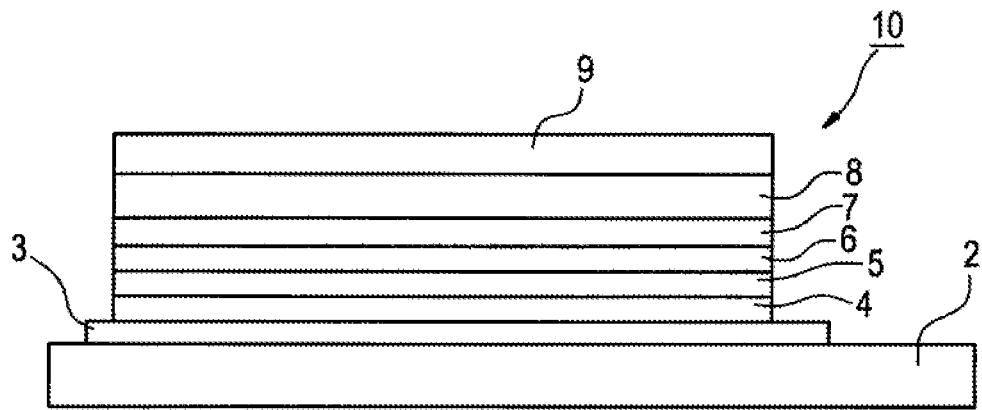
FIG. 1 is a schematic view illustrating an example (first exemplary embodiment) of a layer configuration of an organic EL device according to the present invention.

An organic electroluminescence device of the present invention includes, on a substrate, a pair of electrodes and at least one layer of an organic layer including a light emitting layer containing a light emitting material disposed between the electrodes, wherein the light emitting layer contains at least each one of a compound represented by the following Formula (3) and a compound represented by the following Formula (D-1).

$$Z^3—(Y^3)_{n^3} \tag{3}$$

(wherein $Z^3$ represents benzene, pyridine, triazine, pyrimidine, biphenyl, phenylpyridine, bipyridine, a silicon atom or a carbon atom, and may be further substituted with at least one group selected from an alkyl group, an aryl group, a silyl group, a cyano group, a fluorine atom or a combination thereof. $Y^3$ represents a group represented by the following Formula (3a-1) or (3a-2). $n^3$ represents an integer of 1 to 4.)

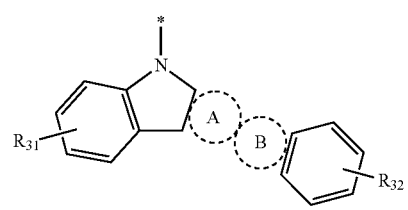
(3a-1)

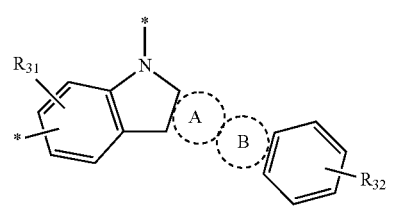
(3a-2)

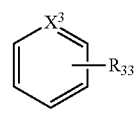
(3b)

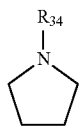
(3c)

(In Formulas (3a-1) and (3a-2), the ring A represents an aromatic ring or a heterocyclic ring, represented by Formula (3b), which is condensed with an adjacent ring, and the ring B represents a heterocyclic ring represented by Formula (3c), which is condensed with an adjacent ring. $X^3$ represents C—R" (R" represents a hydrogen atom or a substituent) or a nitrogen atom. Each of $R_{34}$ and $R_{311}$ independently represents a benzene ring, a naphthalene ring, a pyridine ring, a triazine ring or a pyrimidine ring, and these rings may be further substituted with at least one group selected from a methyl group, an isobutyl group, a t-butyl group, a neopentyl group, a phenyl group, a naphthyl group, a cyano group and a fluorine atom. $R_{33}$ represents a hydrogen atom. Each of $R_{31}$ and $R_{32}$ independently represents a hydrogen atom, an alkyl group, a silyl group, a fluorine atom, a cyano group or a trifluoromethyl group, and these groups may be further substituted with at least one of an alkyl group having 1 to 6 carbon atoms and a phenyl group, if possible. * represents a bond for linking to $Z^3$.)

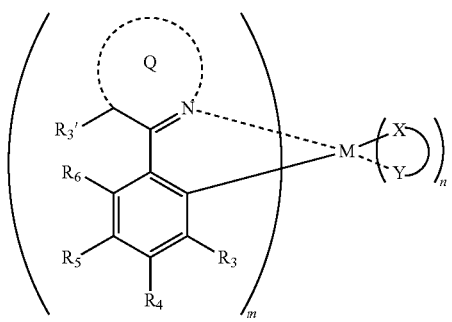
(D-1)

(In Formula (D-1), M represents iridium. Each of $R_3$ to $R_6$ independently represents a hydrogen atom, an alkyl group or an aryl group. $R_3'$ represents a hydrogen atom, an alkyl group or an aryl group. The ring Q represents a pyridine ring, a quinoline ring or an isoquinoline ring, which is coordinated to iridium, and may be further substituted with an alkyl group or an aryl group. $R_5$ represents an aryl group or a heteroaryl group when the ring Q is a pyridine ring, and the aryl group or the heteroaryl group may be further substituted with an alkyl group. $R_3'$ and $R_6$ may be linked to each other by a linking group selected from —$CR_2$—$CR_2$—, —CR=CR—, —$CR_2$—, —O—, —NR—, —O—$CR_2$—, —NR—$CR_2$— and —N=CR— to form a ring, each R independently represents a hydrogen atom, an alkyl group, an alkenyl group, an alkynyl group, an aryl group or a heteroaryl group, and may further have a substituent selected from a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' and —SO$_3$R', and each R' independently represents a hydrogen atom, an alkyl group, a perhaloalkyl group, an alkenyl group, an alkynyl group, an aryl group or a heteroaryl group. (X—Y) represents a ligand represented by any one of the following Formulas (1-1), (I-4) or (1-15). m represents an integer of 1 to 3, and n represents an integer of 0 to 2. However, m+n is 3.)

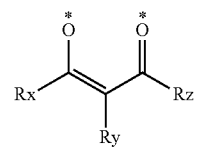
(I-1)

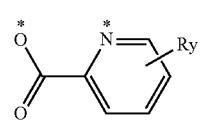
(I-4)

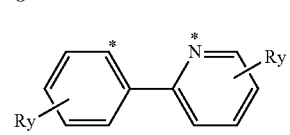
(I-15)

(In Formulas (1-1), (1-4) and (1-15), each of Rx, Ry and Rz independently represents a hydrogen atom, an alkyl group, a perfluoroalkyl group, a halogen atom or an aryl group.)

The organic electroluminescence device of the present invention contains at least each one of the compound represented by Formula (3) and the compound represented by Formula (D-1), and accordingly, is able to have high light emission efficiency (for example, external quantum efficiency) and provide an organic electroluminescence device having high durability.

First, an organic electroluminescence device including, on a substrate, a pair of electrodes and at least one layer of an organic layer including a light emitting layer containing a light emitting material disposed between the electrodes, wherein the light emitting layer contains at least each one of a compound represented by the following Formula (1) and a compound represented by the following Formula (D-1) will be described.

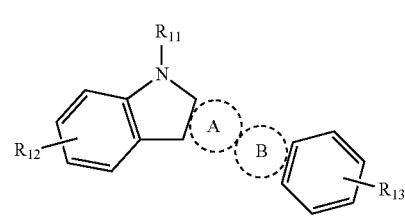
(1)

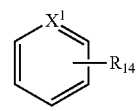
(1a)

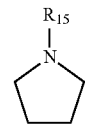
(1b)

(wherein the ring A represents an aromatic ring or a heterocyclic ring represented by Formula (1a), which is condensed with an adjacent ring, the ring B represents a heterocyclic ring represented by Formula (1b), which is condensed with an adjacent ring, $X^1$ represents carbon or nitrogen, each of $R_{11}$ and $R_{15}$ independently represents a substituted or unsubstituted aromatic hydrocarbon group or aromatic heterocyclic group, which is not a condensed ring structure other than a naphthalene ring, $R_{14}$ represents hydrogen, a substituted or unsubstituted aromatic hydrocarbon group or aromatic heterocyclic group, which is not a condensed ring structure, or a ring which is condensed with a ring including $X^1$, and each of $R_{12}$ and $R_{13}$ independently represents a hydrogen atom or a substituent.)

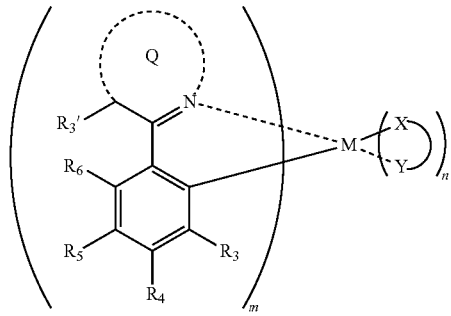

(D-1)

(In Formula (D-1), M represents a metal having an atomic weight of 40 or more. Each of $R_3$ to $R_6$ independently represents a hydrogen atom or a substituent. $R_3'$ represents a hydrogen atom or a substituent. The ring Q represents a pyridine ring, a quinoline ring or an isoquinoline ring, which is coordinated to the metal M, and may be further substituted with a non-aromatic group. $R_5$ represents an aryl group or a heteroaryl group when the ring Q is a pyridine ring. $R_3'$ and $R_6$ may be linked to each other by a linking group selected from —$CR_2$—$CR_2$—, —CR=CR—, —$CR_2$—, —O—, —NR—, —O—$CR_2$—, —NR—$CR_2$— and —N=CR— to form a ring, each R independently represents a hydrogen atom, an alkyl group, an alkenyl group, an alkynyl group, a heteroalkyl group, an aryl group or a heteroaryl group, and may further have a substituent selected from a halogen atom, —R', —OR', —N(R')$_2$, —SR', —C(O)R', —C(O)OR', —C(O)$_N$(R')$_2$, —CN, —NO$_2$, —SO$_2$, —SOR', —SO$_2$R' and —SO$_3$R', and each R' independently represents a hydrogen atom, an alkyl group, a perhaloalkyl group, an alkenyl group, an alkynyl group, a heteroalkyl group, an aryl group or a heteroaryl group. (X—Y) represents an ancillary ligand. m represents a value of 1 to the greatest number of ligands that may be bound to the metal, and n represents a value of 0 to the greatest number of ligands that may be bound to the metal. The value represents a value of the greatest number of ligands that may be bound to the metal or less. m+n is the greatest number of ligands that may be bound to the metal.)

[A compound represented by Formula (1)]

A compound represented by Formula (1) will be described in detail.

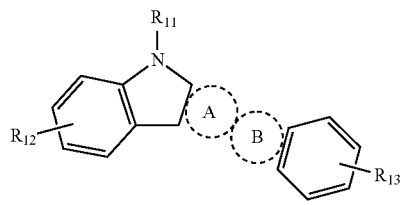

(1)

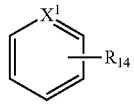

(1a)

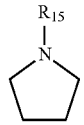

(1b)

(wherein the ring A represents an aromatic ring or a heterocyclic ring represented by Formula (1a), which is condensed with an adjacent ring, the ring B represents a heterocyclic ring represented by Formula (1b), which is condensed with an adjacent ring, $X^1$ represents carbon or nitrogen, each of $R_{11}$ and $R_{15}$ independently represents a substituted or unsubstituted aromatic hydrocarbon group or aromatic heterocyclic group, which is not a condensed ring structure other than a naphthalene ring, $R_{14}$ represents hydrogen, a substituted or unsubstituted aromatic hydrocarbon group or aromatic heterocyclic group, which is not a condensed ring structure, or a ring which is condensed with a ring including $X^1$, and each of $R_{12}$ and $R_{13}$ independently represents a hydrogen atom or a substituent.)

The compound represented by Formula (1) is a heterocyclic compound containing an indolocarbazole structure in which an indole structure is condensed with a carbazole structure. The compound represented by Formula (1), which is highly condensed in this manner, has more extended conjugation than carbazole compounds in the related art, and thus, the electron injection property may be improved while the hole injection property is maintained, and the balance of electric charges in the organic electroluminescence device may be improved. In particular, when the light emitting layer has excessive holes, these compounds are used to facilitate electron injection into the light emitting layer and improve the electric charge balance in the light emitting layer, thereby realizing high efficiency and low voltage driving of the organic electroluminescence device.

Further, the compound represented by Formula (1) has an extended p-conjugated plane and has a small degree of freedom of molecular motion, compared to carbazole compounds of the related art, and thus, it is assumed that the service life of the device is easily shortened by association and aggregation. When the compound represented by Formula (1) is used as a host material, it was thought that it was preferable to use a light emitting material which had a large degree of freedom, and thus, it was difficult to be condensed and associated in order to realize high durability of the device.

If materials having a small degree of freedom of molecular motion are combined, it is thought that interaction between molecules (host-light emitting material or between hosts, between light emitting materials, in any case), such as p-stacking, and the like, may not be overcome, and thus, it becomes easy to form an aggregation-association body.

When the compound represented by Formula (D-1) has many aromatic rings and a condensed ring structure such as a quinoline ring and an isoquinoline ring, the degree of freedom of molecular motion is particularly decreased, and thus, when the compound represented by Formula (1) is used as a host, it was expected that the compound was inappropriate as a light emitting material. However, in the present invention, unexpectedly, the aggregation and association was not generated, and thus, the device durability was improved when driving at a high temperature by using the compound represented by Formula (D-1), which has a small degree of freedom of molecular motion, in combination with the compound represented by Formula (1), which has a small degree of freedom of molecular motion.

Although it is not clear why the aggregation and association is not generated, it is understood that the permittivity and surface energy of host and guest materials are similar, and thus, the materials are not separated in a film, and a homogeneous amorphous film is produced.

Further, it is considered that the device durability is improved when driving at a high temperature because a mutual degradation reaction between host-host materials or between host-guest materials is suppressed by using hosts and guests which have a small degree of freedom of molecular motion.

$X^1$ in Formula (1) represents C—R" (R" represents a hydrogen atom or a substituent) or a nitrogen atom. When R" represents a substituent, the substituent may be exemplified by the following group A of substituents. Since chemical stability of Formula (1) is improved and the service life of the device is increased, $X^1$ is preferably C—H.

As substituents represented by $R_{12}$ and $R_{13}$ in Formula (1), those exemplified by the following group A of substituents may be applied.

(Group A of Substituents)

An alkyl group (having preferably 1 to 30 carbon atoms, more preferably 1 to 20 carbon atoms, and particularly preferably 1 to 10 carbon atoms, and examples thereof include methyl, ethyl, isopropyl, tert-butyl, n-octyl, n-decyl, n-hexadecyl and the like), an alicyclic hydrocarbon group (having preferably 1 to 30 carbon atoms, more preferably 1 to 20 carbon atoms, and particularly preferably 1 to 10 carbon atoms, and examples thereof include adamantyl, cyclopropyl, cyclopentyl, cyclohexyl and the like), an alkenyl group (having preferably 2 to 30 carbon atoms, more preferably 2 to 20 carbon atoms, and particularly preferably 2 to 10 carbon atoms, and examples thereof include vinyl, allyl, 2-butenyl, 3-pentenyl and the like), an alkynyl group (having preferably 2 to 30 carbon atoms, more preferably 2 to 20 carbon atoms, and particularly preferably 2 to 10 carbon atoms, and examples thereof include propargyl, 3-pentynyl and the like), an aryl group (having preferably 6 to 30 carbon atoms, more preferably 6 to 20 carbon atoms, and particularly preferably 6 to 12 carbon atoms, and examples thereof include phenyl, p-methylphenyl, naphthyl, anthranyl and the like), an amino group (having preferably 0 to 30 carbon atoms, more preferably 0 to 20 carbon atoms, and particularly preferably 0 to 10 carbon atoms, and examples thereof include amino, methylamino, dimethylamino, diethylamino, dibenzylamino, diphenylamino, ditolylamino and the like), an alkoxy group (having preferably 1 to 30 carbon atoms, more preferably 1 to 20 carbon atoms, and particularly preferably 1 to 10 carbon atoms, and examples thereof include methoxy, ethoxy, butoxy, 2-ethylhexyloxy and the like), an aryloxy group (having preferably 6 to 30 carbon atoms, more preferably 6 to 20 carbon atoms, and particularly preferably 6 to 12 carbon atoms, and examples thereof include phenyloxy, 1-naphthyloxy, 2-naphthyloxy and the like), a heterocyclic oxy group (having preferably 1 to 30 carbon atoms, more preferably 1 to 20 carbon atoms, and particularly preferably 1 to 12 carbon atoms, and examples thereof include pyridyloxy, pyrazyloxy, pyrimidyloxy, quinolyloxy and the like), an acyl group (having preferably 1 to 30 carbon atoms, more preferably 1 to 20 carbon atoms, and particularly preferably 1 to 12 carbon atoms, and examples thereof include acetyl, benzoyl, formyl, pivaloyl and the like), an alkoxycarbonyl group (having preferably 2 to 30 carbon atoms, more preferably 2 to 20 carbon atoms, and particularly preferably 2 to 12 carbon atoms, and examples thereof include methoxycarbonyl, ethoxycarbonyl and the like), an aryloxycarbonyl group (having preferably 7 to 30 carbon atoms, more preferably 7 to 20 carbon atoms, and particularly preferably having 7 to 12 carbon atoms, and examples thereof include phenyloxycarbonyl and the like), an acyloxy group (having preferably 2 to 30 carbon atoms, more preferably 2 to 20 carbon atoms, and particularly preferably 2 to 10 carbon atoms, and examples thereof include acetoxy, benzoyloxy and the like), an acylamino group (having preferably 2 to 30 carbon atoms, more preferably 2 to 20 carbon atoms, and particularly preferably 2 to 10 carbon atoms, and examples thereof include acetylamino, benzoylamino and the like), an alkoxycarbonylamino group (having preferably 2 to 30 carbon atoms, more preferably 2 to 20 carbon atoms, and particularly preferably 2 to 12 carbon atoms, and examples thereof include methoxycarbonylamino and the like), an aryloxycarbonylamino group (having preferably 7 to 30 carbon atoms, more preferably 7 to 20 carbon atoms, and particularly preferably 7 to 12 carbon atoms, and examples thereof include phenyloxycarbonylamino and the like), a sulfonylamino group (having preferably 1 to 30 carbon atoms, more preferably 1 to 20 carbon atoms, and particularly preferably 1 to 12 carbon atoms, and examples thereof include methanesulfonylamino, benzenesulfonylamino and the like), a sulfamoyl group (having preferably 0 to 30 carbon atoms, more preferably 0 to 20 carbon atoms, and particularly preferably 0 to 12 carbon atoms, and examples thereof include sulfamoyl, methylsulfamoyl, dimethylsulfamoyl, phenylsulfamoyl and the like), a carbamoyl group (having preferably 1 to 30 carbon atoms, more preferably 1 to 20 carbon atoms, and particularly preferably 1 to 12 carbon atoms, and examples thereof include carbamoyl, methylcarbamoyl, diethylcarbamoyl, phenylcarbamoyl and the like), an alkylthio group (having preferably 1 to 30 carbon atoms, more preferably 1 to 20 carbon atoms, and particularly preferably 1 to 12 carbon atoms, and examples thereof include methylthio, ethylthio and the like), an arylthio group (having preferably 6 to 30 carbon atoms, more preferably 6 to 20 carbon atoms, and particularly preferably 6 to 12 carbon atoms, and examples thereof include phenylthio and the like), a heterocyclic thio group (having preferably 1 to 30 carbon atoms, more preferably 1 to 20 carbon atoms, and particularly preferably 1 to 12 carbon atoms, and examples thereof include pyridylthio, 2-benzimizolylthio, 2-benzoxazolylthio, 2-benzthiazolylthio and the like), a sulfonyl group (having preferably 1 to 30 carbon atoms, more preferably 1 to 20 carbon atoms, and particularly preferably 1 to 12 carbon atoms, and examples thereof include mesyl, tosyl and the like), a sulfinyl group (having preferably 1 to 30 carbon atoms, more preferably 1 to 20 carbon atoms, and particularly preferably 1 to 12 carbon atoms, and examples thereof include methanesulfinyl, benzenesulfinyl and the like), a ureido group (having preferably 1 to 30 carbon atoms, more preferably 1 to 20 carbon atoms, and particularly preferably 1 to 12 carbon atoms, and examples thereof include ureido, methylureido, phenylureido and the like), a phosphoric acid amide group (having preferably 1 to 30 carbon atoms, more preferably 1 to 20 carbon atoms, and particularly preferably 1 to 12 carbon atoms, and examples thereof include diethylphosphoric acid amide, phenylphosphoric acid amide and the like), a hydroxyl group, a mercapto group, a halogen atom (for example, a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic group (having preferably 1 to 30 carbon atoms, and more preferably 1 to 12 carbon atoms, and examples of the heteroatom include a nitrogen atom, an oxygen atom, and a sulfur atom, and specifically imidazolyl, pyridyl, quinolyl, furyl, thienyl, piperidyl, morpholino, benzoxazolyl, benzimidazolyl, benzthiazolyl, a carbazolyl group, an azepinyl group and the like), a silyl group (having preferably 3 to 40 carbon atoms, more preferably 3 to 30 carbon atoms, and particularly preferably 3 to 24 carbon atoms, and examples thereof include trimethylsilyl, triphenylsilyl, and the like), a silyloxy group (having preferably 3 to 40 carbon atoms, more preferably 3 to 30 carbon atoms, and particularly preferably 3 to 24 carbon atoms, and examples thereof include trimethylsilyloxy, triphenylsilyloxy and the like)

$R_{12}$ and $R_{13}$ include preferably a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group, a silyloxy group and a trifluoromethyl group, more preferably a hydrogen atom, an alkyl group, an alicyclic hydrocarbon group, an aryl group, a fluorine group, a cyano group, a silyl group, a heterocyclic group and a trifluoromethyl group, even more preferably a hydrogen atom, an alkyl group, an aryl group, a fluorine group, a cyano group, a silyl group and a trifluoromethyl group, and particularly preferably a hydrogen atom, an alkyl group, a silyl group, a fluorine group, a cyano group and a trifluoromethyl group.

$R_{12}$ and $R_{13}$ may further have a substituent, and the above-described group A of substituents may be applied as the substituent, which includes an alkyl group, an aryl group, a cyano group, a halogen atom and a nitrogen-containing aromatic heterocyclic group, more preferably alkyl having 1 to 6 carbon atoms, an aryl group having 6 to 10 carbon atoms, a pyridyl group and a fluorine atom, and more preferably an alkyl group having 1 to 6 carbon atoms and a phenyl group. The number of substituents may be 0 to 4, and preferably 0 to 2. Further, a plurality of substituents may be linked to each other to form a ring.

In Formula (1), a substituted or unsubstituted aromatic hydrocarbon group or aromatic heterocyclic group, which is not a condensed ring structure other than a naphthalene ring, represented by $R_{11}$ and $R_{15}$, includes a benzene ring, a naphthalene ring, a biphenyl ring, an o-terphenyl ring, an m-terphenyl ring, a p-terphenyl ring, a furan ring, a thiophene ring, a pyridine ring, a pyridazine ring, a pyrimidine ring, a pyrazine ring, a triazine ring, an oxadiazole ring, a triazole ring, an imidazole ring, a pyrazole ring, a thiazole ring and the like.

$R_{11}$ and $R_{15}$ include preferably a benzene ring, a naphthalene ring, a biphenyl ring, a pyrazole ring, an imidazole ring, a triazole ring, a pyridine ring, a pyridazine ring, a pyrimidine ring, a pyrazine ring, a triazine ring and a thiophene ring, more preferably a benzene ring, a naphthalene ring, a biphenyl ring, a pyridine ring, a pyrimidine ring and a triazine ring, even more preferably a benzene ring, a naphthalene ring, a pyridine ring, a triazine ring and a pyrimidine ring, particularly preferably a benzene ring, a pyridine ring and a triazine ring, and most preferably a benzene ring and a pyridine ring.

$R_{11}$ and $R_{15}$ may further have a substituent, and the above-described group A of substituents may be applied as the substituent, and includes preferably an alkyl group, an aryl group, a cyano group, a halogen atom, and a nitrogen-containing aromatic heterocyclic group, more preferably alkyl having 1 to 6 carbon atoms, an aryl group having 6 to 10 carbon atoms, pyridyl, a cyano group and a halogen atom, even more preferably a branched alkyl group having 3 to 6 carbon atoms, a phenyl group, a naphthyl group, a cyano group and a fluorine atom, and particularly preferably a methyl group, an isobutyl group, a t-butyl group, a neopentyl group, a phenyl group, a naphthyl group, a cyano group and a fluorine atom. The number of substituents may be 0 to 4, and preferably 0 to 2. Further, a plurality of substituents may be linked to each other to form a ring.

A substituted or unsubstituted aromatic hydrocarbon group or aromatic heterocyclic group, which is not a condensed ring structure, represented by $R_{14}$, includes a benzene ring, a biphenyl ring, an o-terphenyl ring, an m-terphenyl ring, a p-terphenyl group, a furan ring, a thiophene ring, a pyridine ring, a pyridazine ring, a pyrimidine ring, a pyrazine ring, an oxadiazole ring, a triazole ring, an imidazole ring, a pyrazole ring, a thiazole ring and the like. The aromatic heterocycling ring may have a substituent, and as the substituent, those exemplified above for the group A of substituents may be applied.

$R_{14}$ includes preferably a hydrogen atom, a benzene ring, a biphenyl ring, a pyrazole ring, an imidazole ring, a triazole ring, a pyridine ring and a thiophene ring, more preferably a hydrogen atom, a benzene ring, a biphenyl ring and a pyridine ring, and particularly preferably a hydrogen atom.

$R_{14}$ may further have a substituent, and as the substituent, those exemplified above for the group A of substituents may be applied, and may include preferably an alkyl group having 1 to 6 carbon atoms, a phenyl group, a pyridyl group and the like.

Further, a plurality of substituents may be linked to a ring including X' to form a ring.

The compound represented by Formula (3) is preferably represented by Formula (1). In this case, in Formula (1), the ring A represents an aromatic ring or a heterocyclic ring represented by Formula (1a), which is condensed with an adjacent ring, and the ring B represents a heterocyclic ring represented by Formula (1b), which is condensed with an adjacent ring. $X^1$ represents C—R" (R" represents a hydrogen atom or a substituent) or a nitrogen atom. Each of $R_{11}$ and $R_{15}$ independently represents a benzene ring, a naphthalene ring, a pyridine ring, a triazine ring or a pyrimidine ring, and these rings may be further substituted with at least one group selected from a methyl group, an isobutyl group, a t-butyl group, a neopentyl group, a phenyl group, a naphthyl group, a cyano group and a fluorine atom. $R_{14}$ represents a hydrogen atom. Each of $R_{12}$ and $R_{13}$ independently represents a hydrogen atom, an alkyl group, a silyl group, a fluorine atom, a cyano group or a trifluoromethyl group, and these groups may be further substituted with at least one of an alkyl group having 1 to 6 carbon atoms and a phenyl group.

A preferred range of each symbol in the above definition is the same as that described above.

As the compound represented by Formula (1), one of preferable forms is a compound represented by the following Formula (2).

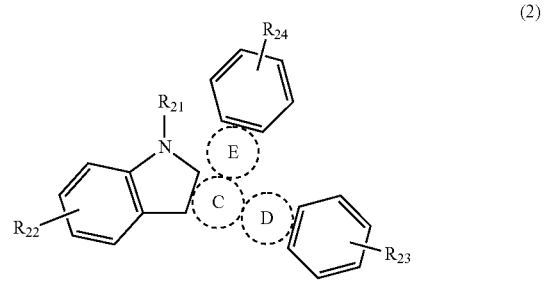

(2)

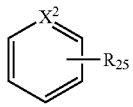

(2a)

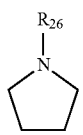

(2b)

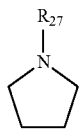

(2c)

(wherein the ring C represents an aromatic ring or a heterocyclic ring represented by Formula (2a), which is condensed with an adjacent ring, the ring D represents a heterocyclic ring represented by Formula (2b), which is condensed with an adjacent ring, the ring E represents a heterocyclic ring represented by Formula (2c), which is condensed with an adjacent ring, $X^2$ represents carbon or nitrogen, each of $R_{21}$, $R_{26}$ and $R_{27}$ independently represents a substituted or unsubstituted aromatic hydrocarbon group or aromatic heterocyclic group, which is not a condensed ring structure other than a naphthalene ring, $R_{25}$ represents hydrogen, a substituted or unsubstituted aromatic hydrocarbon group or aromatic heterocyclic group, which is not a condensed ring structure, or a ring which is condensed with a ring including $X^2$, and each of $R_{22}$, $R_{23}$ and $R_{24}$ independently represents a hydrogen atom or a substituent.)

Each of $R_{21}$, $R_{26}$ and $R_{27}$ independently represents a substituted or unsubstituted aromatic hydrocarbon group or aromatic heterocyclic group, which is not a condensed ring structure other than a naphthalene ring, and has the same meaning as $R_{11}$ and $R_{15}$ in Formula (1), and preferred ranges thereof are also the same.

$R_{25}$ represents hydrogen, a substituted or unsubstituted aromatic hydrocarbon group or aromatic heterocyclic group, which is not a condensed ring structure, or a ring which is condensed with a ring including $X^2$, and has the same meaning as $R_{14}$ in Formula (1), and preferred ranges thereof are also the same.

Each of $R_{22}$, $R_{23}$ and $R_{24}$ independently represents a hydrogen atom or a substituent, and has the same meaning as $R_{12}$ and $R_{13}$ in Formula (1), and preferred ranges thereof are also the same.

As the compound represented by Formula (1), one of the preferable forms is a compound represented by the following Formula (15).

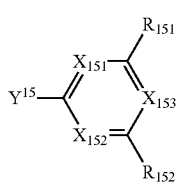

(15)

(wherein $X_{151}$ to $X_{153}$ represent a nitrogen atom or C—$R_{153}$, and $R_{153}$ represents a hydrogen atom, a methyl group, an isobutyl group, a t-butyl group, a neopentyl group, a phenyl group, a naphthyl group, a cyano group or a fluorine atom. Each of $R_{151}$ and $R_{152}$ independently represents a hydrogen atom, a methyl group, an isobutyl group, a t-butyl group, a neopentyl group, a phenyl group, a naphthyl group, a cyano group or a fluorine atom. $Y^{15}$ represents a group represented by any one of the following Formulas (15a) to (15c).)

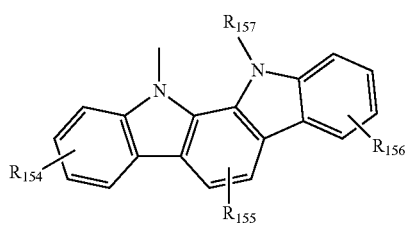

(15a)

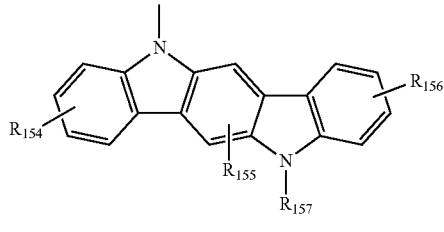

(15b)

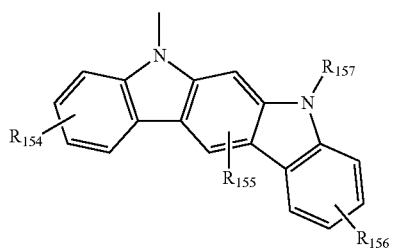

(15c)

(wherein $R_{155}$ represents a hydrogen atom. Each of $R_{154}$ and $R_{156}$ independently represents a hydrogen atom, an alkyl group, a silyl group, a fluorine atom, a cyano group or a trifluoromethyl group, and these groups may be further substituted with at least one of an alkyl group having 1 to 6 carbon atoms and a phenyl group. $R_{157}$ represents a benzene ring, a naphthalene ring, a pyridine ring, a triazine ring or a pyrimidine ring, and these rings may be further substituted with at least one group selected from a methyl group, an isobutyl group, a t-butyl group, a neopentyl group, a phenyl group, a naphthyl group, a cyano group and a fluorine atom.)

$X_{151}$ to $X_{153}$ represent a nitrogen atom or C—$R_{153}$, and $R_{153}$ represents a hydrogen atom or a substituent. A combination of $X_{151}$ to $X_{153}$ is not particularly limited, but the number of nitrogen atoms is preferably 0, 1 or 3, and more preferably 0 or 3.

As the substituent represented by $R_{151}$ and $R_{152}$, those exemplified above for the group A of substituents may be applied.

$R_{151}$ and $R_{152}$ include preferably a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group and a silyloxy group, more preferably a hydrogen atom, an alkyl group, an alicyclic hydrocarbon group, an aryl group, a fluorine group, a cyano group, a silyl group and a heterocyclic group, even more preferably a hydrogen atom, an alkyl group (preferably a methyl group, an isobutyl group, a t-butyl group and a neopentyl group), an aryl group (preferably a phenyl group and a naphthyl group), a cyano group and a fluorine atom, and particularly preferably a hydrogen atom, an alkyl group and aryl group.

$R_{151}$ and $R_{152}$ may further have a substituent, and as the substituent, those exemplified above for the group A of substituents may be applied, and may include preferably alkyl having 1 to 6 carbon atoms, phenyl, pyridyl and the like. The number of substituents is preferably 0 to 4, and more preferably 0 to 2. Further, a plurality of substituents may be linked to each other to form a ring.

As the substituent represented by $R_{153}$, those exemplified above for the group A of substituents may be applied.

$R_{153}$ includes preferably a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group and a silyloxy group, more preferably a hydrogen atom, an alkyl group, an alicyclic hydrocarbon group, an aryl group, a fluorine group, a cyano group, a silyl group and a heterocyclic group, even more preferably a hydrogen atom, an alkyl group (preferably a methyl group, an isobutyl group, a t-butyl group and a neopentyl group), an aryl group (preferably a phenyl group and a naphthyl group), a cyano group, a fluorine atom, a hydrogen atom, an alkyl group and an aryl group, particularly preferably a hydrogen atom and an alkyl group, and most preferably a hydrogen atom.

$R_{153}$ may further have a substituent, and as the substituent, those exemplified above for the group A of substituents may be applied, and may include preferably alkyl having 1 to 6 carbon atoms, phenyl, pyridyl and the like. The number of substituents is preferably 0 to 4, and more preferably 0 to 2. Further, a plurality of substituents may be linked to each other to form a ring.

$Y^{15}$ represents a group represented by any one of Formulas (15a) to (15c), preferably (15a) and (15b), and more preferably (15a).

In Formulas (15a) to (15c), as the substituent represented by $R_{154}$ and $R_{156}$, those exemplified above for the group A of substituents may be applied.

$R_{154}$ and $R_{156}$ include preferably a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group and a silyloxy group, more preferably a hydrogen atom, an alkyl group, an alicyclic hydrocarbon group, an aryl group, a fluorine group, a cyano group, a silyl group and a heterocyclic group, even more preferably a hydrogen atom, an alkyl group and an aryl group, particularly preferably a hydrogen atom and an alkyl group, and most preferably a hydrogen atom.

$R_{154}$ and $R_{156}$ may further have a substituent, and as the substituent, those exemplified above for the group A of substituents may be applied, and may include preferably alkyl having 1 to 6 carbon atoms, phenyl, pyridyl and the like. The number of substituents is preferably 0 to 4, and more preferably 0 to 2. Further, a plurality of substituents may be linked to each other to form a ring.

A substituted or unsubstituted aromatic hydrocarbon group or aromatic heterocyclic group, which is not a condensed ring structure, represented by $R_{155}$, includes a benzene ring, a biphenyl ring, an o-terphenyl ring, an m-terphenyl ring, a p-terphenyl ring, a furan ring, a thiophene ring, a pyridine ring, a pyridazine ring, a pyrimidine ring, a pyrazine ring, an oxadiazole ring, a triazole ring, an imidazole ring, a pyrazole ring, a thiazole ring and, the like. The aromatic heterocyclic ring may have a substituent, and as the substituent, those exemplified above for the group A of substituents may be applied.

$R_{155}$ includes preferably a hydrogen atom, a benzene ring, a biphenyl ring, a pyrazole ring, an imidazole ring, a triazole ring, a pyridine ring and a thiophene ring, more preferably a hydrogen atom, a benzene ring, a biphenyl ring and a pyridine ring, and particularly preferably a hydrogen atom.

$R_{155}$ may further have a substituent, and as the substituent, those exemplified above for the group A of substituents may be applied, and may include preferably alkyl having 1 to 6 carbon atoms, phenyl, pyridyl and the like.

A substituted or unsubstituted aromatic hydrocarbon group or aromatic heterocyclic group, which is not a condensed ring structure other than a naphthalene ring, represented by $R_{157}$, includes a benzene ring, a naphthalene ring, a biphenyl ring, an o-terphenyl ring, an m-terphenyl ring, a p-terphenyl ring, a furan ring, a thiophene ring, a pyridine ring, a pyridazine ring, a pyrimidine ring, a pyrazine ring, an oxadiazole ring, a triazole ring, an imidazole ring, a pyrazole ring, a thiazole ring and the like. The aromatic heterocyclic ring may have a substituent, and as the substituent, those exemplified above for the group A of substituents may be applied.

$R_{157}$ includes preferably a benzene ring, a biphenyl ring, a pyrazole ring, an imidazole ring, a triazole ring, a pyridine ring, a thiophene ring, a naphthalene ring, and a triazine ring, more preferably a benzene ring, a biphenyl ring, a pyridine ring, a naphthalene ring and a triazine ring, particularly preferably a benzene ring, a naphthalene ring, a pyridine ring, a naphthalene ring, and a triazine ring, particularly preferably a benzene ring and a triazine ring, and most preferably a benzene ring.

$R_{157}$ may further have a substituent, and as the substituent, those exemplified above for the group A of substituents may be applied, and may include preferably alkyl having 1 to 6 carbon atoms, phenyl, pyridyl and the like. The number of substituents is preferably 0 to 4, and more preferably 0 to 2. Further, a plurality of substituents may be linked to each other to form a ring.

As the compound represented by Formula (15), one of the preferable forms is a compound represented by the following Formula (16).

(16)

(wherein $X_{161}$ to $X_{163}$ represents a nitrogen atom or C—H, and each of $R_{161}$ and $R_{162}$ independently represents a hydrogen atom or a substituent. $Y^{16}$ represents a group represented by any one of the following Formulas (15a) to (15c).)

$R_{161}$, $R_{162}$ and $Y^{16}$ have the same meaning as $R_{151}$, $R_{152}$ and $Y^{15}$ in Formula (15), and preferred ranges thereof are also the same.

$X_{161}$ to $X_{163}$ represent a nitrogen atom or C—H. A combination of $X_{151}$ to $X_{153}$ is not particularly limited, but the number of nitrogen atoms is preferably 0, 1 or 3 and more preferably 0 or 3.

In the above Formula, it is preferred that $X_{161}$ to $X_{163}$ represents a nitrogen atom or C—H, each of $R_{161}$ and $R_{162}$ independently represents a hydrogen atom, a methyl group, an isobutyl group, a t-butyl group, a neopentyl group, a phenyl group, a naphthyl group, a cyano group or a fluorine atom, and $Y^{16}$ represents a group represented by any one of Formulas (15a) to (15c).

As the compound represented by Formula (16), one of the preferable forms is a compound represented by the following Formula (17).

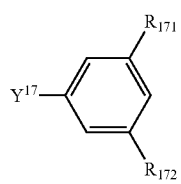

(17)

(wherein each of $R_{171}$ to $R_{172}$ independently represents a hydrogen atom or a substituent. $Y^{17}$ represents a group represented by any one of Formulas (15a) to (15c).)

$R_{171}$, $R_{172}$ and $Y^{17}$ have the same meaning as $R_{161}$, $R_{162}$ and $Y^{16}$ in Formula (16), and preferred ranges thereof are also the same.

In the above Formula, it is preferred that each of $R_{171}$ and $R_{172}$ independently represents a hydrogen atom, a methyl group, an isobutyl group, a t-butyl group, a neopentyl group, a phenyl group, a naphthyl group, a cyano group or a fluorine atom, and $Y^{17}$ represents a group represented by any one of Formulas (15a) to (15c).

As the compound represented by Formula (16), one of the preferable forms is a compound represented by the following Formula (18).

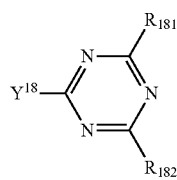

(18)

(wherein each of $R_{181}$ and $R_{182}$ independently represents a hydrogen atom or a substituent. $Y^{18}$ represents a group represented by any one of Formulas (15a) to (15c).)

$R_{181}$, $R_{182}$ and $Y^{18}$ have the same meaning as $R_{161}$, $R_{162}$ and $Y^{16}$ in Formula (16), an preferred ranges thereof are also the same.

In the above Formula, it is preferred that each of $R_{181}$ and $R_{182}$ independently represents a hydrogen atom, a methyl group, an isobutyl group, a t-butyl group, a neopentyl group, a phenyl group, a naphthyl group, a cyano group or a fluorine atom, and $Y'^{8}$ represents a group represented by any one of Formulas (15a) to (15c).

As the compound represented by Formula (1) or (2), one of the preferable forms is a compound represented by the following Formula (3).

(3)

(wherein $Z^3$ represents a $n^3$ valent group including a substituted or unsubstituted aromatic hydrocarbon group or aromatic heterocyclic group which is not a condensed ring structure, a silicon atom or a carbon atom, $Y^3$ represents a group represented by the following Formula (3a-1), (3a-2) or (3e), and $n^3$ represents an integer of 1 or more.)

The substituted or unsubstituted aromatic hydrocarbon group or aromatic heterocyclic group represented by $Z^3$, which is not a condensed ring structure includes preferably benzene, pyridine, triazine, pyrimidine, biphenyl, phenylpyridine, bipyridine, terphenyl, triazole, diazole, phenyltriazole, triphenylthiazole and the like, preferably benzene, pyridine, triazine, pyrimidine, biphenyl, phenylpyridine and bipyridine, and more preferably a benzene ring, a biphenyl ring and a pyridine ring. When these have a substituent, the substituent may include a substituent selected from the group A of substituents, preferably at least one group selected from an alkyl group, an aryl group, a silyl group, a cyano group, a fluorine atom, and a combination thereof, and more preferably alkyl having 1 to 6 carbon atoms, phenyl and pyridyl. The number of substituents may be 0 to 4, and preferably 0 to 2.

When $Z^3$ represents a silicon atom or a carbon atom, the silicon atom and the carbon atom may further have a substituent, if possible, and the substituent may include a substituent selected from the group A of substituents, preferably at least one group selected from an alkyl group, an aryl group, a silyl group, a cyano group, a fluorine atom and a combination thereof, more preferably at least one group selected from an alkyl group, an aryl group and a combination thereof, and even more preferably a methyl group and a phenyl group.

$Y^3$ represents a group represented by the following Formula (3a-1), (3a-2) or (3e).

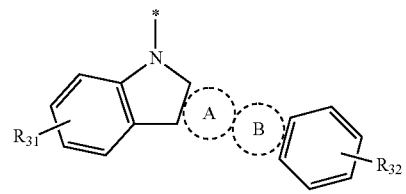

(3a-1)

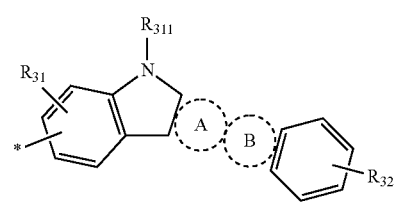

(3a-2)

(3b)

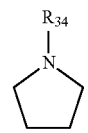

(3c)

(wherein the ring A represents an aromatic ring or a heterocyclic ring represented by Formula (3b), which is condensed with an adjacent ring, the ring B represents a heterocyclic ring represented by Formula (3c), which is condensed with an adjacent ring, $X^3$ represents carbon or nitrogen, each of $R_{34}$ and $R_{311}$ independently represents a substituted or unsubstituted aromatic hydrocarbon group or aromatic heterocyclic group, which is not a condensed ring structure other than a naphthalene ring, $R_{33}$ represents hydrogen, a substituted or unsubstituted aromatic hydrocarbon group or aromatic heterocyclic group, which is not a condensed ring structure, or a ring which is condensed with a ring including $X^3$, and each of $R_{31}$ and $R_{32}$ independently represents a hydrogen atom or a substituent. * represents a bond for linking to $Z^3$.)

$R_{34}$ and $R_{311}$ represent a substituted or unsubstituted aromatic hydrocarbon group or aromatic heterocyclic group, which is not a condensed ring structure other than a naphthalene ring, and has the same meaning as $R_{15}$ in Formula (1), and preferred ranges thereof are also the same.

$R_{33}$ represents hydrogen, a substituted or unsubstituted aromatic hydrocarbon group or aromatic heterocyclic group, which is not a condensed ring structure, or a ring which is condensed with a ring including X, and has the same meaning as $R_{14}$ in Formula (1), and preferred ranges thereof are also the same.

Each of $R_{31}$ and $R_{32}$ independently represents a hydrogen atom or a substituent, and has the same meaning as $R_{12}$ and $R_{13}$ in Formula (1), and preferred ranges thereof are also the same.

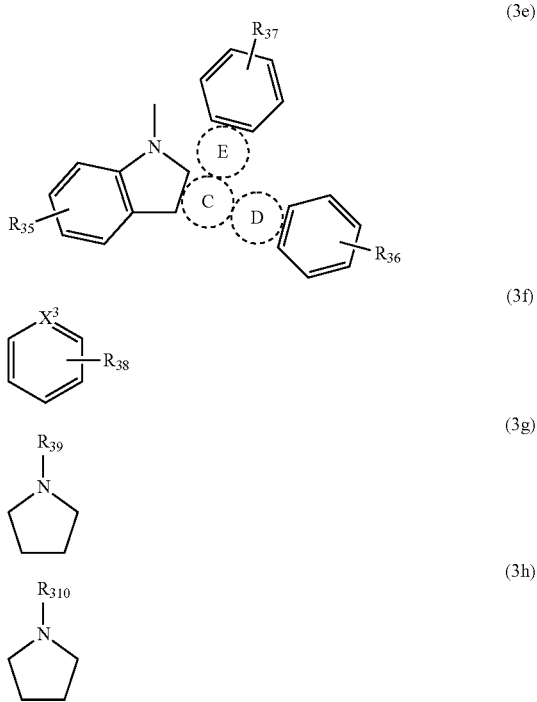

(wherein the ring C represents an aromatic ring or a heterocyclic ring represented by Formula (30, which is condensed with an adjacent ring, the ring D represents a heterocyclic ring represented by Formula (3g), which is condensed with an adjacent ring, the ring E represents a heterocyclic ring represented by Formula (3h), which is condensed with an adjacent ring, $X^3$ represents carbon or nitrogen, each of $R_{39}$ and $R_{310}$ independently represents a substituted or unsubstituted aromatic hydrocarbon group or aromatic heterocyclic group, which is not a condensed ring structure other than a naphthalene ring, $R_{38}$ represents hydrogen, a substituted or unsubstituted aromatic hydrocarbon group or aromatic heterocyclic group, which is not a condensed ring structure, or a ring which is condensed with a ring including $X^3$, and each of $R_{35}$, $R_{36}$ and $R_{37}$ independently represents a hydrogen atom or a substituent.)

Each of $R_{39}$ and $R_{310}$ independently represents a substituted or unsubstituted aromatic hydrocarbon group or aromatic heterocyclic group, which is not a condensed ring structure other than a naphthalene ring, and has the same meaning as $R_{26}$ and $R_{27}$ in Formula (2), and preferred ranges thereof are also the same.

$R_{38}$ represents hydrogen, a substituted or unsubstituted aromatic hydrocarbon group or aromatic heterocyclic group, which is not a condensed ring structure, or a ring which is condensed with a ring including $X^3$, and has the same meaning as $R_{25}$ in Formula (2), and preferred ranges thereof are also the same.

Each of $R_{35}$, $R_{36}$, and $R_{37}$ independently represents a hydrogen atom or a substituent, and has the same meaning as Rn, $R_{23}$ and $R_{24}$ in Formula (1), and preferred ranges thereof are also the same.

$n^3$ in Formula (3) is preferably 1 to 4, more preferably 2 to 4, and even more preferably 2 to 3.

One of the preferable forms of the compound represented by Formula (3) is a compound represented by the following Formula (4).

$$Ar_{41}\text{-}(Y^4)_2 \quad (4)$$

(wherein $Ar_{41}$ represents a divalent linking group consisting of a substituted or unsubstituted aromatic hydrocarbon group or aromatic heterocyclic group, which is not a condensed ring structure, and $Y^4$ represents a group represented by Formula (3a-1), (3a-2) or (3e).)

$Ar_{41}$ in Formula (4) represents a divalent linking group. Specifically, the linking group may include a linking group represented by the following Y-1 to Y-118.

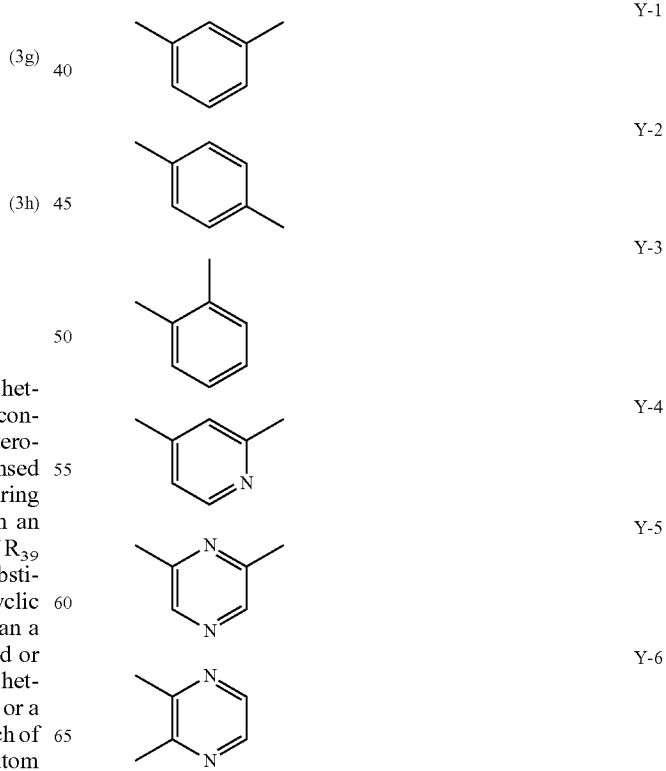

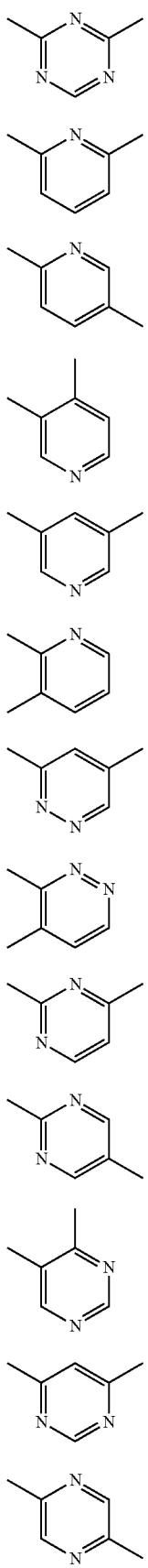
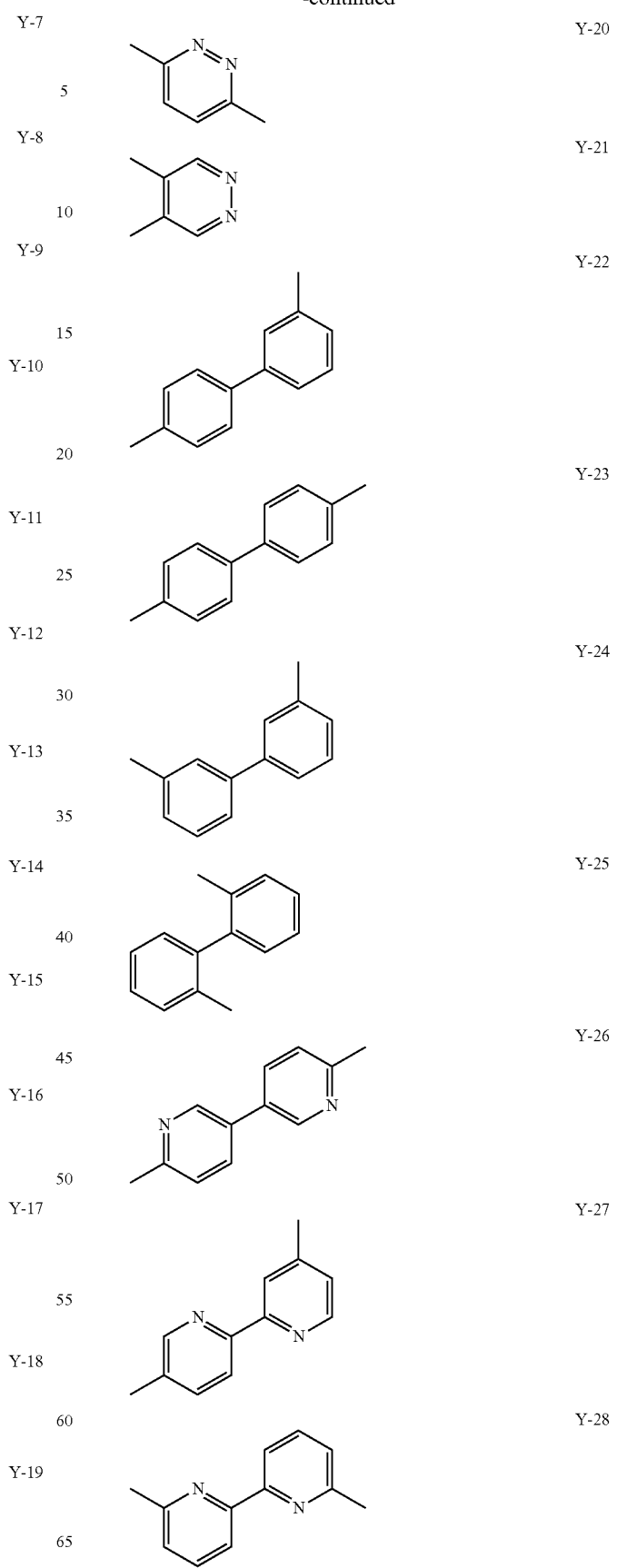

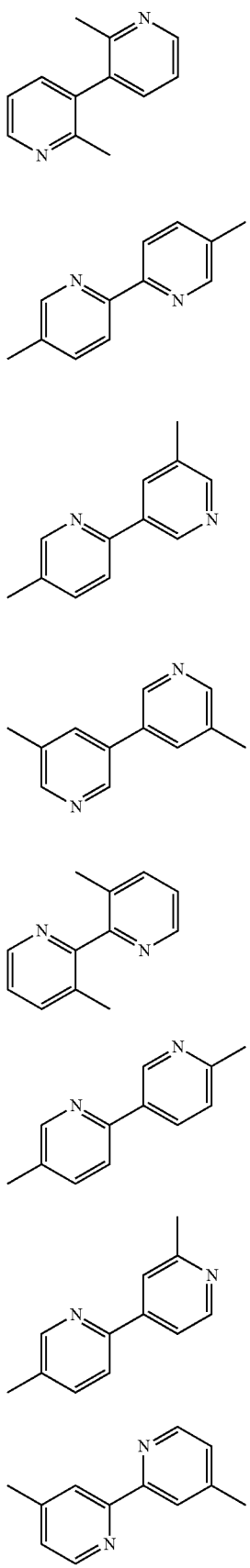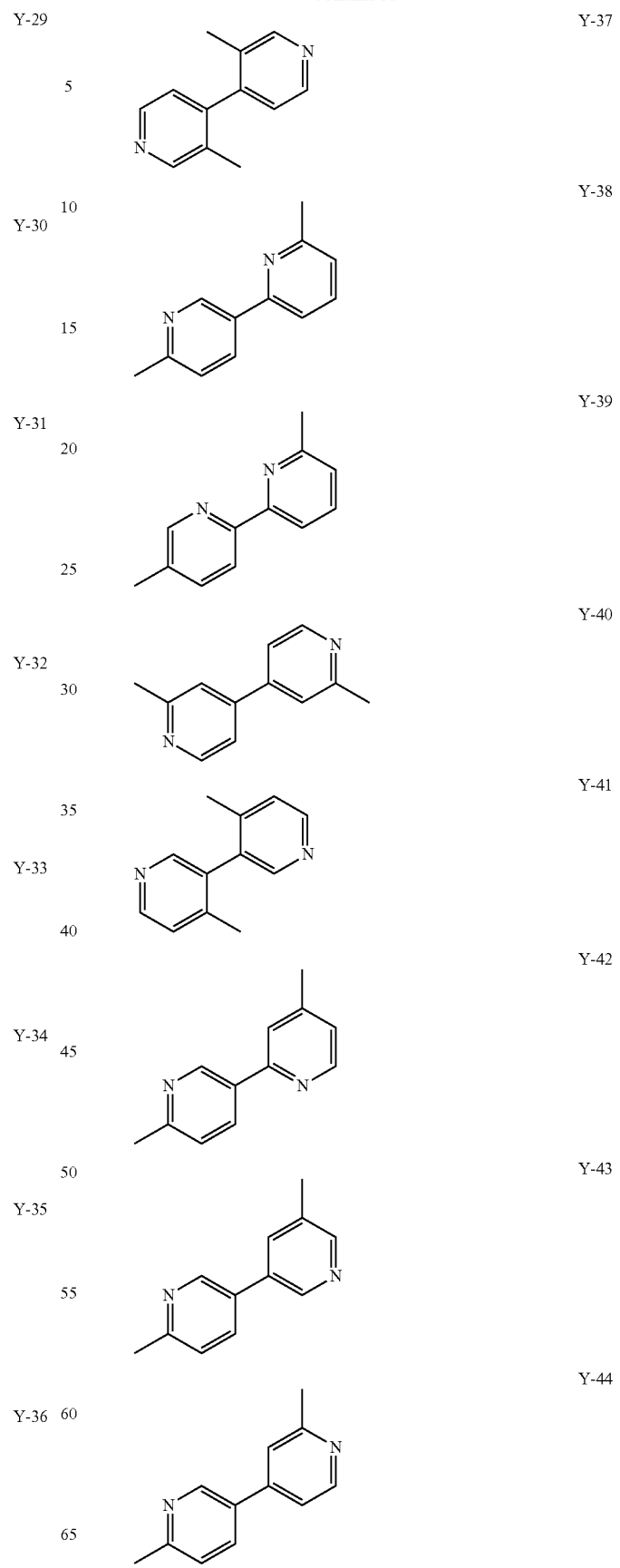

| | |
|---|---|
| Y-45 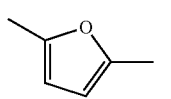 | Y-57 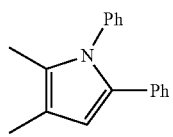 |
| Y-46 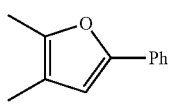 | Y-58 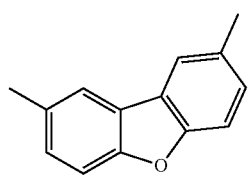 |
| Y-47 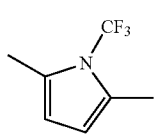 | Y-59 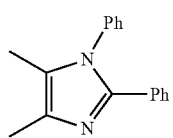 |
| Y-48 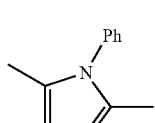 | Y-60 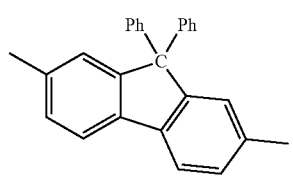 |
| Y-49 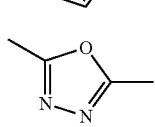 | Y-61 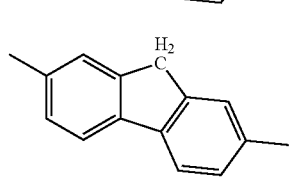 |
| Y-50 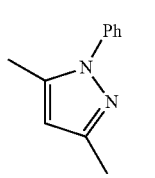 | Y-62 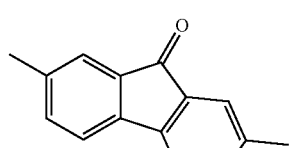 |
| Y-51 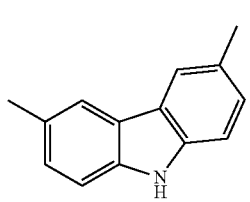 | Y-63 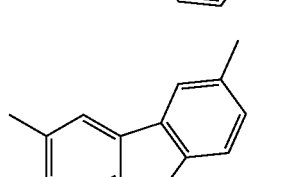 |
| Y-52 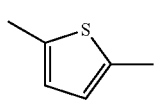 | Y-64 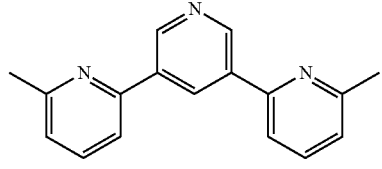 |
| Y-53 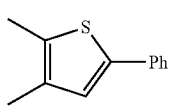 | Y-65 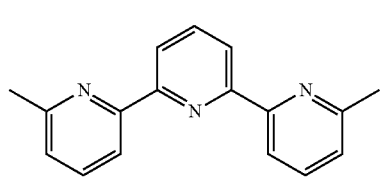 |
| Y-54 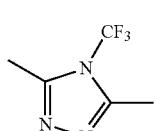 | |
| Y-55 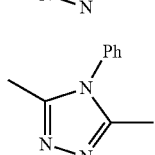 | |
| Y-56  | |

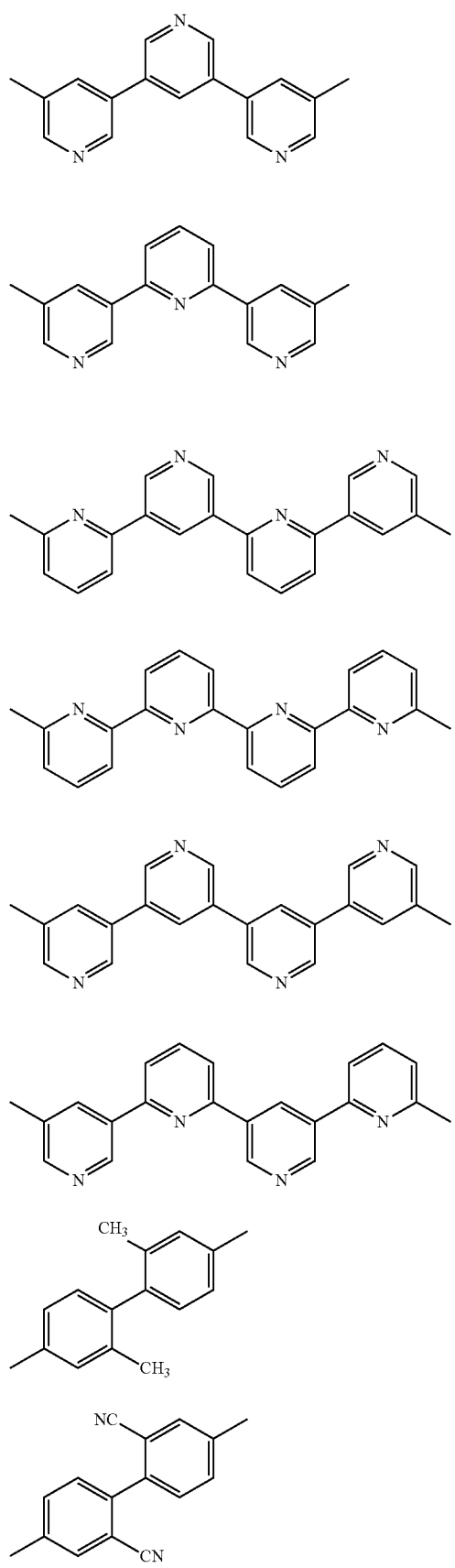
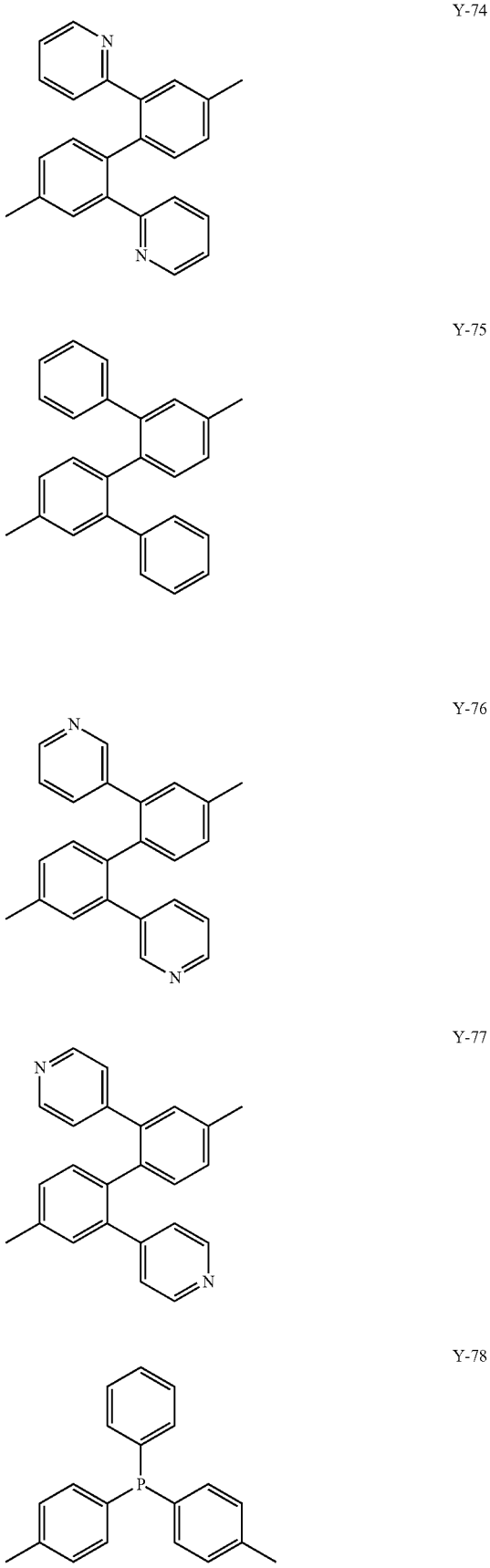

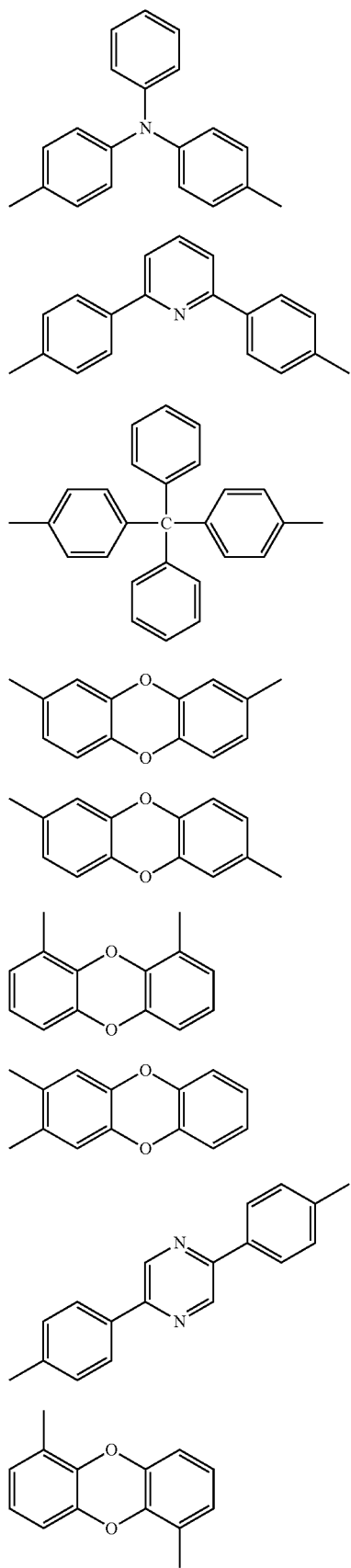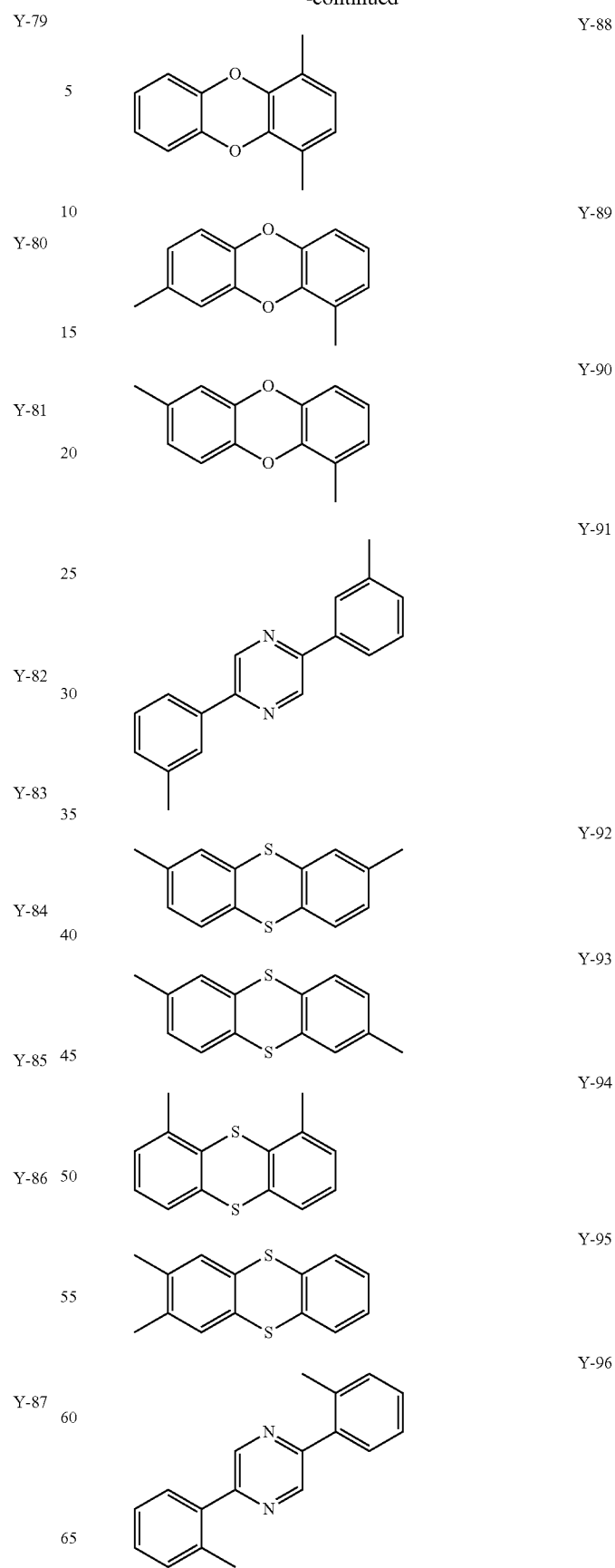

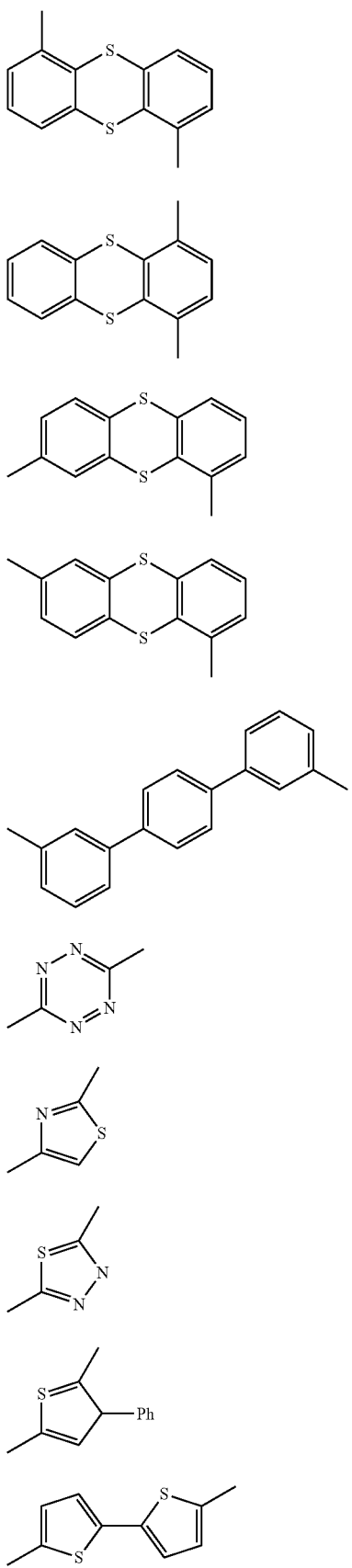
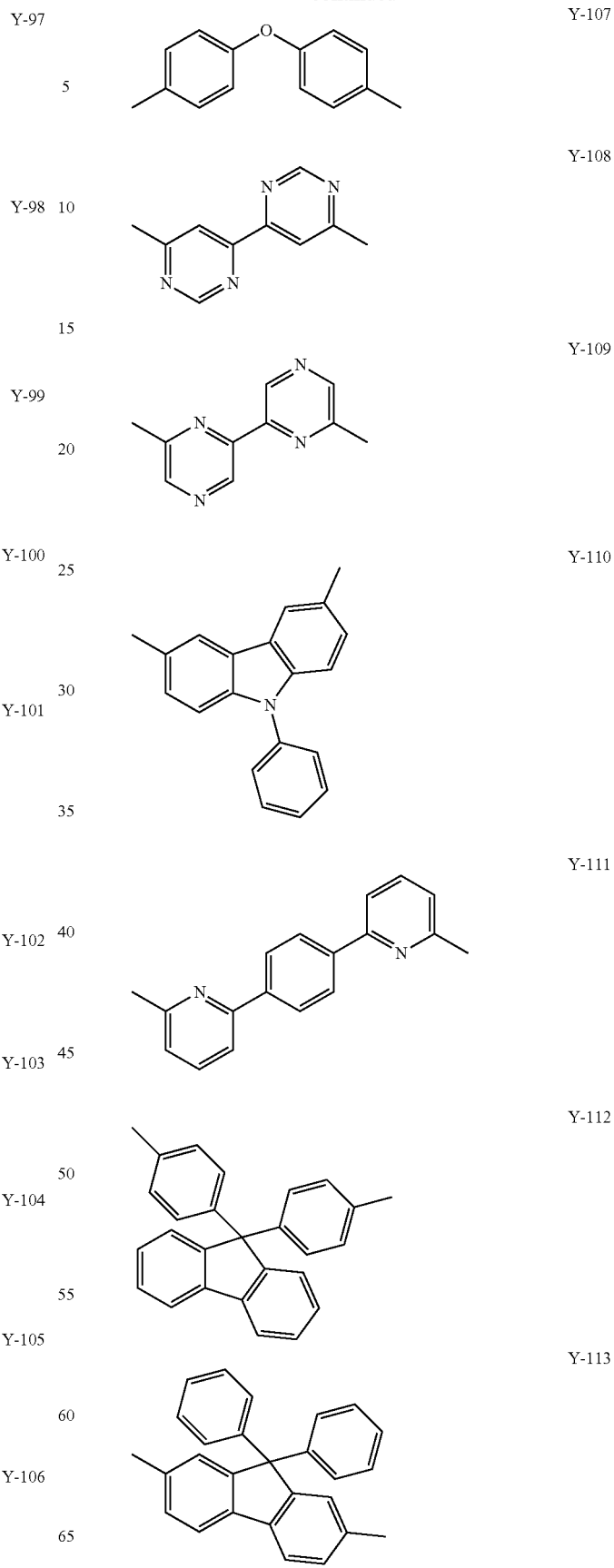

-continued

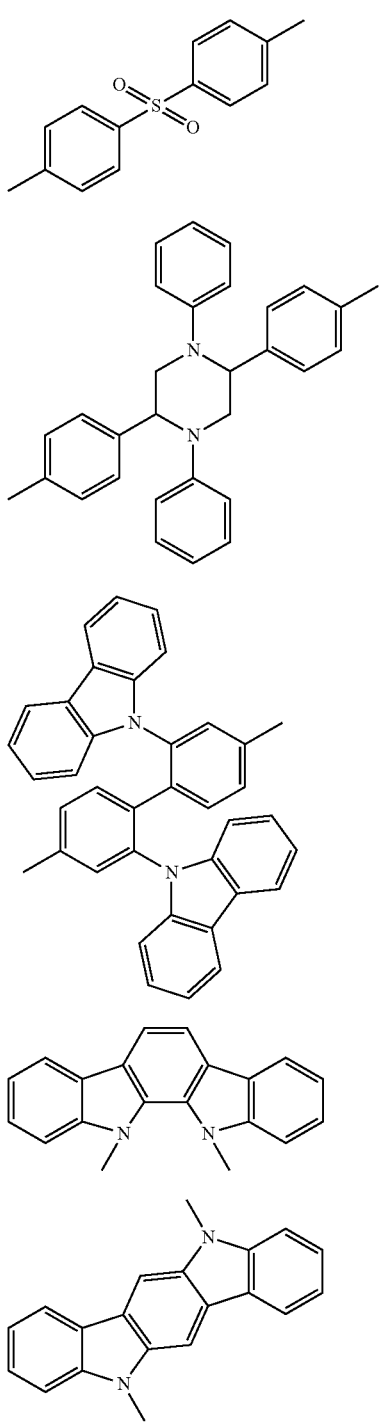

Y-114

Y-115

Y-116

Y-117

Y-118

Further, these linking groups may have a substituent. Examples of the substituent include an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a halogen atom, a haloalkyl group, a hydroxyl group, an amide group, and a substituted or unsubstituted aromatic hydrocarbon group or aromatic heterocyclic group.

Preferred examples of the substituent include a substituent represented by the following Z-1 to Z-138.

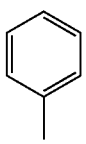 Z-1

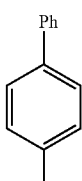 Z-2

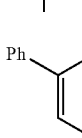 Z-3

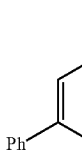 Z-4

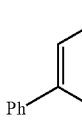 Z-5

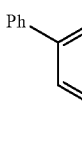 Z-6

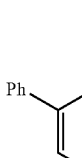 Z-7

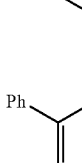 Z-8

 Z-9

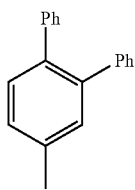 Z-10
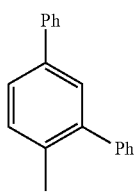 Z-11
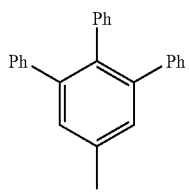 Z-12
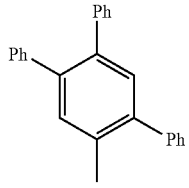 Z-13
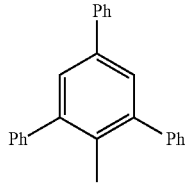 Z-14
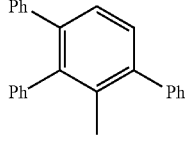 Z-15
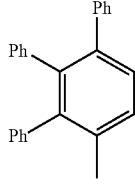 Z-16
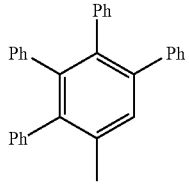 Z-17
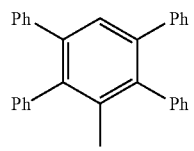 Z-18
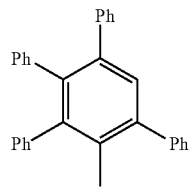 Z-19
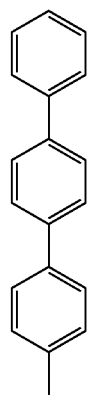 Z-20
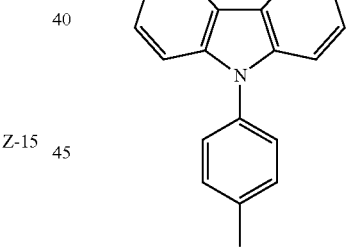 Z-21
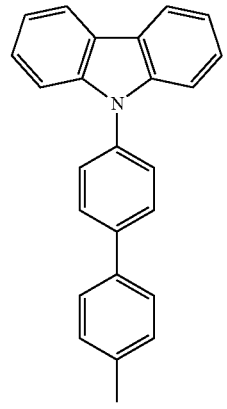 Z-23

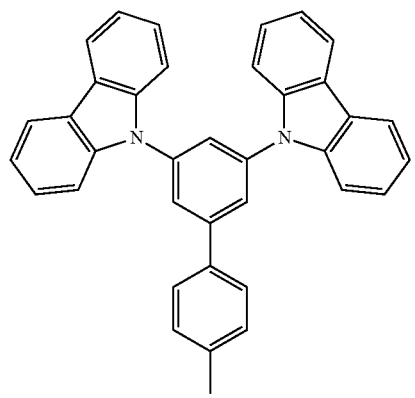
Z-24
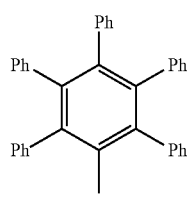
Z-25
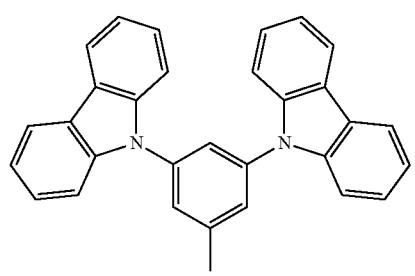
Z-26
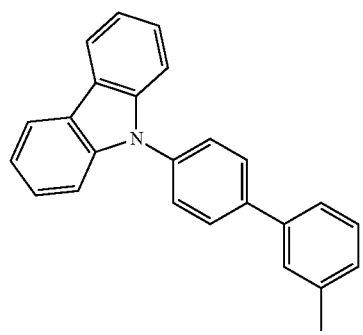
Z-27
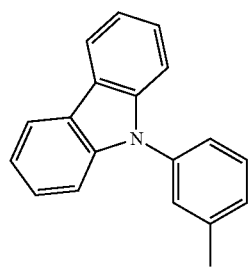
Z-28
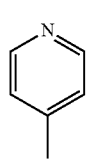
Z-29
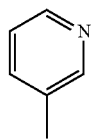
Z-30
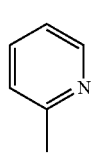
Z-31
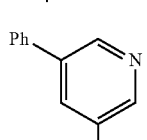
Z-32
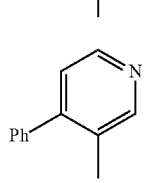
Z-33
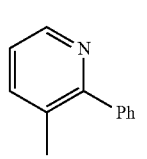
Z-34
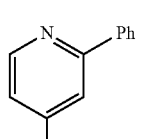
Z-35
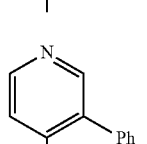
Z-36
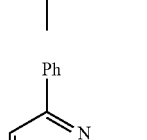
Z-37
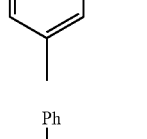
Z-38
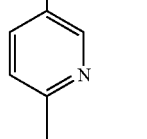
Z-39

Z-40 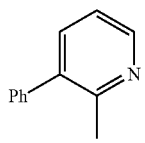
Z-41 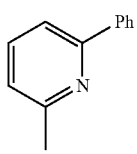
Z-42 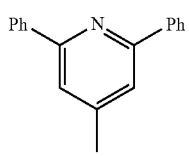
Z-43 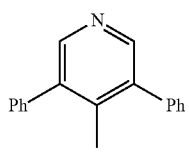
Z-44 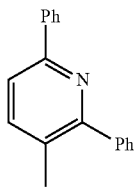
Z-45 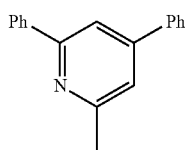
Z-46 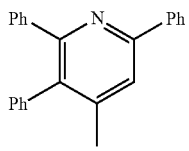
Z-47 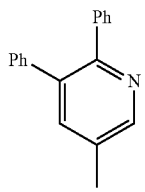
Z-48 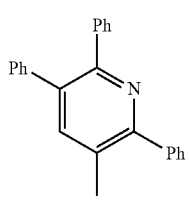
Z-49 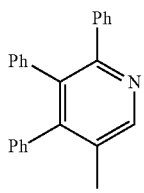
Z-50 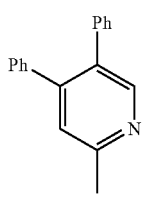
Z-51 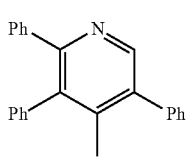
Z-52 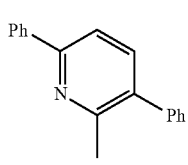
Z-53 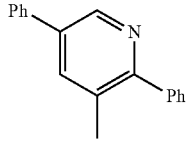
Z-54 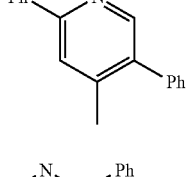
Z-55 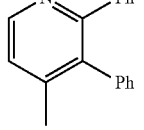
Z-56 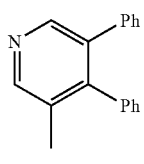
Z-57 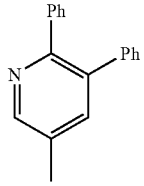

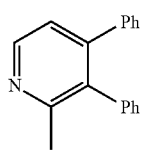 Z-58
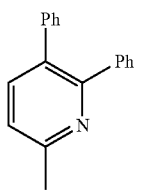 Z-59
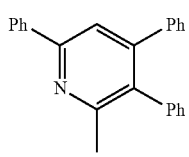 Z-60
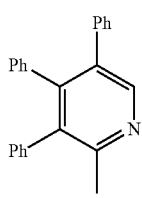 Z-61
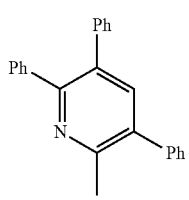 Z-62
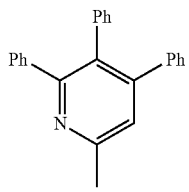 Z-63
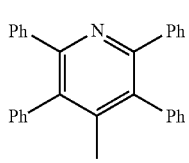 Z-64
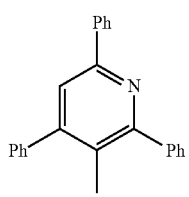 Z-65
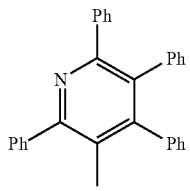 Z-66
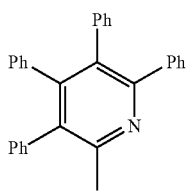 Z-67
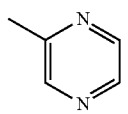 Z-68
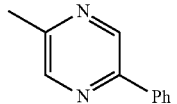 Z-69
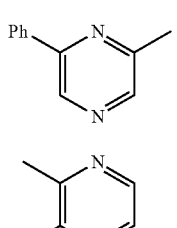 Z-70
Z-71
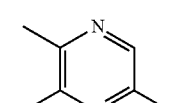 Z-72
Z-73
Z-74
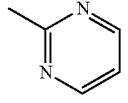 Z-75
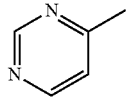 Z-76
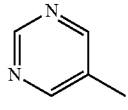 Z-77

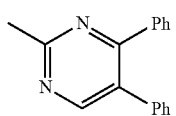 Z-78
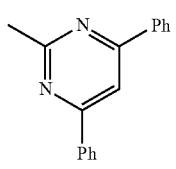 Z-79
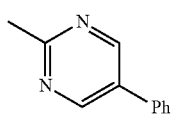 Z-80
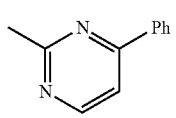 Z-81
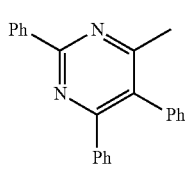 Z-82
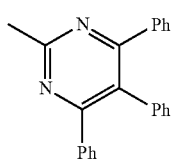 Z-83
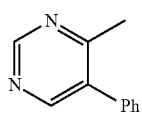 Z-84
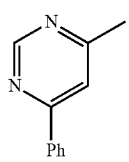 Z-85
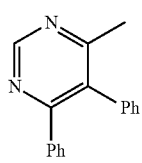 Z-86
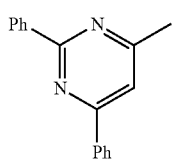 Z-87
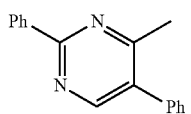 Z-88
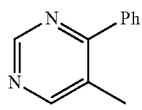 Z-89
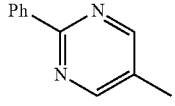 Z-90
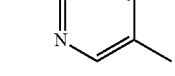 Z-91
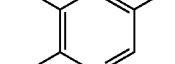 Z-92
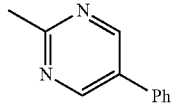 Z-93
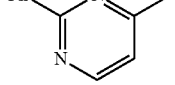 Z-94
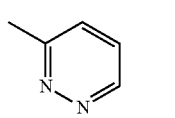 Z-95
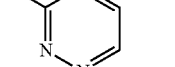 Z-96
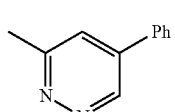 Z-97
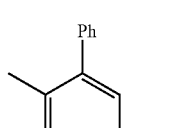 Z-98
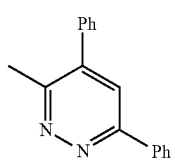 Z-99
Z-100

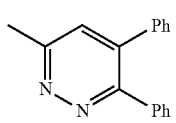 Z-101
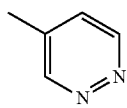 Z-102
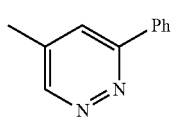 Z-103
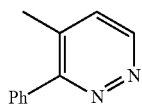 Z-104
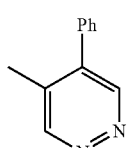 Z-105
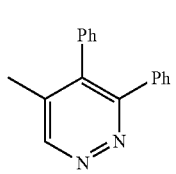 Z-106
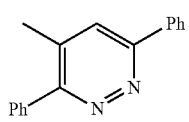 Z-107
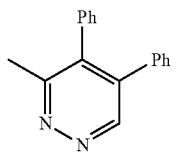 Z-108
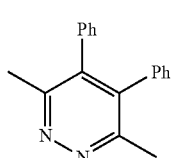 Z-109
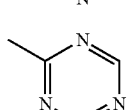 Z-110
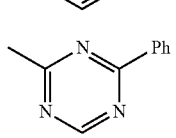 Z-111
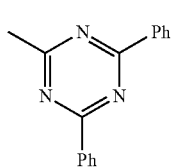 Z-112
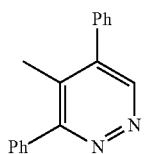 Z-113
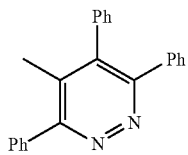 Z-114
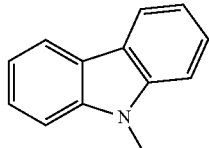 Z-115
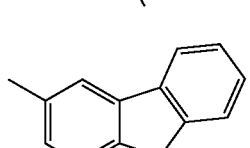 Z-115
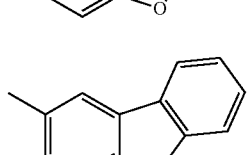 Z-116
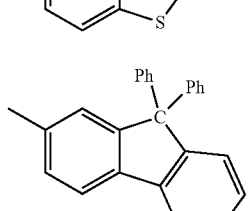 Z-117
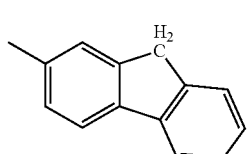 Z-118
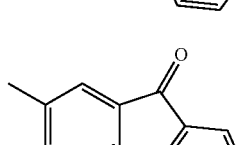 Z-119
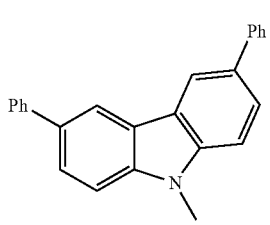 Z-120

-continued

Z-121 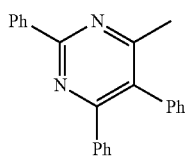

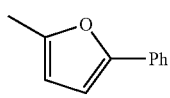 Z-122

Z-123 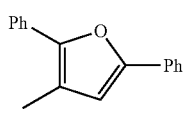

Z-124 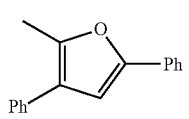

Z-125 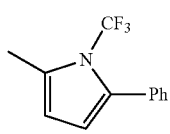

Z-126 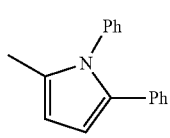

Z-127 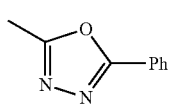

Z-128 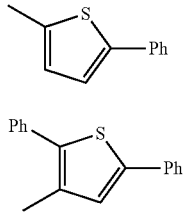

Z-129 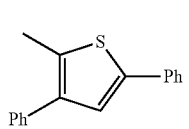

Z-130 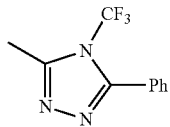

Z-131 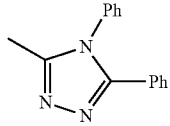

Z-132

-continued

Z-133 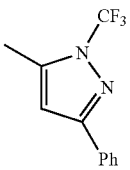

Z-134 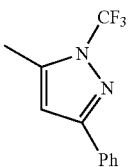

Z-135 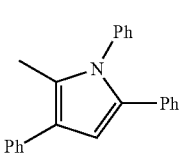

Z-136 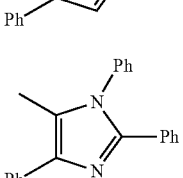

Z-138 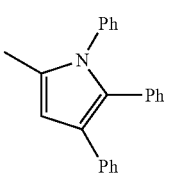

The substituted or unsubstituted aromatic hydrocarbon group or aromatic heterocyclic group represented by the linking group $Ar_{41}$, which is not a condensed ring structure includes preferably benzene, pyridine, triazine, pyrimidine, biphenyl, phenylpyridine, bipyridine, a terphenyl ring, a triazole ring, a diazole ring, a phenyltriazole ring, a triphenylthiazole ring and the like, more preferably benzene, pyridine, triazine, pyrimidine, biphenyl, phenylpyridine and bipyridine, and even more preferably a benzene ring, a biphenyl ring and a pyridine ring. When these have a substituent, the substituent may include a substituent selected from the group A of substituents, preferably at least one group selected from an alkyl group, an aryl group, a silyl group, a cyano group, a fluorine atom and a combination thereof, and more preferably alkyl having 1 to 6 carbon atoms, phenyl and pyridyl. The number of substituents may be 0 to 4, and preferably 0 to 2.

$Y^4$ represents a group represented by Formula (3a-1), (3a-2) or (3e).

One of the preferable forms of the compound represented by Formula (3) is a compound represented by the following Formula (5).

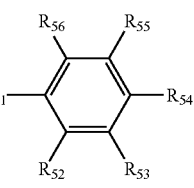

(5)

(wherein each of $R_{51}$ to $R_{56}$ independently represents a hydrogen atom or a substituent, but at least two of $R_{51}$ to $R_{56}$ are a group represented by Formula (3a-1), (3a-2) or (3e).)

Each of $R_{51}$ to $R_{56}$ independently represents a hydrogen atom or a substituent and as the substituent, those exemplified above for the above group A of substituents may be applied, but at least two of $R_{51}$ to $R_{56}$ are a group represented by Formula (3a-1), (3a-2) or (3e).

$R_{51}$ to $R_{56}$ include preferably a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group and a silyloxy group, more preferably a hydrogen atom, an alkyl group, an alicyclic hydrocarbon group, an aryl group, a fluorine group, a cyano group, a silyl group and a heterocyclic group, even more preferably a hydrogen atom, a methyl group, an isobutyl group, a t-butyl group, a neopentyl group, a phenyl group, a naphthyl group, a cyano group and a fluorine atom, particularly preferably a hydrogen atom, a methyl group, a t-butyl group, a phenyl group, a cyano group and a fluorine atom, preferably among them, a hydrogen atom, a methyl group, a phenyl group and a fluorine atom, and most preferably a hydrogen atom.

$R_{51}$ to $R_{56}$ may further have a substituent, and as the substituent, those exemplified above for the group A of substituents may be applied. Further, a plurality of substituents may be linked to each other to form a ring.

In Formula (5), it is preferred that at least two of Formulas $R_{51}$ to $R_{56}$ are preferably (3a-1). At this time, (3a-1) which is one of Formula (5) is preferably substituted in the para position or meta position relative to another (3a-1), and more preferably substituted in the meta position.

In the above Formula, each of $R_{51}$ to $R_{56}$ independently represents a hydrogen atom, a methyl group, an isobutyl group, a t-butyl group, a neopentyl group, a phenyl group, a naphthyl group, a cyano group, a fluorine atom or a group represented by any one of Formula (10), (10-2) or (10-3) as described below, but it is preferred that each of at least two of $R_{51}$ to $R_{56}$ is independently a group represented by any one of Formula (10), (10-2) or (10-3) as described below.

One of the preferable forms of the compound represented by Formula (3) is a compound represented by the following Formula (6).

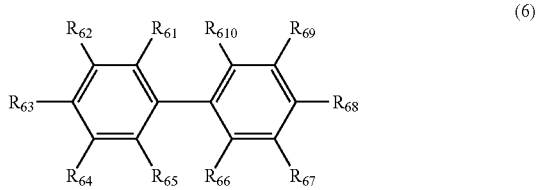

(6)

(wherein each of $R_{61}$ to $R_{610}$ independently represents a hydrogen atom or a substituent. At least two of $R_{61}$ to $R_{610}$ is a group represented by Formula (3a-1), (3a-2) or (3e).

Each of $R_{61}$ to $R_{610}$ independently represents a hydrogen atom or a substituent, and as the substituent, those exemplified above for the following group A of substituents may be applied, but at least two of $R_{61}$ to $R_{610}$ are a group represented by Formula (3a-1), (3a-2) or (3e). In Formula (6), it is preferred that at least one of Formulas $R_{61}$ to $R_{65}$ is (3a-1), and at least one of Formulas $R_{66}$ to $R_{510}$ is (3a-1).

$R_{61}$ to $R_{610}$ include preferably a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group and a silyloxy group, more preferably a hydrogen atom, an alkyl group, an alicyclic hydrocarbon group, an aryl group, a fluorine group, a cyano group, a silyl group and a heterocyclic group, even more preferably a hydrogen atom, even more preferably a hydrogen atom, a methyl group, an isobutyl group, a t-butyl group, a neopentyl group, a phenyl group, a naphthyl group, a cyano group and a fluorine atom, particularly preferably a hydrogen atom, a methyl group, a t-butyl group, a phenyl group, a cyano group and a fluorine atom, preferably among them, a hydrogen atom and a methyl group, and most preferably a hydrogen atom.

$R_{61}$ to $R_{610}$ may further have a substituent, and as the substituent, those exemplified above for the group A of substituents may be applied. Further, a plurality of substituents may be linked to each other to form a ring.

In the above Formula, each of $R_{61}$ to $R_{610}$ independently represents a hydrogen atom, a methyl group, an isobutyl group, a t-butyl group, a neopentyl group, a phenyl group, a naphthyl group, a cyano group, a fluorine atom or a group represented by any one of Formula (10), (10-2) or (10-3) as described below, but it is preferred that each of at least two of $R_{61}$ to $R_{610}$ is independently a group represented by any one of Formula (10), (10-2) or (10-3) as described below.

One of the preferable forms of the compound represented by Formula (6) is a compound represented by the following Formula (7).

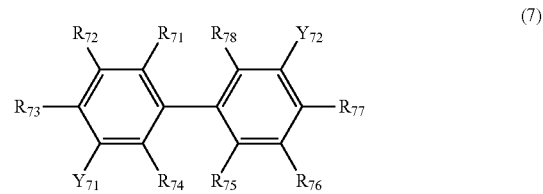

(7)

(wherein each of $R_{71}$ to $R_{78}$ independently represents a hydrogen atom or a substituent. Each of $Y_{71}$ and $Y_{72}$ independently represents a group represented by Formula (3a-1), (3a-2) or (3e).)

Each of $R_{71}$ to $R_{78}$ independently represents a hydrogen atom or a substituent, and is the same meaning as $R_{61}$ to $R_{610}$ in Formula (6), and preferred ranges thereof are also the same.

In the above Formula, each of $R_{71}$ to $R_{78}$ independently represents a hydrogen atom, a methyl group, an isobutyl group, a t-butyl group, a neopentyl group, a phenyl group, a naphthyl group, a cyano group, a fluorine atom or a group represented by one of the following Formula (10), (10-2) or (10-3), and it is preferred that each of $Y_{71}$ and $Y_{72}$ is independently a group represented by any one of the following Formula (10), (10-2) or (10-3).

One of the preferable forms of the compound represented by Formula (6) is a compound represented by the following Formula (8).

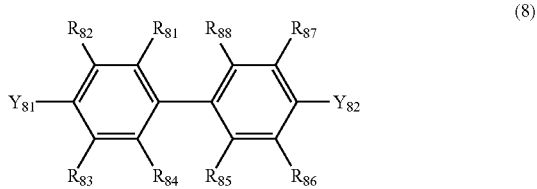

(8)

(wherein each of $R_{81}$ to $R_{88}$ independently represents a hydrogen atom or a substituent. Each of $Y_{81}$ and $Y_{82}$ independently represents a group represented by Formula (3a-1), (3a-2) or (3e).)

Each of $R_{81}$ to $R_{88}$ independently represents a hydrogen atom or a substituent, and has the same meaning as $R_{61}$ to $R_{610}$ in Formula (6), and preferred ranges thereof are also the same.

In the above Formula, each of $R_{81}$ to $R_{88}$ independently represents a hydrogen atom, a methyl group, an isobutyl group, a t-butyl group, a neopentyl group, a phenyl group, a naphthyl group, a cyano group, a fluorine atom or a group represented by any one of Formula (10), (10-2) or (10-3) as described below, and it is preferred that each of $Y_{81}$ and $Y_{82}$ is independently a group represented by any one of Formula (10), (10-2) or (10-3) as described below.

One of the preferable forms of the compound represented by Formula (3) is a compound represented by the following Formula (9).

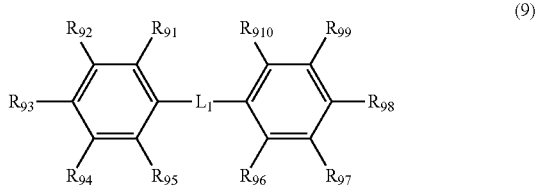

(9)

(wherein each of $R_{91}$ to $R_{910}$ independently represents a hydrogen atom or a substituent, but at least two of $R_{91}$ to $R_{910}$ represents a group represented by Formula (3a-1), (3a-2) or (3e). $L_1$ represents a divalent linking group.)

Each of $R_{91}$ to $R_{910}$ independently represents a hydrogen atom or a substituent, and as the substituent, those exemplified above for the following group A of substituents may be applied, but at least two of $R_{91}$ to $R_{910}$ are a group represented by Formula (3a-1), (3a-2) or (3e). In Formula (6), it is preferred that at least one of $R_{91}$ to $R_{95}$ is Formula (3a-1), and at least one of Formulas $R_{96}$ to $R_{910}$ is Formula (3a-1).

$R_{91}$ to $R_{910}$ include preferably a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group and a silyloxy group, more preferably a hydrogen atom, an alkyl group, an alicyclic hydrocarbon group, an aryl group, a fluorine group, a cyano group, a silyl group and a heterocyclic group, even more preferably a hydrogen atom, a methyl group, an isobutyl group, a t-butyl group, a neopentyl group, a phenyl group, a naphthyl group, a cyano group and a fluorine atom, particularly preferably a hydrogen atom, a methyl group, a t-butyl group, a phenyl group, a cyano group and a fluorine atom, preferably among them, a hydrogen atom, a methyl group and a fluorine atom, and most preferably a hydrogen atom.

$R_{91}$ to $R_{910}$ may further have a substituent, and as the substituent, those exemplified above for the group A of substituents may be applied. Further, a plurality of substituents may be linked to each other to form a ring.

The divalent linking group represented by $L_1$ may include a group including a substituted silicon atom, a substituted germanium atom and a heteroatom (for example, a divalent group including a chalcogen atom such as —O—, —S— and the like, and an —N(R)— group wherein R represents a hydrogen atom or an alkyl group, wherein the alkyl group may be the same as the alkyl group described as the group A of substituents) in addition to a hydrocarbon group such as an alkylene group (for example, a methylene group, an ethylene group, a trimethylene group, a tetramethylene group, a propylene group, an ethylethylene group, a pentamethylene group, a hexamethylene group, a 2,2,4-trimethylhexamethylene group, a heptamethylene group, an octamethylene group, a nonamethylene group, a decamethylene group, an undecamethylene group, a dodecamethylene group, a cyclohexylene group (for example, a 1,6-cyclohexanediyl group and the like), a cyclopentylene group (for example, 1,5-cyclopentanediyl group and the like), and the like), an alkenylene group (for example, a vinylene group, a propenylene group and the like), an alkynylene group (for example, an ethynylene group, a 3-pentenylene group and the like) and an arylene group, and the like.

Further, in each of the above-described alkylene group, alkenylene group, alkynylene group and arylene group, at least one of carbon atoms, which constitute a divalent linking group, may be substituted with a chalcogen atom (such as oxygen, sulfur and the like) or said —N(R)— group, and the like.

In addition, as a divalent linking group represented by $L_1$, for example, a group having a divalent heterocyclic group is used, and examples thereof include an oxazolediyl group, a pyrimidinediyl group, a pyridazinediyl group, a pyrandiyl group, a pyrrolinediyl group, an imidazolinediyl group, an imidazolidinediyl group, a pyrazolidinediyl group, a pyrazolinediyl group, a piperidinediyl group, a piperazinediyl group, a morpholinediyl group, a quinuclidinediyl group and the like, and may also be a divalent linking group derived from a compound having an aromatic heterocyclic ring (also referred to as a heteroaromatic compound) such as a thiophene-2,5-diyl group or a pyrazine-2,3-diyl group.

Furthermore, linking groups through a heteroatom, such as an alkylimino group, a dialkylsilanediyl group and a diarylgermanediyl group may be used.

The divalent linking group represented by $L_1$ includes preferably a methylene group, an ethylene group, a cyclohexylene group, a cyclopentylene group, a substituted silicon atom, a substituted germanium atom, an oxygen atom, a sulfur atom, a 5- or 6-membered aromatic hydrocarbon ring group and an aromatic heterocyclic group, more preferably a methylene group, an ethylene group, a cyclohexylene group, a substituted or unsubstituted nitrogen atom, a substituted silicon atom, a substituted germanium atom, a 5- or 6-membered aromatic hydrocarbon ring group, even more preferably a methylene group, an ethylene group, a substituted silicon atom, a substituted nitrogen atom, and a substituted germanium atom, particularly preferably a methylene group substituted with an alkyl group or a phenyl group, a silicon atom, a germanium atom, and a nitrogen atom, and most preferably a methylene group substituted with an alkyl group or a phenyl group and a silicon atom.

These linking groups may further have a substituent, if possible, and as a substituent which may be introduced, those exemplified for the group A of substituents may be applied.

When an aromatic hydrocarbon ring group or aromatic heterocyclic group is used as the linking group, the size of the ring is a 5- or 6-membered ring.

In the above Formula, each of $R_{91}$ to $R_{910}$ independently represents a hydrogen atom, a methyl group, an isobutyl group, a t-butyl group, a neopentyl group, a phenyl group, a naphthyl group, a cyano group, a fluorine atom or a group represented by any one of Formula (10), (10-2) or (10-3) as described below, but it is preferred that each of at least two of $R_{91}$ to $R_{910}$ is independently a group represented by any one of Formula (10), (10-2) or (10-3) as described below, $L_1$ represents a silicon atom or a carbon atom, and the silicon atom or carbon atom may be further substituted with at least one group selected from an alkyl group and an aryl group.

In Formulas (3) to (9), one of the preferable forms is that the substituent represented by Formula (3a-1) is a compound represented by the following Formula (10).

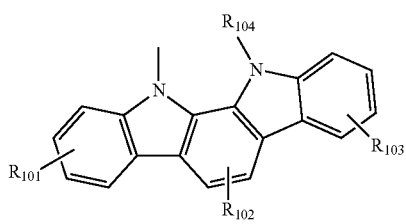

(10)

(wherein $R_{102}$ represents hydrogen and a substituted or unsubstituted aromatic hydrocarbon group or aromatic heterocyclic group, which is not a condensed ring structure, and each of $R_{101}$ and $R_{103}$ independently represents a hydrogen atom or a substituent. $R_{104}$ represents a substituted or unsubstituted aromatic hydrocarbon group or aromatic heterocyclic group, which is not a condensed ring structure other than a naphthalene ring.)

Each of $R_{101}$ and $R_{103}$ independently represents a hydrogen atom or a substituent, and has the same meaning as $R_{31}$ and $R_{32}$ in Formula (3a-1), and preferred ranges thereof are also the same.

$R_{104}$ represents a substituted or unsubstituted aromatic hydrocarbon group or aromatic heterocyclic group, which is not a condensed ring structure other than a naphthalene ring, and has the same meaning as $R_{34}$ in Formula (3c), and preferred ranges thereof are also the same.

A substituted or unsubstituted aromatic hydrocarbon group or aromatic heterocyclic group, which is not a condensed ring structure, represented by $R_{102}$, may include a benzene ring, a biphenyl ring, an o-terphenyl ring, an m-terphenyl ring, a p-terphenyl group, a furan ring, a thiophene ring, a pyridine ring, a pyridazine ring, a pyrimidine ring, a pyrazine ring, an oxadiazole ring, a triazole ring, an imidazole ring, a pyrazole ring, a thiazole ring and the like. The aromatic heterocyclic ring may have a substituent, and as the substituent, those exemplified above for the group A of substituents may be applied.

$R_{102}$ includes preferably a hydrogen atom, a benzene ring, a biphenyl ring, a pyrazole ring, an imidazole ring, a triazole ring, a pyridine ring, and a thiophene ring, more preferably a hydrogen atom, a benzene ring, a biphenyl ring and a pyridine ring, and particularly preferably a hydrogen atom.

$R_{102}$ may further have a substituent, and as the substituent, those exemplified above for the group A of substituents may be applied, and may include preferably alkyl having 1 to 6 carbon atoms, phenyl, pyridyl and the like.

In Formulas (3) to (10) and Formulas (3a-1) to (3h), it is preferred that the ring A and the ring C are a benzene ring, $R_{34}$, $R_{39}$, $R_{310}$ and $R_{104}$ are a substituted or unsubstituted phenyl group or pyridyl group, and further, $R_{31}$ to $R_{32}$, $R_{35}$ to $R_{37}$, and $R_{101}$ to $R_{103}$ are a hydrogen atom or a phenyl group.

Further, in Formulas (3) to (9), it is also preferred that the substituent represented by Formula (3a-1) is a compound represented by the following Formula (10-2).

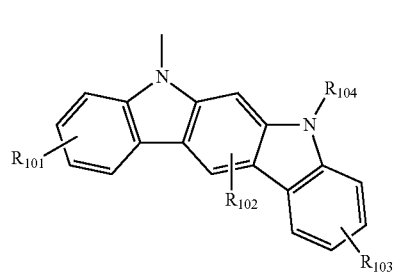

(10-2)

(wherein $R_{102}$ represents hydrogen and a substituted or unsubstituted aromatic hydrocarbon group or aromatic heterocyclic group which is not a condensed ring structure, and each of $R_{101}$ and $R_{103}$ independently represents a hydrogen atom or a substituent. $R_{104}$ represents a substituted or unsubstituted aromatic hydrocarbon group or aromatic heterocyclic group, which is not a condensed ring structure other than a naphthalene ring.)

Each of $R_{101}$ and $R_{103}$ independently represents a hydrogen atom or a substituent, and has the same meaning as $R_{31}$ and $R_{32}$ in Formula (3a-1), and preferred ranges thereof are also the same.

$R_{104}$ represents a substituted or unsubstituted aromatic hydrocarbon group or aromatic heterocyclic group, which is not a condensed ring structure other than a naphthalene ring, and has the same meaning as $R_{34}$ in Formula (3c), and preferred ranges thereof are also the same.

The substituted or unsubstituted aromatic hydrocarbon group or aromatic heterocyclic group represented by $R_{102}$, which is not a condensed ring structure, is the same as $R_{102}$ in Formula (10).

$R_{102}$ may further have a substituent, and as the substituent, those exemplified above for the group A of substituents may be applied, and may include preferably alkyl having 1 to 6 carbon atoms, phenyl, pyridyl and the like.

Further, in Formulas (3) to (9), it is also preferred that the substituent represented by Formula (3a-1) is a compound represented by the following Formula (10-3).

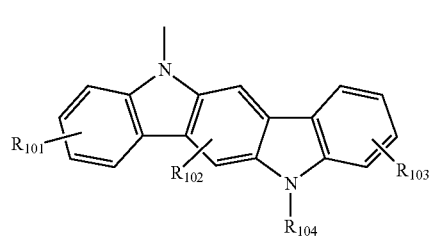

(10-3)

(wherein $R_{102}$ represents hydrogen and a substituted or unsubstituted aromatic hydrocarbon group or aromatic heterocyclic group which is not a condensed ring structure, and each of $R_{101}$ and $R_{103}$ independently represents a hydrogen atom or a substituent. $R_{104}$ represents a substituted or unsubstituted aromatic hydrocarbon group or aromatic heterocyclic group, which is not a condensed ring structure other than a naphthalene ring.)

Each of $R_{101}$ and $R_{103}$ independently represents a hydrogen atom or a substituent, and has the same meaning as $R_{31}$ and $R_{32}$ in Formula (3a-1), and preferred ranges thereof are also the same.

$R_{104}$ represents a substituted or unsubstituted aromatic hydrocarbon group or aromatic heterocyclic group, which is not a condensed ring structure other than a naphthalene ring, and has the same meaning as $R_{34}$ in Formula (3c), and preferred ranges thereof are also the same.

The substituted or unsubstituted aromatic hydrocarbon group or aromatic heterocyclic group represented by $R_{102}$, which is not a condensed ring structure is the same as $R_{102}$ in Formula (10).

$R_{102}$ may further have a substituent, and as the substituent, those exemplified above for the group A of substituents may be applied, and may include preferably alkyl having 1 to 6 carbon atoms, phenyl, pyridyl and the like.

In Formulas (10-2) and (10-3), it is preferred that $R_{104}$ is a substituted or unsubstituted phenyl group or pyridyl group and $R_{101}$ to $R_{103}$ are a hydrogen atom or a phenyl group.

In Formulas (10), (10-2) and (10-3), it is preferred that $R_{102}$ represents a hydrogen atom, each of $R_{101}$ and $R_{103}$ independently represents a hydrogen atom, an alkyl group, a silyl group, a fluorine atom, a cyano group or a trifluoromethyl group, these groups may be further substituted with at least one of an alkyl group having 1 to 6 carbon atoms and a phenyl group, $R_{104}$ represents a benzene ring, a naphthalene ring, a pyridine ring, a triazine ring or a pyrimidine ring, and these rings may be further substituted with at least one selected from a methyl group, an isobutyl group, a t-butyl group, a neopentyl group, a phenyl group, a naphthyl group, a cyano group and a fluorine atom.

Among Formulas (10), (10-2) and (10-3), Formula (10) is particularly preferable.

As the compound represented by Formula (3), one of the preferable forms is a compound represented by the following Formula (11).

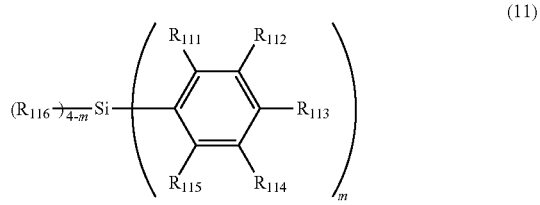

(11)

(wherein each of $R_{111}$ to $R_{116}$ independently represents a hydrogen atom or a substituent. However, at least one of $R_{111}$ to $R_{115}$ is a group represented by Formula (3a-1), (3a-2) or (3e). m represents an integer of 1 to 4.)

Each of $R_{111}$ to $R_{115}$ independently represents a hydrogen atom or a substituent, and as the substituent, those exemplified above for the group A of substituents may be applied.

At least one of $R_{111}$ to $R_{115}$ is a group represented by Formula (3a-1), (3a-2) or (3e), and preferably a group represented by Formula (10).

$R_{111}$ and $R_{115}$ preferably include a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group and a silyloxy group, more preferably a hydrogen atom, an alkyl group, an alicyclic hydrocarbon group, an aryl group, a fluorine group, a cyano group, a silyl group and a heterocyclic group, even more preferably a hydrogen atom, an alkyl group, an alicyclic hydrocarbon group, an aryl group, a fluorine group, a cyano group, a silyl group and a heterocyclic group, and particularly preferably a hydrogen atom, an alkyl group, an alicyclic hydrocarbon group, an aryl group and a heterocyclic group.

In $R_{111}$ to $R_{115}$, $R_{113}$ is particularly preferably a group represented by Formula (3a-1).

$R_{111}$ to $R_{115}$ may further have a substituent, and as the substituent, those exemplified above for the group A of substituents may be applied. Further, a plurality of substituents may be linked to each other to form a ring.

$R_{116}$ represents a hydrogen atom or a substituent. Each $R_{116}$ may be the same as or different from every other $R_{116}$.

As the substituent represented by $R_{116}$, those exemplified above for the group A of substituents may be applied.

$R_{116}$ includes preferably a hydrogen atom, an alkyl group, an aromatic hydrocarbon ring group, an amino group, an alkoxy group, an aryloxy group, an aromatic heterocyclic oxy group, an alkylthio group, an arylthio group, a heterocyclic thio group, a cyano group, an aromatic heterocyclic group, a silyl group and a silyloxy group, more preferably an alkyl group, an aromatic hydrocarbon ring group, an amino group, a cyano group and an aromatic heterocyclic group, even more preferably an alkyl group, an aromatic hydrocarbon ring group, a cyano group and an aromatic heterocyclic group, and particularly preferably an alkyl group and an aromatic hydrocarbon ring group.

m represents an integer of 1 to 4, preferably 1 to 3, and more preferably 2.

In the above Formula, each of $R_{111}$ to $R_{116}$ independently represents a hydrogen atom, a methyl group, an isobutyl group, a t-butyl group, a neopentyl group, a phenyl group, a naphthyl group, a cyano group, a fluorine atom or a group represented by any one of Formula (10), (10-2) or (10-3) as described above, but it is preferred that at least one of $R_{111}$ to $R_{115}$ is a group represented by any one of Formula (10), (10-2) or (10-3) as described above, and m represents an integer of 1 to 4.

As the compound represented by Formula (3), one of the preferable forms is a compound represented by the following Formula (12).

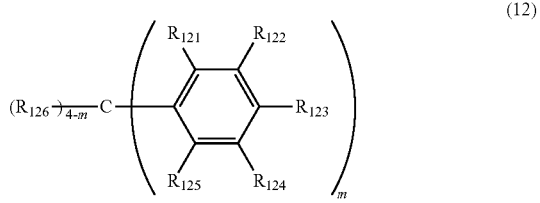

(12)

(wherein each of $R_{121}$ to $R_{126}$ independently represents a hydrogen atom or a substituent. However, at least one of $R_{121}$ to $R_{125}$ is a group represented by Formula (3a-1), (3a-2) or (3e). m represents an integer of 1 to 4.)

Each of $R_{121}$ to $R_{125}$ independently represents a hydrogen atom of a substituent, and as the substituent, those exemplified above for the group A of substituents may be applied. At least one of $R_{121}$ to $R_{125}$ is a group represented by Formula (3a-1), (3a-2) or (3e), and preferably a group represented by Formula (10).

$R_{121}$ and $R_{125}$ preferably include a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group and a silyloxy group, more preferably a hydrogen atom, an alkyl group, an alicyclic hydrocarbon group, an aryl group, a fluorine group, a cyano group, a silyl group and a heterocyclic group, even more preferably a hydrogen atom, an alkyl group, an alicyclic hydrocarbon group, an aryl group, a fluorine group, a cyano group, a silyl group and a heterocyclic group, and particularly preferably a hydrogen atom, an alkyl group, an alicyclic hydrocarbon group, an aryl group and a heterocyclic group.

$R_{121}$ to $R_{125}$ may further have a substituent, and as the substituent, those exemplified above for the group A of substituents may be applied. Further, a plurality of substituents may be linked to each other to form a ring.

$R_{126}$ represents a hydrogen atom or a substituent. Each $R_{126}$ may be the same as or different from every other $R_{126}$.

As the substituent represented by $R_{126}$, those exemplified above for the group A of substituents may be applied.

$R_{126}$ includes preferably a hydrogen atom, an alkyl group, an aromatic hydrocarbon ring group, an amino group, an alkoxy group, an aryloxy group, an aromatic heterocyclic oxy group, an alkylthio group, an arylthio group, a heterocyclic thio group, a cyano group, an aromatic heterocyclic group, a silyl group and a silyloxy group, more preferably an alkyl group, an aromatic hydrocarbon ring group, an amino group, a cyano group and an aromatic heterocyclic group, even more preferably an alkyl group, an aromatic hydrocarbon ring group, a cyano group and an aromatic heterocyclic group, and particularly preferably an alkyl group and an aromatic hydrocarbon ring group.

m represents an integer of 1 to 4, preferably 1 to 3, and more preferably 2.

In the above Formula, each of $R_{121}$ to $R_{126}$ independently represents a hydrogen atom, a methyl group, an isobutyl group, a t-butyl group, a neopentyl group, a phenyl group, a naphthyl group, a cyano group, a fluorine atom or a group represented by any one of Formula (10), (10-2) or (10-3) as described above, but it is preferred that at least one of $R_{121}$ to $R_{125}$ is a group represented by any one of Formula (10), (10-2) or (10-3) as described above and m represents an integer of 1 to 4.

As the compound represented by Formula (1), one of preferable forms is a compound represented by the following Formula (13).

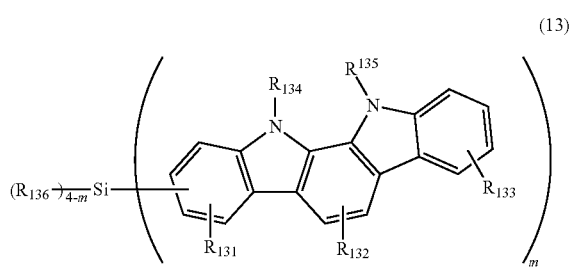

(13)

($R_{132}$ represents hydrogen or a substituted or unsubstituted aromatic hydrocarbon group or aromatic heterocyclic group which is not a condensed ring structure, and each of $R_{131}$ and $R_{133}$ independently represents a hydrogen atom or a substituent. $R_{134}$ and $R_{135}$ represent a substituted or unsubstituted aromatic hydrocarbon group or aromatic heterocyclic group, which is not a condensed ring structure other than a naphthalene ring. $R_{136}$ represents a hydrogen atom or a substituent. m represents an integer of 1 to 4. A silicon linking group as $R_{131}$ is substituted to a carbon atom.)

Each of $R_{131}$ and $R_{133}$ independently represents a hydrogen atom or a substituent, and has the same meaning as $R_{12}$ and $R_{13}$ in Formula (1), and preferred ranges thereof are also the same.

$R_{134}$ and $R_{135}$ represent a substituted or unsubstituted aromatic hydrocarbon group or aromatic heterocyclic group, which is not a condensed ring structure other than a naphthalene ring, and has the same meaning as $R_{11}$ and $R_{15}$ in Formula (1), and preferred ranges thereof are also the same.

A substituted or unsubstituted aromatic hydrocarbon group or aromatic heterocyclic group represented by $R_{132}$, which is not a condensed ring structure, may include a benzene ring, a biphenyl ring, an o-terphenyl ring, an m-terphenyl ring, a p-terphenyl ring, a furan ring, a thiophene ring, a pyridine ring, a pyridazine ring, a pyrimidine ring, a pyrazine ring, an oxadiazole ring, a triazole ring, an imidazole ring, a pyrazole ring, a thiazole ring and the like. The aromatic heterocyclic ring may have a substituent, and as the substituent, those exemplified above for the group A of substituents may be applied.

$R_{132}$ includes preferably a hydrogen atom, a benzene ring, a biphenyl ring, a pyrazole ring, an imidazole ring, a triazole ring, a pyridine ring and a thiophene ring, more preferably a hydrogen atom, a benzene ring, a biphenyl ring and a pyridine ring, and particularly preferably a hydrogen atom.

$R_{132}$ may further have a substituent, and as the substituent, those exemplified above for the group A of substituents may be applied, and may include preferably alkyl having 1 to 6 carbon atoms, phenyl, pyridyl and the like.

$R_{136}$ represents a hydrogen atom or a substituent. Each $R_{136}$ may be the same as or different from every other $R_{136}$.

As the substituent represented by $R_{136}$, those exemplified above for the group A of substituents may be applied.

$R_{136}$ includes preferably a hydrogen atom, an alkyl group, an aromatic hydrocarbon ring group, an amino group, an alkoxy group, an aryloxy group, an aromatic heterocyclic oxy group, an alkylthio group, an arylthio group, a heterocyclic thio group, a cyano group, an aromatic heterocyclic group, a silyl group and a silyloxy group, more preferably an alkyl group, an aromatic hydrocarbon ring group, an amino group, a cyano group and an aromatic heterocyclic group, even more preferably, an alkyl group, an aromatic hydrocarbon ring group, a cyano group and an aromatic heterocyclic group, and particularly preferably an alkyl group and an aromatic hydrocarbon ring group.

m represents an integer of 1 to 4, preferably 1 to 3, and more preferably 2.

In the above Formula, it is preferred that $R_{132}$ represents a hydrogen atom, each of $R_{131}$ and $R_{133}$ independently represents a hydrogen atom, an alkyl group, a silyl group, a fluorine atom, a cyano group or a trifluoromethyl group, these groups may be further substituted with at least one of an alkyl group having 1 to 6 carbon atoms and a phenyl group, each of $R_{134}$ and $R_{135}$ independently represents a benzene ring; a naphthalene ring, a pyridine ring, a triazine ring or a pyrimidine ring, these rings may be further substituted with at least one group selected from a methyl group, an isobutyl group, a t-butyl group, a neopentyl group, a phenyl group, a naphthyl group, a cyano group and a fluorine atom, $R_{136}$ represents a hydrogen atom, a methyl group, an isobutyl group, a t-butyl group, a neopentyl group, a phenyl group, a naphthyl group, a cyano group or a fluorine atom, m represents an integer of 1 to 4, and a silicon linking group as one of $R_{131}$ is substituted to a carbon atom.

As the compound represented by Formula (1), one of preferable forms is a compound represented by the following Formula (14).

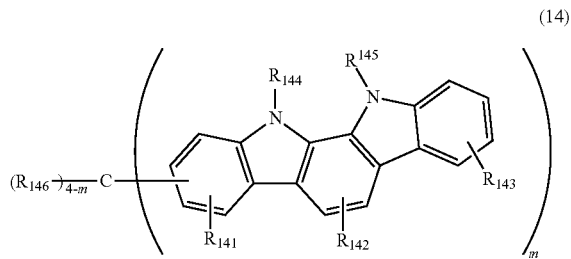

(14)

(wherein $R_{142}$ represents hydrogen or a substituted or unsubstituted aromatic hydrocarbon group or aromatic heterocyclic group, which is not a condensed ring structure, each of $R_{141}$ and $R_{143}$ independently represents a hydrogen atom or a substituent, and $R_{144}$ and $R_{145}$ represent a substituted or unsubstituted aromatic hydrocarbon group or aromatic heterocyclic group, which is not a condensed ring structure other than a naphthalene ring. A carbon linking group as $R_{141}$ is substituted to a carbon atom. $R_{146}$ represents a hydrogen atom or a substituent. m represents an integer of 1 to 4.)

Each of $R_{141}$ and $R_{143}$ independently represents a hydrogen atom or a substituent, and has the same meaning as $R_{12}$ and $R_{13}$ in Formula (1), and preferred ranges thereof are also the same.

$R_{144}$ and $R_{145}$ represent a substituted or unsubstituted aromatic hydrocarbon group or aromatic heterocyclic group, which is not a condensed ring structure other than a naphthalene ring, and has the same meaning as $R_{11}$ and $R_{15}$ in Formula (1), and preferred ranges thereof are also the same.

A substituted or unsubstituted aromatic hydrocarbon group or aromatic heterocyclic group represented by $R_{142}$, which is not a condensed ring structure may include a benzene ring, a biphenyl ring, an o-terphenyl ring, an m-terphenyl ring, a p-terphenyl ring, a furan ring, a thiophene ring, a pyridine ring, a pyridazine ring, a pyrimidine ring, a pyrazine ring, an oxadiazole ring, a triazole ring, an imidazole ring, a pyrazole ring, a thiazole ring and the like. The aromatic heterocyclic ring may have a substituent, and as the substituent, those exemplified above for the group A of substituents may be applied.

$R_{142}$ includes preferably a hydrogen atom, a benzene ring, a biphenyl ring, a pyrazole ring, an imidazole ring, a triazole ring, a pyridine ring and a thiophene ring, more preferably a hydrogen atom, a benzene ring, a biphenyl ring and a pyridine ring, and particularly preferably a hydrogen atom.

$R_{142}$ may further have a substituent, and as the substituent, those exemplified above for the group A of substituents may be applied, and may include preferably alkyl having 1 to 6 carbon atoms, phenyl, pyridyl and the like.

$R_{146}$ represents a hydrogen atom or a substituent. Each $R_{146}$ may be the same as or different from every other $R_{146}$.

As the substituent represented by $R_{146}$, those exemplified above for the group A of substituents may be applied.

$R_{146}$ includes preferably a hydrogen atom, an alkyl group, an aromatic hydrocarbon ring group, an amino group, an alkoxy group, an aryloxy group, an aromatic heterocyclic oxy group, an alkylthio group, an arylthio group, a heterocyclic thio group, a cyano group, an aromatic heterocyclic group, a silyl group and a silyloxy group, more preferably an alkyl group, an aromatic hydrocarbon ring group, an amino group, a cyano group and an aromatic heterocyclic group, even more preferably an alkyl group, an aromatic hydrocarbon ring group, a cyano group and an aromatic heterocyclic group, and even more preferably an alkyl group and an aromatic hydrocarbon ring group.

m represents an integer of 1 to 4, preferably 1 to 3, and more preferably 2.

In the above Formula, it is preferred that $R_{142}$ represents a hydrogen atom, each of $R_{141}$ and $R_{143}$ independently represents a hydrogen atom, an alkyl group, a silyl group, a fluorine atom, a cyano group or a trifluoromethyl group, these groups may be substituted with at least one of an alkyl group having 1 to 6 carbon atoms and a phenyl group, each of $R_{144}$ and $R_{145}$ independently represents a benzene ring, a naphthalene ring, a pyridine ring, a triazine ring or a pyrimidine ring, these rings may be further substituted with at least one group selected from a methyl group, an isobutyl group, a t-butyl group, a neopentyl group, a phenyl group, a naphthyl group, a cyano group and a fluorine atom, a carbon linking group is substituted to a carbon atom as one of $R_{141}$, $R_{146}$ represents a hydrogen atom, a methyl group, an isobutyl group, a t-butyl group, a neopentyl group, a phenyl group, a naphthyl group, a cyano group or a fluorine atom, and m represents an integer of 1 to 4.

Preferred specific examples of the compounds represented by Formulas (1) to (18) are represented below, but are not limited thereto.

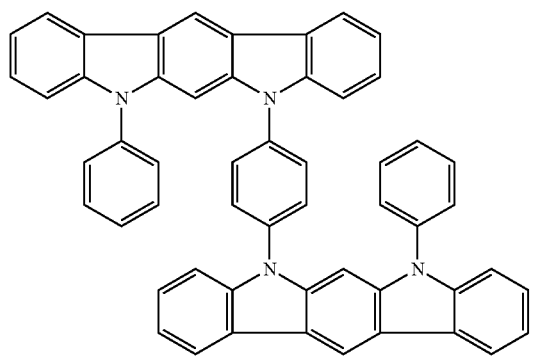

1

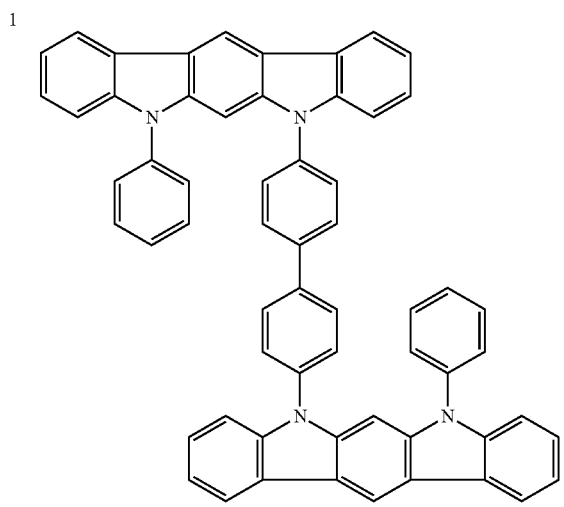

2

87
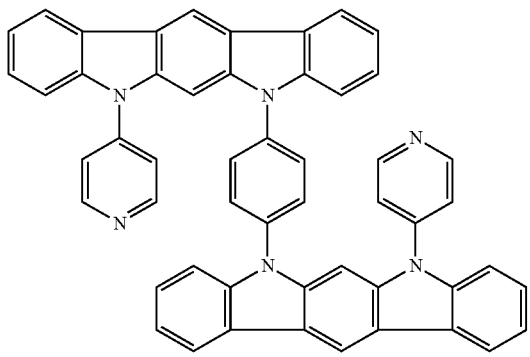
88
-continued
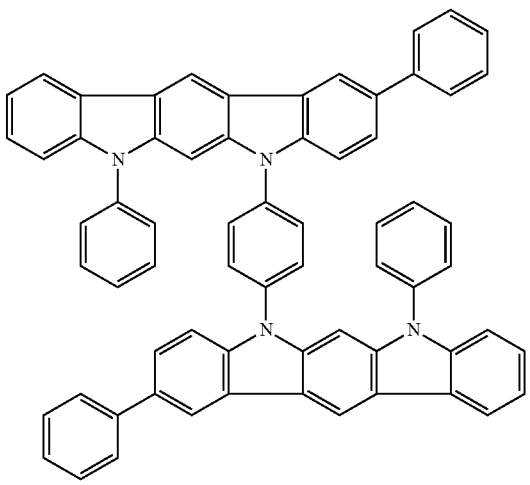
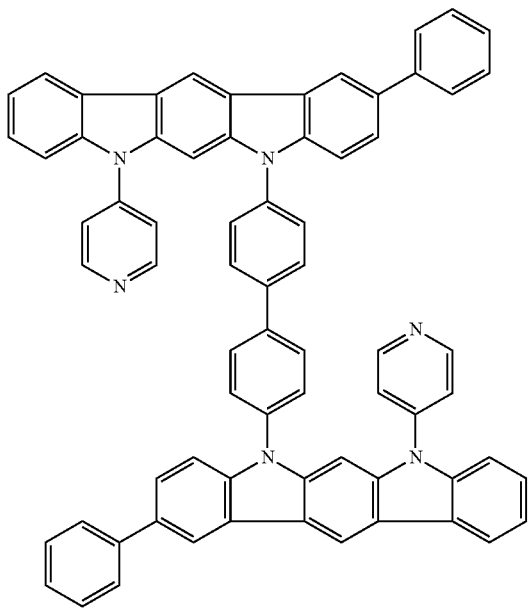
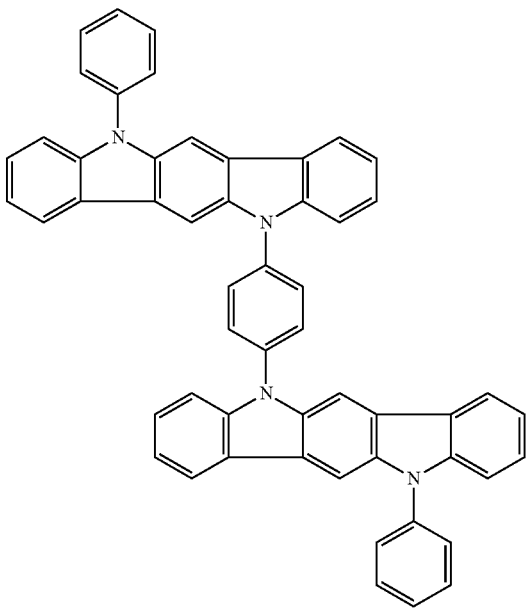

-continued
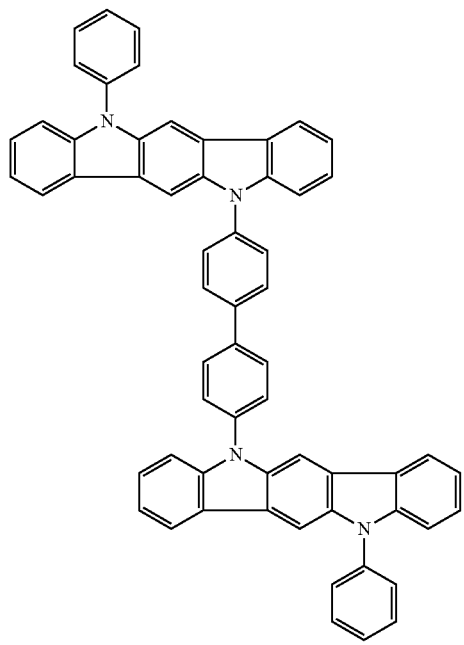
7
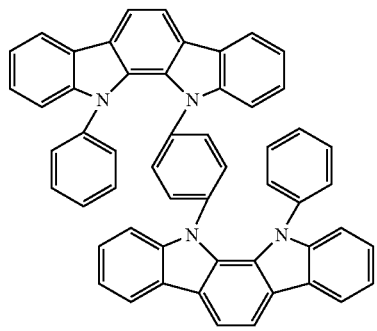
8
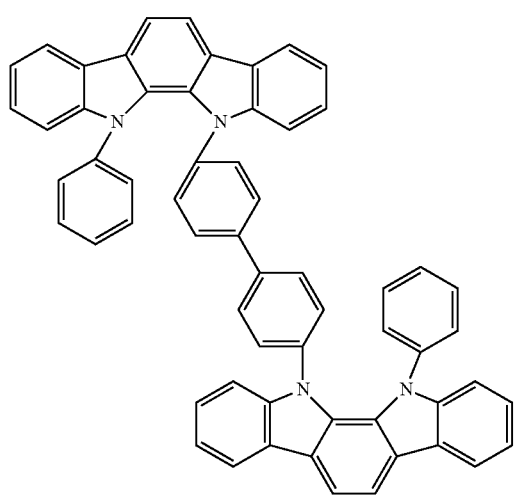
9
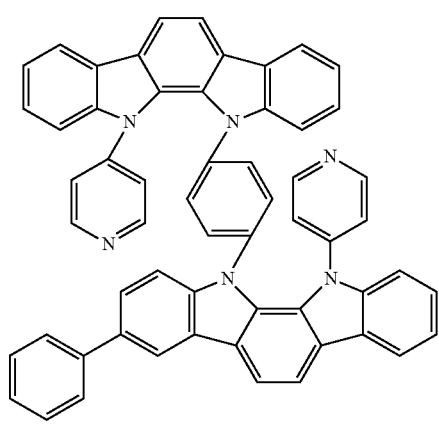
10

11
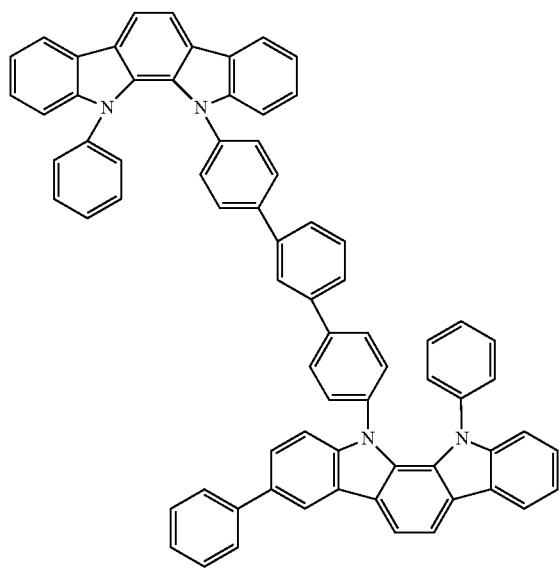
12
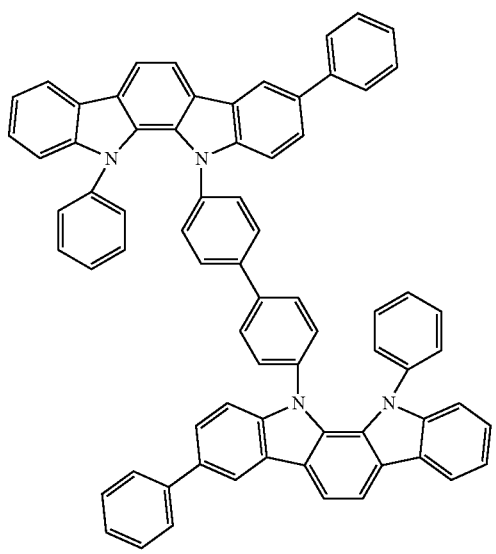
13
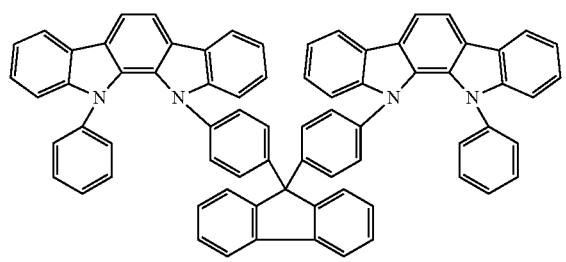
14
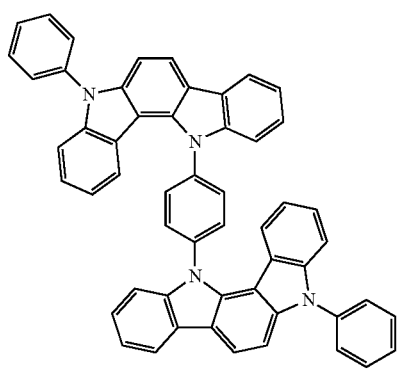
15
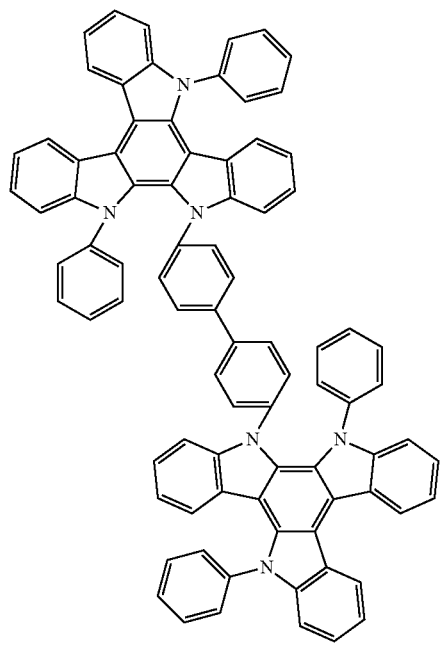
16
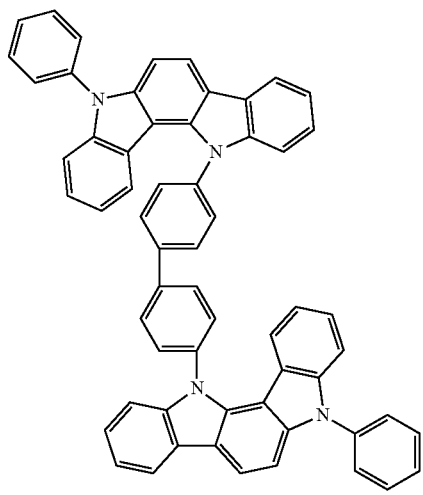

-continued
17
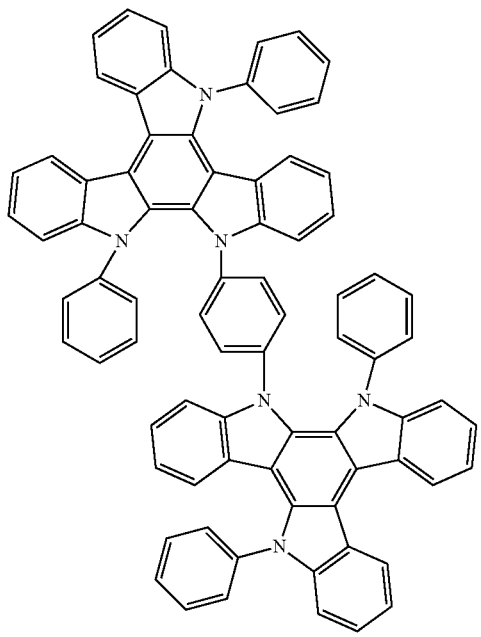
18
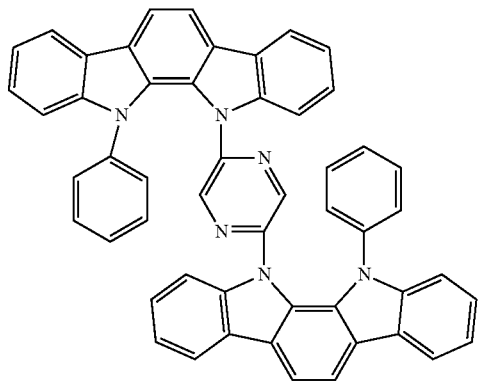
19
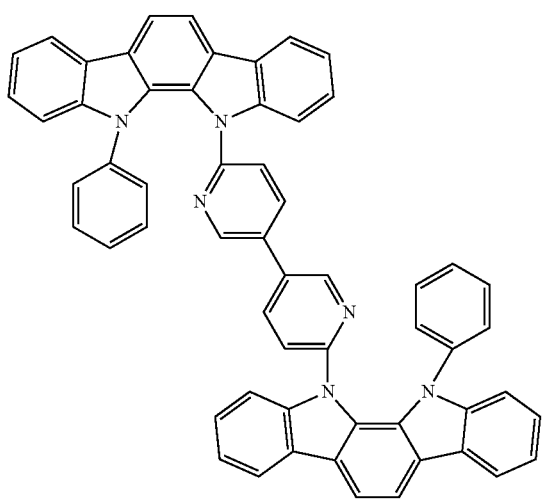
20
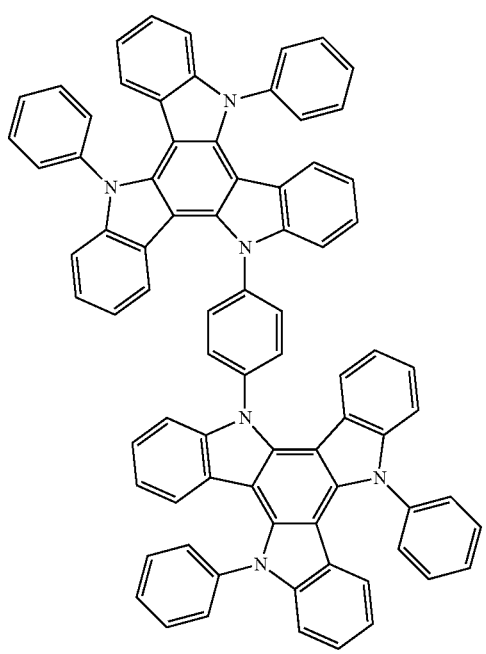

21
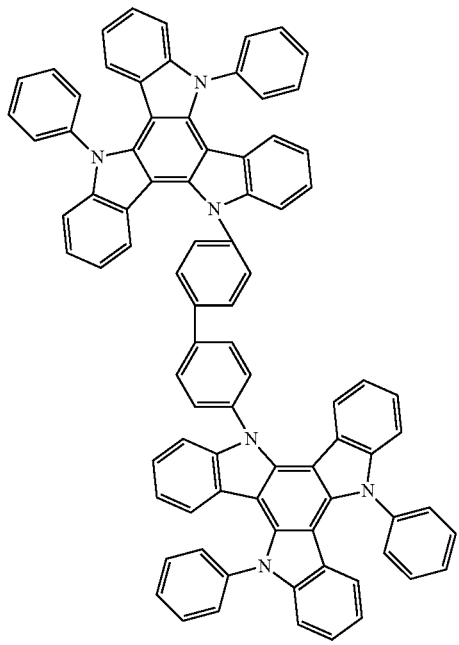
22
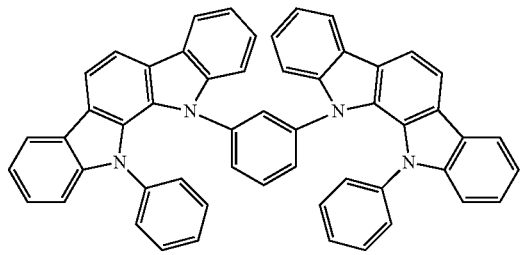
23
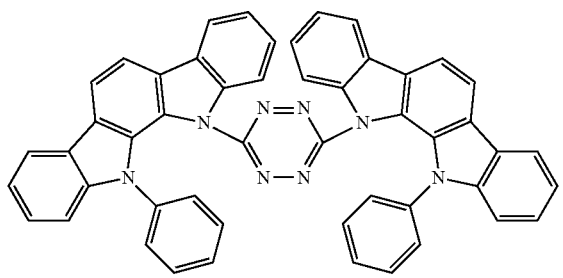
24
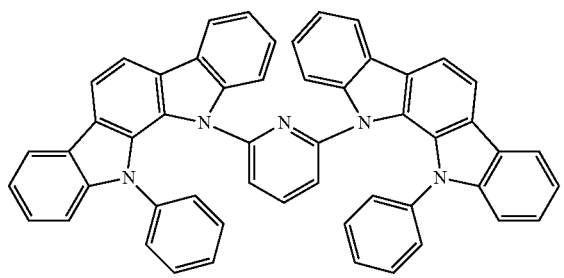
25
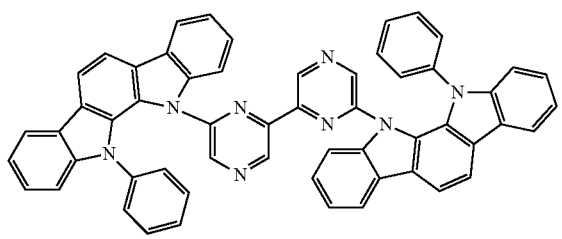
26
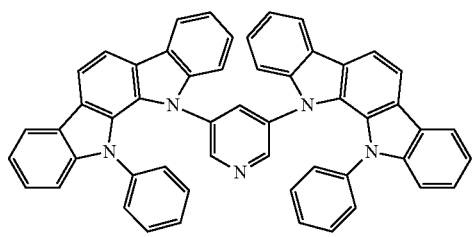
27
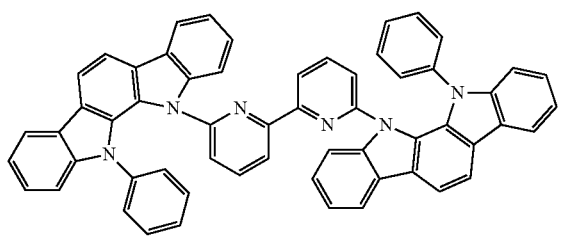
28
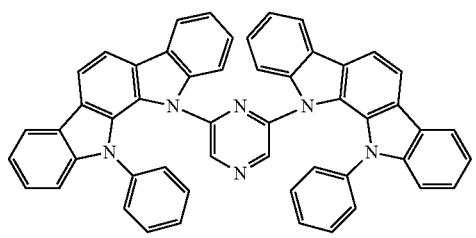

-continued
29
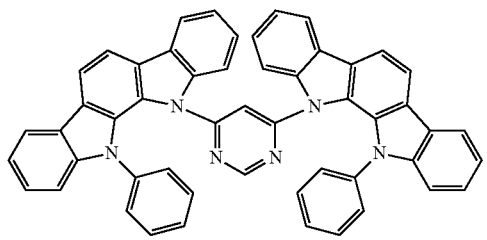
30
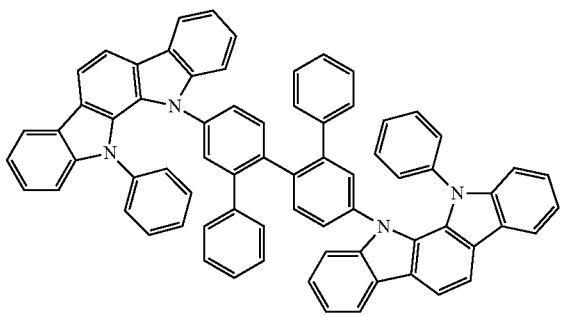
31
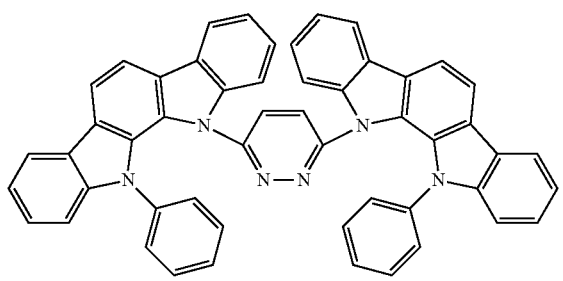
32
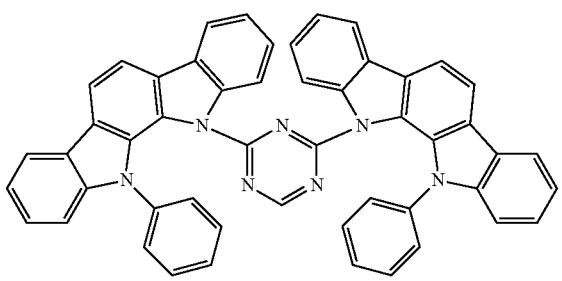
33
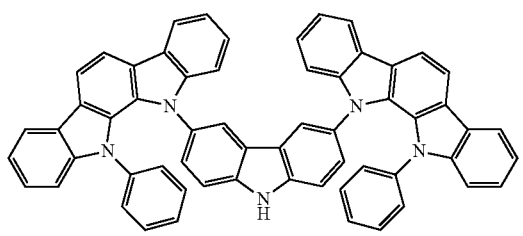
34
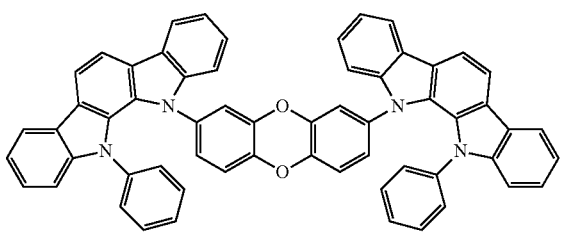
35
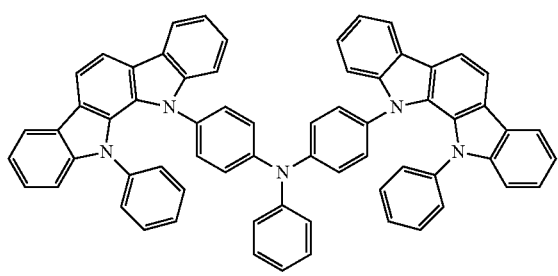
36
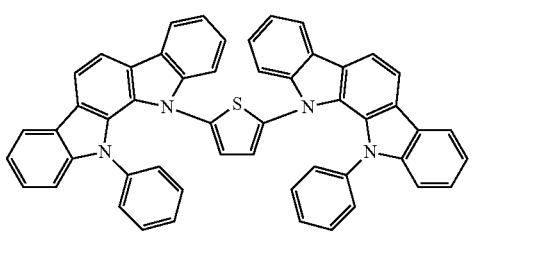
37
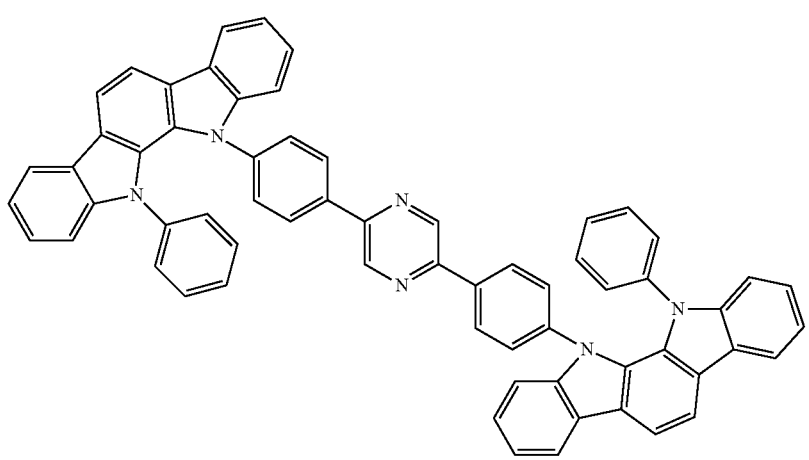

-continued
38
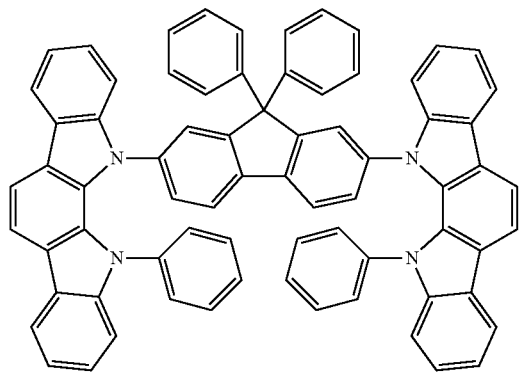
39
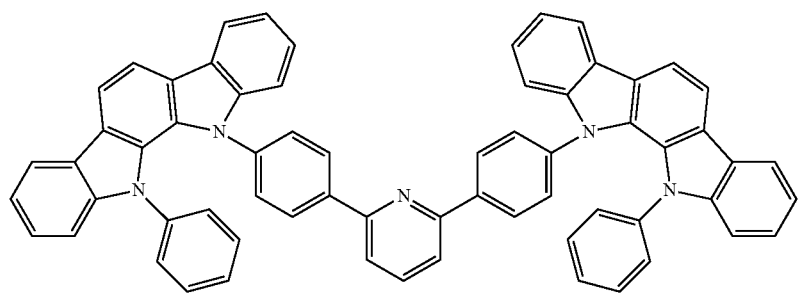
40
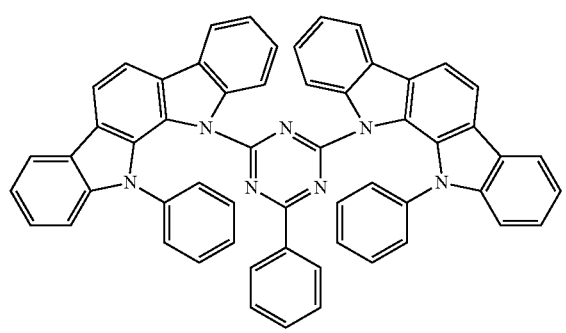
41
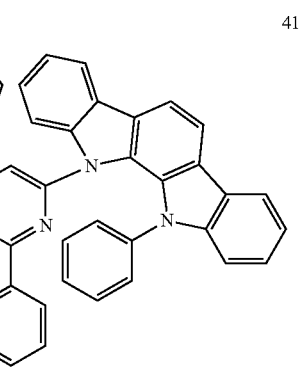
42
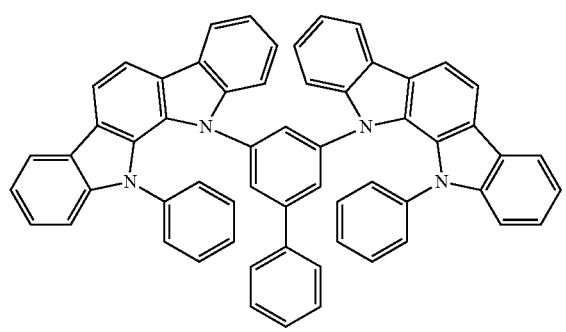
43
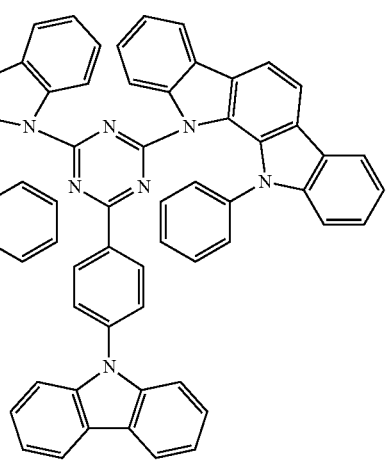

-continued
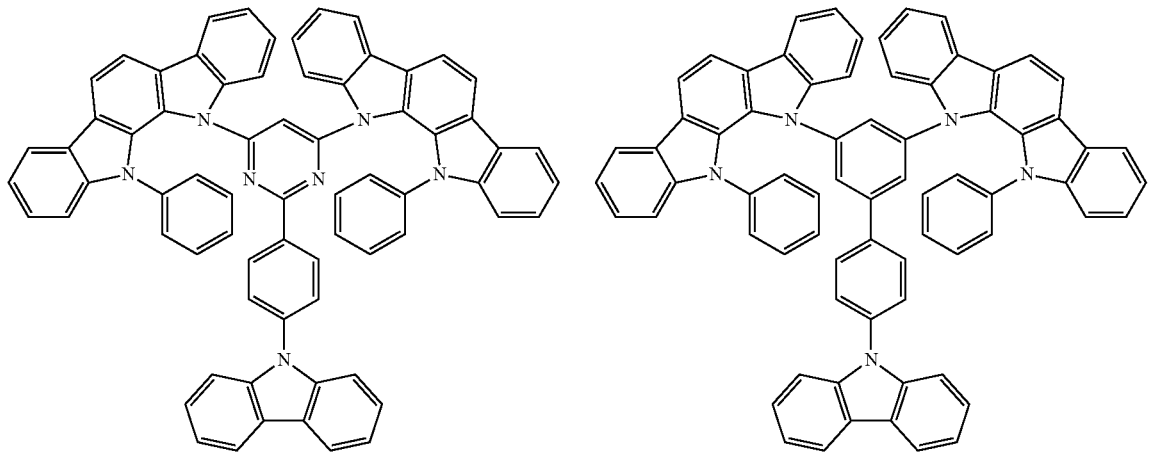
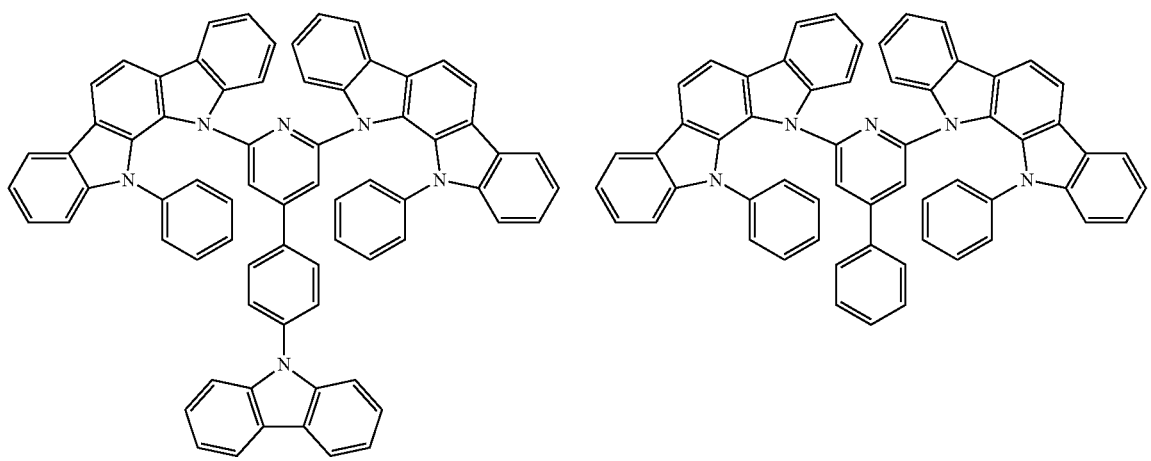
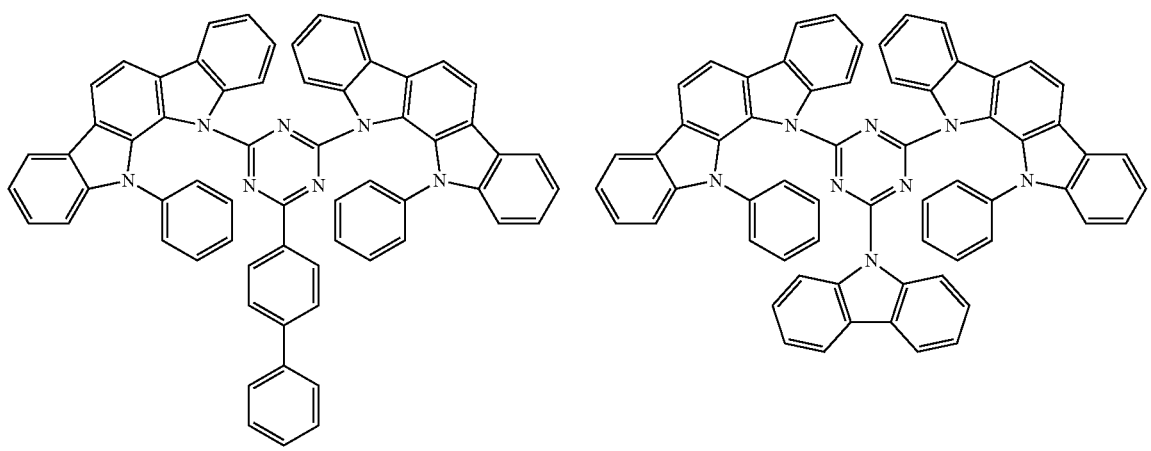

-continued
50
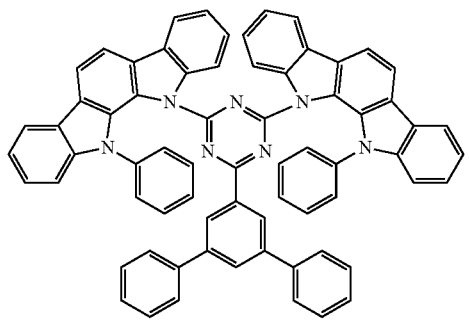
51
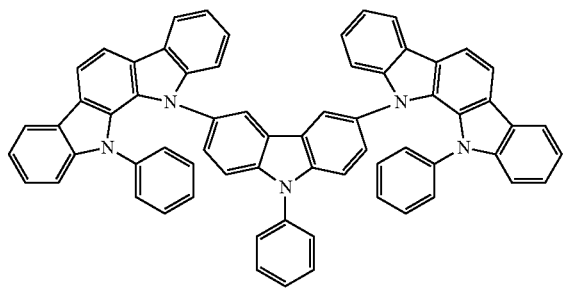
52
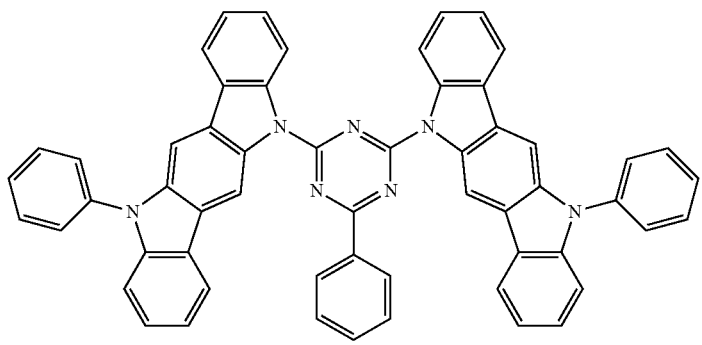
53
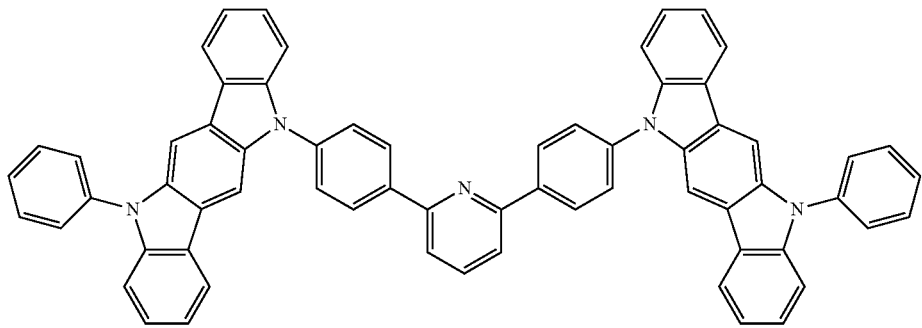
54
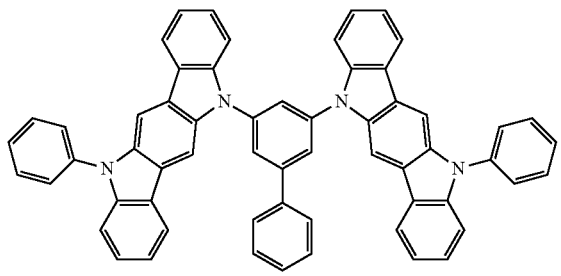
55
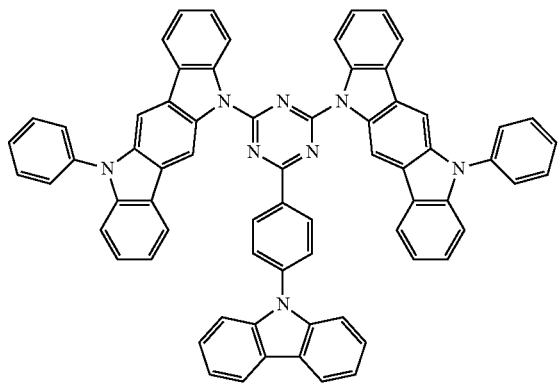

56
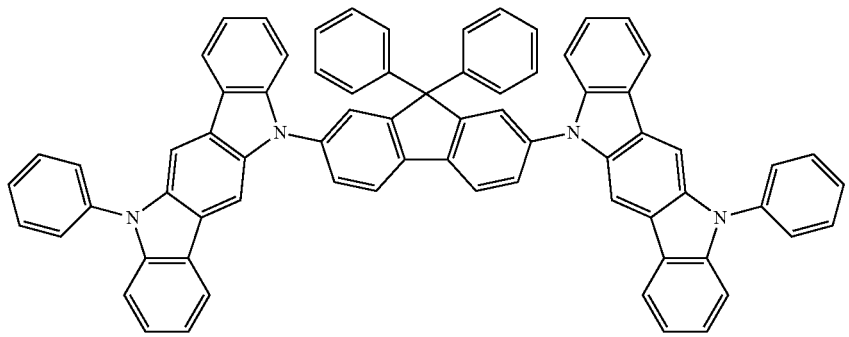
57
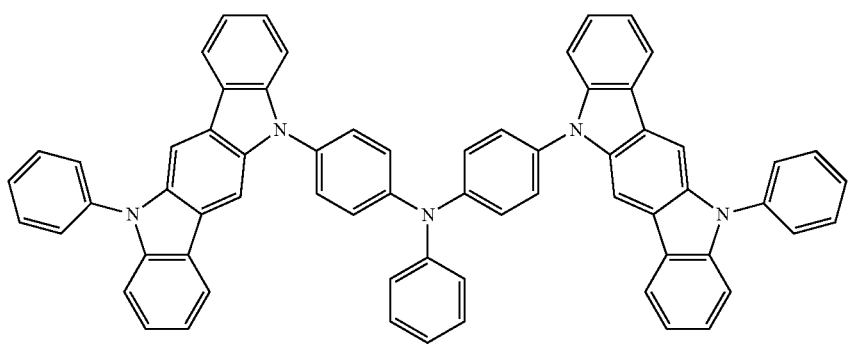
58
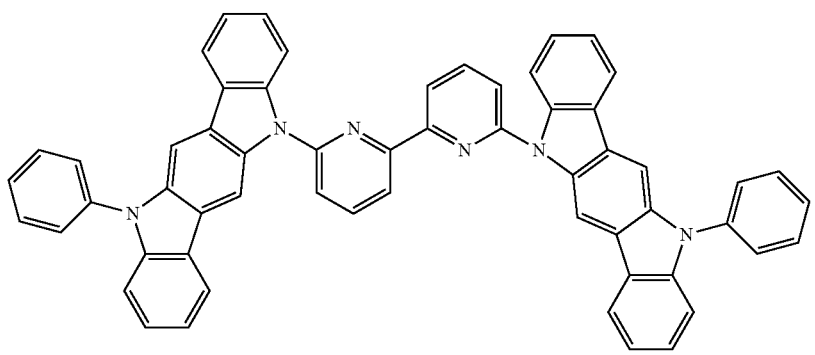
59 60
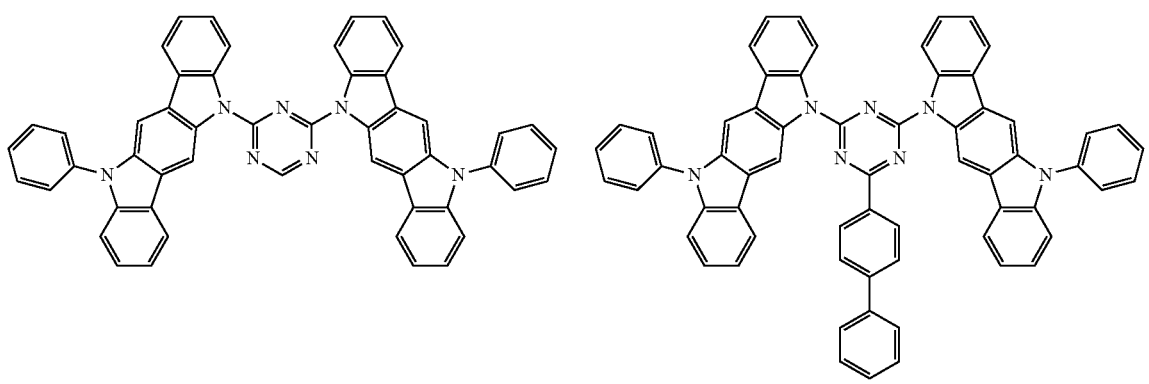

61
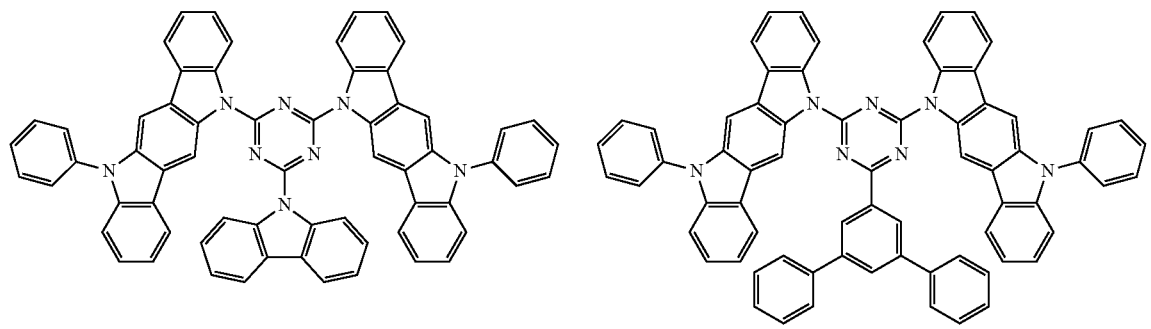
63
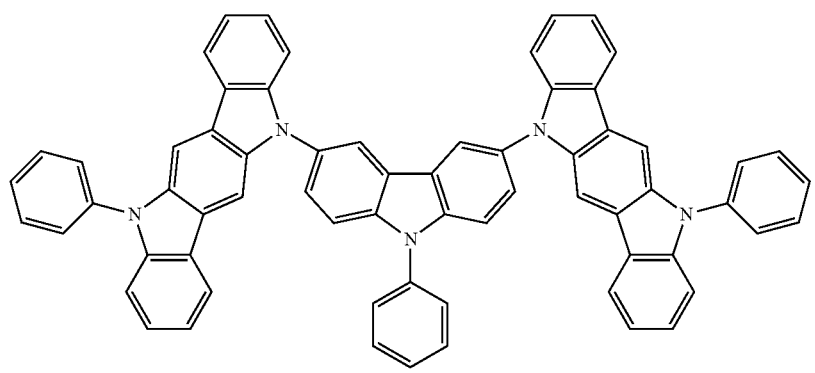
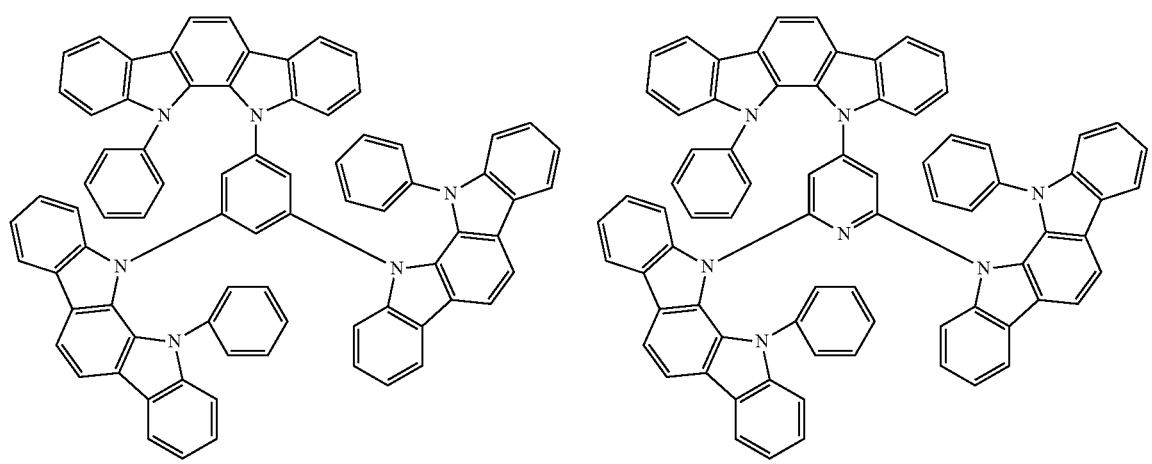

-continued
103
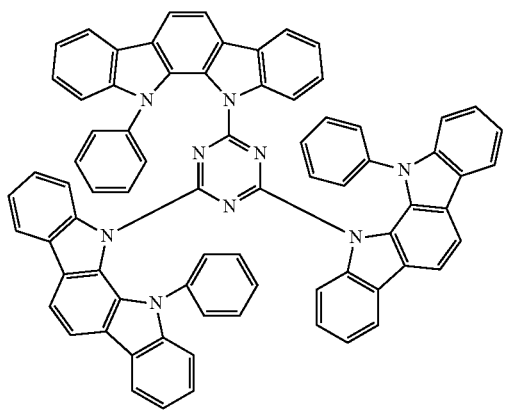
104
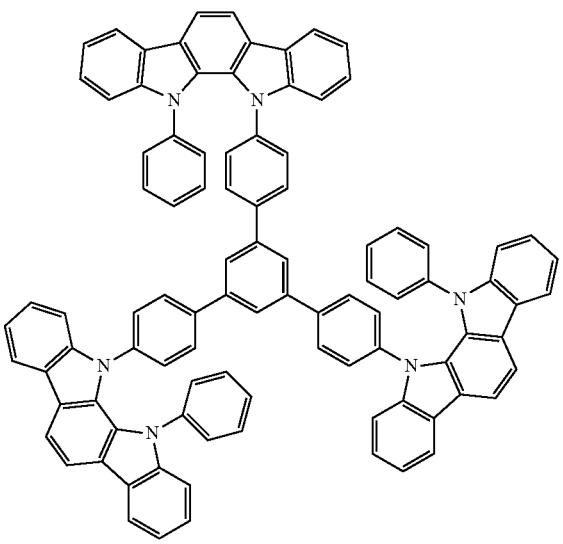
105
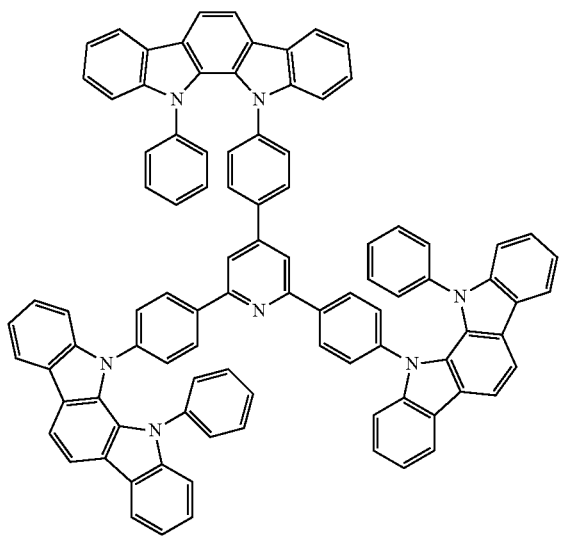
106
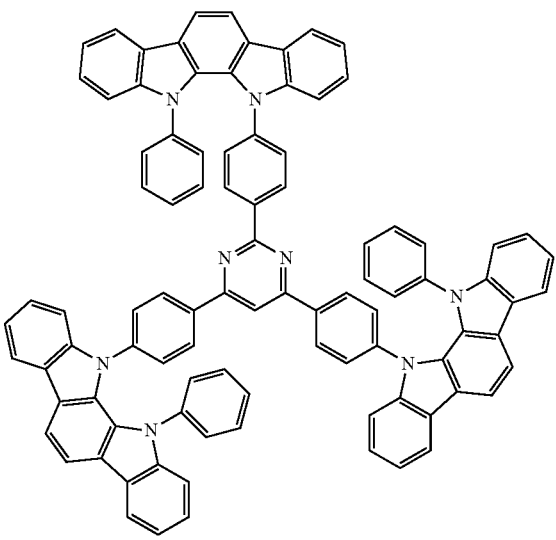
107
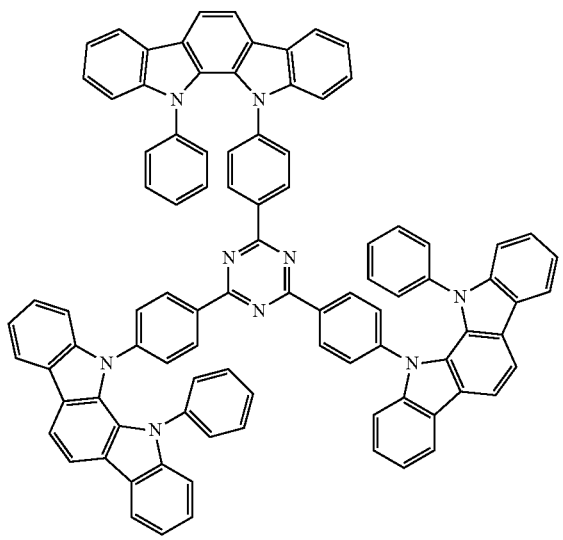
108
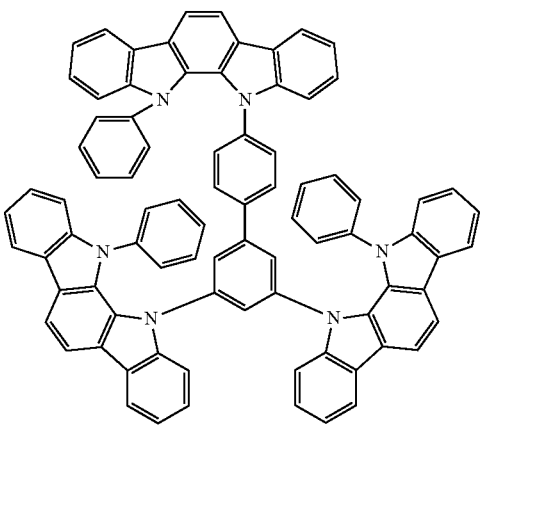

-continued
109
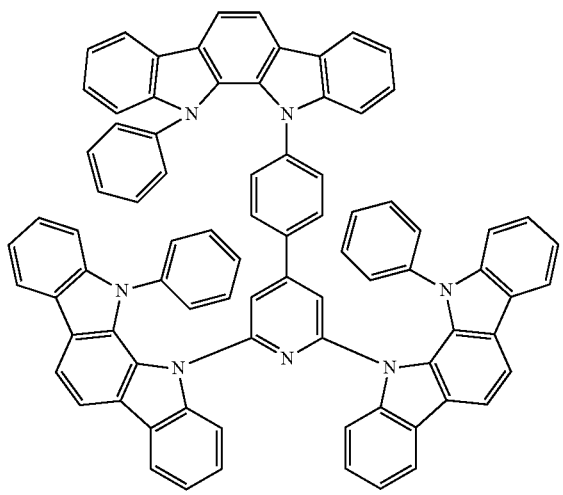
110
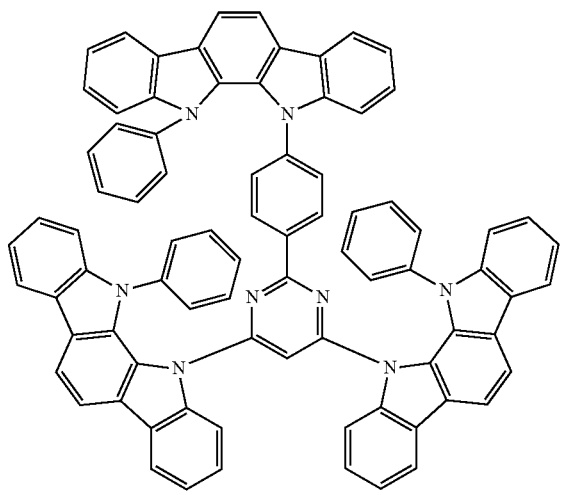
111
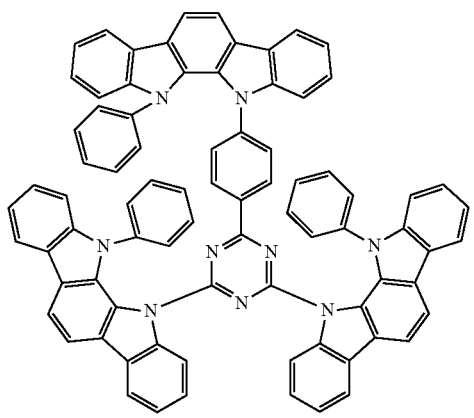
112
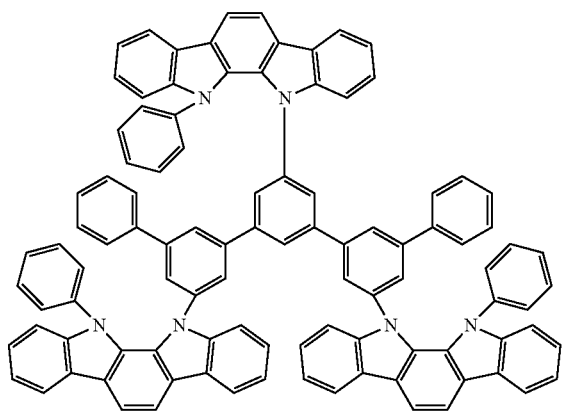
113
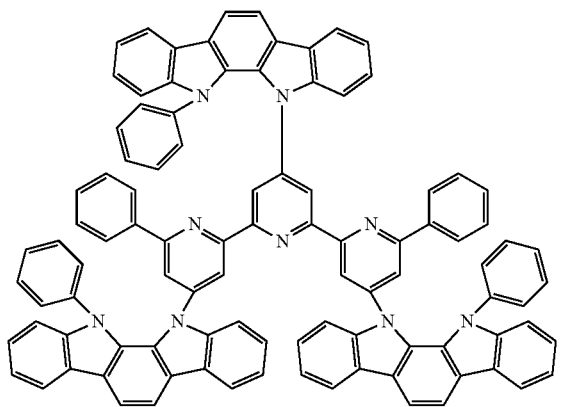
114
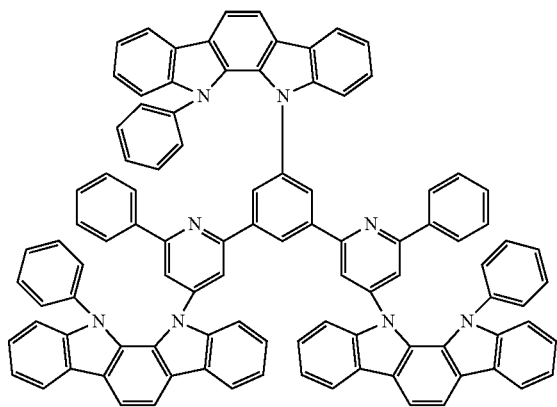

-continued
115
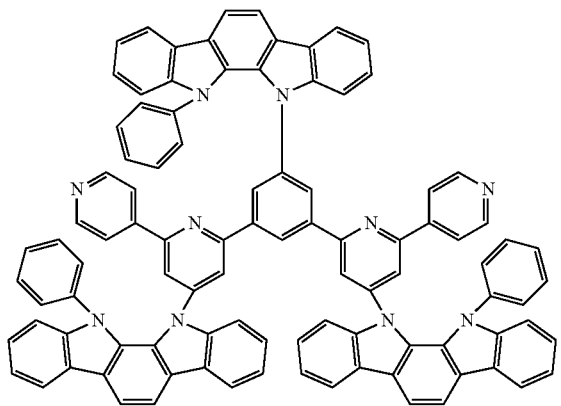
116
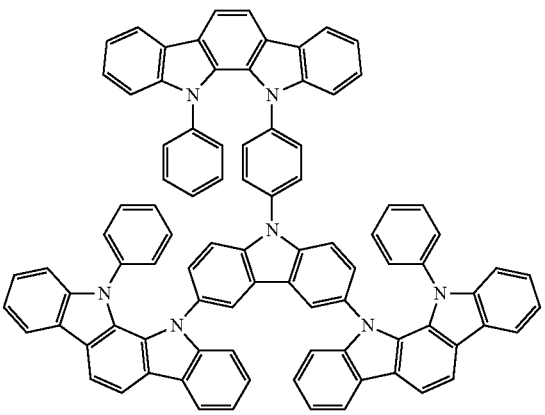
117
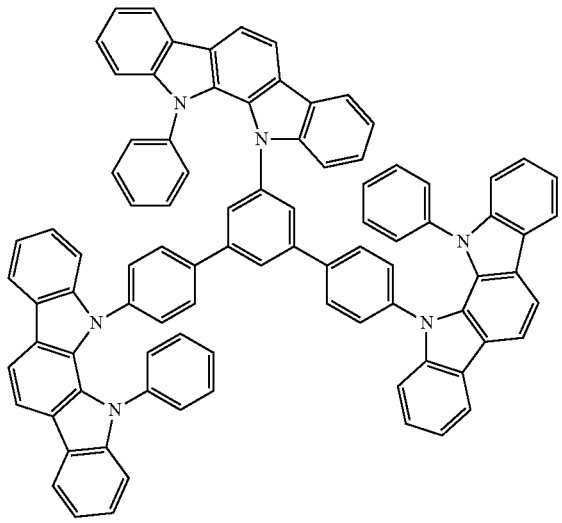
118
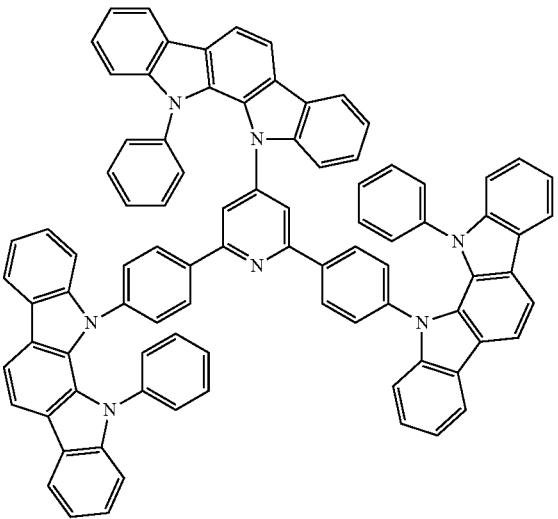
119
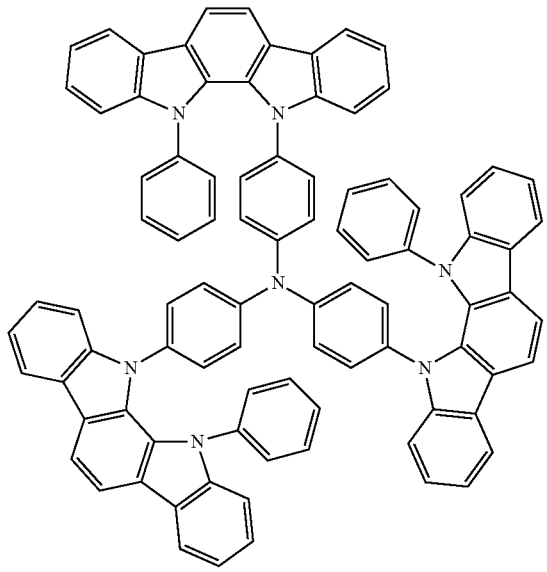
120
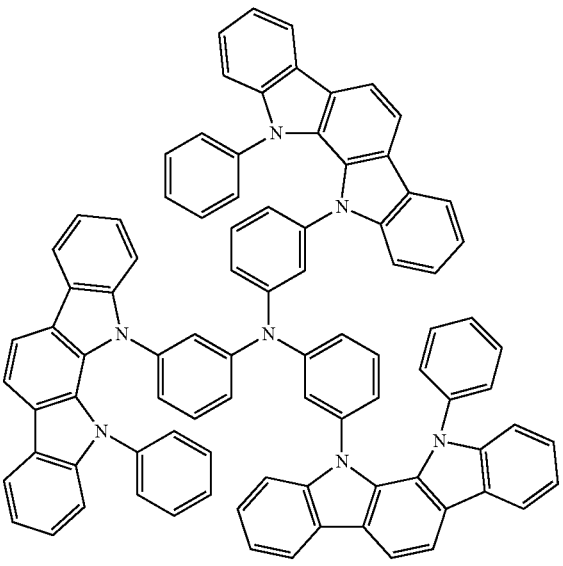

-continued
121 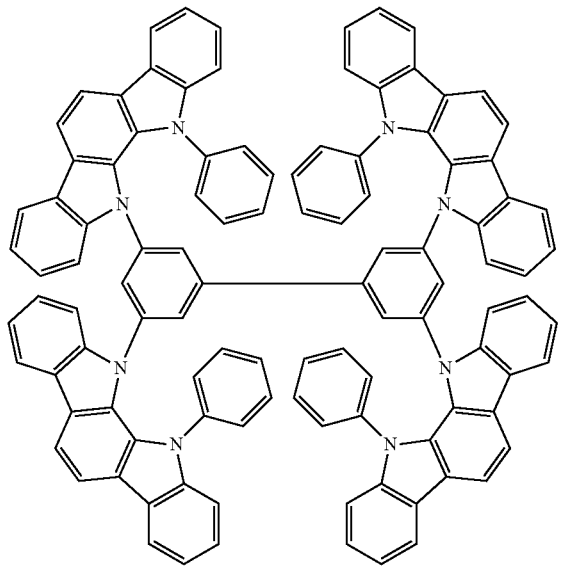
122 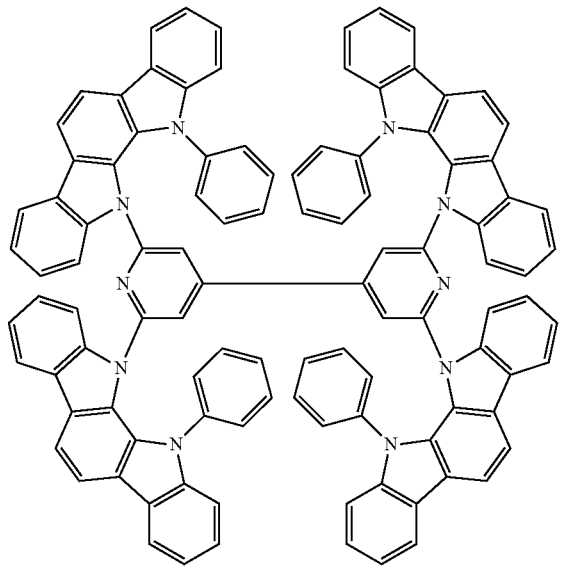
123 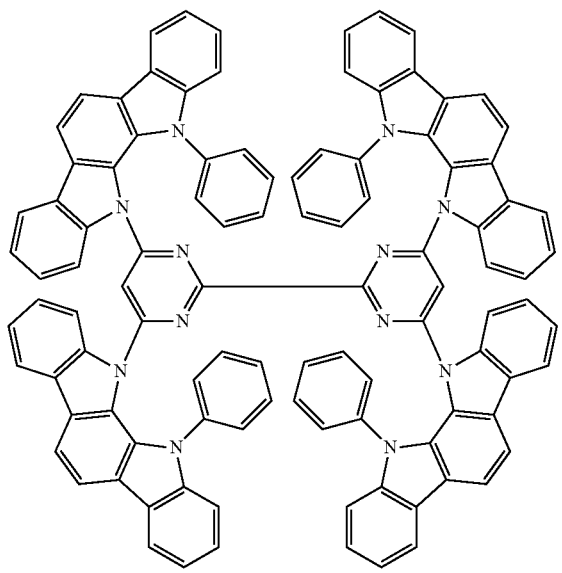
124 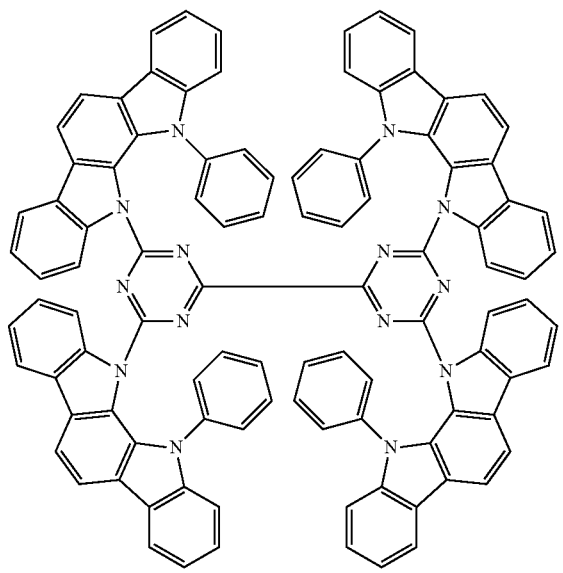

-continued
125
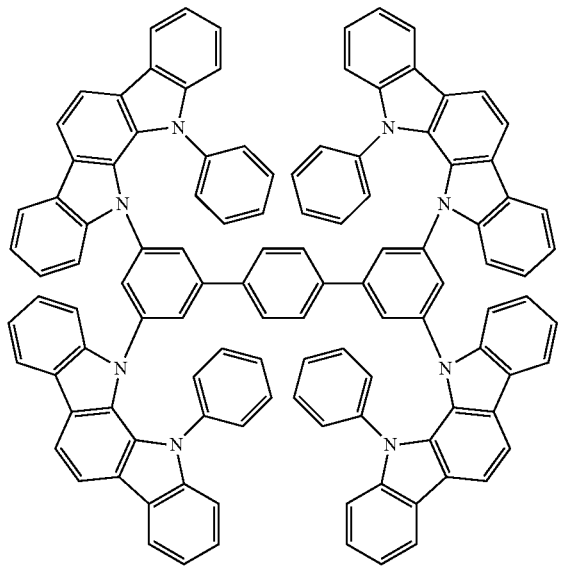
126
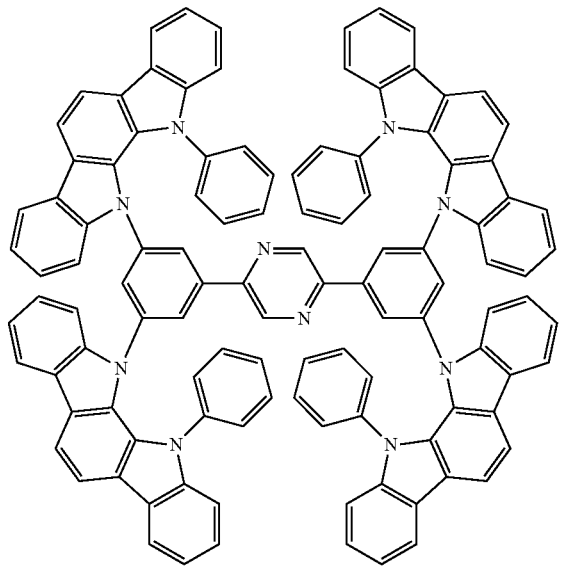
127
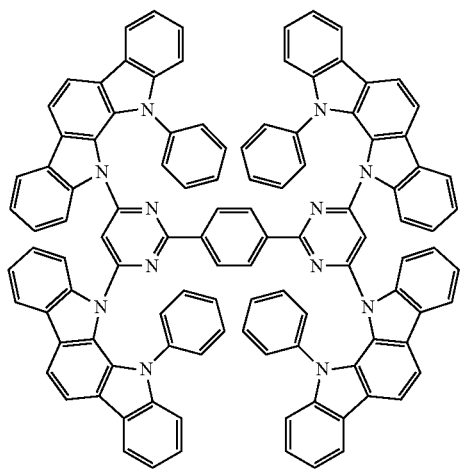
128
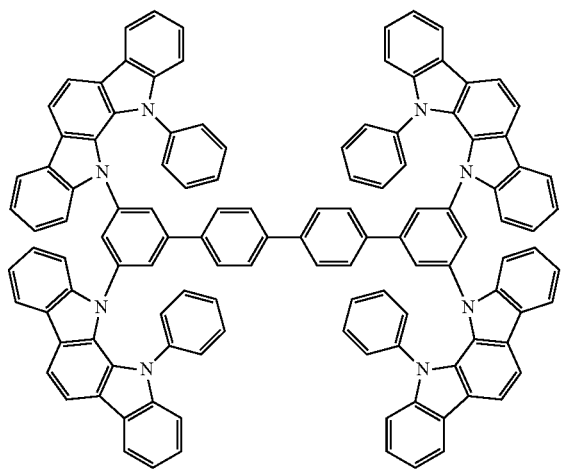
129
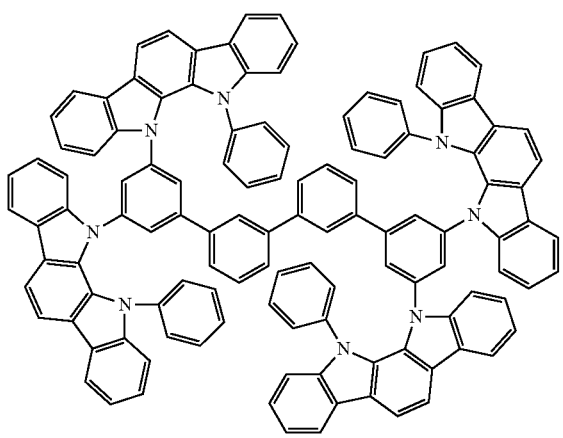
130
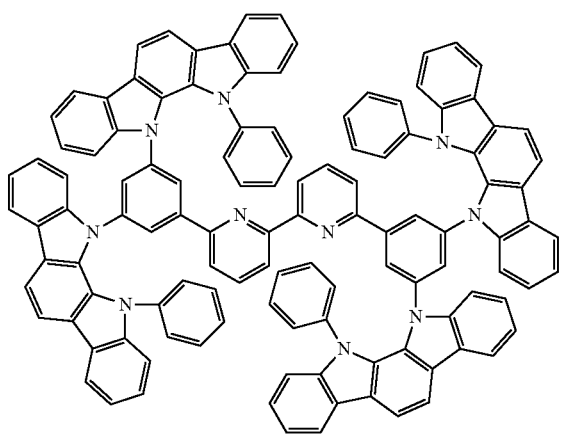

131
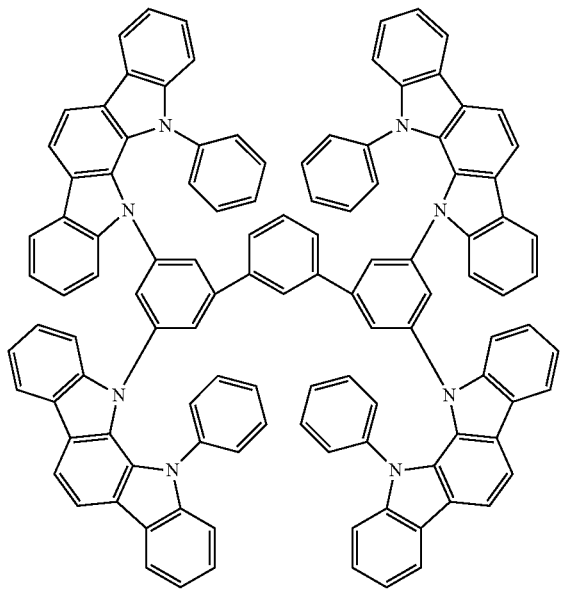
132
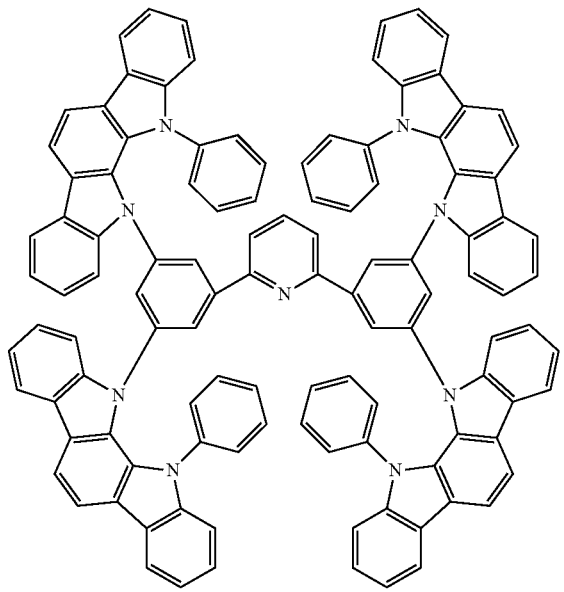
133
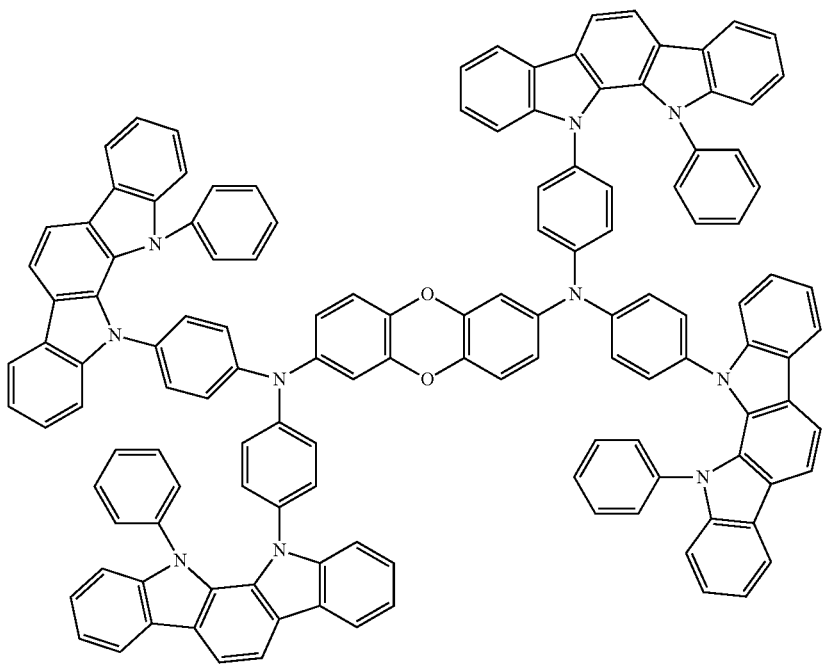

134
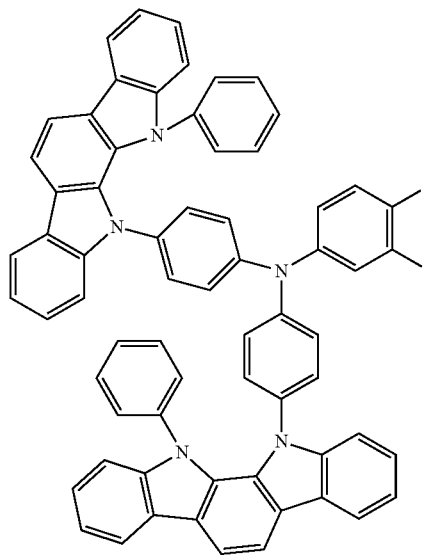
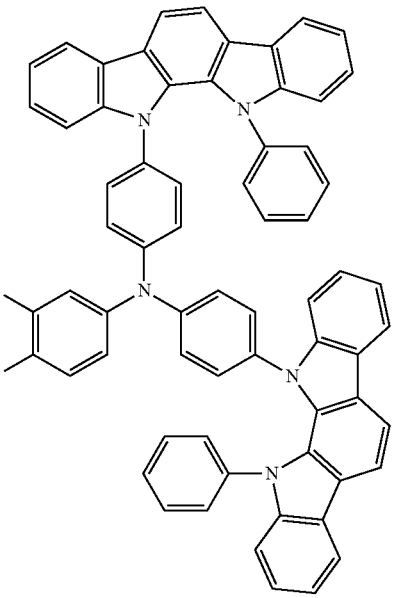
135
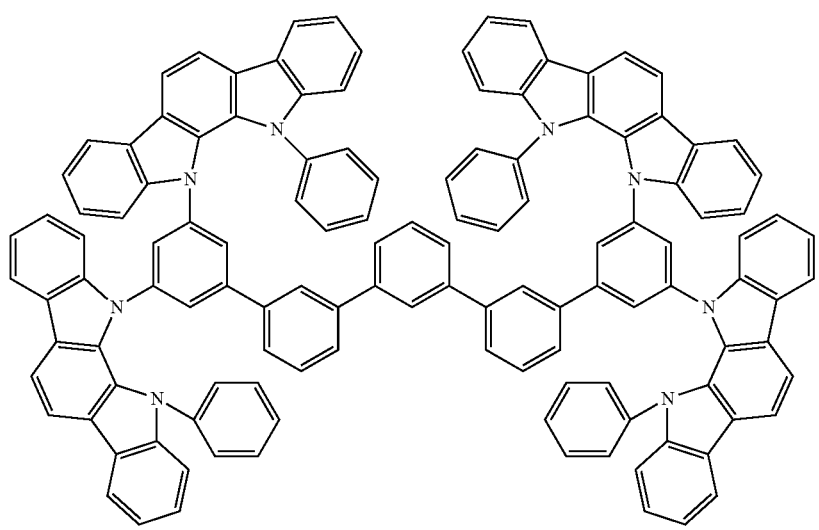

-continued
123
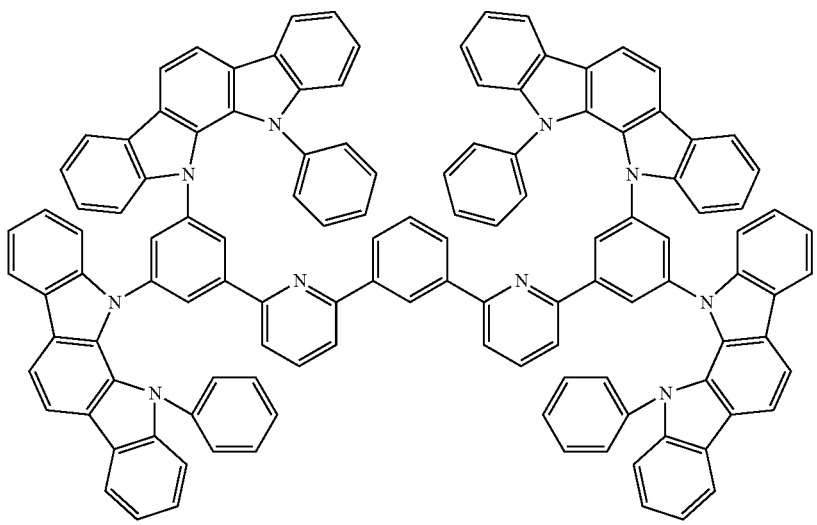
124
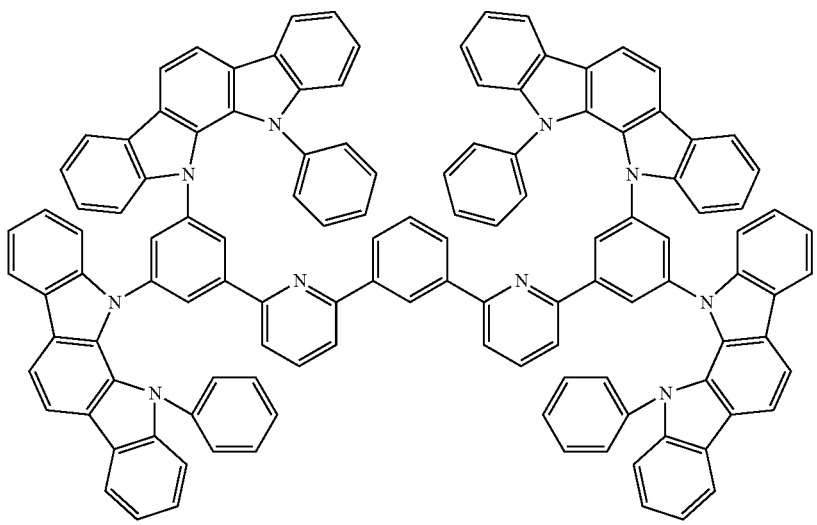
136
137
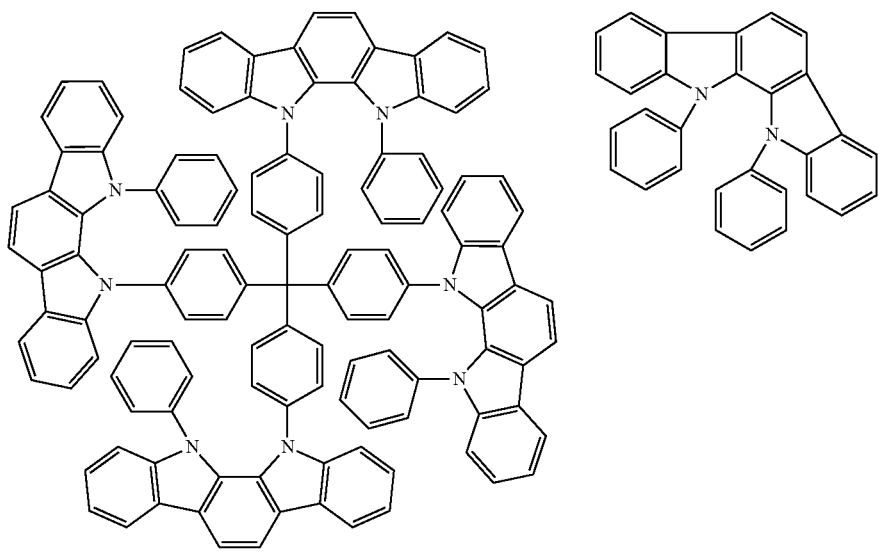
138
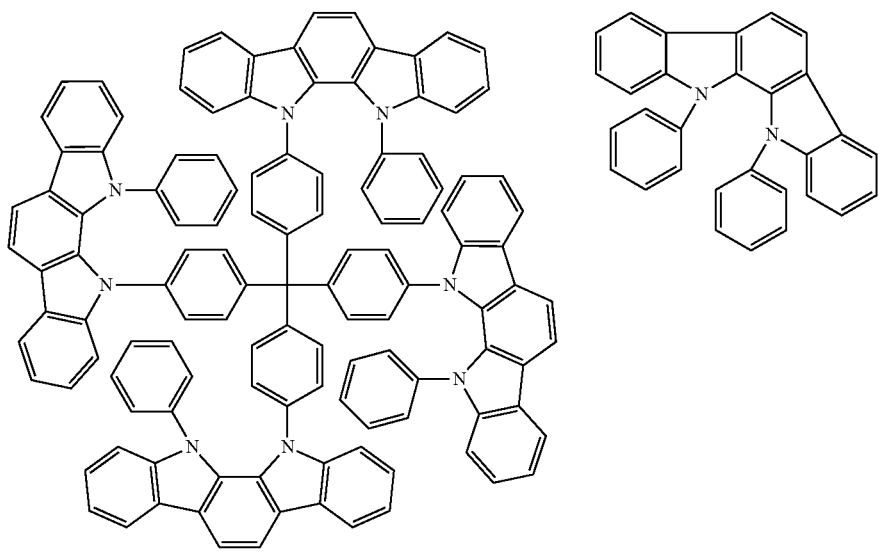
139
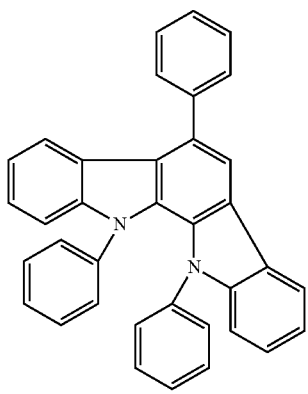
140
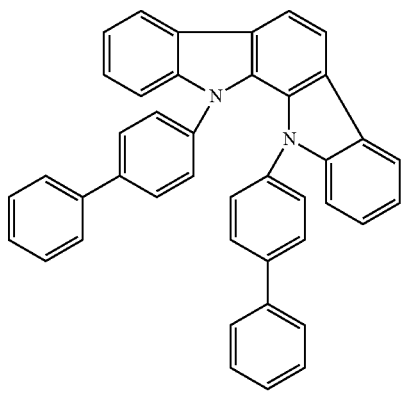

-continued
125
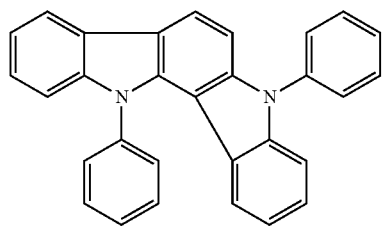
126
141
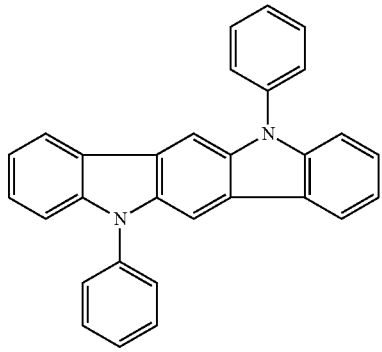
142
143
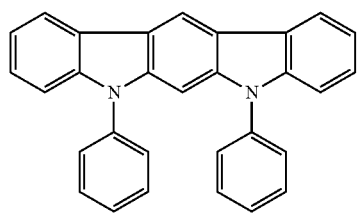
144
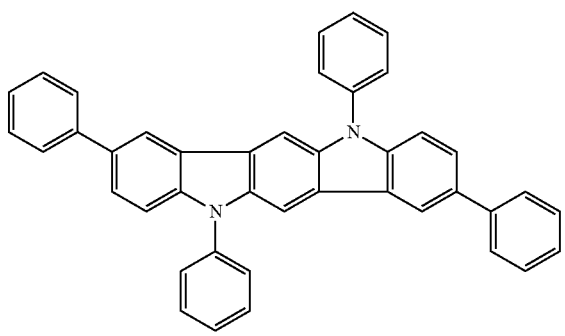
145
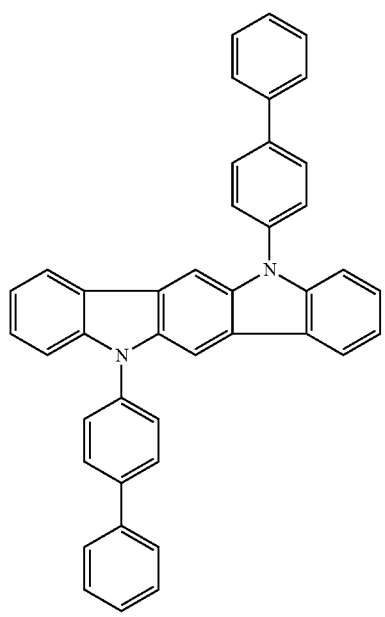
146
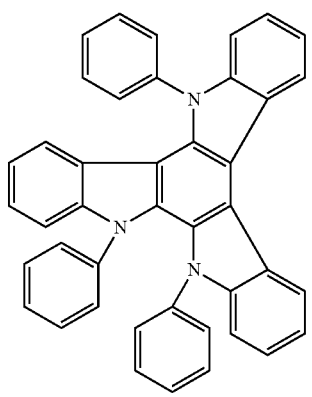

-continued
147
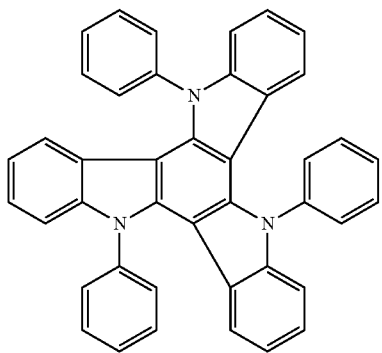
| Compound | Central Skeleton | A |
|---|---|---|
| 148 | A—⌬—O—⌬—A | [N-methyl, N-phenyl indolocarbazole] |
| 149 | A—⌬—O—⌬—A | [N-methyl, N-phenyl indolocarbazole isomer] |
| 150 | A—⌬—S—⌬—A | [N-methyl, N-(2-pyridyl) indolocarbazole] |
| 151 | A—⌬—SO₂—⌬—A | [N-methyl, N-phenyl pyrido-indolocarbazole] |

-continued

| Compound | Central Skeleton | A |
| --- | --- | --- |
| 152 | | |
| 153 | | |
| 154 | | |
| 155 | | |
| 156 | | |
| 157 | | |

-continued

| Compound | Central Skeleton | A |
|---|---|---|
| 158 | | |
| 159 | | |
| 160 | | |
| 161 | | |
| 162 | | |
| 163 | | |

-continued
| Compound | Central Skeleton | A |
|---|---|---|
| 164 | 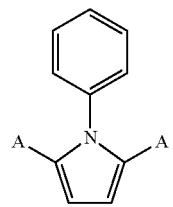 | 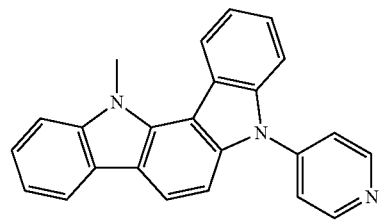 |
| 165 |  | 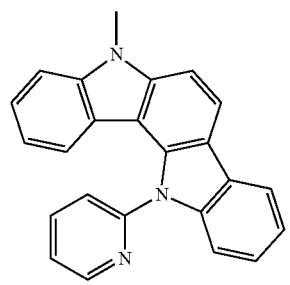 |
| 166 | 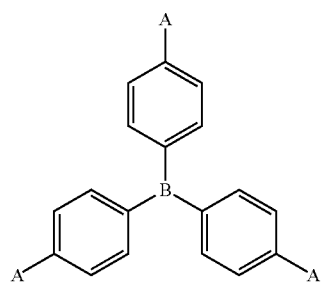 | 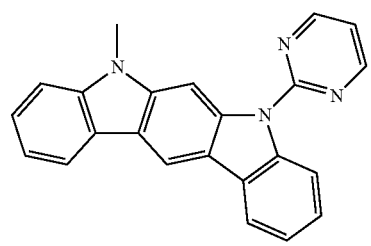 |
| 167 | 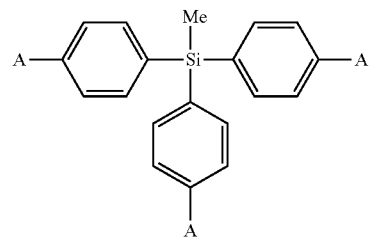 | 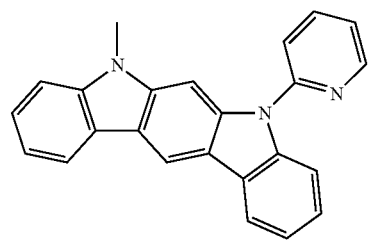 |
| 168 | 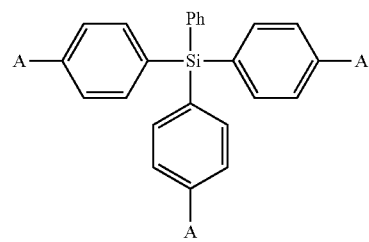 | 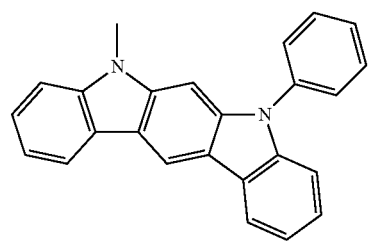 |

-continued
| Compound | Central Skeleton | A |
|---|---|---|
| 169 | 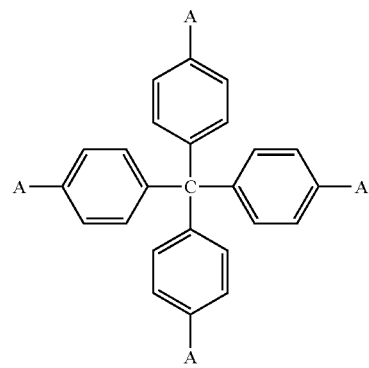 | 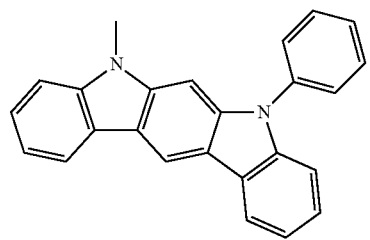 |
| 170 | 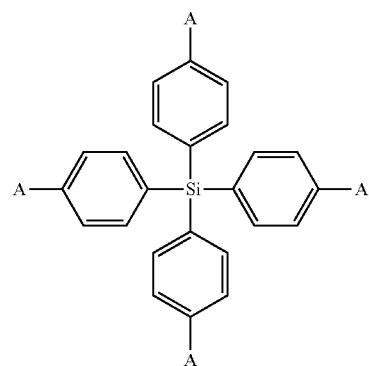 | 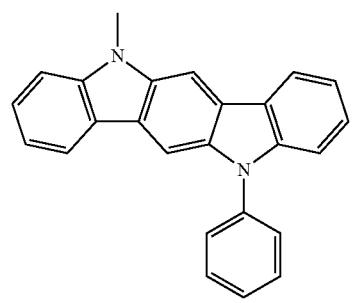 |
| 171 | 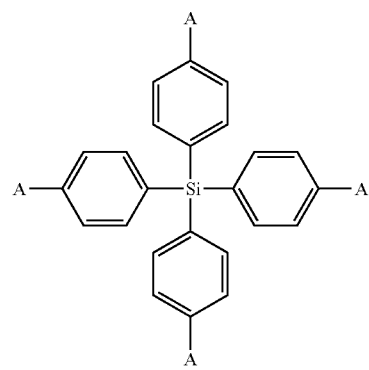 | 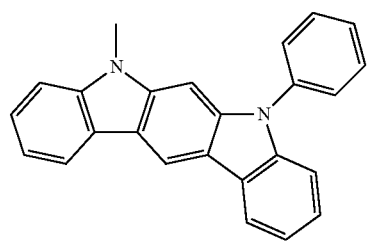 |
| 172 | 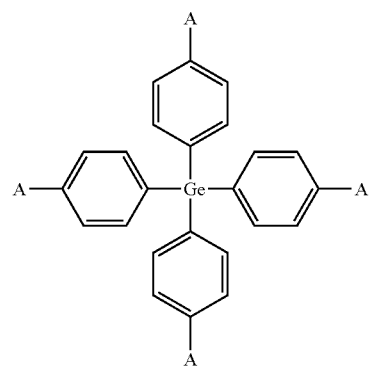 | 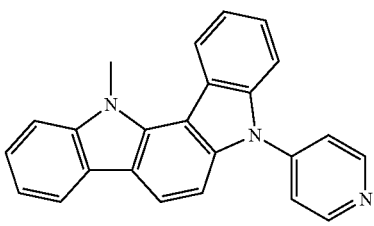 |

-continued
| Compound | Central Skeleton | A |
|---|---|---|
| 173 | 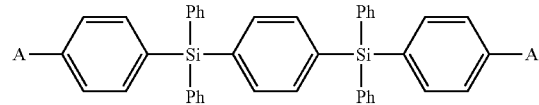 | 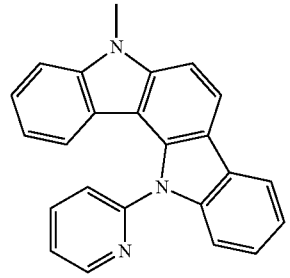 |
| 174 | 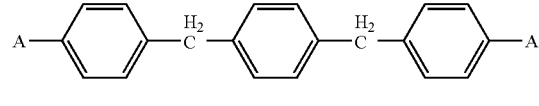 | 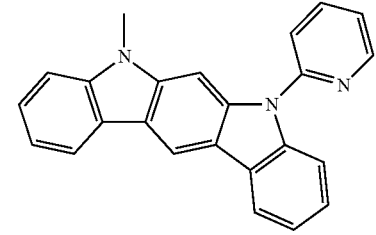 |
| 175 | 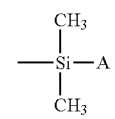 | 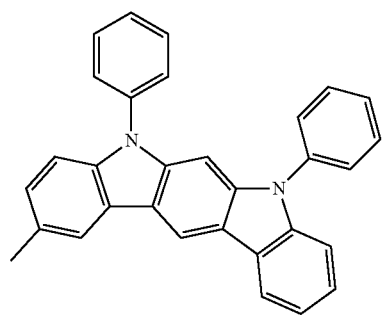 |
| 176 | 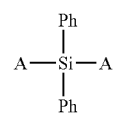 | 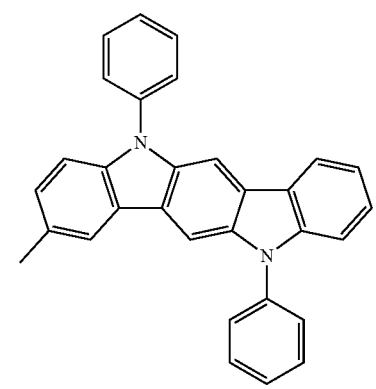 |
| 177 | 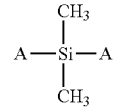 | 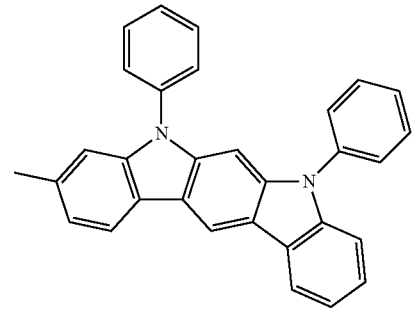 |

-continued

| Compound | Central Skeleton | A |
|---|---|---|
| 178 | A—Si(Ph)(Ph)—A | (N-phenyl, N-phenyl indolocarbazole with methyl) |
| 179 | A—Si(CH₃)(CH₃)—A | (N-pyridin-4-yl, N-pyridin-4-yl indolocarbazole with methyl) |
| 180 | A—Si(Ph)(Ph)—A | (N-phenyl, N-phenyl indolocarbazole isomer with methyl) |
| 181 | A—Si(CH₃)(A)—A | (N-phenyl, N-phenyl indolocarbazole with methyl) |
| 182 | A—Si(Ph)(Ph)—A | (N-pyridin-3-yl, N-pyridin-3-yl indolocarbazole with methyl) |

-continued

| Compound | Central Skeleton | A |
|---|---|---|
| 183 | A—Si(A)(A)—A | (phenyl-substituted indolocarbazole with methyl and N-phenyl groups) |
| 184 | A—Si(Ph)(A)—A | (phenyl-substituted indolo-pyridino-carbazole with methyl group) |
| 185 | (CH₃)₂C(A)— | (phenyl-substituted indolocarbazole with methyl group) |
| 186 | A—C(Ph)(Ph)—A | (phenyl-substituted indolocarbazole with methyl group) |

| Compound | Central Skeleton | A |
|---|---|---|
| 187 | A—C(CH₃)(CH₃)—A | 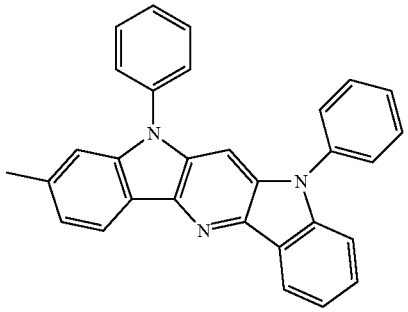 |
| 188 | A—C(Ph)(Ph)—A | 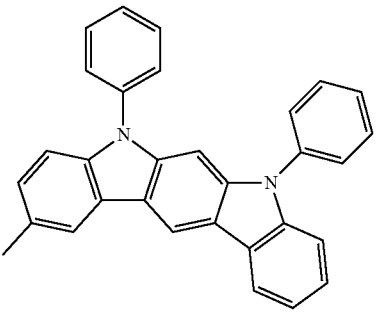 |
| 189 | A—C(CH₃)(CH₃)—A | 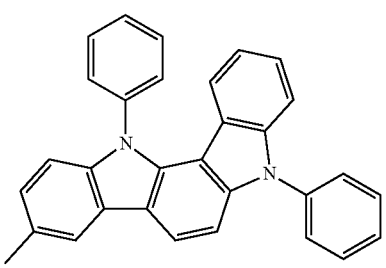 |
| 190 | A—C(Ph)(Ph)—A | 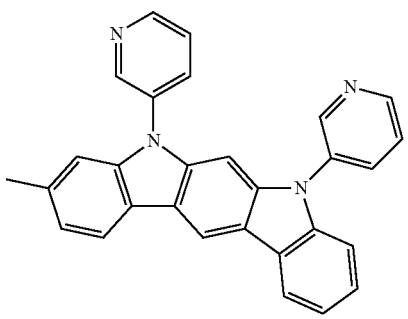 |
| 191 | A—C(CH₃)(A)—A | 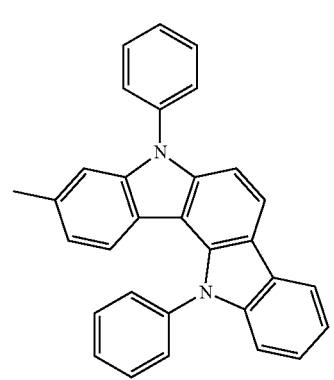 |

-continued
| Compound | Central Skeleton | A |
|---|---|---|
| 192 | 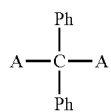 | 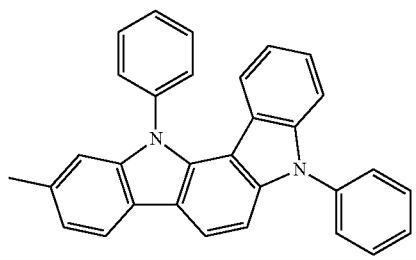 |
| 193 | 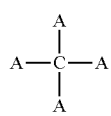 | 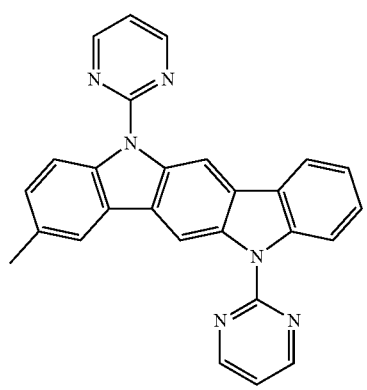 |
| 194 | 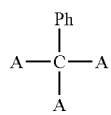 | 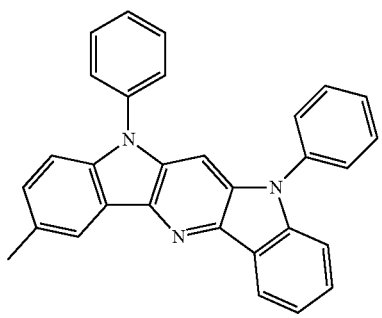 |
| 195 | 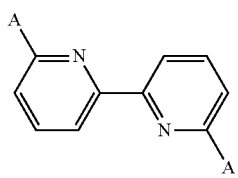 | 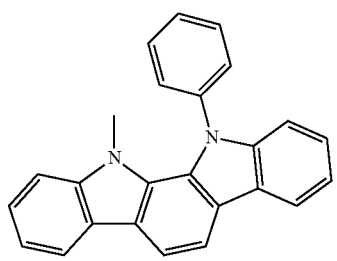 |

| 147 | 148 |
|---|---|
| 196 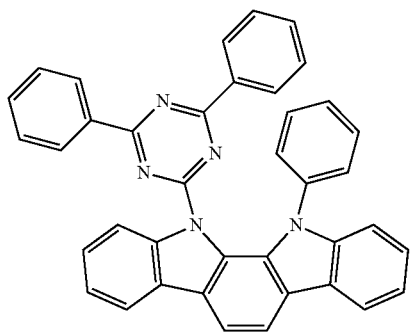 | 197 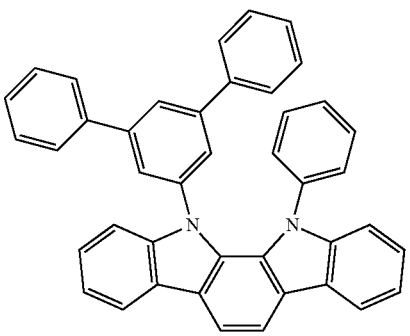 |
| 198 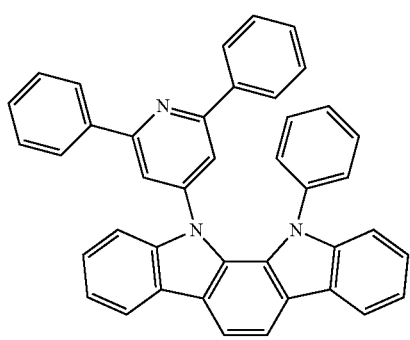 | 199 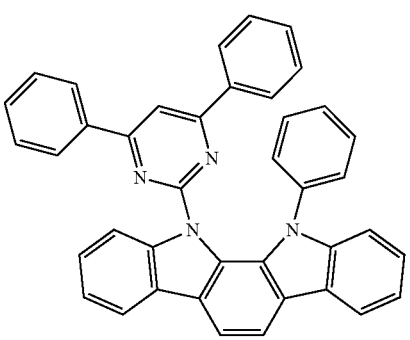 |
| 200 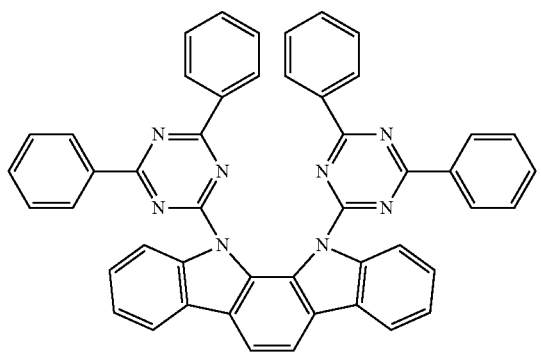 | 201 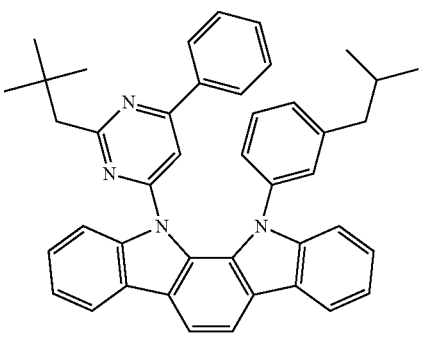 |
| 202 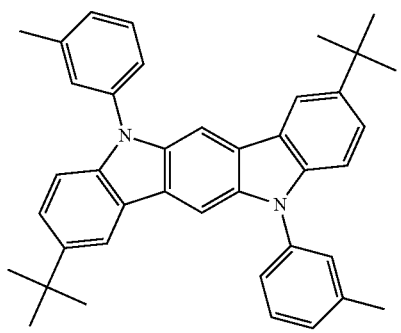 | 203 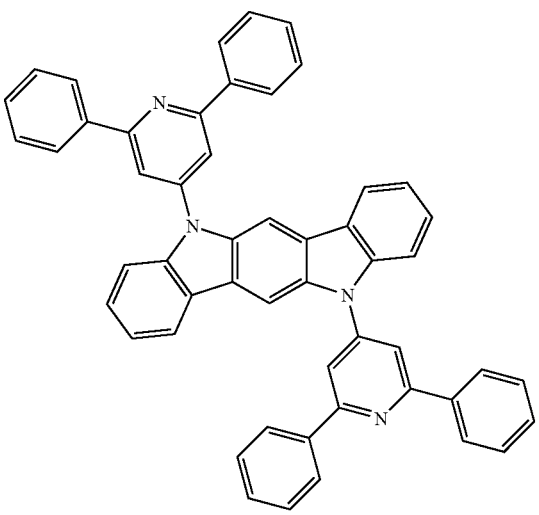 |

-continued
| 204 | 205 |
|---|---|
| 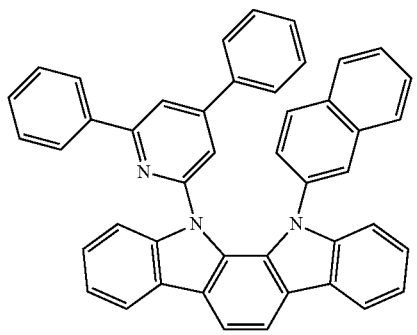 | 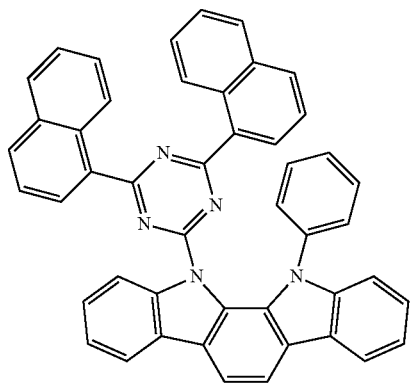 |
| 206 | 207 |
| 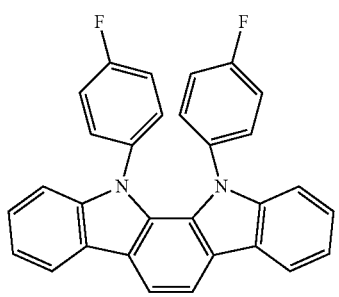 | 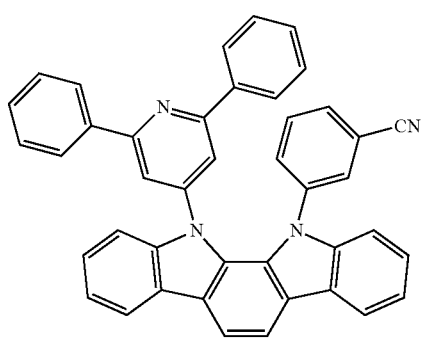 |
| 208 | 209 |
| 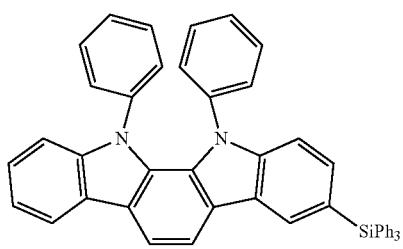 | 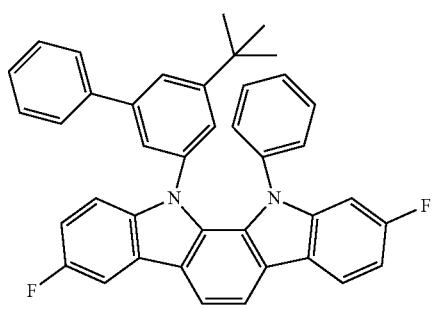 |
| 210 | 211 |
| 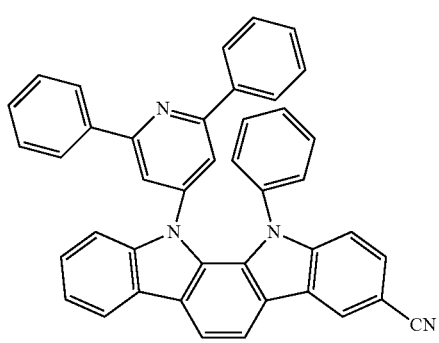 | 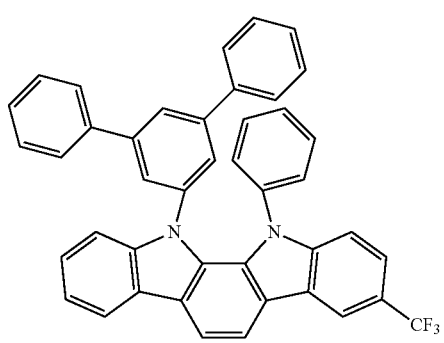 |

-continued
212
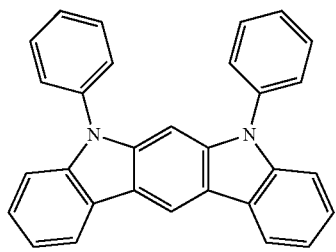
213
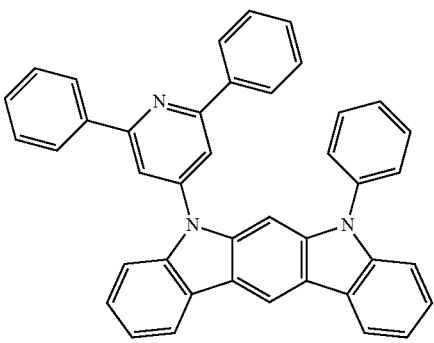
214
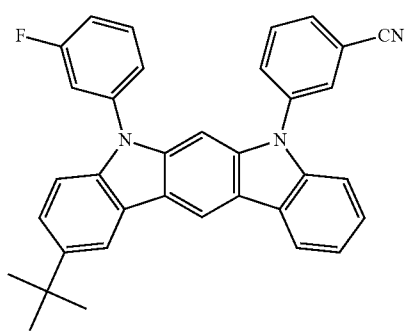
215
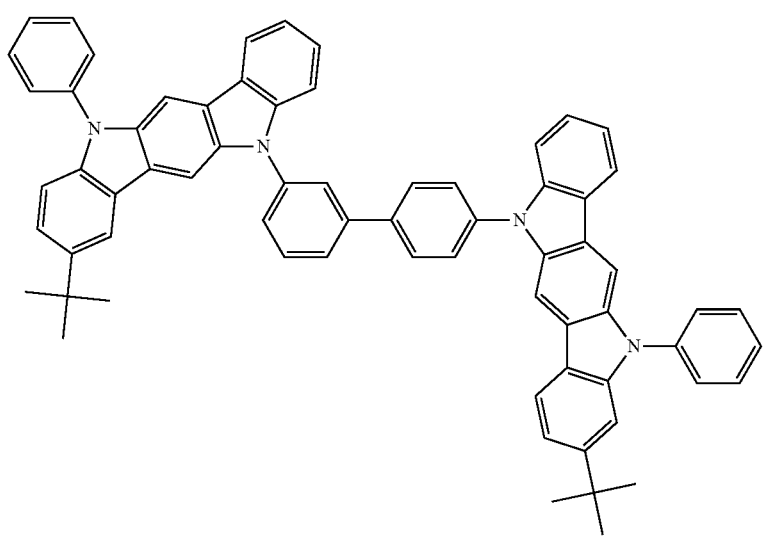
216
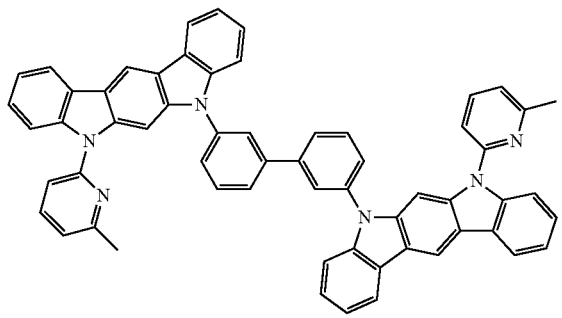
217
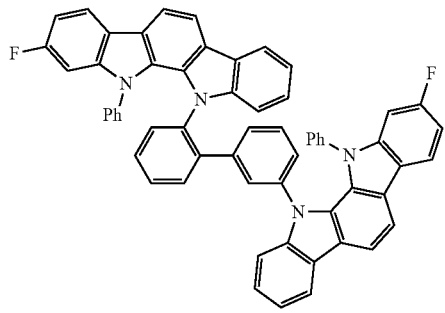

-continued
218
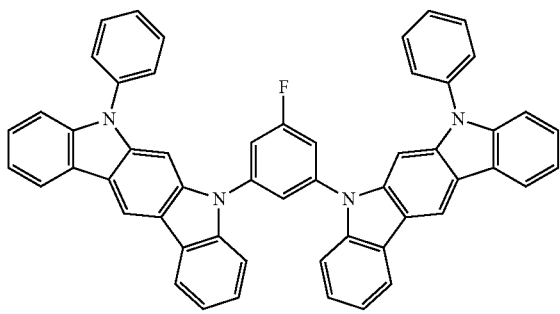
219
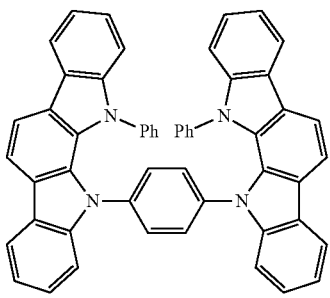
220
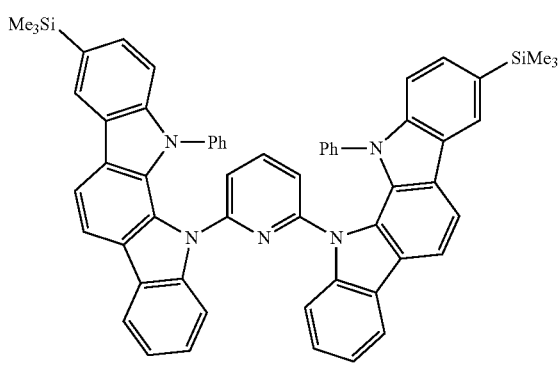
221
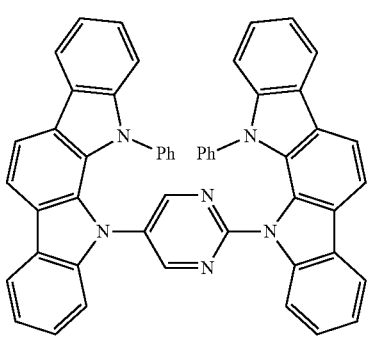
222
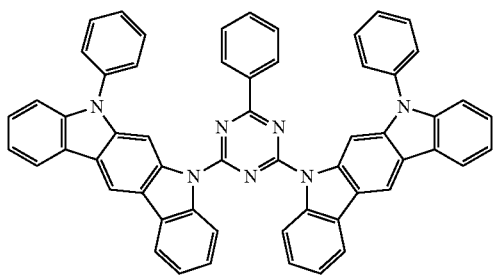
223
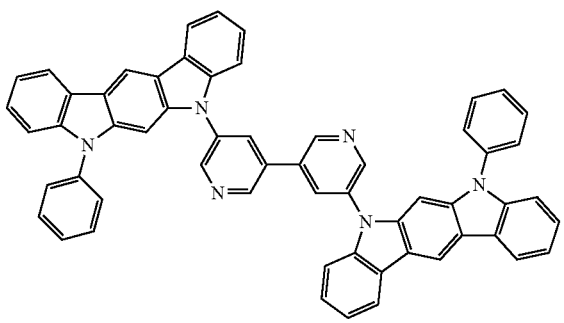
224
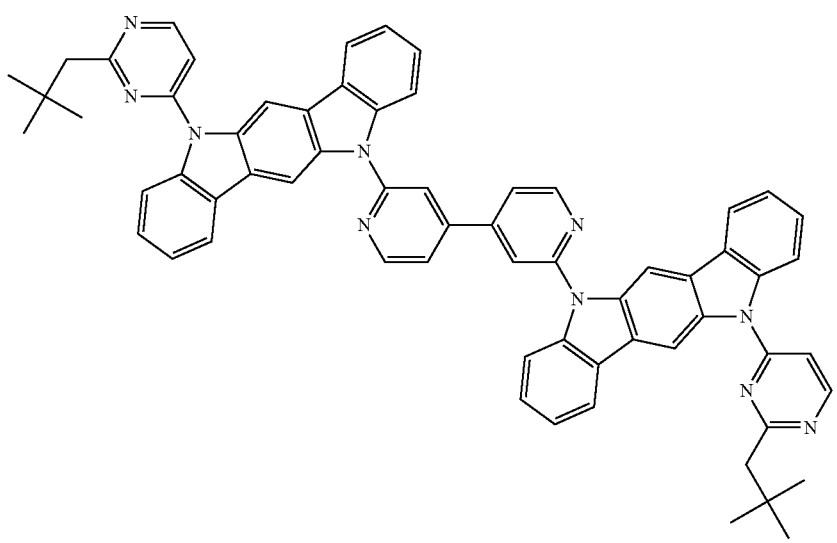

-continued
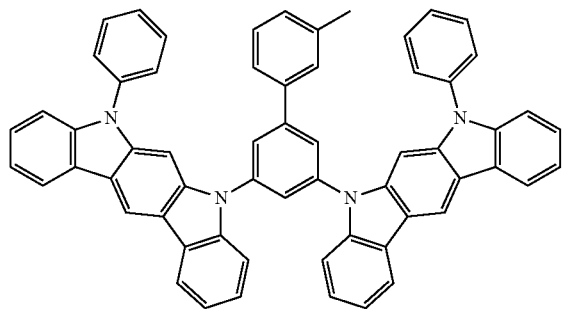
225
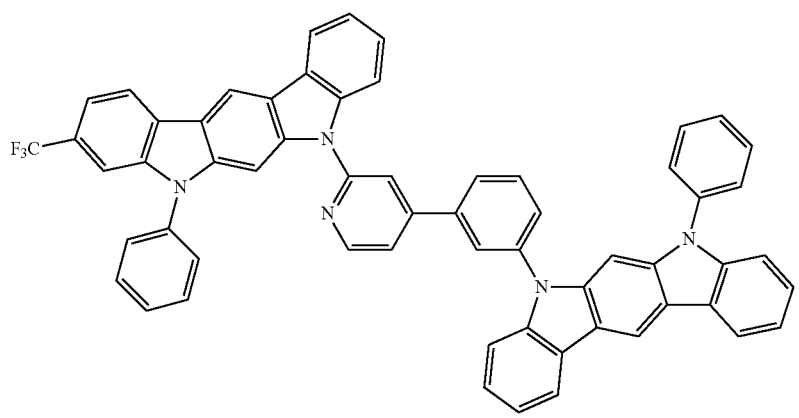
226
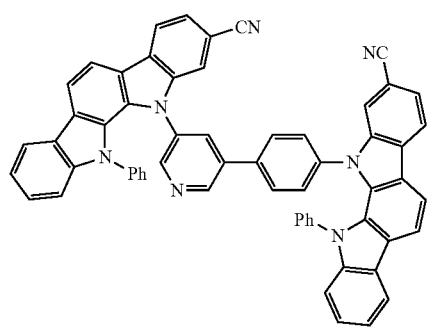
227
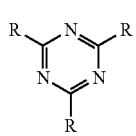
228
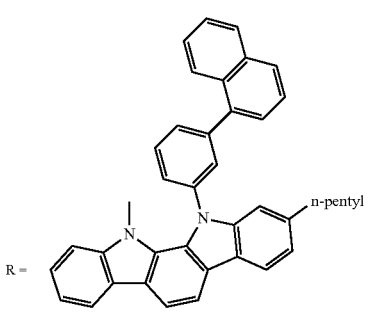

-continued
229
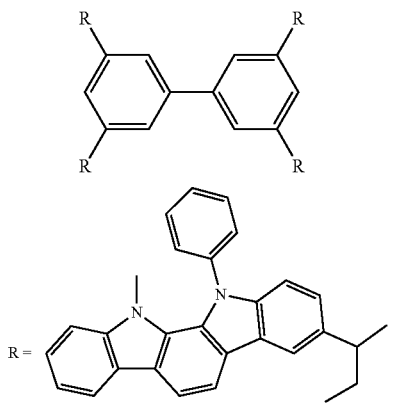
230
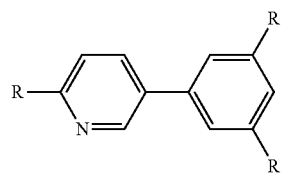
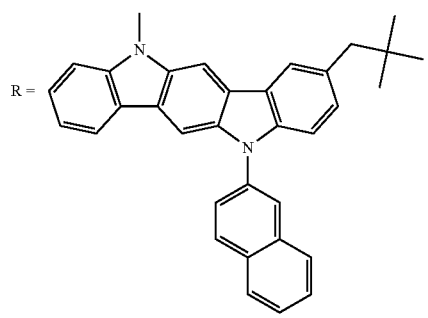
231
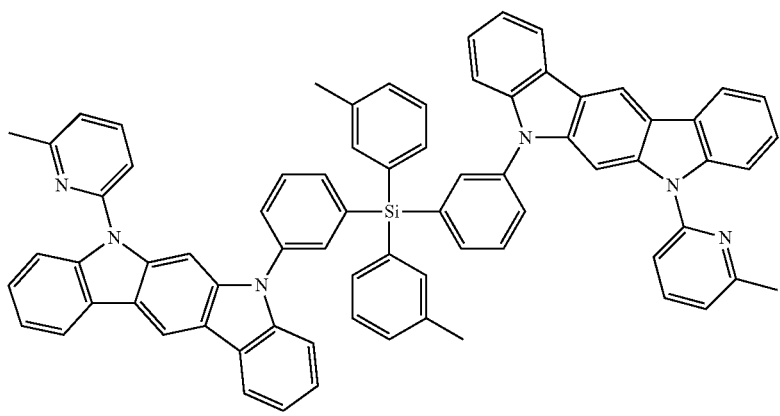
232
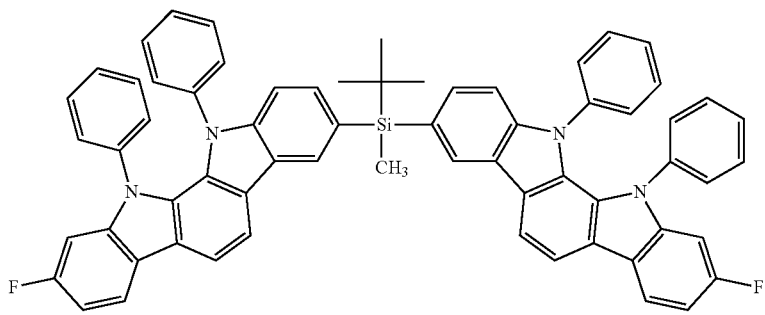
233
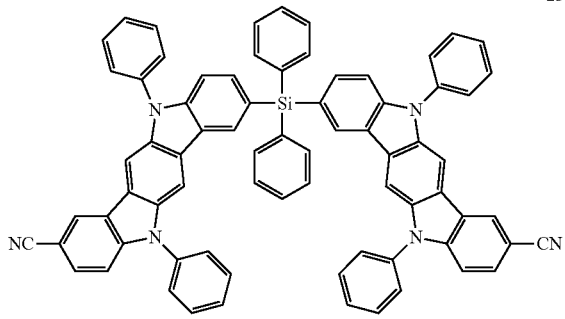
234
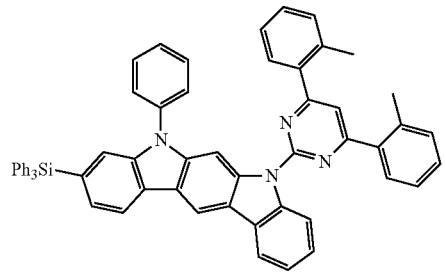

235
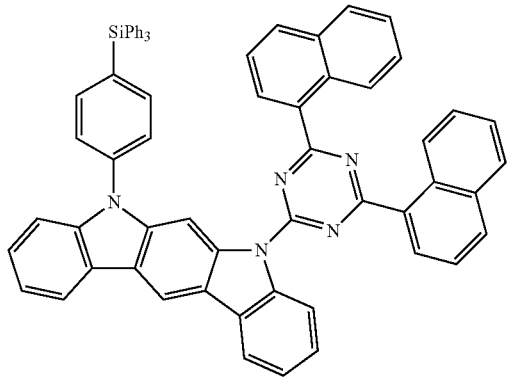
236
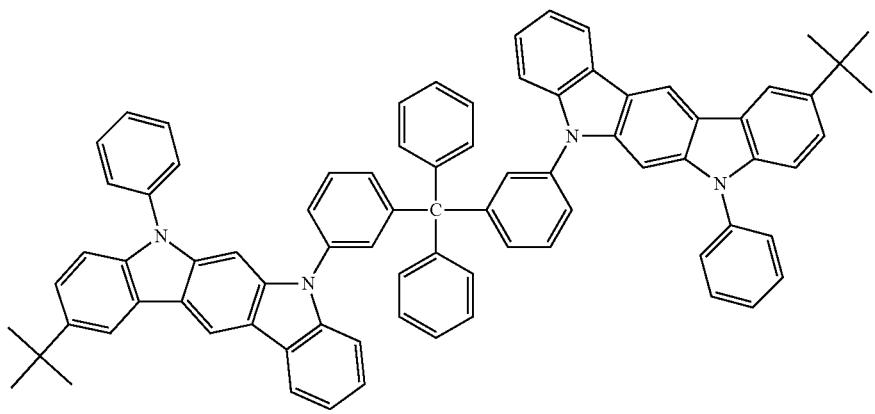
237
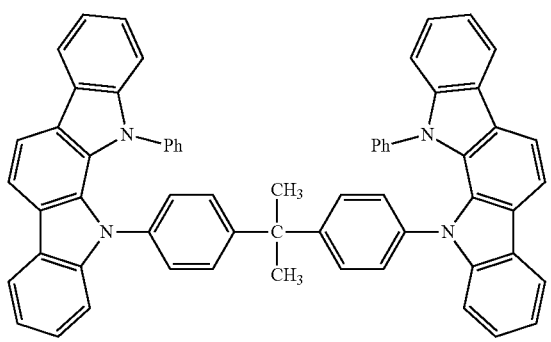
238
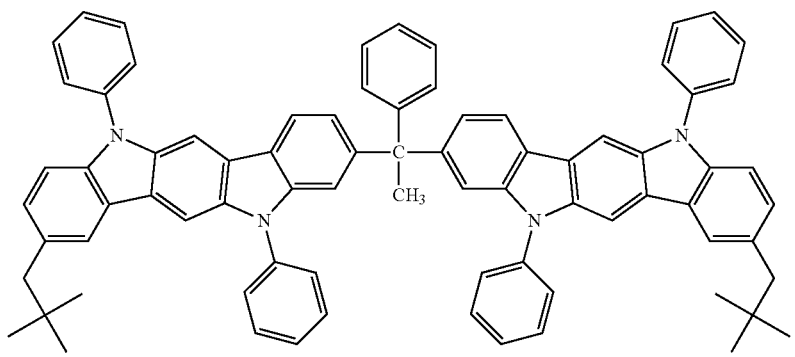

239
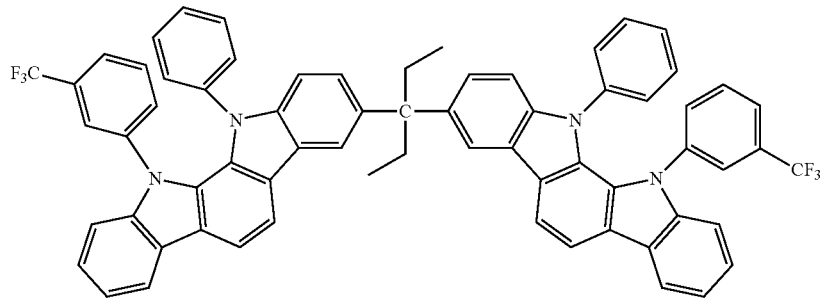
240
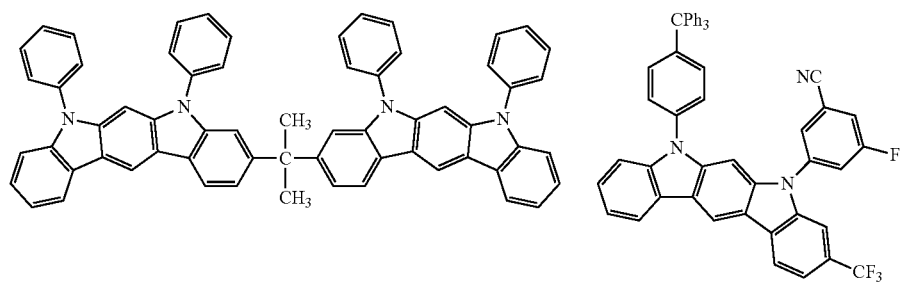
241
242
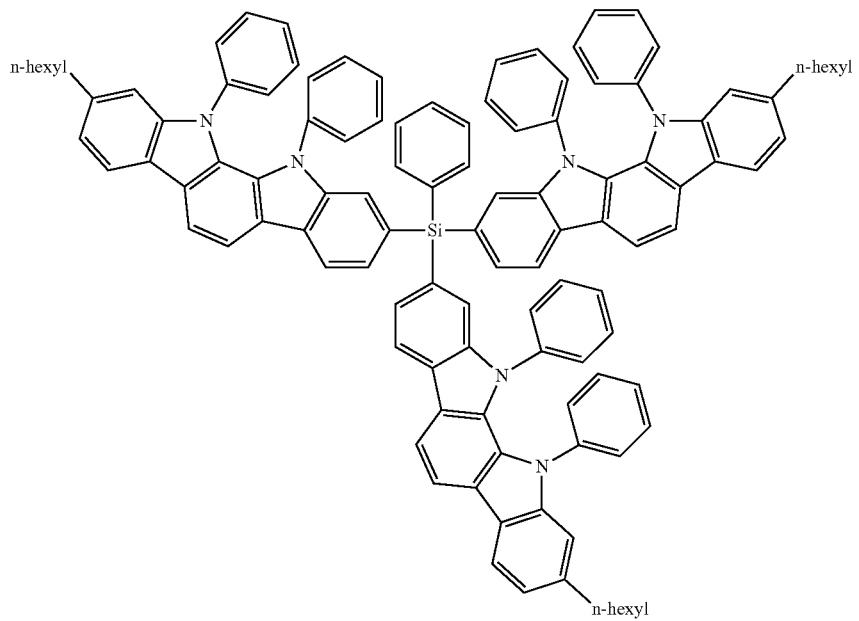

-continued

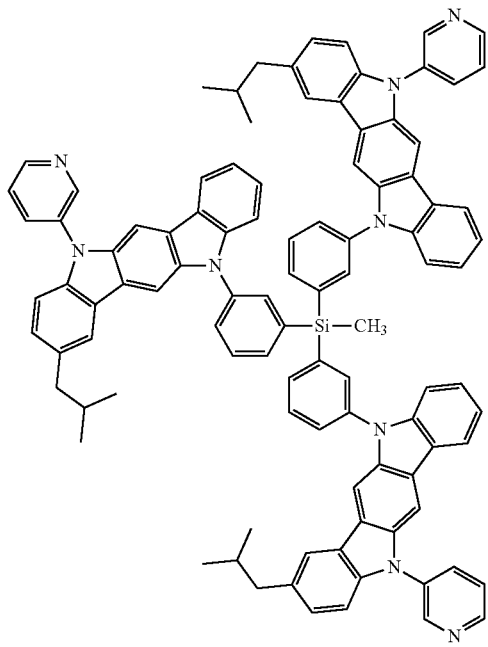

243

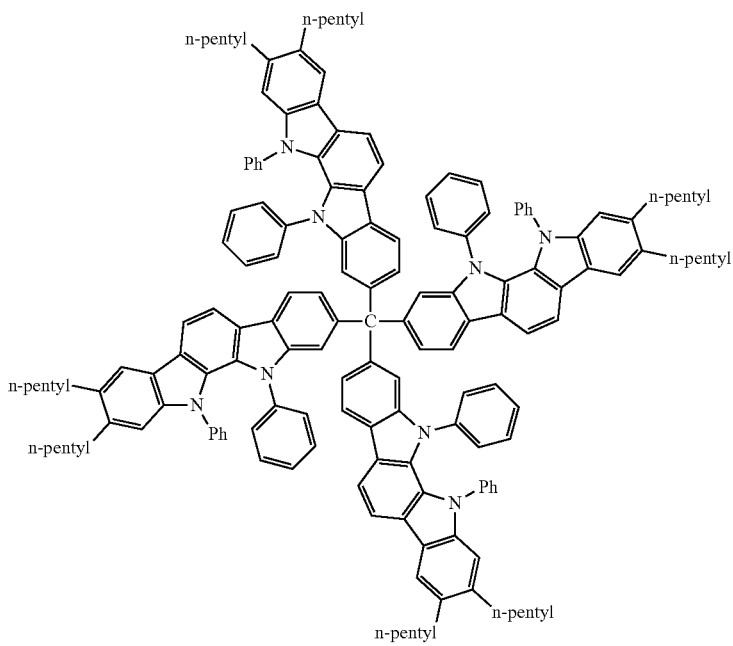

244

The compound represented by Formula (1) may be easily prepared by methods known in the art. For example, preparation may be performed with reference to Synthetic Examples shown in Tetrahedron, 47, 7739-7750 (1991), Synlett, 42-48 (2005).

In the present invention, the compound represented by Formula (1) is included in a light emitting layer from the viewpoint of improving light emission efficiency and durability (in particular, durability when driving at a high temperature), but the use thereof is not limited and may be included in any layer in addition to the light emitting layer within the organic layer. It is preferred that as a layer which introduces the compound represented by Formula (1), the compound is included in one of a hole injection layer, a hole transporting layer, an electron transporting layer, an electron injection layer, an exciton blocking layer and a charge blocking layer, or a plurality thereof in addition to a light emitting layer.

Further, the compound represented by Formula (1) may be contained in both layers of the light emitting layer and the layer adjacent to the light emitting layer.

[Compound represented by Formula (D-1)]

A compound represented by Formula (D-1) will be described in detail.

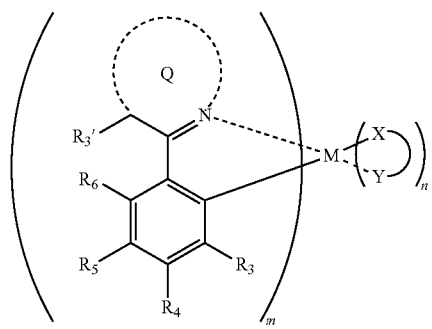

(D-1)

(In Formula (D-1), M represents a metal having an atomic weight of 40 or more. Each of $R_3$ to $R_6$ independently represents a hydrogen atom or a substituent. $R_3'$ represents a hydrogen atom or a substituent. The ring Q represents a pyridine ring, a quinoline ring or an isoquinoline ring, which is coordinated to the metal M, and may be further substituted with a non-aromatic group. $R_5$ represents an aryl group or a heteroaryl group when the ring Q is a pyridine ring. $R_3'$ and $R_6$ may be linked to each other by a linking group selected from —$CR_2$—$CR_2$—, CR=CR—, —$CR_2$—, —O—, —NR—, —O—$CR_2$—, —NR—$CR_2$— and —N=CR— to form a ring, each R independently represents a hydrogen atom, an alkyl group, an alkenyl group, an alkynyl group, a heteroalkyl group, an aryl group or a heteroaryl group, and may further have a substituent selected from a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' and —SO$_3$R', and each R' independently represents a hydrogen atom, an alkyl group, a perhaloalkyl group, an alkenyl group, an alkynyl group, a heteroalkyl group, an aryl group or a heteroaryl group. (X—Y) represents an ancillary ligand. m represents a value of 1 to the greatest number of ligands that may be bound to the metal, and n represents a value of 0 to the greatest number of ligands that may be bound to the metal. m+n is the greatest number of ligands that may be bound to the metal.)

In Formula (D-1), M represents a metal having an atomic weight of 40 or more, and may include Ir, Pt, Cu, Re, W, Rh, Ru, Pd, Os, Eu, Tb, Gd, Dy and Ce. Preferably, M is Ir, Pt or Re, and among them, Ir, Pt or Re, which may form a coordination mode of a metal-carbon bond or a metal-nitrogen bond, is preferable, and Ir is particularly preferable from the viewpoint of high light emission quantum efficiency.

Each of $R_3$ to $R_6$ and $R_3'$ independently represents a hydrogen atom or a substituent. As the substituent represented by $R_3$ to $R_6$ and $R_3'$, those exemplified above for the group A of substituents may be applied.

The aryl group represented by $R_3$ to $R_6$ and $R_3'$ may include preferably a substituted or unsubstituted aryl group having 6 to 30 carbon atoms, for example, a phenyl group, a tolyl group, a naphthyl group, and the like.

The heteroaryl group represented by $R_3$ to $R_6$ and $R_3'$ may include preferably a heteroaryl group having 5 to 8 carbon atoms, more preferably a 5- or 6-membered, substituted or unsubstituted heteroaryl group, for example, a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group and the like.

Preferable examples of the heterocyclic group represented by $R_3'$ include a pyridyl group, a pyrimidinyl group, an imidazolyl group, a thienyl group, and more preferably a pyridiyl group and a pyrimidinyl group.

$R_3'$ includes preferably a hydrogen atom, an alkyl group, a cyano group, a trifluoromethyl group, a perfluoroalkyl group, a dialkylamino group, a fluoro group, an aryl group and a heteroaryl group, more preferably a hydrogen atom, an alkyl group, a cyano group, a trifluoromethyl group, a fluoro group and an aryl group, and even more preferably a hydrogen atom, an alkyl group and aryl group.

$R_3$, $R_4$, and $R_6$ include preferably a hydrogen atom, an alkyl group, a cycloalkyl group, a cyano group, a perfluoroalkyl group, a dialkylamino group, a fluoro group, an aryl group and a heteroaryl group, more preferably a hydrogen atom, an alkyl group, a cyano group, a trifluoromethyl group, a fluoro group and an aryl group, and even more preferably a hydrogen atom, an alkyl group and an aryl group.

Further, $R_3$ to $R_6$ and $R_3'$ may further have a substituent, and as the substituent, those exemplified above for the group A of substituents may be applied. The substituent includes an alkyl group, an aryl group, a cyano group, a halogen atom and a nitrogen-containing aromatic heterocyclic group, and more preferably alkyl having 1 to 6 carbon atoms, an aryl group having 6 to 10 carbon atoms, pyridyl, a fluorine atom and a cyano group, and even more preferably an alkyl group having 1 to 6 carbon atoms, a phenyl group and a cyano group. in addition, $R_3$ to $R_6$ may be linked to each other to form a condensed ring, and a ring to be formed may include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring, a carbazole ring and the like.

$R_5$ becomes an aryl group or a heteroaryl group when the ring Q is a pyridine ring. The aryl group or heteroaryl group may further have a substituent, and the substituent includes preferably an alkyl group, a cyano group, a perfluoroalkyl group, a dialkylamino group, a fluoro group, an aryl group and a heteroaryl group, and more preferably a hydrogen atom, an alkyl group, a cyano group, a trifluoromethyl group, a fluoro group and an aryl group, and even more preferably a hydrogen atom, an alkyl group, a cyano group and an aryl group.

$R_5$ includes preferably a phenyl group, a p-tolyl group and a naphthyl group, and more preferably a phenyl group.

When the ring Q is a quinoline ring or an isoquinoline ring, $R_5$ includes preferably an alkyl group, an alkoxy group, a fluoro group, a cyano group, an alkylamino group and a diarylamino group, more preferably an alkyl group, a fluoro group and a cyano group, even more preferably an alkyl group, and particularly preferably a methyl group. Further, when the ring Q is a quinoline ring or an isoquinoline ring and $R_5$ is an alkyl group, $R_3$ is also preferably an alkyl group, and more preferably a methyl group.

The ring Q represents a pyridine ring, a quinoline ring or an isoquinoline ring, which is coordinated to the metal M, and may be further substituted with a substituent. The substituent includes an alkyl group, an aryl group, a cyano group, a perfluoroalkyl group, a dialkylamino group, a fluoro group, a pyridyl group, a thienyl group and an alkoxy group, more preferably an alkyl group, an aryl group, an alkoxy group, a cyano group, a dialkylamino group, a fluoro group, a pyridyl group and a thienyl group, even more preferably an alkyl group and an aryl group, and particularly preferably an alkyl group.

It is preferred that the ring Q does not further have the above-mentioned substituent or is substituted with an alkyl group or an aryl group, and it is more preferred that the ring Q has no further substituent or is substituted with an alkyl group.

m is preferably 1 to 6, and more preferably 1 to 3. When M is Ir, m is preferably 1 to 3, and more preferably 2. n is preferably 0 to 3, and more preferably 0 to 1. When M is Ir, n is preferably 1 to 3. It is more preferable that m is 2 and n is 1.

(X—Y) represents a bidendate ligand. The bidendate ligand represented by (X—Y) is not particularly limited, but specific examples thereof include, for example, substituted or unsubstituted phenylpyridine, phenylpyrazole, phenylimidazole, phenyltriazole, phenyltetrazole, pyridylpyridine, imidazolylpyridine, pyrazolylpyridine, triazolylpyridine, pyrazabole, diphenylphosphinoethylene, picolinic acid, acetylacetone and the like. Among them, phenylpyridine, phenylpyrazole, phenyl imidazole, pyridylpyridine, pyrazabole, picolinic acid, acetylacetone and the like are preferable, and phenylpyridine, picolinic acid and acetylacetone are more preferable.

Further, specific examples of the bidendate ligand represented by (X—Y) include a ligand represented by any one of the following Formulas (1-1) to (1-15).

(I-1)
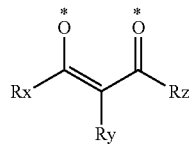

(I-2)
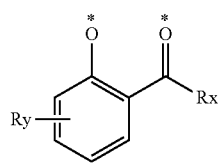

(I-3)
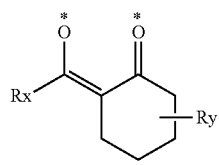

(I-4)
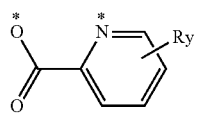

(I-5)
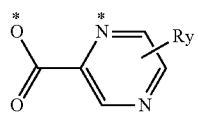

(I-6)

(I-7)
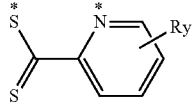

(I-8)
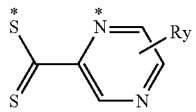

(I-9)

(I-10)
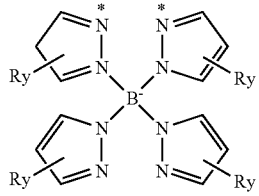

(I-11)
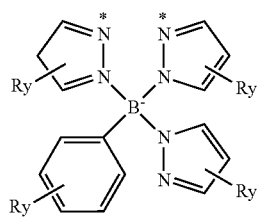

(I-12)
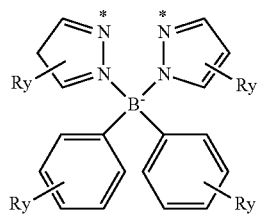

(I-13)
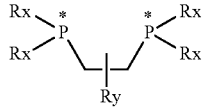

(I-14)
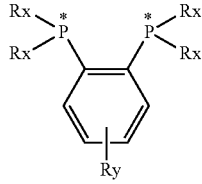

(I-15)
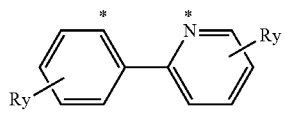

In the above Formula, * represents a coordination position as a metal.

Each of Rx, Ry and Rz independently represents a hydrogen atom or a substituent. The substituent may include a substituent selected from the group A of substituents.

Rx and Rz are preferably any one of an alkyl group, a perfluoroalkyl group, a halogen atom and an aryl group, and more preferably an alkyl group.

Ry is preferably one of a hydrogen atom, an alkyl group, a perfluoroalkyl group, a halogen atom, and an aryl group, and more preferably a hydrogen atom or an alkyl group.

In Formulas (1-1) to (1-14), Formula (1-1), (1-4) or (1-15) is more preferable.

One of the preferable forms of the compound represented by Formula (D-1) is a compound represented by the following Formula (D-2).

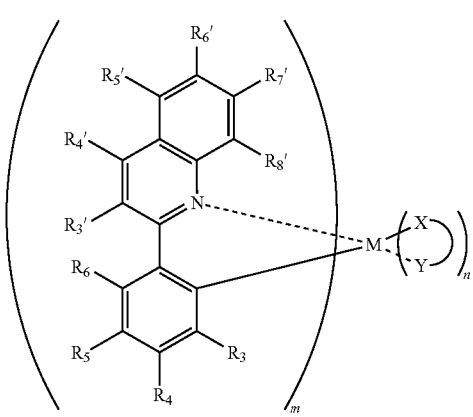

(In Formula (D-2), M represents a metal having an atomic weight of 40 or more. Each of $R_3$ to $R_6$ independently represents a hydrogen atom or a substituent. Each of $R_3$ to $R_8$ independently represents a hydrogen atom or a substituent. $R_3'$ and $R_6$ may be linked to each other by a linking group selected from —$CR_2$—$CR_2$—, —CR=CR—, —$CR_2$—, —O—, —NR—, —O—$CR_2$—, —NR—$CR_2$— and —N=CR— to form a ring, and each R independently represents a hydrogen atom, an alkyl group, an alkenyl group, an alkynyl group, a heteroalkyl group, an aryl group or a heteroaryl group, and may further have a substituent Z. Each Z independently represents a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' or —SO$_3$R', and each R' represents a hydrogen atom, an alkyl group, a perhaloalkyl group, an alkenyl group, an alkynyl group, a heteroalkyl group, an aryl group or a heteroaryl group. (X—Y) represents an ancillary ligand. m represents a value of 1 to the greatest number of ligands that may be bound to the metal, and n represents a value of 0 to the greatest number of ligands that may be bound to the metal. m+n is the greatest number of ligands that may be bound to the metal.)

M, $R_3'$, m and n in Formula (D-2) have the same meaning as M, $R_3'$, m and n in Formula (D-1), and preferred ranges thereof are also the same.

Each of $R_3$ to $R_6$ independently represents a hydrogen atom or a substituent. As the substituent represented by $R_3$ to $R_6$, those exemplified above for the group A of substituents may be applied.

$R_3$ to $R_6$ may further have a substituent, and as the substituent, those exemplified above for the group A of substituents may be applied. The substituent includes an alkyl group, an aryl group, a cyano group, a halogen atom and a nitrogen-containing aromatic heterocyclic group, and more preferably alkyl having 1 to 6 carbon atoms, an aryl group having 6 to 10 carbon atoms, pyridyl, a fluorine atom and a cyano group, and even more preferably an alkyl group having 1 to 6 carbon atoms, a phenyl group and a cyano group. Further, $R_3$ to $R_6$ may be linked to each other to form a condensed ring, and a ring to be formed may include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring and the like.

The aryl group represented by $R_3$ to $R_6$ may include preferably a substituted or unsubstituted aryl group having 6 to 30 carbon atoms, for example, a phenyl group, a tolyl group, a naphthyl group and the like.

The heteroaryl group represented by $R_3$ to $R_6$ may include preferably a heteroaryl group having 5 to 8 carbon atoms, more preferably a 5- or 6-membered, substituted or unsubstituted heteroaryl group, for example, a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group and the like.

$R_3$ to $R_6$ include preferably a hydrogen atom, an alkyl group, a cyano group, a trifluoromethyl group, a perfluoroalkyl group, a dialkylamino group, a fluoro group, an aryl group and a heteroaryl group, more preferably a hydrogen atom, an alkyl group, a cyano group, a trifluoromethyl group, a fluoro group and an aryl group, and even more preferably a hydrogen atom, an alkyl group and an aryl group. In particular, $R_3$ and $R_5$ include preferably an alkyl group, more preferably an ethyl group, an isobutyl group, a t-butyl group, a neopentyl group and a methyl group, particularly preferably an ethyl group, an isobutyl group, a neopentyl group and a methyl group, and even more preferably a methyl group.

Each of $R_4'$ to $R_8'$ independently represents a hydrogen atom or a substituent. As the substituent represented by $R_4'$ to $R_8'$, those exemplified above for the group A of substituents may be applied.

The aryl group represented by $R_4'$ to $R_8'$ may include preferably a substituted or unsubstituted aryl group having 6 to 30 carbon atoms, for example, a phenyl group, a tolyl group, a naphthyl group and the like.

The heteroaryl group represented by $R_4'$ to $R_8'$ may include preferably a heteroaryl group having 5 to 8 carbon atoms, more preferably a 5- or 6-membered, substituted or unsubstituted heteroaryl group, for example, a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group and the like.

$R_4'$ to $R_8'$ includes preferably a hydrogen atom, an alkyl group, a cyano group, a trifluoromethyl group, a perfluoroalkyl group, a dialkylamino group, a fluoro group, an aryl group, a heteroaryl group and an alkoxy group, more preferably a hydrogen atom, an alkyl group, a cyano group, a trifluoromethyl group, a fluoro group, an aryl group, an alkoxy group and a thienyl group, and even more preferably a hydrogen atom, an alkyl group and an aryl group, and particularly preferably a hydrogen atom and an alkyl group.

Further, $R_4'$ to $R_8'$ may further have a substituent, and as the substituent, those exemplified above for the group A of substituents may be applied. The substituent includes preferably an alkyl group, an aryl group, a cyano group, a halogen atom and a nitrogen-containing aromatic heterocyclic group, and more preferably alkyl having 1 to 6 carbon atoms, an aryl group having 6 to 10 carbon atoms, pyridyl, a cyano group and a halogen atom, even more preferably a branched alkyl group having 3 to 6 carbon atoms, a phenyl group, a naphthyl group, a cyano group and a fluorine atom, and particularly preferably an isobutyl group, a t-butyl group, a neopentyl group, a phenyl group, a naphthyl group, a cyano group and a fluorine atom. The number of substituents is 0 to 4, and preferably 0 to 2. Further, a plurality of substituents may be linked to each other to form a ring.

In addition, $R_4'$ to $R_8'$ may be linked to each other to form a condensed ring, and a ring to be formed may include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring and the like.

$R_4'$ to $R_6'$ and $R_8'$ are particularly preferably a hydrogen atom.

In particular, $R_7'$ is preferably an alkyl group, and more preferably a branched alkyl group. Specifically, the branched alkyl group may include the following substituents (a) to (x), and is preferably substituents (a) to (h), more preferably substituents (b) to (e), and particularly preferably substituent (c) or (d).

(a)
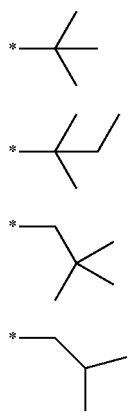

(b)

(c)

(d)

-continued (e)

(f)
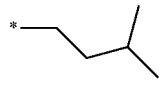

(g)
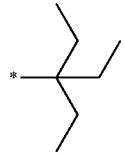

(h)
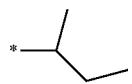

(i)
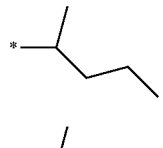

(j)
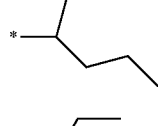

(k)
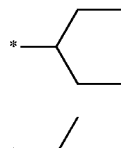

(l)
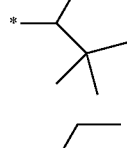

(m)
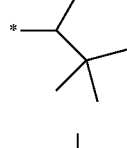

(n)
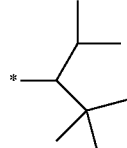

(o)
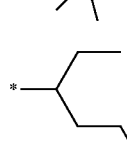

(p)
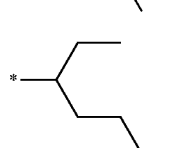

(q)
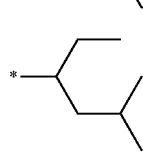

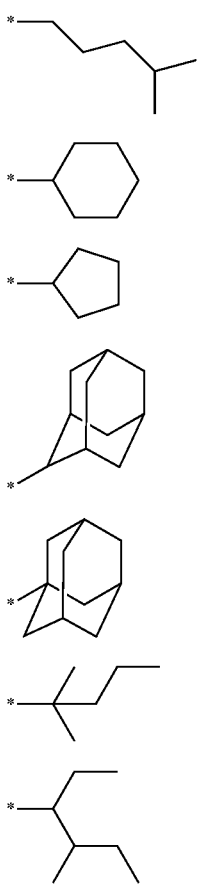

(r)

(s)

(t)

(u)

(v)

(w)

(x)

(X—Y) represents a bidendate ligand. The bidendate ligand represented by (X—Y) is not particularly limited, but specific examples thereof include, for example, substituted or unsubstituted phenylpyridine, phenylpyrazole, phenylimidazole, phenyltriazole, phenyltetrazole, pyridylpyridine, imidazolylpyridine, pyrazolylpyridine, triazolylpyridine, pyrazabole, diphenylphosphinoethylene, picolinic acid, acetylacetone and the like. Among these, phenylpyridine, phenylpyrazole, phenylimidazole, pyridylpyridine, pyrazabole, picolinic acid, acetylacetone, and the like are preferable, and phenylpyridine, picolinic acid and acetylacetone are more preferable. Acetylacetonate is particularly preferable from the viewpoint that stability and high light emission efficiency of the complex may be obtained. Further, these groups may be further substituted by the above substituent.

The preferred range of (X—Y) is the same as (X—Y) in Formula (D-1).

In the above Formula (D-2), M represents iridium, each of $R_3$ to $R_6$ independently represents a hydrogen atom, an alkyl group or an aryl group, $R_3'$ to $R_8'$ represent a hydrogen atom, an alkyl group or an aryl group, $R_3'$ and $R_6$ may be linked by a linking group selected from —$CR_2$—$CR_2$—, —CR=CR—, —$CR_2$—, —O—, —NR—, —O—$CR_2$—, —NR—$CR_2$— and —N=CR— to form a ring, each R independently represents a hydrogen atom, an alkyl group, an alkenyl group, an alkynyl group, an aryl group or a heteroaryl group, and may further have a substituent selected from a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' and —SO$_3$R', each R' independently represents a hydrogen atom, an alkyl group, a perhaloalkyl group, an alkenyl group, an alkynyl group, an aryl group or a heteroaryl group, (X—Y) represents a ligand represented by any one of the above Formula (1-1), (1-4) or (1-15), m represents an integer of 1 to 3, n represents an integer of 0 to 2, provided that m+n is preferably 3.

One of the preferable forms of the compound represented by Formula (D-1) is a compound represented by Formula (D-3).

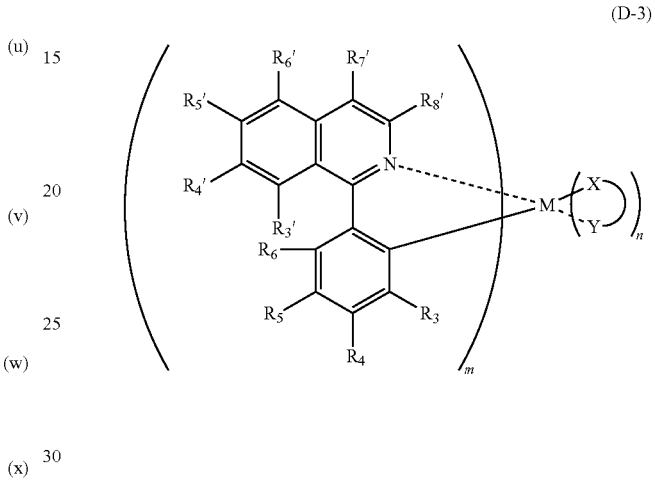

(D-3)

(In Formula (D-3), M represents a metal having an atomic weight of 40 or more. Each of $R_3$ to $R_6$ independently represents a hydrogen atom or a substituent. Each of $R_3'$ to $R_8'$ independently represents a hydrogen atom or a substituent. $R_3'$ and $R_6$ may be linked to each other by a linking group selected from —$CR_2$—$CR_2$—, —CR=CR—, —$CR_2$—, —O—, —NR—, —O—$CR_2$—, —NR—$CR_2$— and —N=CR— to form a ring, and each R independently represents a hydrogen atom, an alkyl group, an alkenyl group, an alkynyl group, a heteroalkyl group, an aryl group or a heteroaryl group, and may further have a substituent Z. Each Z independently represents a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' or —SO$_3$R', and each R' independently represents a hydrogen atom, an alkyl group, a perhaloalkyl group, an alkenyl group, an alkynyl group, a heteroalkyl group, an aryl group or a heteroaryl group. (X—Y) represents an ancillary ligand. m represents a value of 1 to the greatest number of ligands that may be bound to the metal, and n represents a value of 0 to the greatest number of ligands that may be bound to the metal. m+n is the greatest number of ligands that may be bound to the metal.)

M, $R_3'$, (X—Y), m and n in Formula (D-3) have the same meaning as M, $R_3'$, (X—Y), m and n in Formula (D-1), and preferred ranges thereof are also the same.

Each of $R_3$ to $R_6$ independently represents a hydrogen atom or a substituent. As the substituent represented by $R_3$ to $R_6$, those exemplified above for the group A of substituents may be applied.

$R_3$ to $R_6$ may further have a substituent, and as the substituent, those exemplified above for the group A of substituents may be applied. The substituent includes an alkyl group, an aryl group, a cyano group, a halogen atom and a nitrogen-containing aromatic heterocyclic group, and more preferably alkyl having 1 to 6 carbon atoms, an aryl group having 6 to 10 carbon atoms, pyridyl, a fluorine atom and a cyano group, and even more preferably an alkyl group having 1 to 6 carbon atoms, a phenyl group and a cyano group. Further, $R_3$ to $R_6$ may be linked to each other to form a condensed ring, and a ring to be formed may include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring and the like.

The aryl group represented by $R_3$ to $R_6$ may include preferably a substituted or unsubstituted aryl group having 6 to 30 carbon atoms, for example, a phenyl group, a tolyl group, a naphthyl group and the like.

The heteroaryl group represented by $R_3$ to $R_6$ may include preferably a heteroaryl group having 5 to 8 carbon atoms, more preferably a 5- or 6-membered, substituted or unsubstituted heteroaryl group, for example, a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group and the like.

$R_3$ to $R_6$ include preferably a hydrogen atom, an alkyl group, a cyano group, a trifluoromethyl group, a perfluoroalkyl group, a dialkylamino group, a fluoro group, an aryl group and a heteroaryl group, more preferably a hydrogen atom, an alkyl group, a cyano group, a trifluoromethyl group, a fluoro group and an aryl group, and even more preferably a hydrogen atom, an alkyl group and an aryl group.

$R_4$ and $R_6$ are particularly preferably a hydrogen atom.

$R_3$ and $R_5$ are particularly preferably an alkyl group, more preferably an ethyl group, an isobutyl group, a t-butyl group, a neopentyl group and a methyl group, particularly preferably an ethyl group, an isobutyl group, a neopentyl group and a methyl group, and even more preferably a methyl group.

Each of $R_4'$ to $R_8'$ independently represents a hydrogen atom or a substituent. As the substituent represented by $R_4'$ to $R_8'$, those exemplified above for the group A of substituents may be applied.

Further, $R_4'$ to $R_8'$ may further have a substituent, and as the substituent, those exemplified above for the group A of substituents may be applied. In addition, $R_4'$ to $R_8'$ may be linked to each other to form a condensed ring, and a ring to be formed may include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring and the like.

The aryl group represented by $R_4'$ to $R_3'$ may include preferably a substituted or unsubstituted aryl group having 6 to 30 carbon atoms, for example, a phenyl group, a tolyl group, a naphthyl group and the like.

The heteroaryl group represented by $R_4'$ to $R_8'$ may include preferably a heteroaryl group having 5 to 8 carbon atoms, more preferably a 5- or 6-membered, substituted or unsubstituted heteroaryl group, for example, a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group and the like.

$R_4'$ to $R_8'$ include preferably a hydrogen atom, an alkyl group, a cyano group, a trifluoromethyl group, a perfluoroalkyl group, a dialkylamino group, a fluoro group, an aryl group and a heteroaryl group, more preferably a hydrogen atom, an alkyl group, a cyano group, a trifluoromethyl group, a fluoro group and an aryl group, and even more preferably a hydrogen atom, an alkyl group and an aryl group. In particular, $R_4'$ is preferably an alkyl group.

(X—Y) represents a bidendate ligand. The bidendate ligand represented by (X—Y) is not particularly limited, but specific examples thereof include, for example, substituted or unsubstituted phenylpyridine, phenylpyrazole, phenylimidazole, phenyltriazole, phenyltetrazole, pyridylpyridine, imidazolylpyridine, pyrazolylpyridine, triazolylpyridine, pyrazabole, diphenylphosphinoethylene, picolinic acid, acetylacetone and the like. Among them, phenylpyridine, phenylpyrazole, phenylimidazole, pyridylpyridine, pyrazabole, picolinic acid, acetylacetone and the like are preferable, and phenylpyridine, picolinic acid and acetylacetone are more preferable. Acetylacetonate is particularly preferable from the viewpoint that stability and high light emission efficiency of the complex may be obtained. Further, these groups may be further substituted by the above substituent.

The preferred range of (X—Y) is the same as (X—Y) in Formula (D-1).

In the above Formula (D-3), M represents iridium, each of $R_3$ to $R_6$ independently represents a hydrogen atom, an alkyl group or an aryl group, each of $R_3'$ to $R_8'$ independently represents a hydrogen atom, an alkyl group or an aryl group, $R_3'$ and $R_6$ may be linked by a linking group selected from —$CR_2$—$CR_2$—, —CR═CR—, —$CR_2$—, —O—, —NR—, —NR—$CR_2$— and —N═CR— to form a ring, each R independently represents a hydrogen atom, an alkyl group, an alkenyl group, an alkynyl group, an aryl group or a heteroaryl group, and may further have a substituent selected from a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' and —SO$_3$R', each R' independently represents a hydrogen atom, an alkyl group, a perhaloalkyl group, an alkenyl group, an alkynyl group, an aryl group or a heteroaryl group, (X—Y) represents a ligand represented by any one of the above Formula (1-1), (1-4) or (1-15), m represents an integer of 1 to 3, n represents an integer of 0 to 2, provided that m+n is preferably 3.

One of the preferable forms of the compound represented by Formula (D-1) is a compound represented by Formula (D-4).

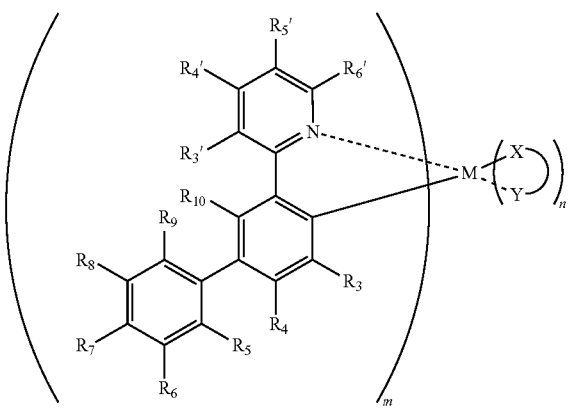

(D-4)

(In Formula (D-4), M represents metal having an atomic weight of 40 or more. Each of $R_3$ to $R_{10}$ independently represents a hydrogen atom or a substituent. Each of $R_3'$ to $R_6'$ independently represents a hydrogen atom or a substituent. $R_3'$ and $R_{10}$ may be linked to each other by a linking group selected from —$CR_2$—$CR_2$—, —CR=CR—, —$CR_2$—, —O—, —NR—, —O—$CR_2$—, —NR—$CR_2$— and —N=CR— to form a ring, and each R independently represents a hydrogen atom, an alkyl group, an alkenyl group, an alkynyl group, a heteroalkyl group, an aryl group or a heteroaryl group, and may further have a substituent Z. Each Z independently represents a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' or —SO$_3$R', and each R' independently represents a hydrogen atom, an alkyl group, a perhaloalkyl group, an alkenyl group, an alkynyl group, a heteroalkyl group, an aryl group or a heteroaryl group. (X—Y) represents an ancillary ligand. m represents a value of 1 to the greatest number of ligands that may be bound to the metal, and n represents a value of 0 to the greatest number of ligands that may be bound to the metal. m+n is the greatest number of ligands that may be bound to the metal.)

M, $R_3'$, (X—Y), m and n in Formula (D-4) have the same meaning as M, $R_3'$, (X—Y), m and n in Formula (D-1), and preferred ranges thereof are also the same.

Each of $R_3$ to $R_{10}$ independently represents a hydrogen atom or a substituent. As the substituent represented by $R_3$ to $R_{10}$, those exemplified above for the group A of substituents may be applied.

$R_3$ to $R_{10}$ may further have a substituent, and as the substituent, those exemplified above for the group A of substituents may be applied. The substituent includes an alkyl group, an aryl group, a cyano group, a halogen atom and a nitrogen-containing aromatic heterocyclic group, and more preferably alkyl having 1 to 6 carbon atoms, an aryl group having 6 to 10 carbon atoms, pyridyl, a fluorine atom and a cyano group, and even more preferably an alkyl group having 1 to 6 carbon atoms, a phenyl group and a cyano group. Further, $R_3$ to $R_{10}$ may be linked to each other to form a condensed ring, and a ring to be formed may include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring and the like.

The aryl group represented by $R_3$ to $R_{10}$ may include preferably a substituted or unsubstituted aryl group having 6 to 30 carbon atoms, for example, a phenyl group, a tolyl group, a naphthyl group and the like.

The heteroaryl group represented by $R_3$ to $R_{10}$ may include preferably a heteroaryl group having 5 to 8 carbon atoms, more preferably a 5- or 6-membered, substituted or unsubstituted heteroaryl group, for example, a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group and the like.

$R_3$ to $R_{10}$ include preferably a hydrogen atom, an alkyl group, a cyano group, a trifluoromethyl group, a perfluoroalkyl group, a dialkylamino group, a fluoro group, an aryl group and a heteroaryl group, more preferably a hydrogen atom, an alkyl group, a cyano group, a trifluoromethyl group, a fluoro group and an aryl group, and even more preferably a hydrogen atom, an alkyl group, a cyano group and an aryl group, and particularly preferably a hydrogen atom, an alkyl group and an aryl group.

$R_3$ to $R_6$ and $R_3$ to $R_{10}$ are particularly preferably a hydrogen atom.

$R_7$ is particularly preferably an alkyl group, preferably a methyl group, an isobutyl group and a neopentyl group, and more preferably a methyl group.

Each of $R_3'$ to $R_6'$ independently represents a hydrogen atom or a substituent. As the substituent represented by $R_3'$ to $R_6'$, those exemplified above for the group A of substituents may be applied.

Further, $R_3'$ to $R_6'$ may further have a substituent, and as the substituent, those exemplified above for the group A of substituents may be applied. In addition, $R_3'$ to $R_6'$ may be linked to each other to form a condensed ring, and a ring to be formed may include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring and the like.

The aryl group represented by $R_3'$ to $R_6'$ may include preferably a substituted or unsubstituted aryl group having 6 to 30 carbon atoms, for example, a phenyl group, a tolyl group, a naphthyl group and the like.

The heteroaryl group represented by $R_3'$ to $R_6'$ may include preferably a heteroaryl group having 5 to 8 carbon atoms, more preferably a 5- or 6-membered, substituted or unsubstituted heteroaryl group, for example, a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group and the like.

$R_3'$ to $R_6'$ include preferably a hydrogen atom, an alkyl group, a cyano group, a trifluoromethyl group, a perfluoroalkyl group, a dialkylamino group, a fluoro group, an aryl group and a heteroaryl group, more preferably a hydrogen atom, an alkyl group, a cyano group, a trifluoromethyl group, a fluoro group and an aryl group, and even more preferably a hydrogen atom, an alkyl group and an aryl group.

(X—Y) represents a bidendate ligand. The bidendate ligand represented by (X—Y) is not particularly limited, but specific examples thereof include, for example, substituted or unsubstituted phenylpyridine, phenylpyrazole, phenylimidazole, phenyltriazole, phenyltetrazole, pyridylpyridine, imidazolylpyridine, pyrazolylpyridine, triazolylpyridine, pyrazabole, diphenylphosphinoethylene, picolinic acid, acetylacetone and the like. Among them, phenylpyridine, phenylpyrazole, phenylimidazole, pyridylpyridine, pyrazabole, picolinic acid, acetylacetone and the like are preferable, and phenylpyridine, picolinic acid and acetylacetone are more preferable, and penylpyridine is particularly preferable from the viewpoint of stability of the complex. Further, these groups may be further substituted by the above substituent.

The preferred range of (X—Y) is the same as (X—Y) in Formula (D-1).

In the above Formula (D-4), M represents iridium, each of $R_3$ to $R_{10}$ independently represents a hydrogen atom, an alkyl group or an aryl group, each of $R_3'$ to $R_6'$ independently represents a hydrogen atom, an alkyl group or an aryl group, $R_3'$ and $R_{10}$ may be linked by a linking group selected from —$CR_2$—$CR_2$—, —CR=CR—, —$CR_2$—, —O—, —NR—, —O—$CR_2$—, —NR—$CR_2$— and —N=CR— to form a ring, each R independently represents a hydrogen atom, an alkyl group, an alkenyl group, an alkynyl group, an aryl group or a heteroaryl group, and may further have a substituent selected from a halogen atom, —R', —OR', —N(R')$_2$, —SR', —C(O)R', —C(O)OR', —C(O)N(R')$_2$, —CN, —NO$_2$, —SO$_2$, —SOR', —SO$_2$R' and —SO$_3$R', each R' independently represents a hydrogen atom, an alkyl group, a perhaloalkyl group, an alkenyl group, an alkynyl group, an aryl group or a heteroaryl group, (X—Y) represents a ligand represented by any one of the above Formula (1-1), (1-4) or (1-15), m represents an integer of 1 to 3, n represents an integer of 0 to 2, but m+n is preferably 3.

The compounds represented by Formulas (D-1) to (D-4) may be synthesized with reference to, for example, various known synthetic methods such as Inorg. Chem., 30, 1685-1687 (1991), J. Am. Chem. Soc., vol. 123, 4304 (2001), Inorg. Chem., vol. 40, 1704-1711(2001), Inorg. Chem., 41, 3055-3066 (2002), Eur. J. Org. Chem., 4, 695-709 (2004) and the like, and International Publication No. WO09/073,245 and International Publication No. WO08/109,824.

Preferred specific examples of the compounds represented by Formulas (D-1) to (D-4) are represented below, but are not limited thereto.

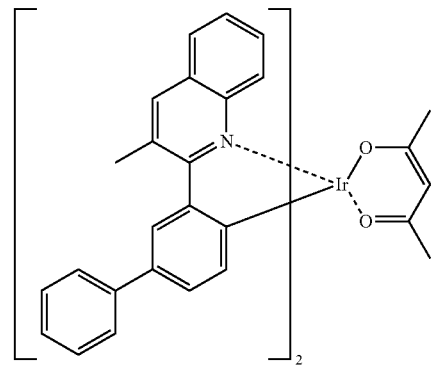

TM-1

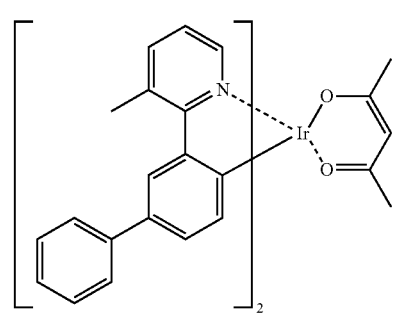

TM-2

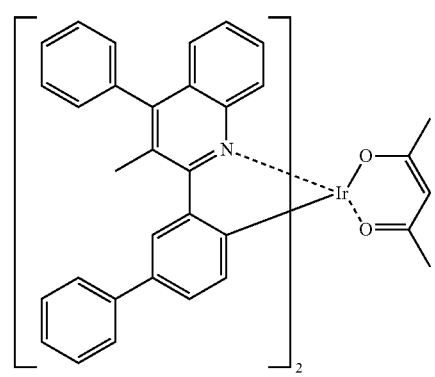

TM-3

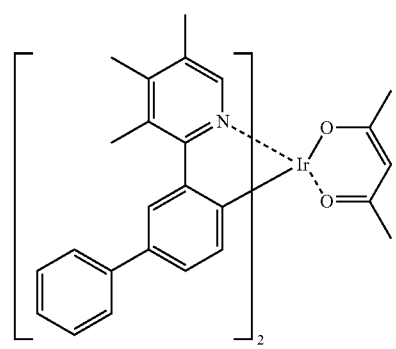

TM-4

-continued
TM-5
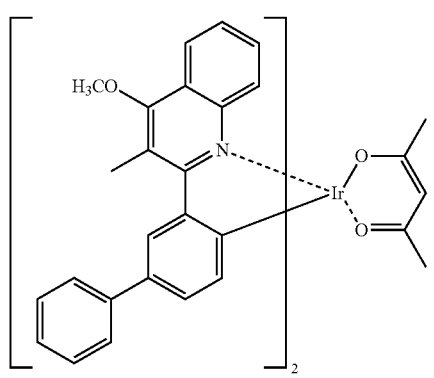
TM-9
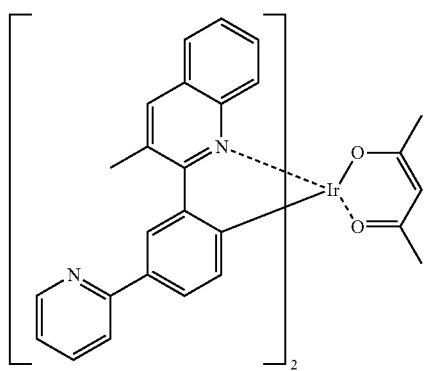
TM-6
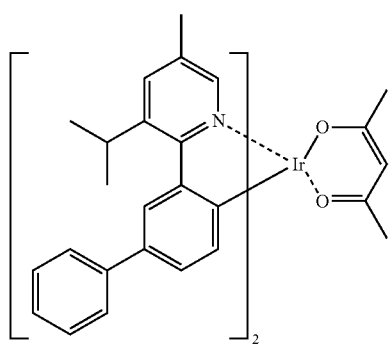
TM-10
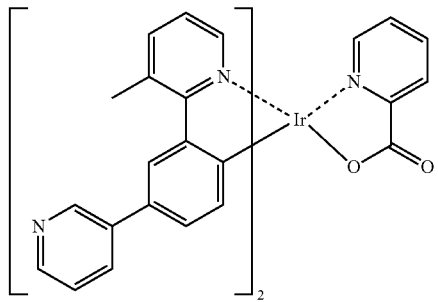
TM-7
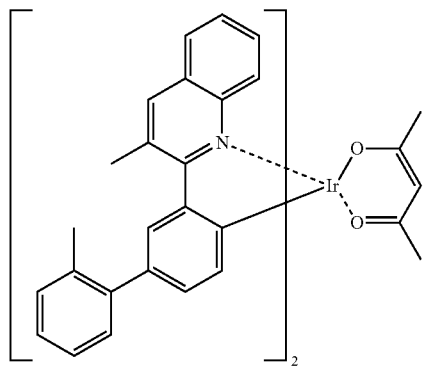
TM-11
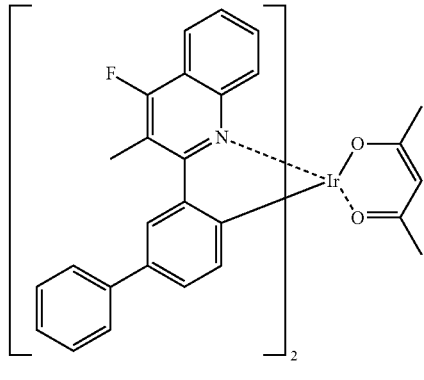
TM-8
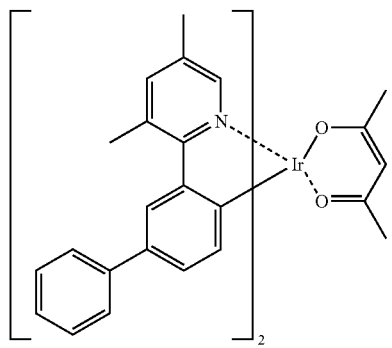
TM-12
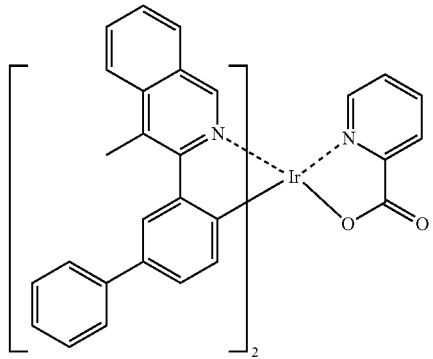

-continued
TM-13
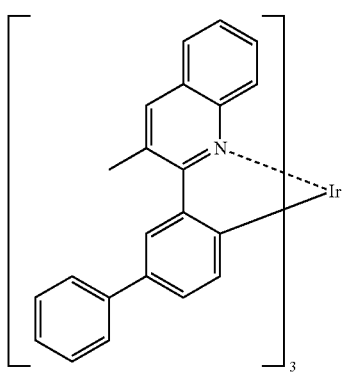
TM-17
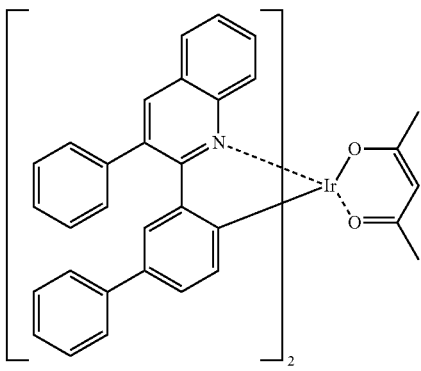
TM-14
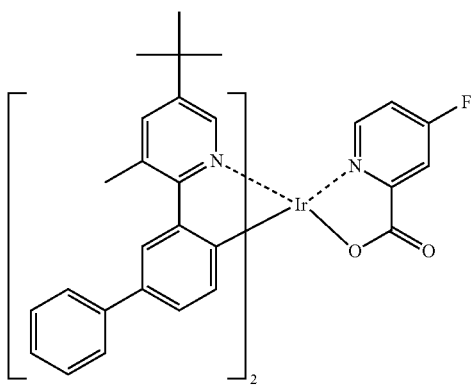
TM-18
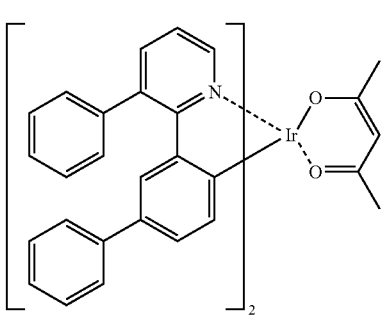
TM-15
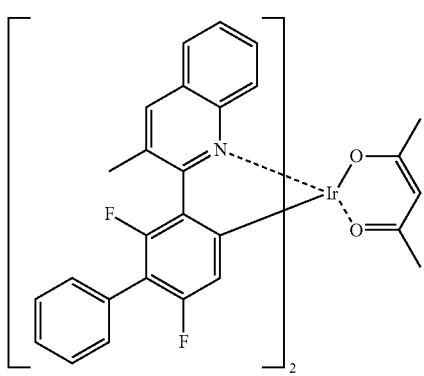
TM-19
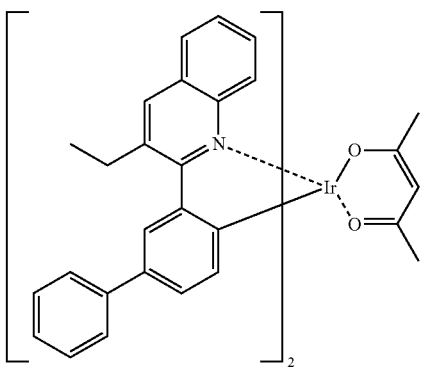
TM-16
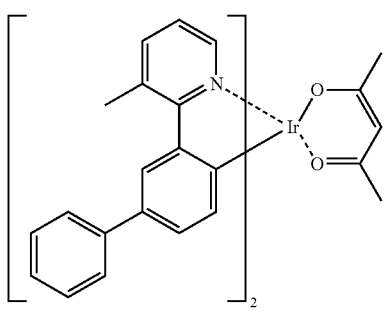
TM-20
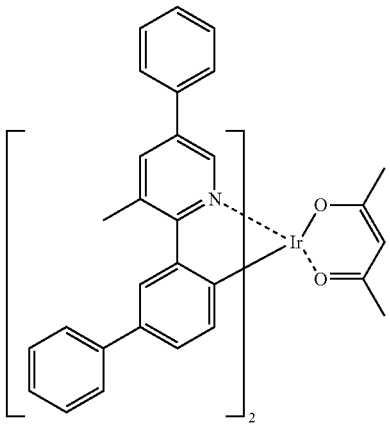

TM-21
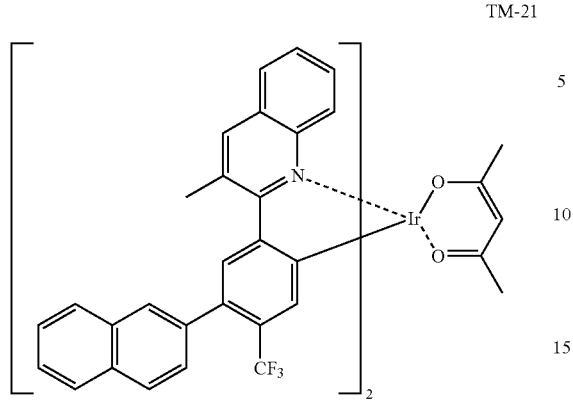
TM-25
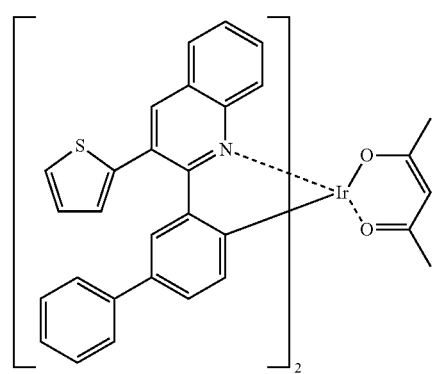
TM-22
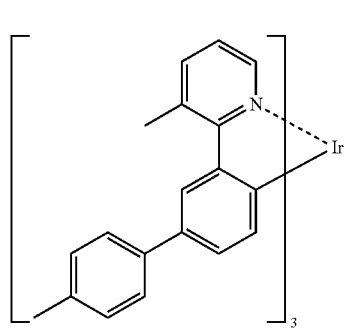
TM-26
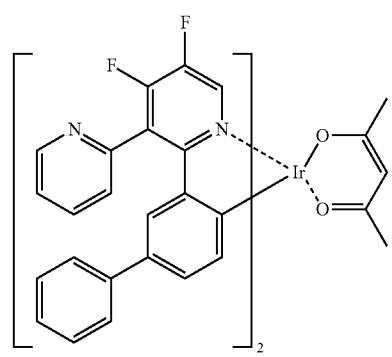
TM-23
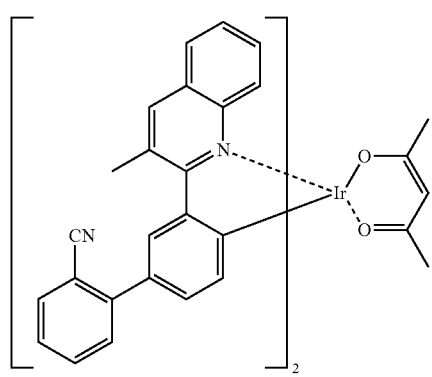
TM-27
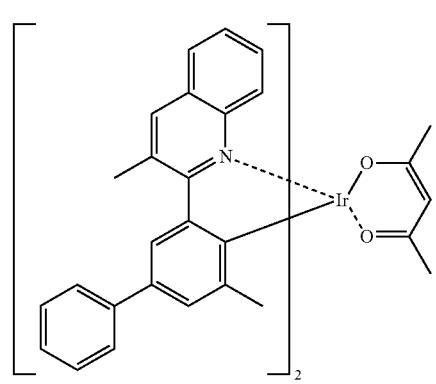
TM-24
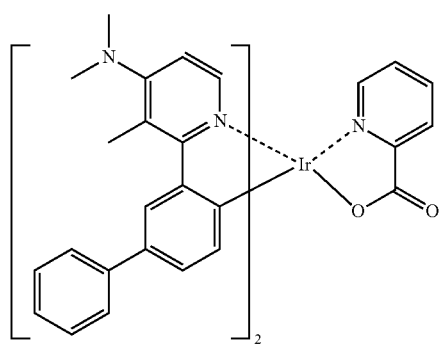
TM-28
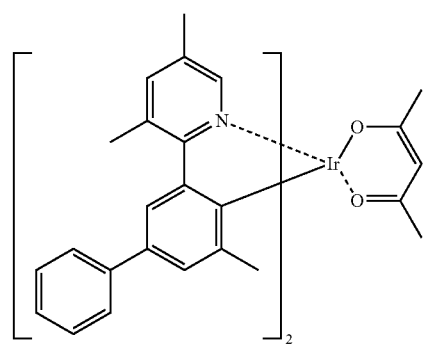

TM-29
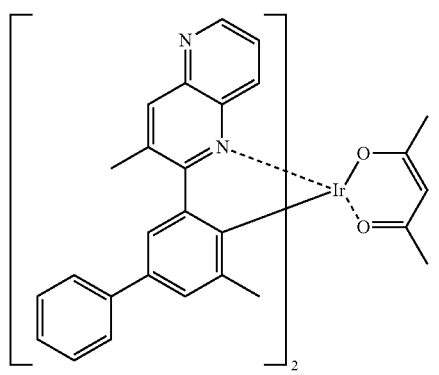
TM-30
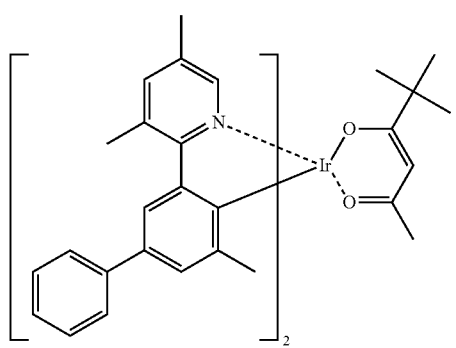
TM-31
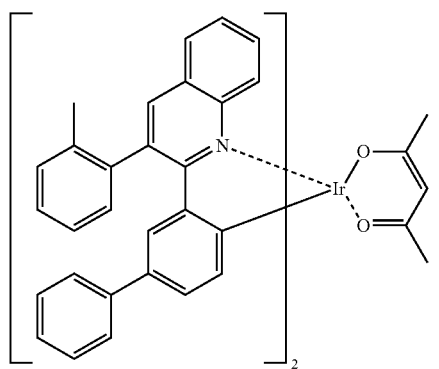
TM-32
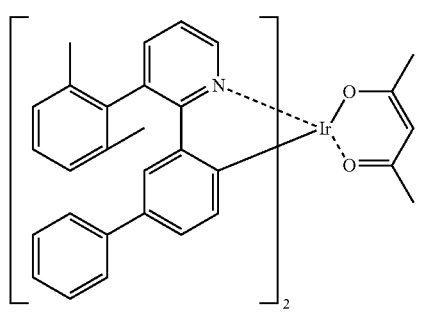
TM-33
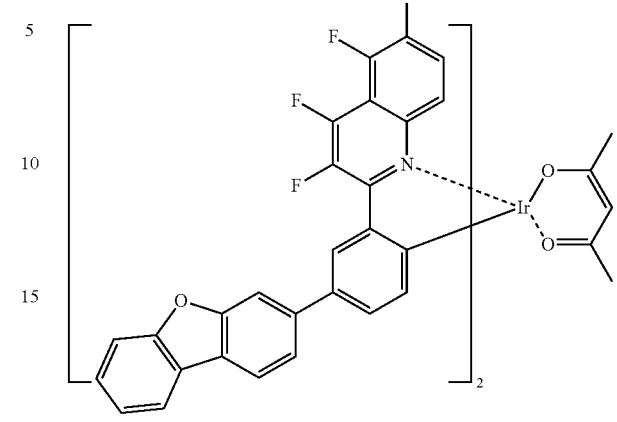
TM-34
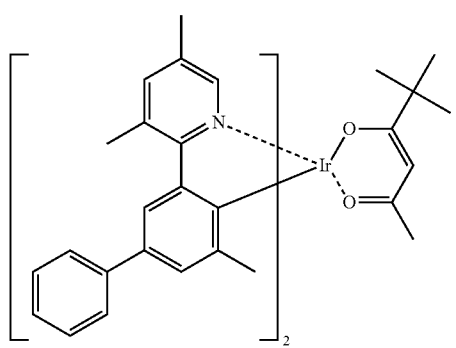
TM-35
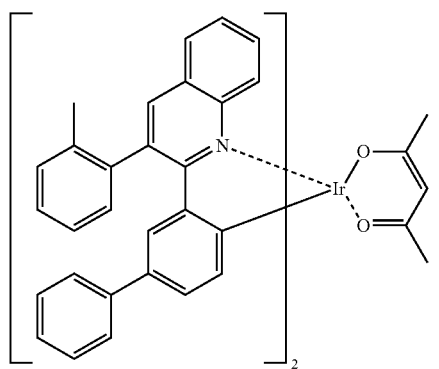
TM-36
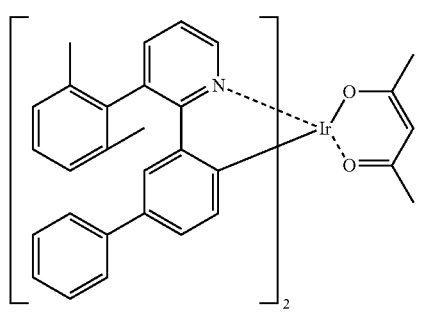

TM-37
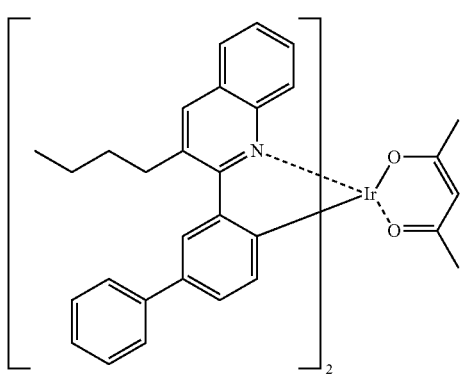
TM-38
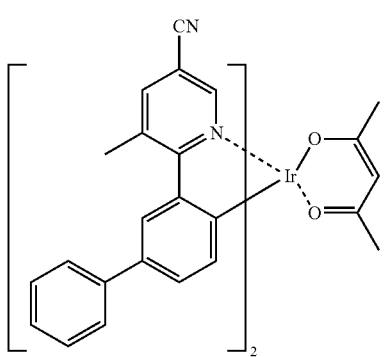
TM-39
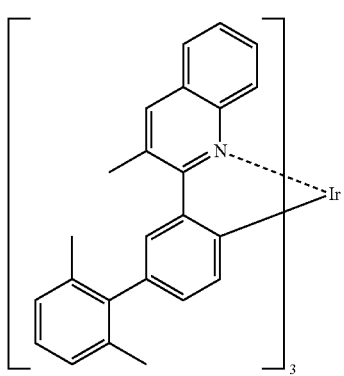
TM-40
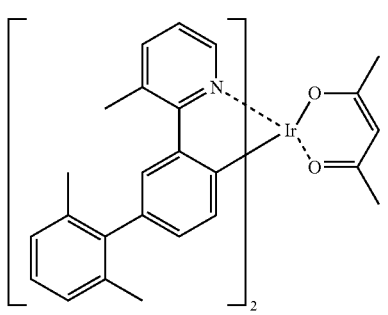
TM-41
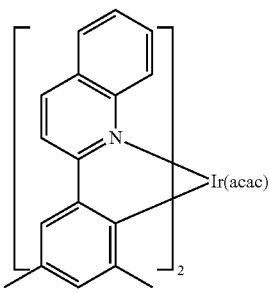
TM-42
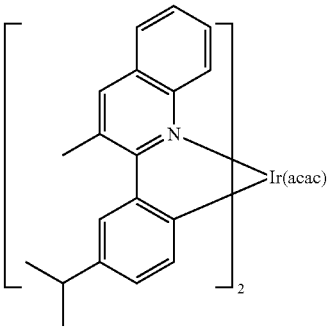
TM-43
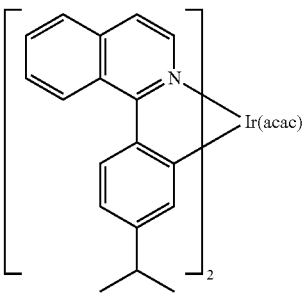
TM-44
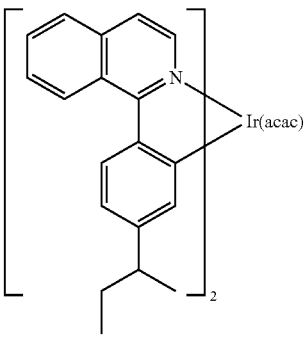
TM-45
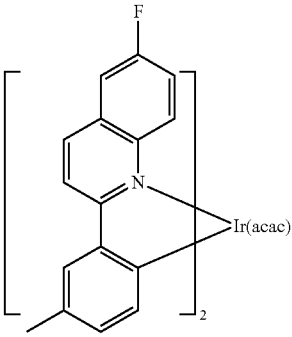

-continued
TM-46
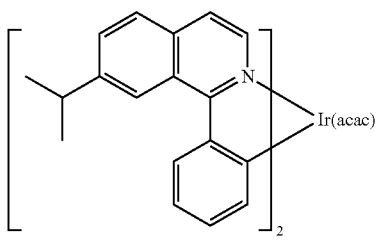
TM-47
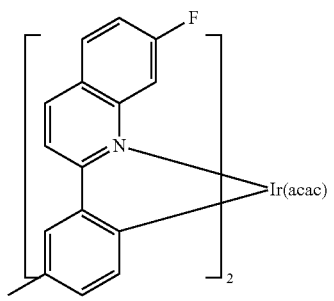
TM-48
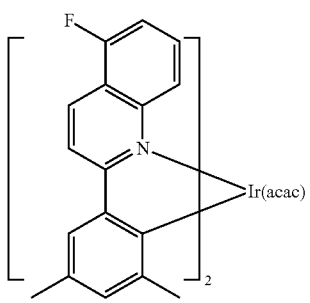
TM-49
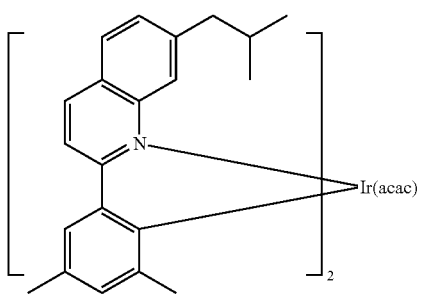
TM-50
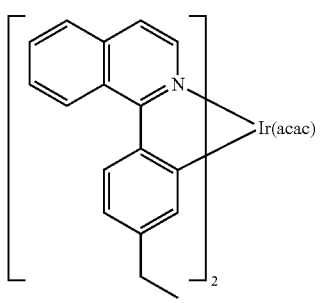
-continued
TM-51
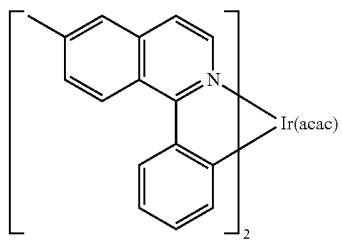
TM-52
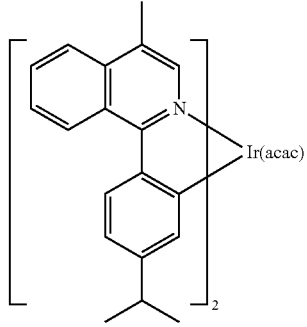
TM-53
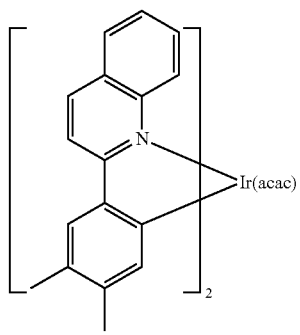
TM-54
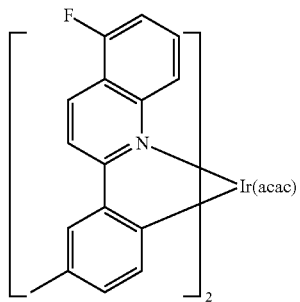
TM-55
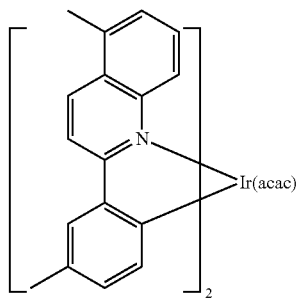

-continued
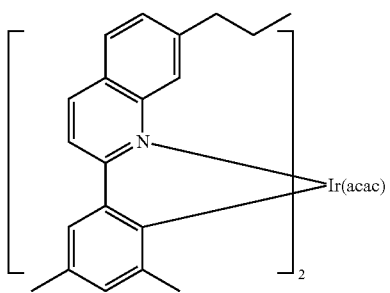
TM-56
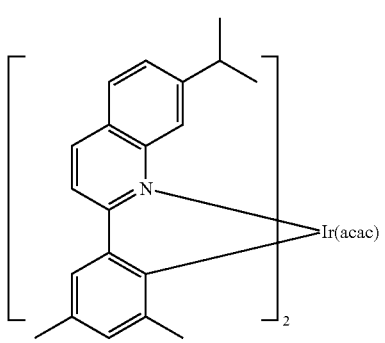
TM-57
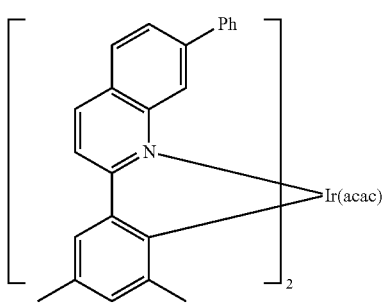
TM-58
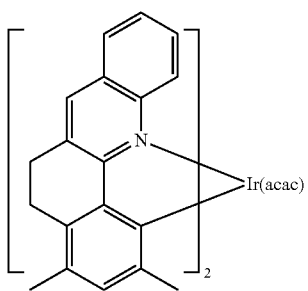
TM-59
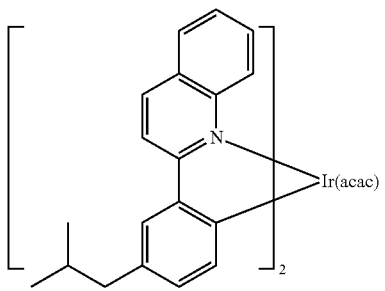
TM-60
-continued
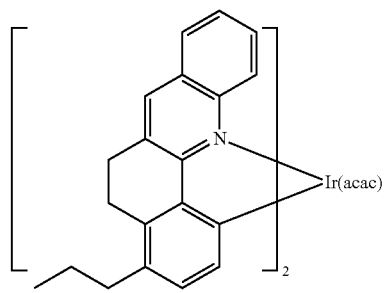
TM-61
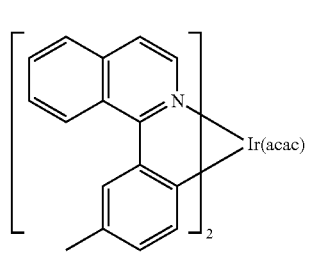
TM-62
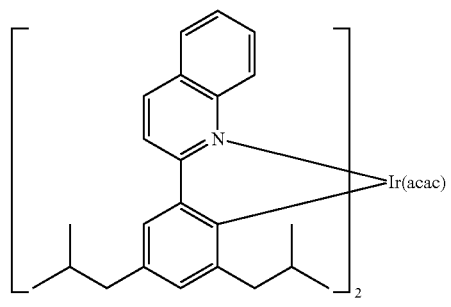
TM-63
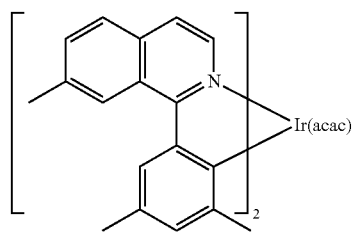
TM-64
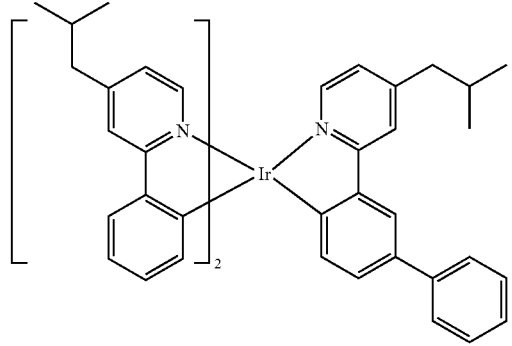
TM-66

TM-67
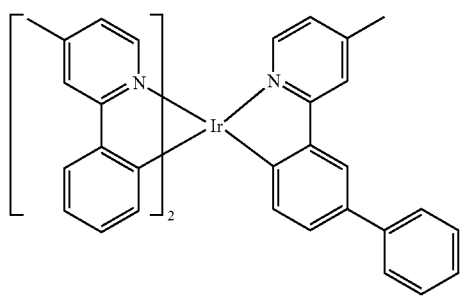
TM-68
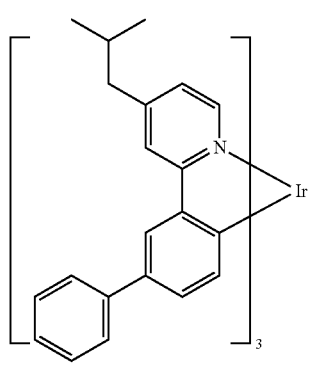
TM-69
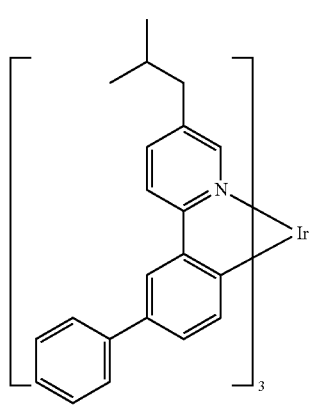
TM-70
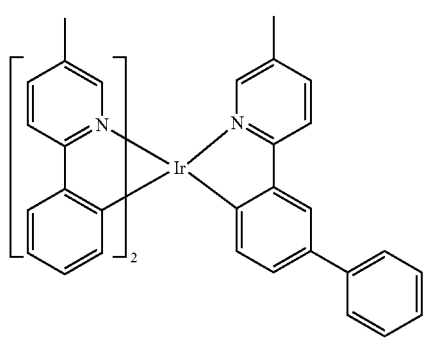
TM-72
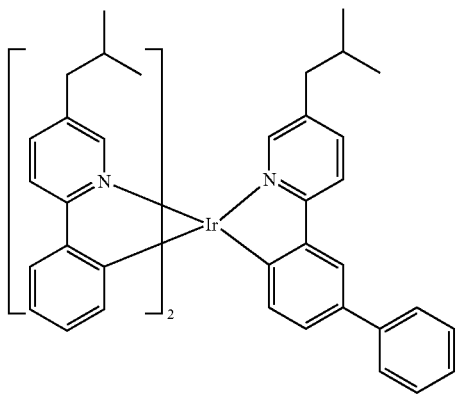
TM-74
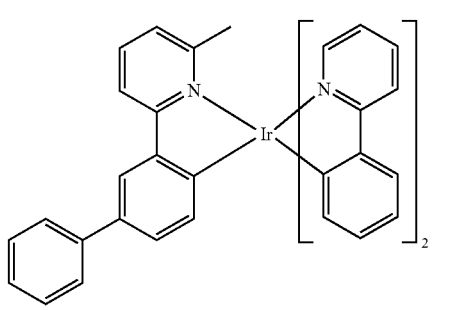
TM-75
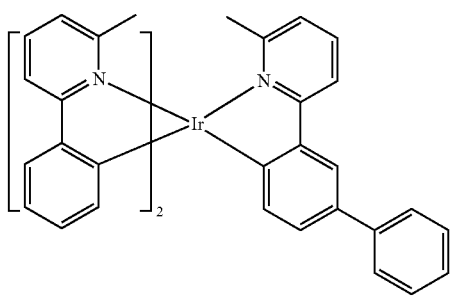
TM-76
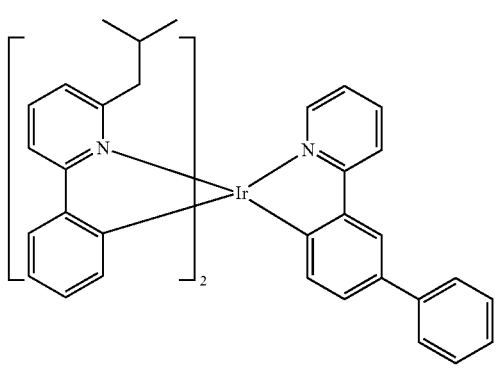

TM-77
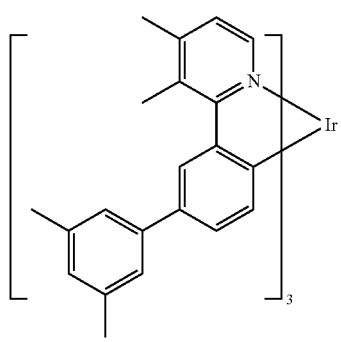
TM-78
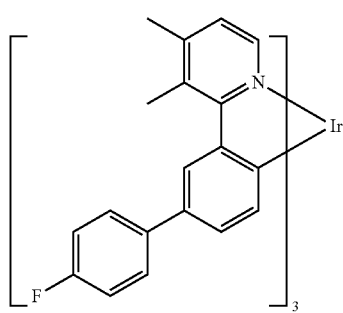
TM-82
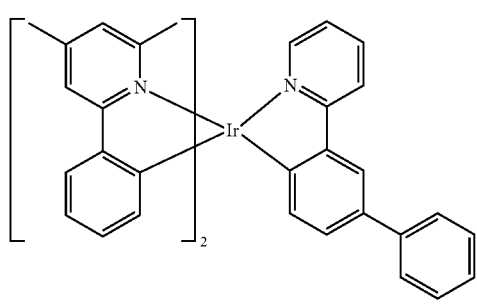
TM-83
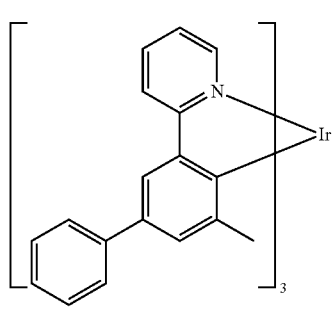
TM-84
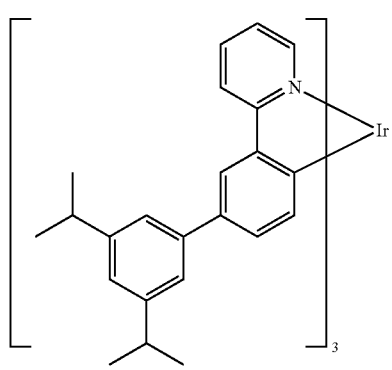
TM-85
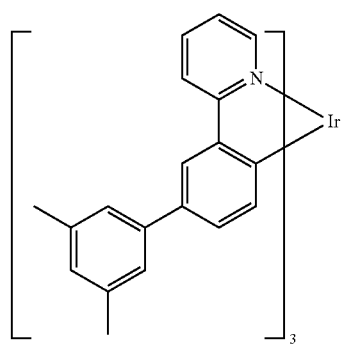
TM-86
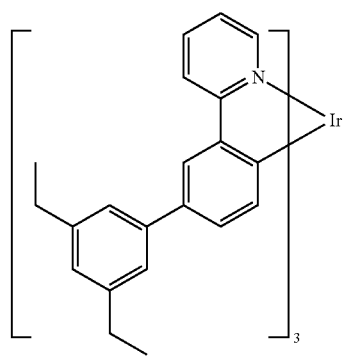
TM-87
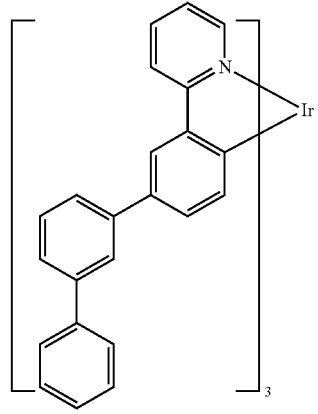
TM-88
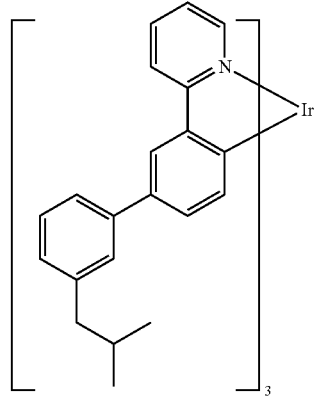

TM-89
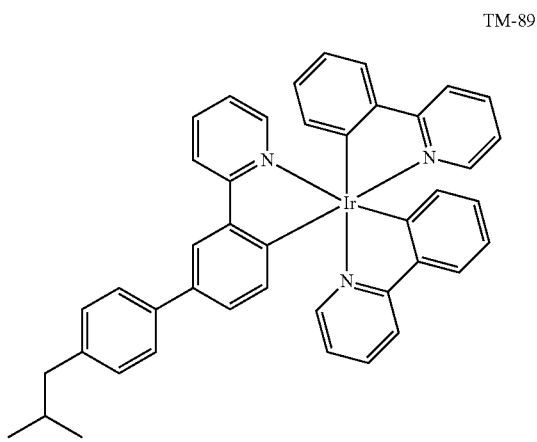
TM-90
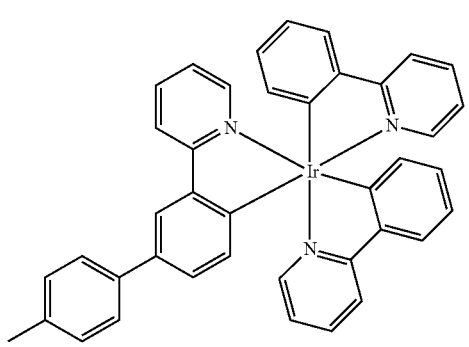
TM-91
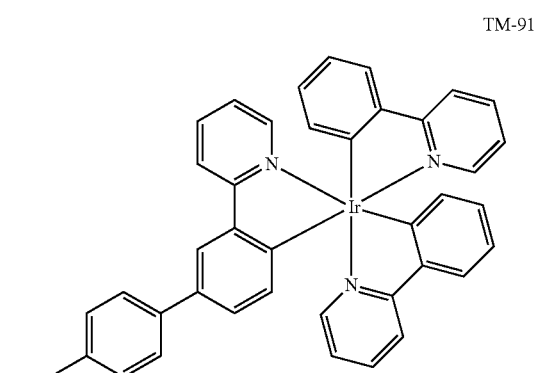
TM-92
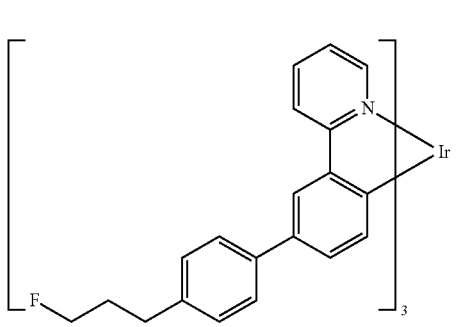
TM-93
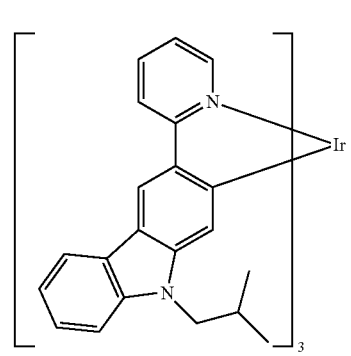
TM-94
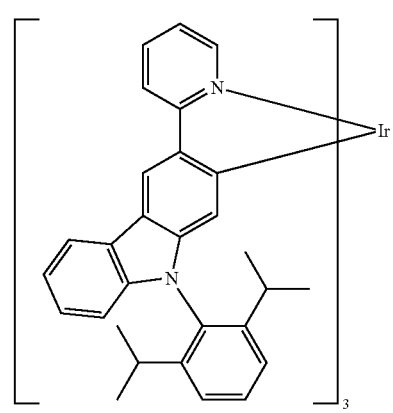
TM-99
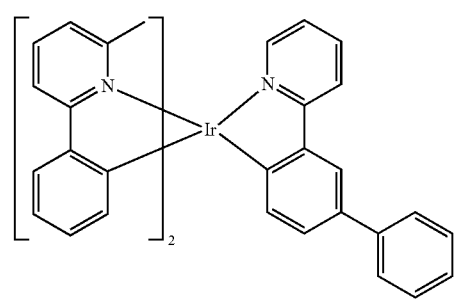
TM-100
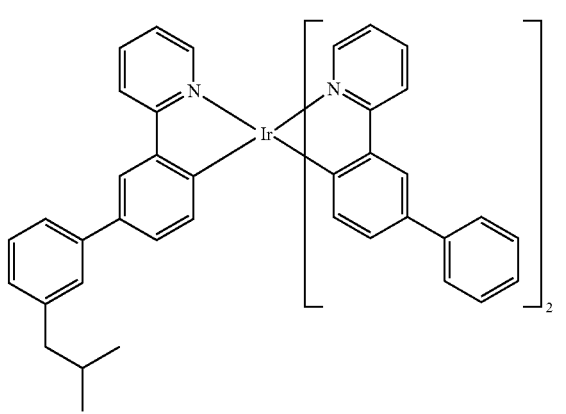

-continued
TM-101
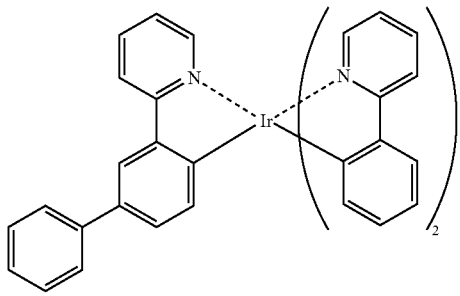
TM-102
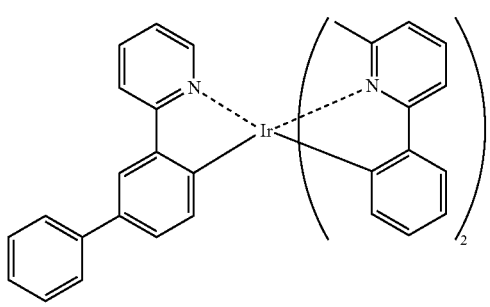
TM-103
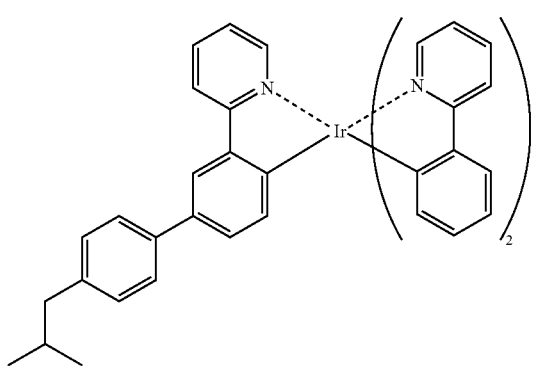
TM-104
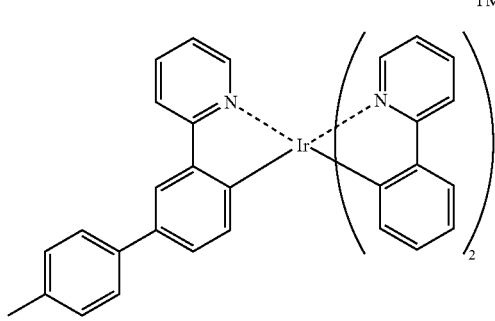
TM-105
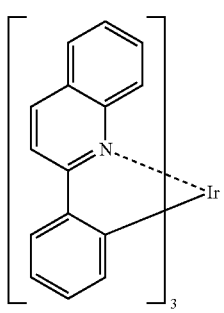
-continued
TM-106
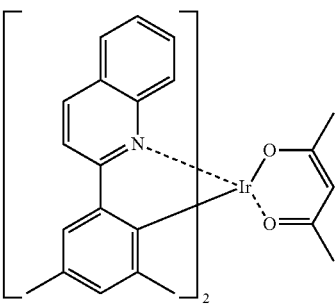
TM-107
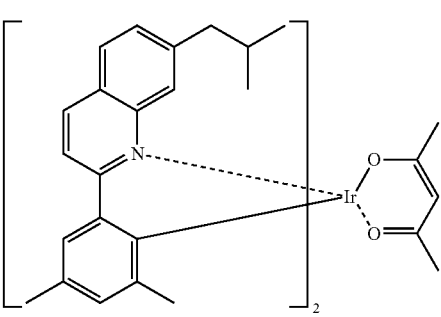
TM-108
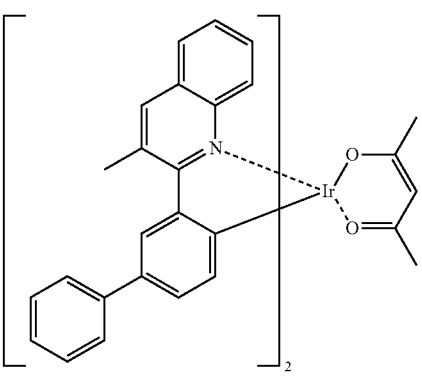
TM-109
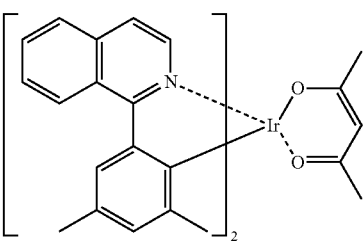
Further, in the structural formulas, acac represents a ligand (acetylacetonate) having the following structure.
(acac)
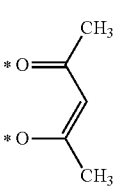
In the present invention, the compound represented by Formula (D-1) is included in a light emitting layer from the viewpoint of improving light emission efficiency and durability (in particular, durability when driving at a high temperature), but the use thereof is not limited, and may be included in any layer in addition to the light emitting layer within the organic layer. It is preferred that as a layer which introduces the compound represented by Formula (D-1), the compound is included in any one of a hole injection layer, a hole transporting layer, an electron transporting layer, an electron injection layer, an exciton blocking layer and a charge blocking layer, or a plurality thereof in addition to a light emitting layer.

[A Composition Containing a Compound Represented by Formula (1) and a Compound Represented by Formula (D-1)]

The present invention also relates to a composition containing the compound represented by Formula (1) and the compound represented by Formula (D-1).

The content of the compound represented by Formula (1) included in the composition of the present invention is preferably 50 to 99% by mass, and more preferably 70 to 95% by mass.

The content of the compound represented by Formula (D-1) included in the composition of the present invention is preferably 1 to 30% by mass, and more preferably 5 to 15% by mass.

Other components which may be contained in the composition of the present invention may be organic materials or inorganic materials, and as organic materials, materials which are exemplified as a host material, a fluorescent light emitting material, and a phosphorescent light emitting material, which are described below, may be applied.

The composition of the present invention may form an organic layer of an organic electroluminescence device by dry film-forming methods such as a vapor deposition method, a sputtering method, and the like, a transfer method, a printing method and the like.

[Organic Electroluminescence Device]

An organic electroluminescence device of the present invention is an organic electroluminescence device, including, on a substrate, a pair of electrodes and at least one layer of an organic layer including a light emitting layer containing a light emitting material between the electrodes, wherein the light emitting layer contains at least each one of the compound represented by Formula (1) and the compound represented by Formula (D-1).

In the organic electroluminescence device of the present invention, the light emitting layer is an organic layer, but may further have a plurality of organic layers.

Due to properties of the luminescence device, at least one electrode of the anode and cathode is preferably transparent or semi-transparent.

FIG. 1 illustrates an example of the configuration of an organic electroluminescence device according to the present invention. The organic electroluminescence device 10 according to the present invention, which is illustrated in FIG. 1, is on a supporting substrate 2, and a light emitting layer 6 is interposed between an anode 3 and a cathode 9. Specifically, a hole injection layer 4, a hole transporting layer 5, the light emitting layer 6, a hole blocking layer 7, and an electron transporting layer 8 are stacked in this order between the anode 3 and the cathode 9.

<Configuration of an Organic Layer>

The layer configuration of the organic layer is not particularly limited, and may be appropriately selected according to the use and purpose of the organic electroluminescence device, but is preferably formed on the transparent electrode or on the rear electrode. In this case, the organic layer is formed on the front surface or one surface on the transparent electrode or the rear electrode.

The shape, size, thickness and the like of the organic layer are not particularly limited and may be appropriately selected according to the purpose.

The specific layer configuration may include the followings, but the present invention is not limited to the configurations.

Anode/hole transporting layer/light emitting layer/electron transporting layer/cathode, Anode/hole transporting layer/light emitting layer/blocking layer/electron transporting layer/cathode, Anode/hole transporting layer/light emitting layer/blocking layer/electron transporting layer/electron injection layer/cathode, Anode/hole injection layer/hole transporting layer/light emitting layer/blocking layer/electron transporting layer/cathode, and Anode/hole injection layer/hole transporting layer/light emitting layer/blocking layer/electron transporting layer/electron injection layer/cathode.

The device configuration, substrate, cathode, and anode of the organic electroluminescence device are described in detail in, for example, Japanese Patent Application Laid-Open No. 2008-270736, and the subject matters described in the publication may be applied to the present invention.

<Substrate>

It is preferred that the substrate which is used in the present invention is a substrate which does not scatter or decay light generated from the organic layer. In the case of an organic material, it is preferred that the organic material is excellent in heat resistance, dimensional stability, solvent resistance, electrical insulation properties and processibility.

<Anode>

Typically, the anode may have a function as an electrode for supplying holes into the organic layer, is not particularly limited with respect to shape, structure, size, and the like and may be appropriately selected among the known electrode materials depending upon a use or purpose of the luminescence device. As described above, the anode is usually provided as a transparent anode.

<Cathode>

Typically, the cathode may have a function as an electrode for injecting electrons into the organic layer, is not particularly limited with respect to shape, structure, size and the like, and may be appropriately selected among the known electrode materials depending upon a use or purpose of the luminescence device.

With respect to the substrate, the anode, and the cathode, subject matters described in paragraph Nos. [0070] to [0089] of Japanese Patent Application Laid-Open No. 2008-270736 may be applied to the present invention.

<Organic Layer>

An organic layer in the present invention will be described.

—Formation of an Organic Layer—

In the organic electroluminescence device of the present invention, each organic layer may be appropriately formed by any one of dry film-forming methods such as a vapor deposition method, a sputtering method, and the like, and wet film-forming methods (wet process) such as a transfer method, a printing method, a spin-coat method, and the like.

In the present invention, it is preferred that a light emitting layer containing at least each one of the compound represented by Formula (1) and the compound represented by Formula (D-1) is formed by the wet process from the viewpoint of reducing manufacturing costs.

(Light Emitting Layer)

The light emitting layer of the present invention contains at least each one of the compound represented by Formula (1) and the compound represented by Formula (D-1).

<Light Emitting Material>

A light emitting material in the present invention is preferably the compound represented by Formula (D-1).

The light emitting material in the light emitting layer is preferably included in an amount of 0.1% by mass to 50% by mass, more preferably 1% by mass to 50% by mass from the viewpoint of durability and external quantum efficiency, and even more preferably 2% by mass to 40% by mass, with respect to the mass of the total compound which generally forms the light emitting layer in the light emitting layer.

The compound represented by Formula (D-1) in the light emitting layer is preferably included in an amount of 1% by mass to 30% by mass, and more preferably 4% by mass to 20% by mass from, the viewpoint of durability and external quantum efficiency in the light emitting layer.

A thickness of the light emitting layer is not particularly limited, but typically, the thickness is preferably 2 nm to 500 nm. Among the numbers of thicknesses, from the viewpoint of external quantum efficiency, the thickness of the light emitting layer is more preferably 3 nm to 200 nm, and even more preferably 5 nm to 100 nm.

The light emitting layer in the device of the present invention may have a configuration of a mixed layer of a light emitting material and a host material.

The light emitting layer may be a fluorescent light emitting material or a phosphorescent light emitting material, and the dopant may be used either alone or in combination of two or more kinds. The host material is preferably a charge transporting material. The host material may be used either alone or in combination of two or more kinds, and may have, for example, a configuration of a mixture of an electron transporting host material and a hole transporting host material. Further, the host material may include a material which does not have a charge transporting property in the light emitting layer and does not emit light.

In addition, the light emitting layer may be a single layer or a multi layer of two or more layers. Furthermore, each light emitting layer may emit light with different light emission colors.

The present invention also relates to a light emitting layer including the compound represented by Formula (1) and the compound represented by Formula (D-1). The light emitting layer of the present invention may be used in an organic electroluminescence device.

<Host Material>

The host material used in the present invention may include the following compounds. Examples of the host material include pyrrole, indole, carbazole (for example, CBP (4,4'-di (9-carbazoyl)biphenyl)), azaindole, azacarbazole, triazole, oxazole, oxadiazole, pyrazole, imidazole, thiophene, polyarylalkane, pyrazoline, pyrazolone, phenylenediamine, arylamine, amino substituted chalcone, styrylanthracene, fluorenone, hydrazone, stilbene, silazane, aromatic tertiary amine compounds, styrylamine compounds, porphyrin-based compounds, polysilane-based compounds, poly(N-vinylcarbazole), aniline-based copolymers, electrically conductive high-molecular oligomers such as thiophene oligomers, polythiophene and the like, organosilanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene and the like, phthalocyanine, a variety of metal complexes represented by metal complexes of a 8-quinolinol derivative, metal phthalocyanine, and metal complexes having benzoxazole or benzothiazole as the ligand thereof, and derivatives thereof (which may have a substituent or a condensed ring), and the like.

In the light emitting layer in the present invention, it is preferred that the lowest triplet excitation energy ($T_1$ energy) of the host material is higher than the $T_1$ energy of the phosphorescent light emitting material from the viewpoint of color purity, light emission efficiency and driving durability.

The host material is preferably the compound represented by Formula (1).

Further, although the content of the host compound included in the present invention is not particularly limited, the content is preferably 15% by mass to 95% by mass with respect to the total mass of the compounds forming the light emitting layer, from the viewpoint of light emission efficiency and driving voltage.

The compound represented by Formula (1) in the light emitting layer is preferably 15% by mass to 95% by mass, and more preferably 40% by mass to 96% by mass with respect to the total mass of the compounds forming the light emitting layer, from the viewpoint of light emission efficiency and driving voltage in the light emitting layer.

(Fluorescent Light Emitting Material)

Examples of the fluorescent light emitting material which may be used in the present invention include, for example, benzoxazole derivatives, benzoimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perynone derivatives, oxadiazole derivatives, oxazine derivatives, aldazine derivatives, pyralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrole derivatives, aromatic dimethylidine compounds, various complexes represented by a complex of 8-quinolinol derivatives or a complex of pyromethene derivatives and the like, polymer compounds such as polythiophene, polyphenylene, polyphenylenevinylene, and the like, compounds such as organic silane derivatives, and the like.

(Phosphorescent Light Emitting Material)

Examples of the phosphorescent light emitting material which may be used in the present invention include phosphorescent light emitting compounds and the like as described in patent documents such as U.S. Pat. No. 6,303,238B1, U.S. Pat. No. 6,097,147, WO00/57676, WO00/70655, WO01/08230, W001/39234A2, W001/41512A1, WO02/02714A2, WO02/15645A1, WO02/44189A1, WO05/19373A2, Japanese Patent Application Laid-Open No. 2001-247859, Japanese Patent Application Laid-Open No. 2002-302671, Japanese Patent Application Laid-Open No. 2002-117978, Japanese Patent Application Laid-Open No. 2003-133074, Japanese Patent Application Laid-Open No. 2002-235076, Japanese Patent Application Laid-Open No. 2003-123982, Japanese Patent Application Laid-Open No. 2002-170684, EP1211257, Japanese Patent Application Laid-Open No. 2002-226495, Japanese Patent Application Laid-Open No. 2002-234894, Japanese Patent Application Laid-Open No. 2001-247859, Japanese Patent Application Laid-Open No. 2001-298470, Japanese Patent Application Laid-Open No. 2002-173674, Japanese Patent Application Laid-Open No. 2002-203678, Japanese Patent Application Laid-Open No.

2002-203679, Japanese Patent Application Laid-Open No. 2004-357791, Japanese Patent Application Laid-Open No. 2006-256999, Japanese Patent Application Laid-Open No. 2007-19462, Japanese Patent Application Laid-Open No. 2007-84635, Japanese Patent Application Laid-Open No. 2007-96259, and the like. Among them, as for light emitting material (light emitting dopant), an Ir complex, a Pt complex, a Cu complex, a Re complex, a W complex, a Rh complex, a Ru complex, a Pd complex, an Os complex, an Eu complex, a Tb complex, a Gd complex, a Dy complex and a Ce complex are even more preferable. An Ir complex, a Pt complex or a Re complex are particularly preferable, and among them, an Ir complex, a Pt complex or a Re complex including at least one coordination mode of a metal-carbon bond, a metal-nitrogen bond, a metal-oxygen bond, and a metal-sulfur bond are preferable. Further, from the viewpoint of light emission efficiency, driving durability, chromaticity and the like, an Ir complex, a Pt complex or a Re complex including a tridentate or higher polydentate ligand are particularly preferable.

The content of the phosphorescent light emitting material included in the light emitting layer is preferably 0.1% by mass to 50% by mass, more preferably 0.2% by mass to 50% by mass, even more preferably 0.3% by mass to 40% by mass, and most preferably 4% by mass to 30% by mass, with respect to the total mass of the light emitting layer.

The content of the phosphorescent light emitting material which may be used in the present invention is preferably 0.1% by mass to 50% by mass, more preferably 1% by mass to 40% by mass, and most preferably 4% by mass to 30% by mass, with respect to the total mass of the light emitting layer. In particular, within the range of 4% by mass to 30% by mass, the luminescence chromaticity of the organic electroluminescence device has low dependency on the concentration of the phosphorescent light emitting material added.

—Electron Injection Layer and Electron Transporting Layer—

Each of the hole injection layer and the hole transporting layer is a layer having a function of accepting a hole from the anode or the anode side to transport the hole into the cathode side.

For the present invention, a hole injection layer or hole transporting layer containing an electron accepting dopant is preferably included as an organic layer.

—Electron Injection Layer and Electron Transporting Layer—

Each of the electron injection layer and the electron transporting layer is a layer having a function of accepting an electron from the cathode or the cathode side to transport the electron into the anode side.

With respect to the hole injection layer, the hole transporting layer, the electron injection layer and the electron transporting layer, the subject matters described in paragraph Nos. [0165] to [0167] of Japanese Patent Application Laid-Open No. 2008-270736 may be applied to the present invention.

—Hole Blocking Layer—

The hole blocking layer is a layer having a function of preventing a hole transported to the light emitting layer from the anode side from penetrating to the cathode side. In the present invention, the hole blocking layer may be provided as an organic layer adjacent to the light emitting layer on the cathode side.

Examples of the organic compound constituting the hole blocking layer include an aluminum complex such as aluminum(III)bis(2-methyl-8-quinolinato)-4-phenylphenolate (simply referred to as BAlq) and the like, triazole derivatives, and phenanthroline derivatives such as 2,9-dimethyl-4,7-diphenyl-1,10-phenanthroline (simply referred to as BCP) and the like.

The thickness of the hole blocking layer is preferably 1 nm to 500 nm, more preferably 5 nm to 200 nm, and even more preferably 10 nm to 100 nm.

The hole blocking layer may have a single layer structure composed of one or two or more kinds of the above-described materials or may have a multilayer structure composed of a plurality of layers of the same or different compositions.

—Electron Blocking Layer—

The electron blocking layer is a layer having a function of preventing an electron transported to the light emitting layer from the cathode side from penetrating to the anode side. In the present invention, the electron blocking layer may be provided as an organic layer adjacent to the light emitting layer on the anode side.

Examples of the organic compound constituting the electron blocking layer include those described above as the hole transporting material.

The thickness of the electron blocking layer is preferably 1 nm to 500 nm, more preferably 5 nm to 200 nm, and even more preferably 10 nm to 100 nm.

The electron blocking layer may have a single layer structure composed of one or two or more kinds of the above-described materials or may have a multilayer structure composed of a plurality of layers of the same or different compositions.

<Protective Layer>

In the present invention, the entire organic EL device may be protected by a protective layer.

With respect to the protective layer, the subject matters described in paragraph Nos. and [0170] of Japanese Patent Application Laid-Open No. 2008-270736, may be applied to the present invention.

<Sealing Vessel>

In the device of the present invention, the entire device may be sealed using a sealing vessel.

With respect to the sealing vessel, the subject matters described in paragraph No. of Japanese Patent Application Laid-Open No. 2008-270736 may be applied to the present invention.

(Driving)

In the organic electroluminescence device of the present invention, light emission may be obtained by applying a voltage (typically 2 volts to 15 volts) of direct current (may include an alternating current component if necessary) or a current of direct current between the anode and the cathode.

With respect to the driving method of the organic electroluminescence device of the present invention, driving methods described in each official gazette of Japanese Patent Application Laid-Open No. Hei 2-148687, Japanese Patent Application Laid-Open No. Hei 6-301355, Japanese Patent Application Laid-Open No. Hei 5-29080, Japanese Patent Application Laid-Open No. Hei 7-134558, Japanese Patent Application Laid-Open No. Hei 8-234685, and Japanese Patent Application Laid-Open No. Hei 8-241047, and Japanese Patent No. 2784615, U.S. Pat. Nos. 5,828,429, and 6,023,308, and the like may be applied.

The light collection efficiency of the luminescence device of the present invention may be enhanced by various known devices. For example, the light collection efficiency may be enhanced to enhance the external quantum efficiency by processing the substrate surface shape (for example, forming a fine uneven pattern), by controlling the refractive index of the substrate ITO layer or organic layer, by controlling the film thickness of the substrate-ITO layer-organic layer, and the like.

The luminescence device of the present invention may be in a so-called top emission mode of collecting light emission from the anode side.

The organic EL device in the present invention may have a resonator structure. For example, a multilayer mirror composed of a plurality of laminated films having the different refractive index, a transparent or semi-transparent electrode, a light emitting layer, and a metal electrode are superimposed on a transparent substrate. Light generated in the light emitting layer is repeatedly reflected and resonated between the multilayer film mirror and the metal electrode as a reflection plate.

In another preferred aspect, each of a transparent or semi-transparent electrode and a metal electrode functions as a reflecting plate on a transparent substrate, and light generated in the light emitting layer repeats reflection and resonates therebetween.

In order to form a resonance structure, the effective refractive index of two reflecting plates and the optical path length determined from the refractive index and thickness of each layer between the reflecting plates may be adjusted to be optimal values to obtain a desired resonance wavelength. The calculating formula in the case of the first aspect is described in Japanese Patent Application Laid-Open No. Hei 9-180883. The calculating formula in the case of the second aspect is described in Japanese Patent Application Laid-Open No. 2004-127795.

The external quantum efficiency of the organic electroluminescence device of the present invention is preferably 5% or more, and more preferably 7% or more. As values of external quantum efficiency, a maximum value of external quantum efficiency, or a value of external quantum efficiency near 100 to 300 $cd/m^2$ may be used when driving the device at 20° C.

The internal quantum efficiency of the organic electroluminescence device of the present invention is preferably 30% or more, more preferably 50% or more, and even more preferably 70% or more. The internal quantum efficiency of the device is calculated by dividing the external quantum efficiency by the light collection efficiency. Although typical organic EL devices have an light collection efficiency of about 20%, it is possible to achieve a light collection efficiency of 20% or more by studying the shape of the substrate, the shape of the electrode, the film thickness of the organic layer, the film thickness of the inorganic layer, the refractive index of the organic layer, the refractive index of the inorganic layer and the like.

The organic electroluminescence device of the present invention has ultra-high power emission wavelength (maximum strength wavelength of the emission spectrum) of preferably 350 nm or more and 700 nm or less, more preferably 350 nm or more and 600 nm or less, even more preferably 400 nm or more and 520 nm or less, and particularly preferably 400 nm or more and 465 nm or less.

(Use of Luminescence Device of the Present Invention)

The luminescence device of the present invention may be suitably used for light emission apparatuses, pixels, display devices, displays, backlights, electrophotography, illumination light sources, recording light sources, exposure light sources, reading light sources, indicators, signboards, interiors, optical communication or the like. In particular, the luminescence device of the present invention is preferably used for a device that is driven in a region with high luminescence intensity, such as a light emission apparatus, an illumination apparatus, a display apparatus, and the like.

Next, the light emission apparatus of the present invention will be described by referring to FIG. 2.

The light emission apparatus of the present invention is configured by using the above-described organic electroluminescence device.

Figure 2:
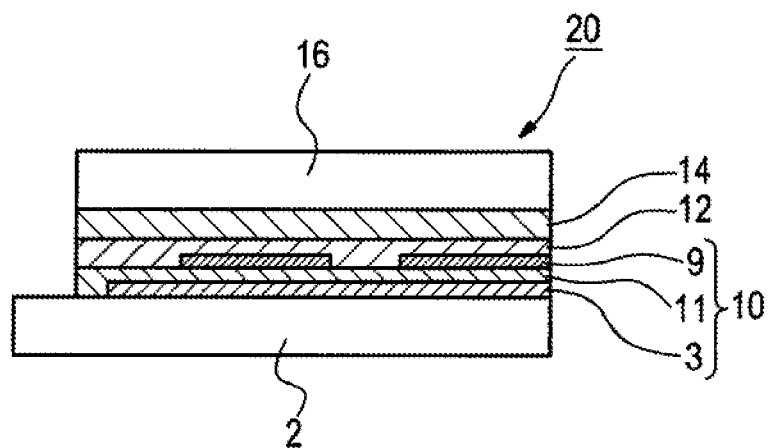
FIG. 2 is a schematic view illustrating an example (second exemplary embodiment) of a light emission apparatus according to the present invention.

FIG. 2 is a cross-sectional view schematically illustrating an example of a light emission apparatus of the present invention:

The light emission apparatus 20 of FIG. 2 is composed of a transparent substrate (supporting substrate) 2, an organic electroluminescence device 10, a sealing vessel 16, and the like.

The organic electroluminescence device 10 is configured by sequentially laminating an anode (first electrode) 3, an organic layer 11, and a cathode (second electrode) 9 on the substrate 2. Further, a protective layer 12 is laminated on the cathode 9, and the sealing vessel 16 is further provided on the protective layer 12 through an adhesive layer 14. In addition, a part of each of electrodes 3 and 9, a partition wall, an insulating layer, and the like are omitted.

Here, as the adhesive layer 14, a photocurable or thermosetting adhesive such as an epoxy resin, and the like may be used and, for example, a thermosetting adhesive sheet may also be used.

The use of the light emission apparatus of the present invention is not particularly limited and, for example, the light emission apparatus may be used not only for an illumination apparatus but also as a display apparatus such as a television set, a personal computer, a cellular phone, an electronic paper and the like.

(Illumination Apparatus)

Next, an illumination apparatus according to an embodiment of the present invention will be described by referring to FIG. 3.

Figure 3:
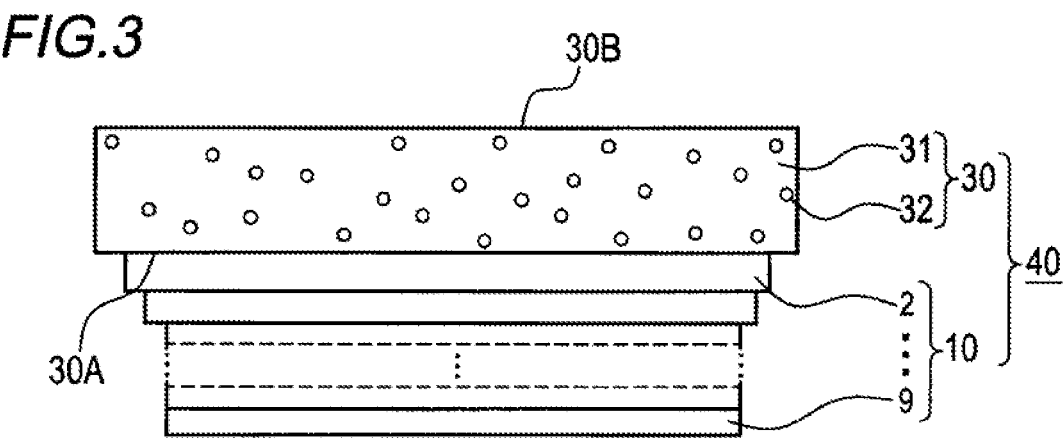
FIG. 3 is a schematic view illustrating an example (third exemplary embodiment) of an illumination apparatus according to the present invention.

FIG. 3 is a cross-sectional view schematically illustrating an example of the illumination apparatus according to the embodiment of the present invention.

The illumination apparatus 40 according to the embodiment of the present invention includes, as illustrated in FIG. 3, the above-described organic EL device 10 and a light scattering member 30. More specifically, the illumination apparatus 40 is configured such that the substrate 2 of the organic EL device 10 and the light scattering member 30 are in contact with each other.

The light scattering member 30 is not particularly limited so long as the member may scatter light, but in FIG. 3, a member obtained by dispersing microparticulates 32 in a transparent substrate 31 is used. Suitable examples of the transparent substrate 31 include a glass substrate. Suitable examples of the microparticulate 32 include a transparent resin microparticulate. As the glass substrate and the transparent resin microparticulate, products known in the art may be used. In such an illumination apparatus 40, when light emitted from the organic electroluminescence device 10 is incident on a light incident surface 30A of the scattering member 30, the incident light is scattered by the light scattering member 30 and the scattered light is reflected as illuminating light from a light reflecting surface 30B.

EXAMPLE (Synthesis of Exemplary Compound 156 (C-6)

Exemplary compound (156) of a compound represented by Formula (1) may be prepared by the following reaction scheme.

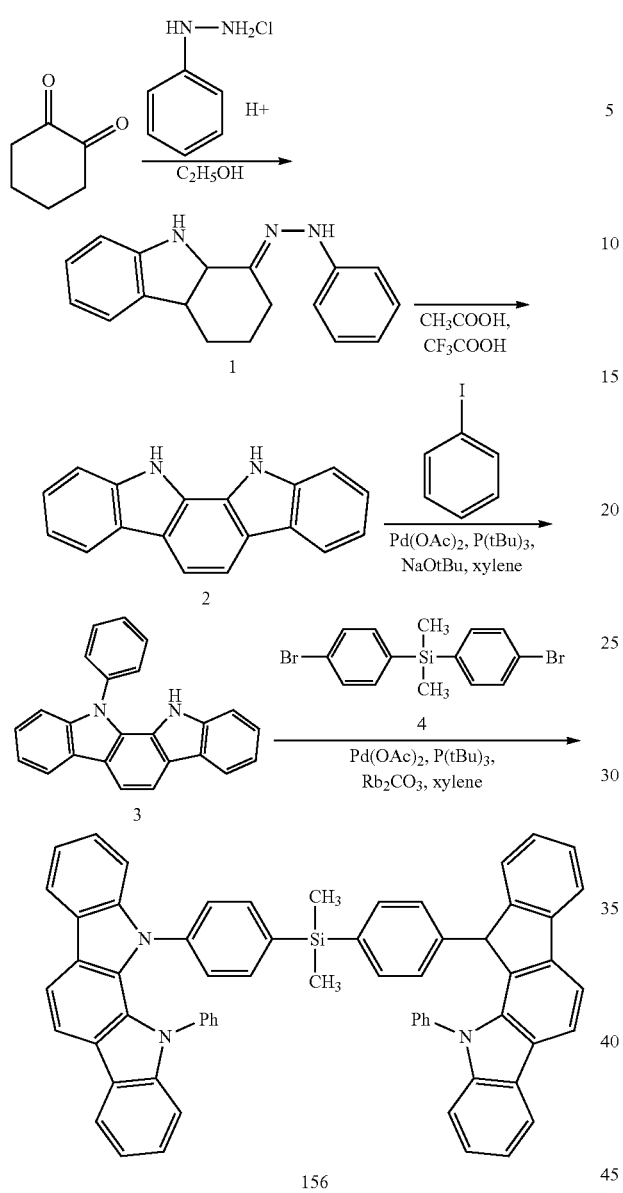

156

2 equivalents of phenylhydrazine hydrochloride were added to 1,2-cyclohexanedione in ethanol, and 0.1 equivalents of concentrated sulfuric acid was added dropwise under nitrogen atmosphere over 5 min. Thereafter, the solution was refluxed at a boiling temperature for 4 hr, and intermediate 1 was obtained in a yield of 90%. Intermediate 1 was stirred in a mixed solvent of acetic acid-trifluoroacetic acid at 100° C. for 15 hr, and intermediate 2 was obtained in a yield of 39%. Intermediate 2, 0.05 equivalents of palladium acetate, 0.15 equivalents of tri(t-butyl)phosphine, 2.4 equivalents of sodium-tert-butoxide, and 1 equivalent of iodobenzene were dissolved in xylene and refluxed at a boiling temperature for 10 hr to synthesize intermediate 3 (yield: 35%). Intermediate 3, 0.05 equivalents of palladium acetate, 0.15 equivalents of tri(t-butyl)phosphine, 2.4 equivalents of rubidium carbonate and 0.5 equivalent of intermediate 4 were dissolved in xylene and refluxed at a boiling temperature to react for 13 hr. Ethyl acetate and water were added to the reaction mixture to separate an organic phase, the organic phase was washed with water and saturated saline solution and concentrated under reduced pressure, and the obtained residue was purified by silica gel column chromatography, recrystallization, sublimation purification, and the like to obtain exemplary compound 156 in a yield of 56%. Further, the compound C-6 used in Example corresponds to exemplary compound 156.

(Synthesis of Exemplary Compound 162 (C-4))

Exemplary compound (162) of a compound represented by Formula (1) may be prepared by the following reaction scheme.

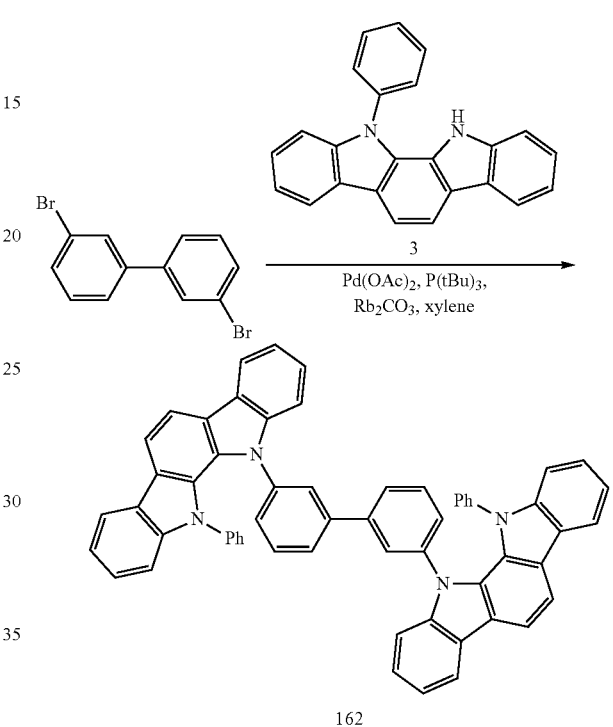

162

3,3'-dibromophenyl and 0.05 equivalents of palladium acetate, 0.15 equivalents of tri(t-butyl)phosphine, 2.4 equivalents of rubidium carbonate and 2 equivalents of 3 were dissolved in xylene and refluxed at a boiling temperature to react for 13 hr. Ethyl acetate and water were added to the reaction mixture to separate an organic phase, the organic phase was washed with water and saturated saline solution and concentrated under reduced pressure, and the obtained residue was purified by silica gel column chromatography, recrystallization, sublimation purification and the like to obtain exemplary compound 162 in a yield of 76%. Further, the compound C-4 used in Example corresponds to exemplary compound 162.

(Synthesis of Exemplary Compound 138 (C-1))

Exemplary compound 138 (C-1) of a compound represented by Formula (1) may be prepared by the following reaction scheme.

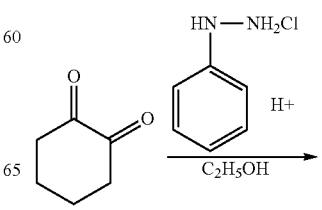

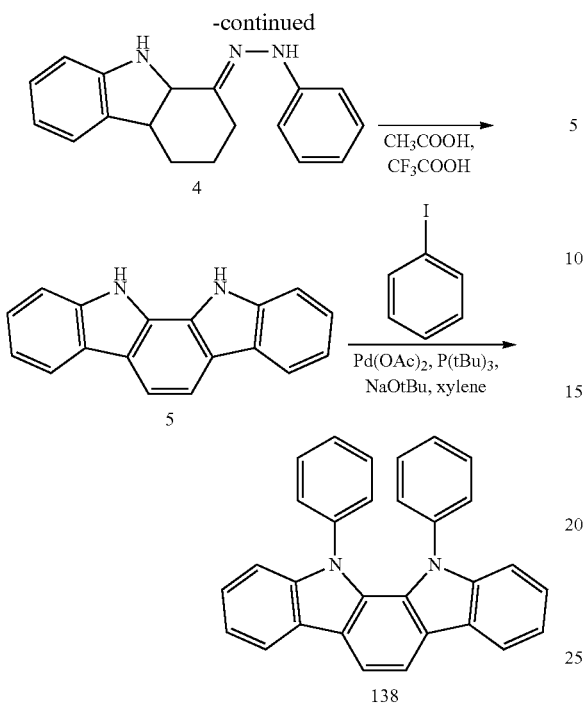

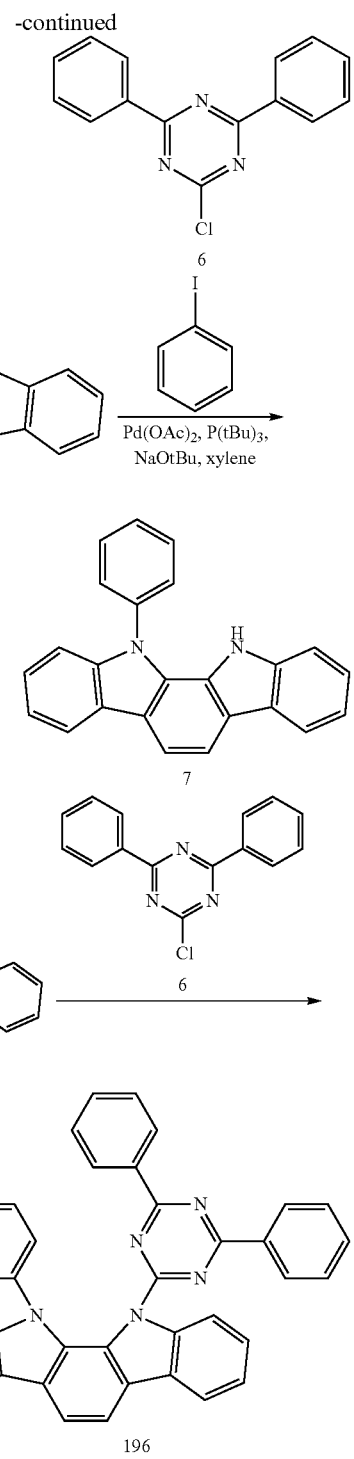

2 equivalents of phenylhydrazine hydrochloride were added to 1,2-cyclohexanedione in ethanol, and 0.1 equivalents of concentrated sulfuric acid was added dropwise under nitrogen atmosphere over 5 min. Thereafter, the solution was refluxed at a boiling temperature for 4 hr, and intermediate 4 was obtained in a yield of 90%. Intermediate 4 was stirred under a mixed solvent of acetic acid-trifluoroacetic acid at 100° C. for 15 hr, and intermediate 5 was obtained in a yield of 39%. Intermediate 5, 0.05 equivalents of palladium acetate, 0.15 equivalents of tri(t-butyl)phosphine, 2.4 equivalents of sodium-tert-butoxide and 2.2 equivalents of iodobenzene were dissolved in xylene and refluxed at a boiling temperature to react for 10 hr. Ethyl acetate and water were added to the reaction mixture to separate an organic phase, the organic phase was washed with water and saturated saline solution and then concentrated under reduced pressure, and the obtained residue was purified by silica gel column chromatography, recrystallization, sublimation purification and the like to obtain exemplary compound 138 in a yield of 66%. Further, compound C-1 used in the Example corresponds to exemplary compound 138.

(Synthesis of Exemplary Compound 196 (C-14))

Exemplary compound 196 (C-14) of a compound represented by Formula (1) may be prepared by the following reaction scheme.

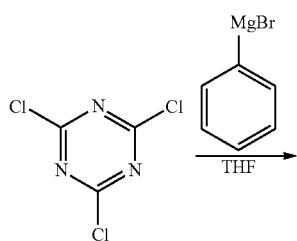

1 equivalent of cyanil chloride was dissolved in dry THF. 32% phenylmagnesium bromide THF solution (2.5 equivalents) was added dropwise in an ice bath under nitrogen atmosphere and stirred for 2 hr to synthesize intermediate 6 (yield: 37%). Intermediate 2, 0.05 equivalents of palladium acetate, 0.15 equivalents of tri(t-butyl)phosphine, 2.4 equivalents of sodium-tert-butoxide and 1 equivalent of iodobenzene were dissolvdd in xylene and refluxed at a boiling temperature for 10 hr to synthesize intermediate 7 (yield: 35%). 1.1 equivalents of sodium hydride was dispersed in dry N,N'-dimethylformamide (DMF) and stirred under nitrogen atmosphere. A DMF solution of 1 equivalent of intermediate 7 was added dropwise and stirred for 1 hr. Thereafter, a DMF solution of 1 equivalent of intermediate 6 was added dropwise and stirred for 3 hr. Water was added, and precipitated crystals were separated by filtration. Recrystallization was performed from an ethanol/chloroform solution and the resulting solution was subjected to purification by sublimation to obtain exemplary compound 196 in a yield of 32%. Further, compound C-14 used in the Example corresponds to exemplary compound 196.

Example 1

Manufacture of Organic Electroluminescence Device

Comparative Example 1-1

A washed ITO substrate was put in a vapor deposition apparatus to vapor-deposit copper phthalocyanine to a thickness of 10 nm, and NPD (N,N'-di-a-naphthyl-N,N'-diphenyl) benzidine) was vapor-deposited thereon to a thickness of 40 nm (hole transporting layer). Thereon, A-1 and C-1 were vapor-deposited at a ratio of 9:91 (mass ratio) to a thickness of 30 nm (light emitting layer), and H-1 was vapor-deposited thereon to a thickness of 5 nm (adjacent layer). Thereon, BAlq [bis-(2-methyl-8-quinolinolate)-4-(phenylphenolate)aluminum] was vapor-deposited to a thickness of 30 nm (electron transporting layer). Thereon, lithium fluoride was vapor-deposited to a thickness of about 3 nm, and aluminum was vapor-deposited thereon to a thickness of 60 nm. This was placed in a glove box substituted with argon gas so as not to be exposed to the atmosphere and sealed using a stainless steel-made sealing tube and a UV-curable adhesive (XNR5516HV, manufactured by Nagase-CHIBA Ltd.) to obtain an organic electroluminescence device in Comparative Example 1-1. A direct current constant voltage was applied to the EL device to emit light by means of a source measure unit Model 2400 manufactured by Toyo Technica, and, as a result, a phosphorescent light emission derived from A-1 could be obtained.

Examples 1-1 to 1-198 and Comparative Examples 1-2 to 1-16

A device was manufactured and evaluated in the same manner as in Comparative Example 1-1, except that the compounds used for the light emitting material and the host material were changed into those described in Table 1. In any of the devices, a phosphorescent light emission derived from a light emitting material used could be obtained. The obtained results were incorporated into Table 1.

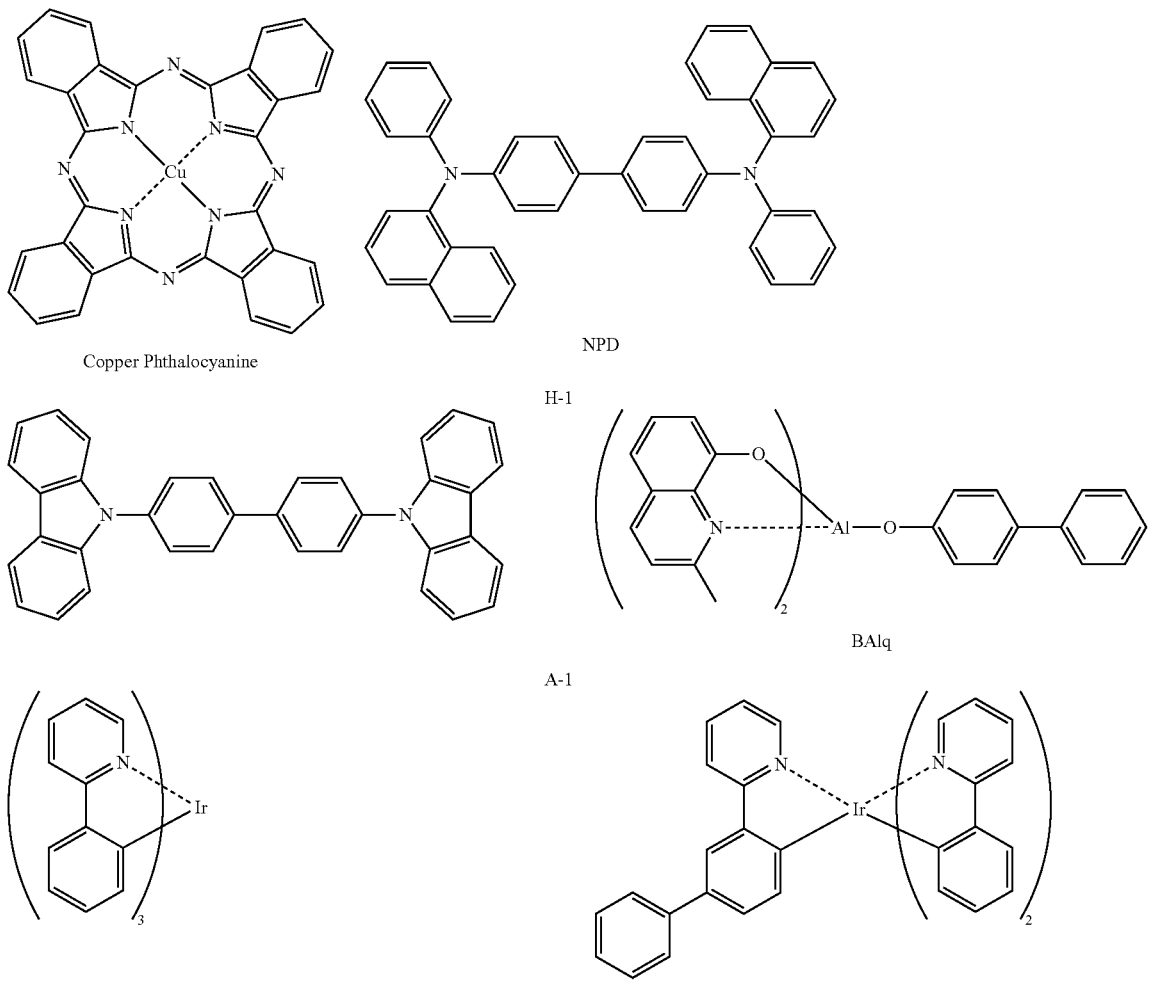

-continued
A-3
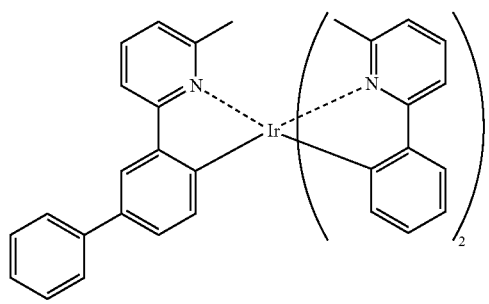
A-4
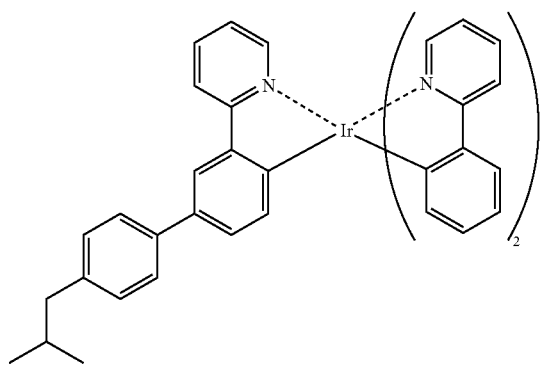
A-5
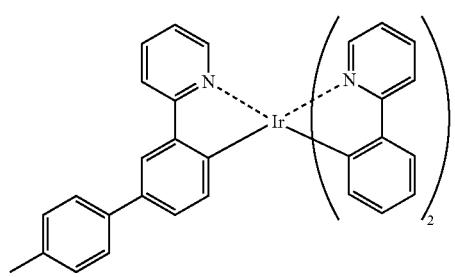
A-6
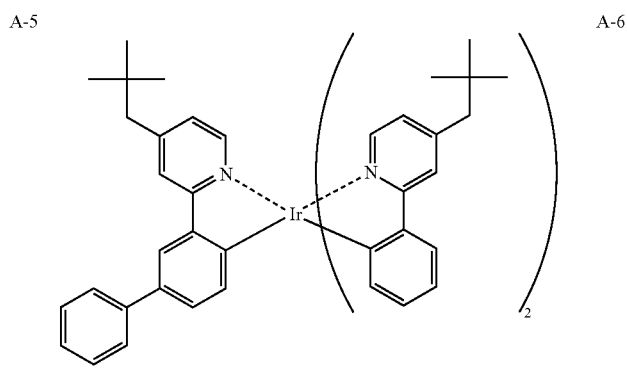
(A-7)
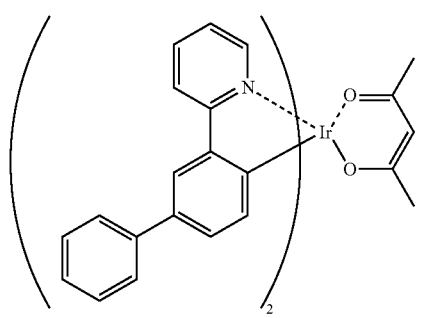
C-1
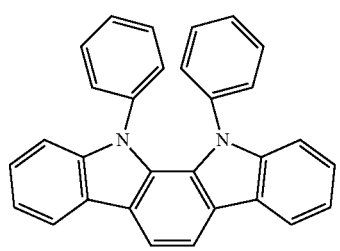
C-2
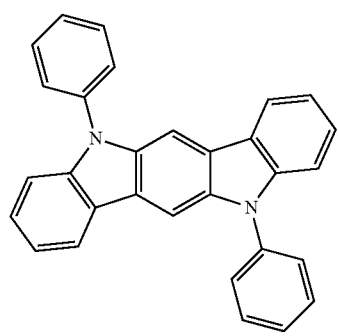
C-3
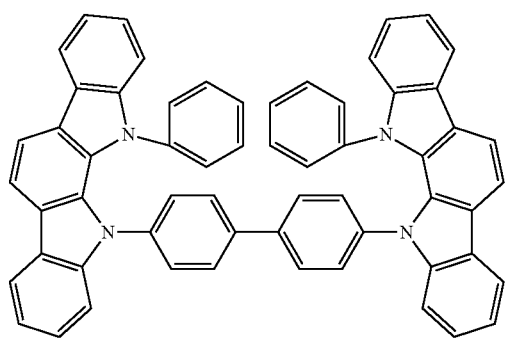

-continued
C-4
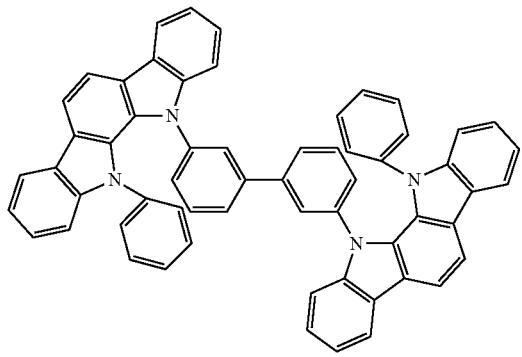
C-5
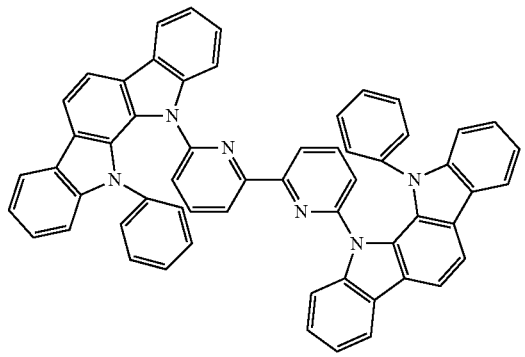
C-6
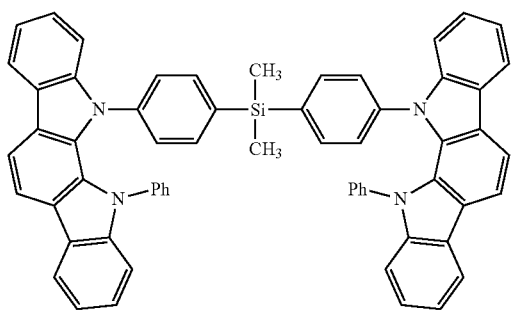
C-7
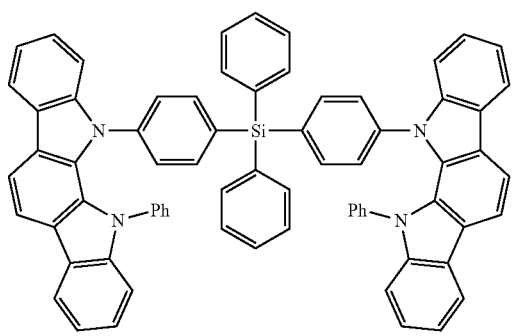
C-8
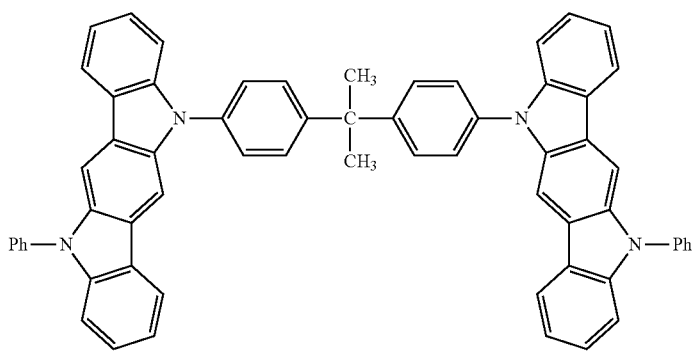
C-9
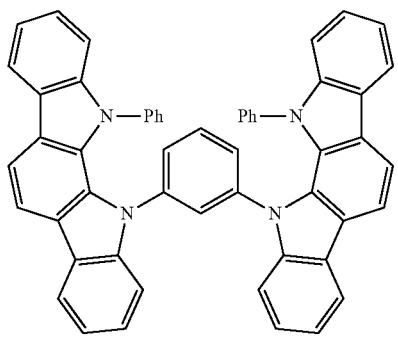
C-11
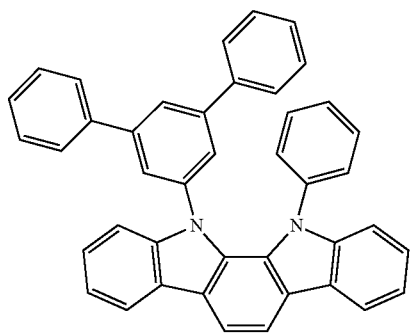

-continued
C-12
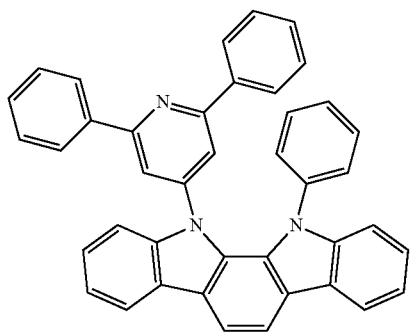
C-13
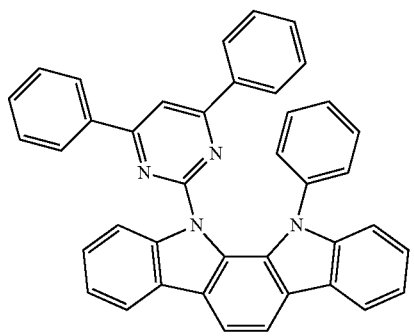
C-14
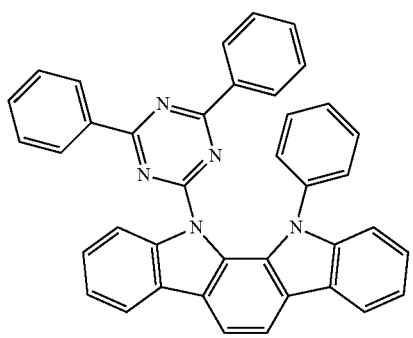
C-15
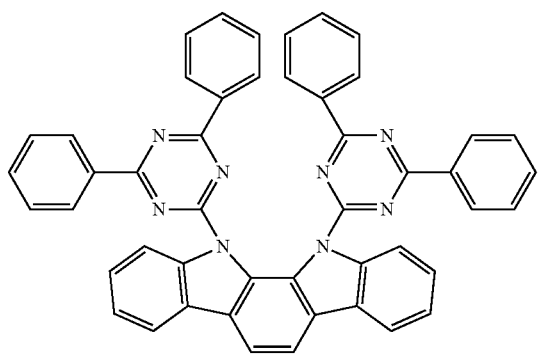
C-16
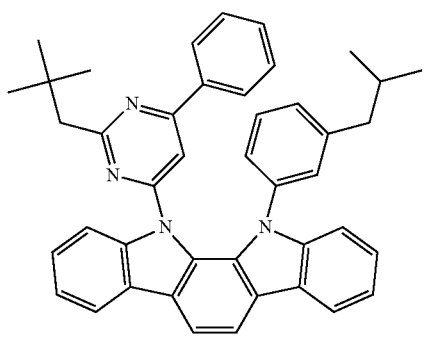
C-17
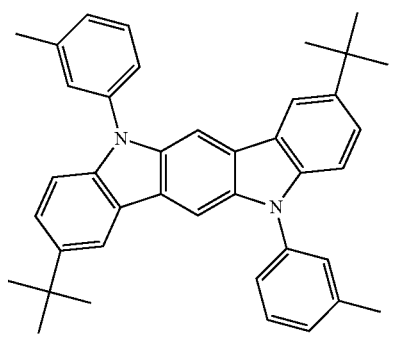
C-18
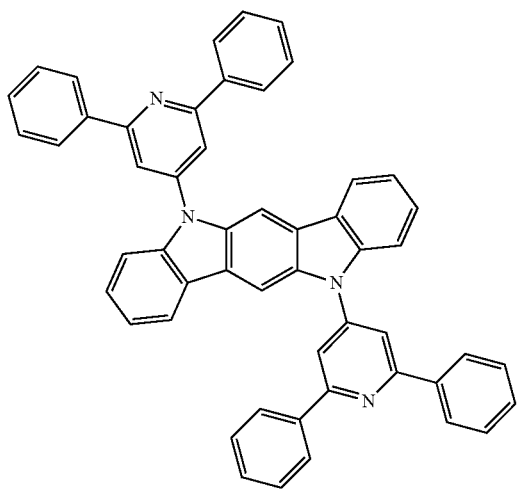
C-19
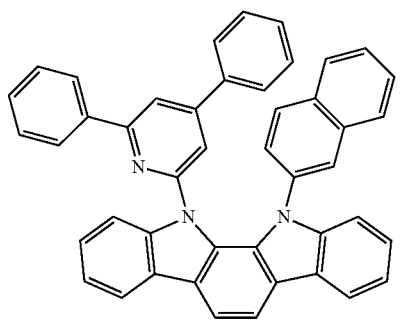

-continued
C-20
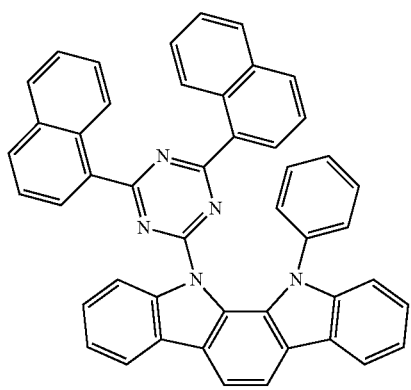
C-21
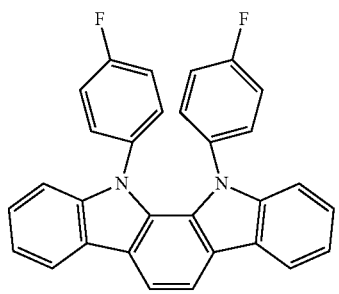
C-22
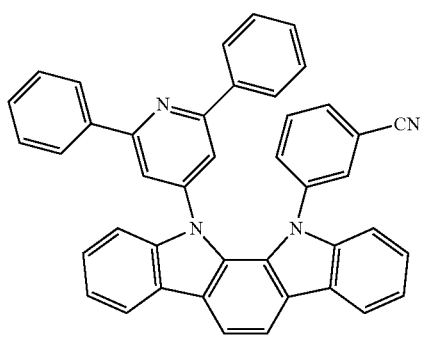
C-23
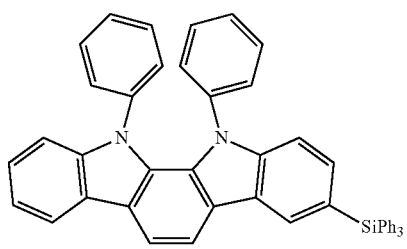
C-24
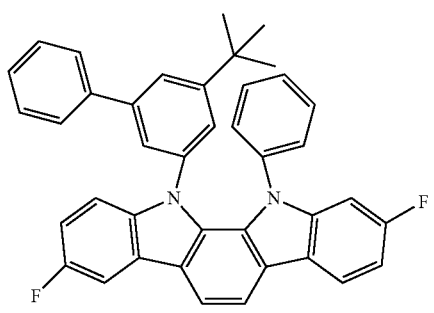
C-25
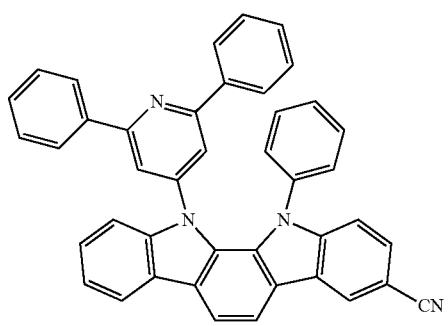
C-26
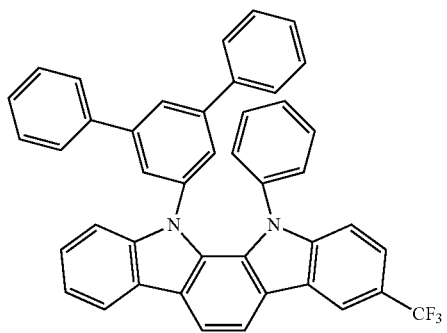
C-27
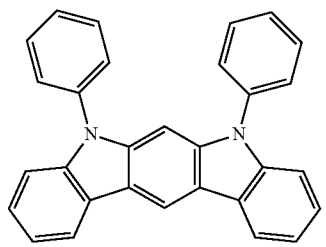

-continued
C-28
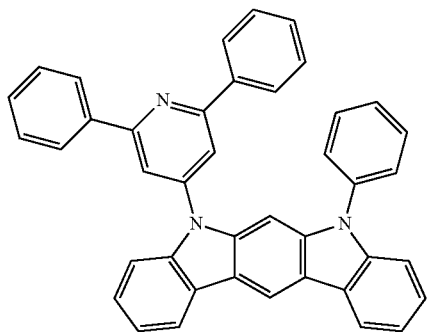
C-29
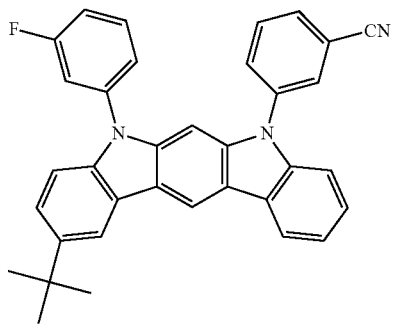
C-30
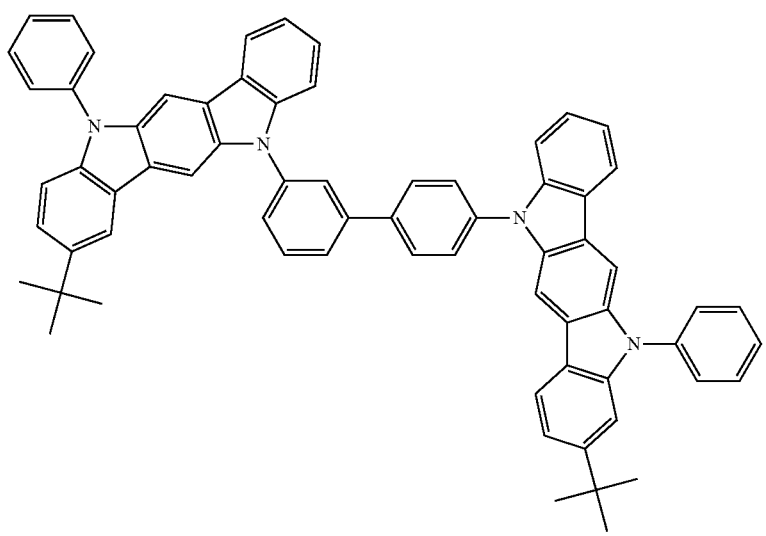
C-31
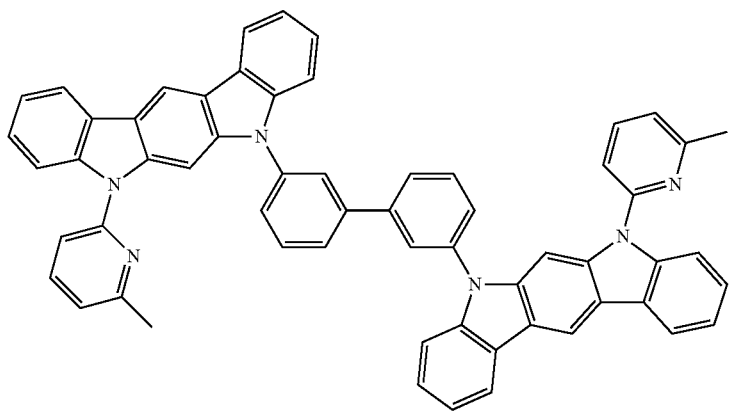
C-32
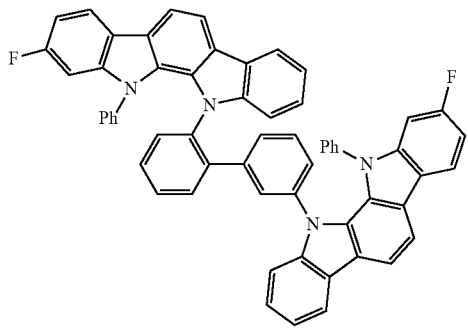
C-33
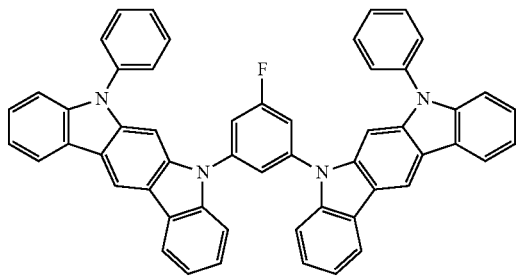

-continued
C-34
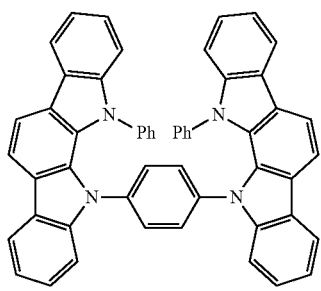
C-35
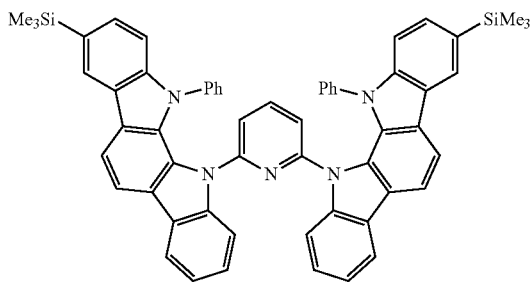
C-36
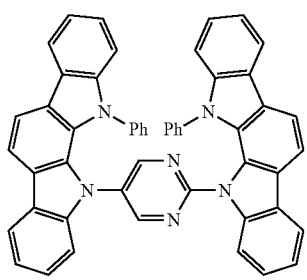
C-37
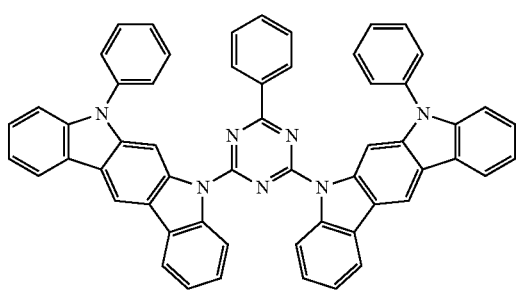
C-38
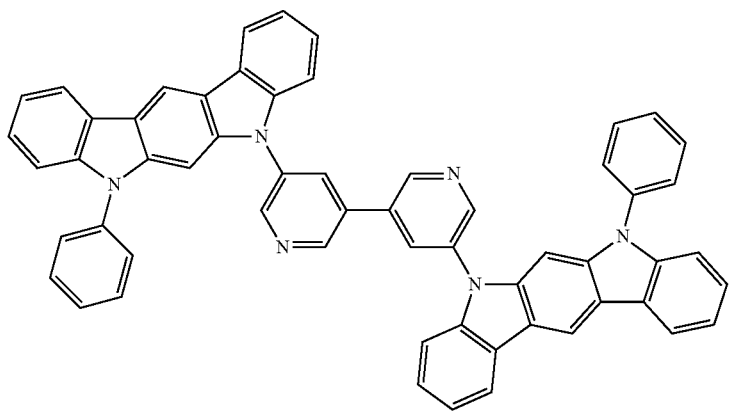
C-39
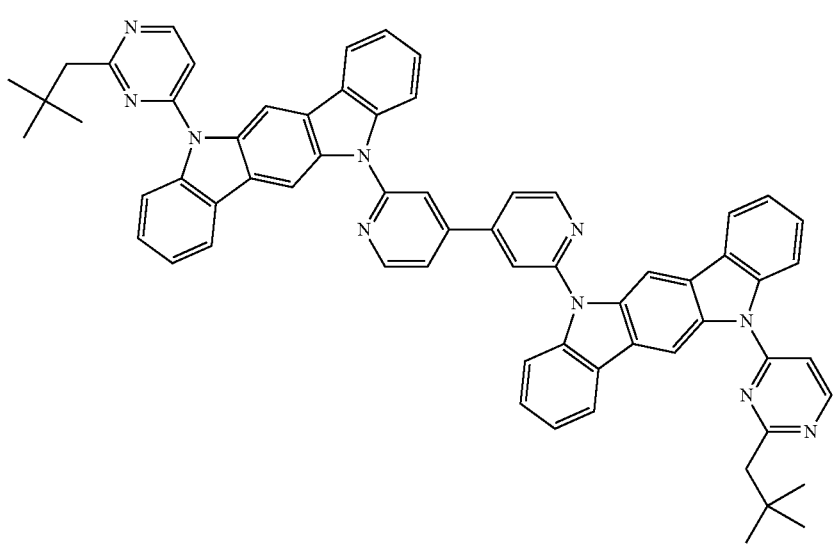

-continued
C-40
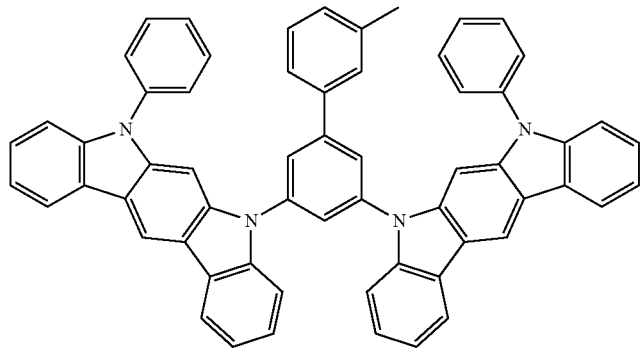
C-41
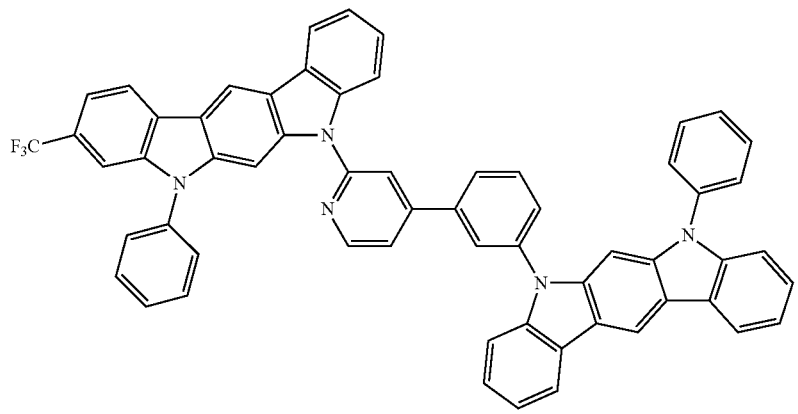
C-42
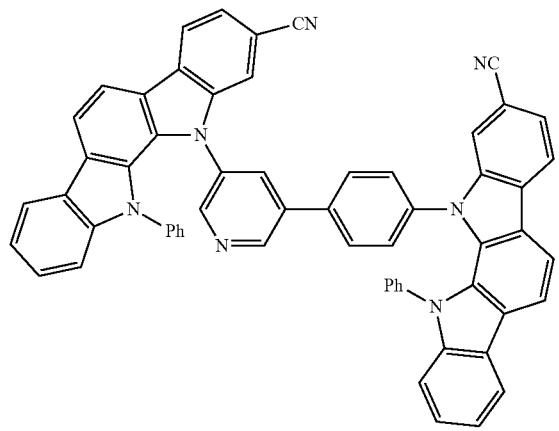
C-46
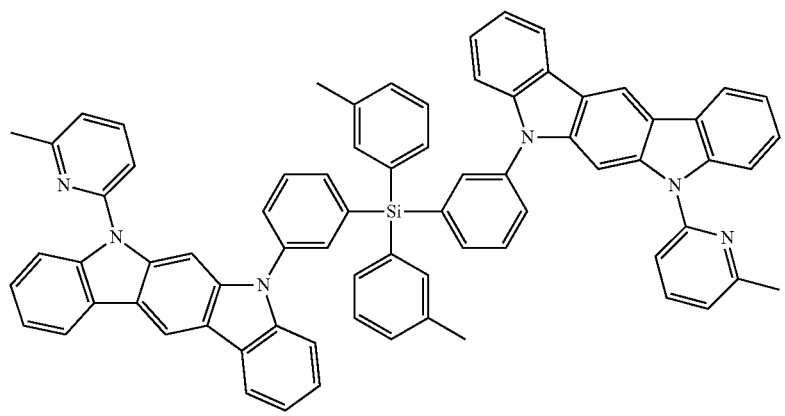

-continued
C-47
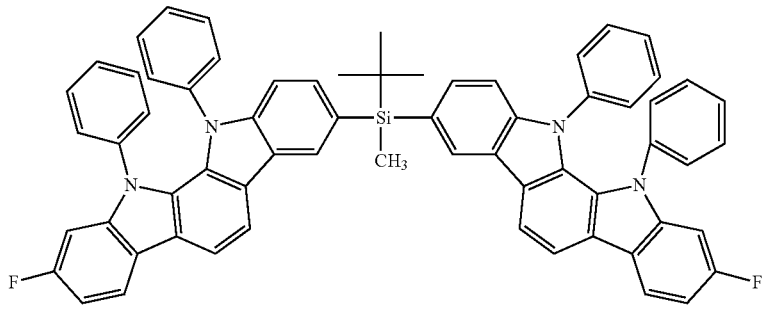
C-48
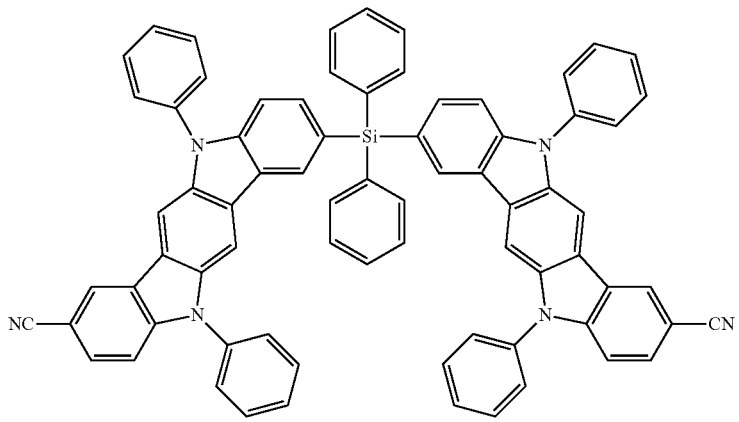
C-49 C-50
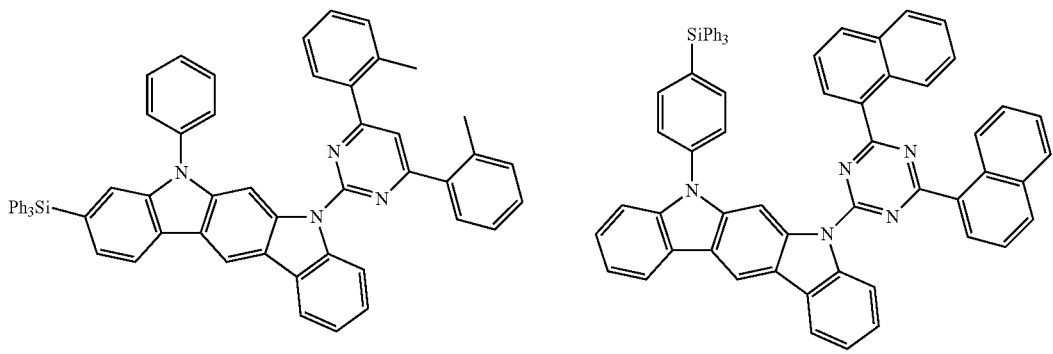
C-51
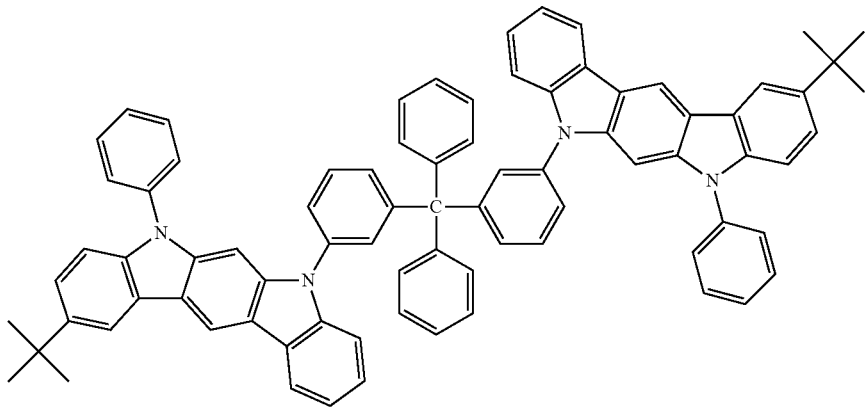

-continued
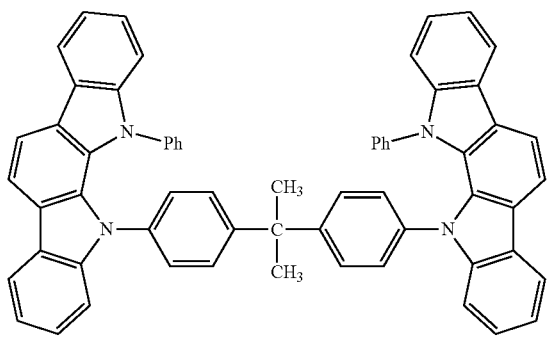
C-52
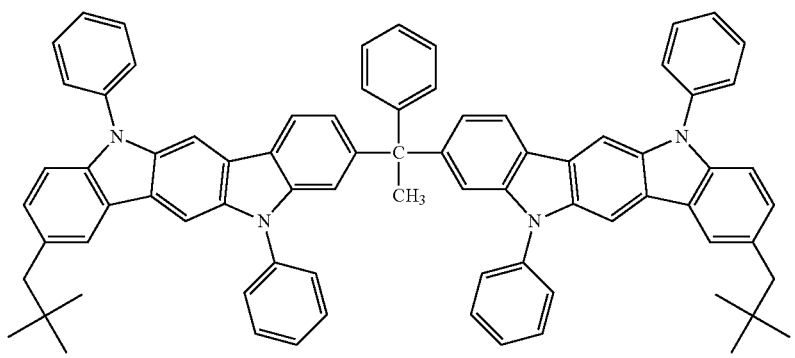
C-53
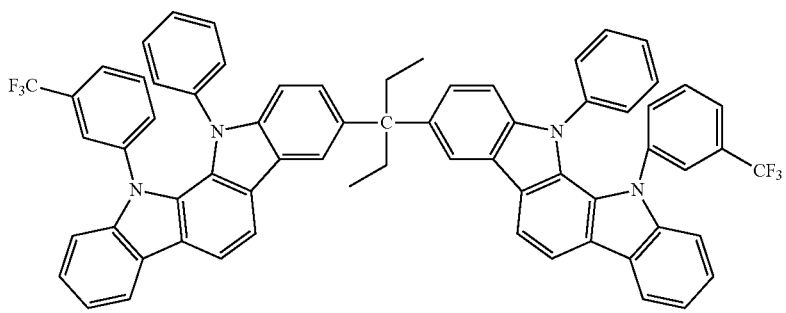
C-54
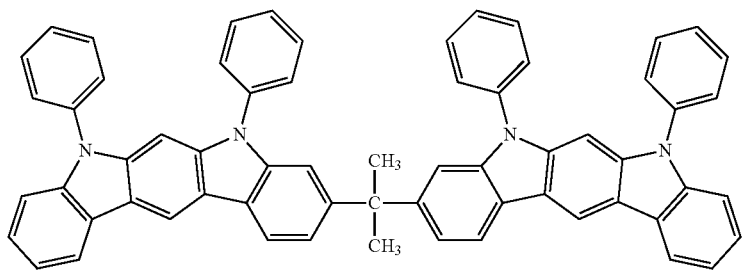
C-55

-continued

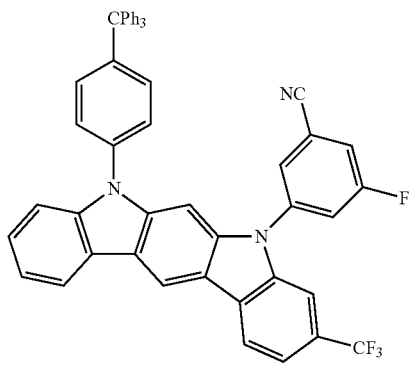
C-56

(Measurement of Driving Voltage)

Each organic electroluminescence device was set on an emission spectrum measurement system (ELS 1500), manufactured by Shimadzu Corporation, and an applied voltage at the time when the luminance intensity was 100 cd/m² was measured.

(Evaluation of External Quantum Efficiency)

Light emission was performed by applying a direct current constant voltage to each organic electroluminescence device using a source measure unit MODEL 2400, manufactured by Toyo Technica. An external quantum efficiency (%) was calculated from the front luminance intensity at the time of 1000 cd/m2.

(Evaluation of Driving Durability)

Each organic electroluminescence device was set on an OLED test system, MODEL ST-D, manufactured by Tokyo Systems Development Co., Ltd. and driven in a constant current mode under a condition of an initial luminance intensity of 1,000 cd/cm² at an ambient air temperature of 70° C., thereby measuring a half-luminance intensity time.

Further, each of values of the devices in Comparative Example 1-1, Comparative Example 2-1, Comparative Example 3-1, and Comparative Example 4-1 was made to be 100, and with reference to those values, relative values are shown in Tables 1 to 4.

TABLE 1

| | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
| | Light emitting material | Host material | | | |
| Comparative example 1-1 | A-1 | C-1 | 10.6 | 6.2 | 100 |
| Comparative example 1-2 | A-1 | C-3 | 11.1 | 5.9 | 104 |
| Comparative example 1-3 | A-1 | C-6 | 10.8 | 6 | 97 |
| Comparative example 1-4 | A-1 | C-8 | 11.8 | 5.7 | 85 |
| Comparative example 1-5 | A-1 | C-9 | 11.1 | 5.9 | 103 |
| Comparative example 1-6 | A-1 | H-1 | 10.88 | 5.8 | 95 |
| Comparative example 1-7 | A-2 | H-1 | 10.3 | 7.6 | 151 |
| Comparative example 1-8 | A-3 | H-1 | 10.2 | 7.5 | 68 |
| Comparative example 1-9 | A-5 | H-1 | 10.1 | 7.8 | 201 |
| Comparative example 1-10 | A-7 | H-1 | 10.6 | 6.5 | 85 |
| Example 1-1 | A-2 | C-1 | 9.7 | 8.2 | 204 |
| Example 1-2 | A-2 | C-3 | 9.6 | 8.3 | 233 |
| Example 1-3 | A-2 | C-4 | 9.5 | 8.7 | 244 |
| Example 1-4 | A-2 | C-5 | 9.3 | 8.7 | 198 |
| Example 1-5 | A-2 | C-6 | 9.7 | 8.4 | 253 |
| Example 1-6 | A-2 | C-7 | 9.7 | 8.2 | 262 |
| Example 1-7 | A-3 | C-1 | 9.8 | 8.7 | 133 |
| Example 1-8 | A-3 | C-2 | 9.9 | 8.8 | 142 |
| Example 1-9 | A-3 | C-4 | 9.8 | 8.9 | 157 |
| Example 1-10 | A-3 | C-5 | 9.5 | 9.4 | 133 |

TABLE 1-continued

| | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
| | Light emitting material | Host material | | | |
| Example 1-11 | A-3 | C-6 | 9.6 | 8.8 | 159 |
| Example 1-12 | A-3 | C-8 | 9.9 | 8.6 | 138 |
| Example 1-13 | A-3 | C-9 | 9.8 | 8.8 | 148 |
| Example 1-14 | A-4 | C-2 | 9.8 | 9.1 | 249 |
| Example 1-15 | A-4 | C-3 | 9.9 | 9.2 | 257 |
| Example 1-16 | A-4 | C-4 | 9.7 | 9 | 296 |
| Example 1-17 | A-4 | C-5 | 9.2 | 9.6 | 221 |
| Example 1-18 | A-4 | C-7 | 9.7 | 9.3 | 251 |
| Example 1-19 | A-4 | C-9 | 9.7 | 9.3 | 249 |
| Example 1-20 | A-5 | C-1 | 9.7 | 9.4 | 268 |
| Example 1-21 | A-5 | C-2 | 9.9 | 9.3 | 279 |
| Example 1-22 | A-5 | C-3 | 10 | 9.3 | 301 |
| Example 1-23 | A-5 | C-4 | 9.9 | 9.5 | 342 |
| Example 1-24 | A-5 | C-6 | 9.8 | 9.5 | 356 |
| Example 1-25 | A-5 | C-7 | 9.9 | 9.2 | 339 |
| Example 1-26 | A-5 | C-8 | 9.9 | 9.3 | 312 |
| Example 1-27 | A-6 | C-1 | 9.8 | 9.3 | 243 |
| Example 1-28 | A-6 | C-2 | 9.7 | 9.3 | 228 |
| Example 1-29 | A-6 | C-3 | 9.5 | 9.4 | 234 |
| Example 1-30 | A-6 | C-4 | 9.7 | 9.5 | 255 |
| Example 1-31 | A-6 | C-5 | 9.2 | 9.7 | 262 |
| Example 1-32 | A-6 | C-7 | 9.5 | 9.3 | 261 |
| Example 1-33 | A-6 | C-8 | 9.9 | 9.2 | 226 |
| Example 1-34 | A-7 | C-1 | 10.1 | 7.9 | 143 |
| Example 1-35 | A-7 | C-4 | 9.9 | 8.4 | 152 |
| Example 1-36 | A-7 | C-6 | 9.9 | 8.2 | 159 |
| Comparative example 1-11 | A-1 | C-11 | 10.1 | 6.6 | 121 |
| Comparative example 1-12 | A-1 | C-14 | 9.5 | 7.3 | 104 |
| Comparative example 1-13 | A-1 | C-16 | 10.3 | 6.8 | 88 |
| Comparative example 1-14 | A-1 | C-18 | 10.1 | 6.4 | 109 |
| Comparative example 1-15 | A-1 | C-21 | 10.3 | 6.5 | 92 |
| Comparative example 1-16 | A-1 | C-23 | 10.8 | 6.1 | 97 |
| Example 1-37 | A-2 | C-2 | 9.9 | 8.0 | 198 |
| Example 1-38 | A-2 | C-11 | 9.5 | 8.4 | 232 |
| Example 1-39 | A-2 | C-12 | 8.6 | 9.0 | 198 |
| Example 1-40 | A-2 | C-13 | 8.4 | 9.4 | 177 |
| Example 1-41 | A-2 | C-14 | 8.2 | 9.8 | 179 |
| Example 1-42 | A-2 | C-15 | 8.4 | 9.2 | 171 |
| Example 1-43 | A-2 | C-16 | 8.9 | 9.1 | 167 |
| Example 1-44 | A-2 | C-17 | 10.0 | 8.0 | 210 |
| Example 1-45 | A-2 | C-18 | 8.9 | 8.8 | 188 |
| Example 1-46 | A-2 | C-21 | 9.6 | 8.3 | 189 |
| Example 1-47 | A-2 | C-22 | 8.4 | 9.1 | 187 |
| Example 1-48 | A-2 | C-23 | 9.8 | 8.0 | 195 |
| Example 1-49 | A-3 | C-11 | 9.5 | 9.1 | 158 |
| Example 1-50 | A-3 | C-12 | 9.1 | 9.3 | 138 |
| Example 1-51 | A-3 | C-13 | 8.5 | 9.8 | 119 |
| Example 1-52 | A-3 | C-14 | 8.3 | 10.6 | 121 |
| Example 1-53 | A-3 | C-17 | 10.5 | 8.3 | 130 |
| Example 1-54 | A-3 | C-18 | 9.3 | 9.1 | 125 |
| Example 1-55 | A-3 | C-21 | 9.6 | 8.7 | 126 |
| Example 1-56 | A-4 | C-11 | 9.5 | 9.7 | 286 |
| Example 1-57 | A-4 | C-12 | 9.3 | 9.8 | 241 |
| Example 1-58 | A-4 | C-13 | 9.1 | 10.0 | 226 |
| Example 1-59 | A-4 | C-14 | 8.7 | 10.8 | 233 |
| Example 1-60 | A-4 | C-15 | 8.9 | 10.5 | 219 |
| Example 1-61 | A-4 | C-17 | 10.1 | 8.7 | 233 |
| Example 1-62 | A-4 | C-22 | 9.2 | 9.9 | 234 |
| Example 1-63 | A-4 | C-23 | 9.9 | 9.0 | 230 |
| Example 1-64 | A-5 | C-11 | 9.7 | 9.6 | 299 |
| Example 1-65 | A-5 | C-12 | 9.5 | 9.8 | 259 |
| Example 1-66 | A-5 | C-14 | 9.0 | 10.8 | 243 |
| Example 1-67 | A-5 | C-15 | 9.2 | 10.2 | 231 |

TABLE 1-continued

|  | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
|  | Light emitting material | Host material |  |  |  |
| Example 1-68 | A-5 | C-16 | 9.4 | 9.8 | 228 |
| Example 1-69 | A-5 | C-18 | 9.6 | 9.9 | 239 |
| Example 1-70 | A-5 | C-21 | 9.5 | 9.5 | 252 |
| Example 1-71 | A-5 | C-22 | 9.4 | 9.8 | 247 |
| Example 1-72 | A-6 | C-11 | 9.6 | 9.6 | 266 |
| Example 1-73 | A-6 | C-12 | 9.3 | 9.8 | 222 |
| Example 1-74 | A-6 | C-13 | 8.6 | 10.2 | 205 |
| Example 1-75 | A-6 | C-14 | 8.3 | 10.7 | 211 |
| Example 1-76 | A-6 | C-15 | 8.8 | 10.0 | 191 |
| Example 1-77 | A-6 | C-16 | 9.0 | 9.9 | 189 |
| Example 1-78 | A-6 | C-21 | 9.6 | 9.5 | 229 |
| Example 1-79 | A-6 | C-23 | 9.9 | 9.1 | 237 |
| Example 1-80 | A-7 | C-11 | 9.7 | 8.3 | 167 |
| Example 1-81 | A-7 | C-12 | 9.5 | 8.4 | 133 |
| Example 1-82 | A-7 | C-14 | 9.0 | 9.1 | 138 |
| Example 1-83 | A-7 | C-18 | 9.5 | 8.3 | 129 |
| Example 1-84 | A-7 | C-22 | 9.4 | 8.6 | 126 |
| Example 1-85 | A-2 | C-24 | 9.8 | 8.1 | 178 |
| Example 1-86 | A-3 | C-25 | 8.5 | 9.7 | 135 |
| Example 1-87 | A-4 | C-26 | 9.3 | 9.7 | 231 |
| Example 1-88 | A-5 | C-24 | 9.6 | 9.6 | 250 |
| Example 1-89 | A-5 | C-25 | 9.2 | 10.2 | 249 |
| Example 1-90 | A-6 | C-25 | 9.1 | 10.2 | 218 |
| Example 1-91 | A-6 | C-26 | 9.4 | 9.6 | 216 |
| Example 1-92 | A-7 | C-26 | 9.5 | 8.4 | 131 |
| Example 1-93 | A-2 | C-27 | 9.8 | 8.0 | 186 |
| Example 1-94 | A-3 | C-28 | 9.3 | 9.1 | 123 |
| Example 1-95 | A-4 | C-29 | 9.0 | 10.1 | 217 |
| Example 1-96 | A-5 | C-27 | 9.9 | 9.1 | 256 |
| Example 1-97 | A-5 | C-28 | 9.6 | 9.8 | 240 |
| Example 1-98 | A-6 | C-27 | 9.6 | 9.2 | 221 |
| Example 1-99 | A-6 | C-29 | 8.6 | 9.3 | 216 |
| Example 1-100 | A-7 | C-28 | 9.6 | 8.3 | 127 |
| Example 1-101 | A-2 | C-30 | 9.6 | 8.5 | 232 |
| Example 1-102 | A-2 | C-32 | 9.5 | 8.6 | 208 |
| Example 1-103 | A-2 | C-34 | 9.6 | 8.3 | 214 |
| Example 1-104 | A-2 | C-36 | 9.2 | 9.0 | 174 |
| Example 1-105 | A-2 | C-38 | 9.2 | 9.1 | 179 |
| Example 1-106 | A-2 | C-39 | 9.0 | 9.5 | 165 |
| Example 1-107 | A-2 | C-40 | 9.5 | 8.6 | 226 |
| Example 1-108 | A-2 | C-42 | 9.2 | 9.5 | 183 |
| Example 1-109 | A-3 | C-30 | 9.8 | 8.6 | 150 |
| Example 1-110 | A-3 | C-31 | 9.6 | 9.3 | 136 |
| Example 1-111 | A-3 | C-33 | 9.7 | 8.6 | 125 |
| Example 1-112 | A-3 | C-34 | 10.0 | 8.4 | 133 |
| Example 1-113 | A-3 | C-35 | 9.7 | 8.8 | 122 |
| Example 1-114 | A-3 | C-37 | 9.0 | 9.7 | 119 |
| Example 1-115 | A-3 | C-39 | 9.2 | 9.5 | 116 |
| Example 1-116 | A-3 | C-41 | 9.4 | 9.2 | 119 |
| Example 1-117 | A-4 | C-30 | 10.1 | 9.2 | 289 |
| Example 1-118 | A-4 | C-31 | 9.7 | 9.8 | 258 |
| Example 1-119 | A-4 | C-32 | 10.0 | 9.3 | 244 |
| Example 1-120 | A-4 | C-33 | 10.0 | 9.1 | 233 |
| Example 1-121 | A-4 | C-34 | 10.2 | 9.1 | 248 |
| Example 1-122 | A-4 | C-35 | 9.9 | 9.5 | 230 |
| Example 1-123 | A-4 | C-36 | 9.5 | 9.9 | 217 |
| Example 1-124 | A-4 | C-37 | 9.3 | 10.3 | 212 |
| Example 1-125 | A-4 | C-38 | 9.5 | 9.9 | 219 |
| Example 1-126 | A-4 | C-39 | 9.6 | 10.3 | 207 |
| Example 1-127 | A-4 | C-40 | 9.6 | 9.4 | 283 |
| Example 1-128 | A-4 | C-41 | 9.5 | 9.5 | 213 |
| Example 1-129 | A-4 | C-42 | 9.4 | 10.0 | 217 |
| Example 1-130 | A-5 | C-30 | 10.1 | 9.3 | 331 |
| Example 1-131 | A-5 | C-31 | 9.6 | 9.8 | 305 |
| Example 1-132 | A-5 | C-32 | 9.9 | 9.5 | 292 |
| Example 1-133 | A-5 | C-33 | 9.8 | 9.4 | 272 |

TABLE 1-continued

| | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
| | Light emitting material | Host material | | | |
| Example 1-134 | A-5 | C-34 | 10.1 | 9.2 | 289 |
| Example 1-135 | A-5 | C-35 | 9.9 | 9.6 | 270 |
| Example 1-136 | A-5 | C-36 | 9.4 | 9.8 | 243 |
| Example 1-137 | A-5 | C-37 | 9.2 | 10.2 | 235 |
| Example 1-138 | A-5 | C-38 | 9.3 | 10.1 | 239 |
| Example 1-139 | A-5 | C-39 | 9.8 | 10.6 | 221 |
| Example 1-140 | A-5 | C-40 | 9.9 | 9.2 | 298 |
| Example 1-141 | A-5 | C-41 | 9.6 | 9.7 | 223 |
| Example 1-142 | A-5 | C-42 | 9.4 | 10.3 | 246 |
| Example 1-143 | A-6 | C-30 | 9.9 | 9.6 | 245 |
| Example 1-144 | A-6 | C-31 | 9.5 | 9.8 | 229 |
| Example 1-145 | A-6 | C-32 | 9.8 | 9.6 | 216 |
| Example 1-146 | A-6 | C-35 | 9.6 | 9.8 | 202 |
| Example 1-147 | A-6 | C-36 | 9.2 | 10.1 | 187 |
| Example 1-148 | A-6 | C-39 | 9.3 | 10.7 | 176 |
| Example 1-149 | A-6 | C-40 | 9.9 | 9.6 | 220 |
| Example 1-150 | A-7 | C-30 | 9.9 | 8.2 | 149 |
| Example 1-151 | A-7 | C-33 | 9.8 | 8.4 | 135 |
| Example 1-152 | A-7 | C-34 | 9.8 | 8.1 | 140 |
| Example 1-153 | A-7 | C-37 | 9.0 | 9.0 | 124 |
| Example 1-154 | A-7 | C-38 | 9.2 | 8.8 | 129 |
| Example 1-155 | A-7 | C-41 | 9.4 | 8.6 | 122 |
| Example 1-156 | A-7 | C-42 | 9.1 | 8.8 | 130 |
| Example 1-157 | A-2 | C-46 | 9.3 | 9.0 | 223 |
| Example 1-158 | A-2 | C-48 | 9.0 | 9.2 | 220 |
| Example 1-159 | A-2 | C-51 | 9.8 | 8.1 | 231 |
| Example 1-160 | A-2 | C-53 | 9.7 | 8.2 | 239 |
| Example 1-161 | A-2 | C-55 | 9.7 | 8.2 | 226 |
| Example 1-162 | A-3 | C-47 | 9.4 | 9.0 | 132 |
| Example 1-163 | A-3 | C-49 | 8.9 | 9.5 | 127 |
| Example 1-164 | A-3 | C-52 | 9.7 | 8.7 | 147 |
| Example 1-165 | A-3 | C-54 | 9.3 | 9.2 | 134 |
| Example 1-166 | A-3 | C-56 | 9.1 | 9.3 | 115 |
| Example 1-167 | A-4 | C-46 | 9.6 | 9.8 | 238 |
| Example 1-168 | A-4 | C-47 | 9.8 | 9.4 | 216 |
| Example 1-169 | A-4 | C-48 | 9.2 | 10.0 | 224 |
| Example 1-170 | A-4 | C-49 | 9.1 | 9.9 | 208 |
| Example 1-171 | A-4 | C-51 | 9.8 | 8.7 | 236 |
| Example 1-172 | A-4 | C-52 | 9.8 | 8.8 | 234 |
| Example 1-173 | A-4 | C-53 | 9.8 | 9.0 | 245 |
| Example 1-174 | A-4 | C-54 | 9.6 | 9.6 | 211 |
| Example 1-175 | A-4 | C-55 | 9.7 | 9.2 | 230 |
| Example 1-176 | A-4 | C-56 | 9.2 | 9.8 | 198 |
| Example 1-177 | A-5 | C-46 | 9.5 | 9.8 | 291 |
| Example 1-178 | A-5 | C-47 | 9.7 | 9.6 | 273 |
| Example 1-179 | A-5 | C-48 | 9.3 | 10.0 | 287 |
| Example 1-180 | A-5 | C-49 | 9.2 | 10.0 | 262 |
| Example 1-181 | A-5 | C-51 | 9.9 | 9.1 | 298 |
| Example 1-182 | A-5 | C-52 | 9.8 | 9.3 | 303 |
| Example 1-183 | A-5 | C-53 | 9.7 | 9.4 | 288 |
| Example 1-184 | A-5 | C-54 | 9.6 | 9.7 | 259 |
| Example 1-185 | A-5 | C-55 | 9.8 | 9.5 | 283 |
| Example 1-186 | A-5 | C-56 | 9.3 | 9.7 | 238 |
| Example 1-187 | A-6 | C-46 | 9.3 | 9.7 | 240 |
| Example 1-188 | A-6 | C-47 | 9.4 | 9.5 | 227 |
| Example 1-189 | A-6 | C-51 | 9.6 | 9.0 | 241 |
| Example 1-190 | A-6 | C-52 | 9.6 | 9.2 | 238 |
| Example 1-191 | A-6 | C-55 | 9.5 | 9.4 | 229 |
| Example 1-192 | A-6 | C-56 | 8.8 | 9.9 | 200 |
| Example 1-193 | A-7 | C-46 | 9.6 | 8.7 | 144 |
| Example 1-194 | A-7 | C-48 | 9.4 | 9.1 | 137 |
| Example 1-195 | A-7 | C-49 | 9.3 | 9.1 | 129 |
| Example 1-196 | A-7 | C-51 | 10.0 | 8.0 | 145 |
| Example 1-197 | A-7 | C-54 | 9.6 | 8.6 | 131 |
| Example 1-198 | A-7 | C-55 | 9.9 | 8.1 | 134 |

As apparent from the above results, the device of the present invention had higher external quantum efficiency and lower driving voltage than the comparative devices. In particular, high durability was shown when driving at a high temperature (70° C.).
Example 2
Comparative Example 2-1
B-1
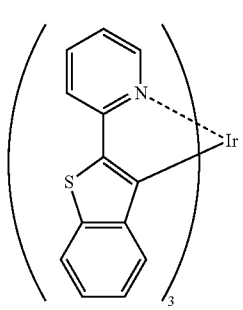
B-2
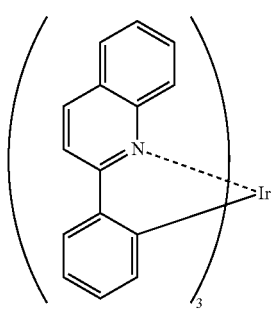
B-3
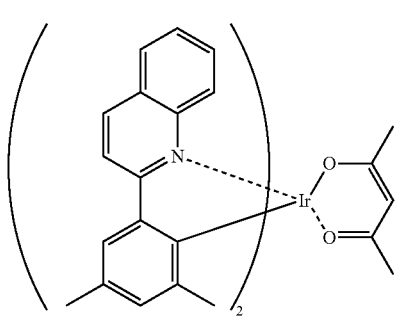
B-4
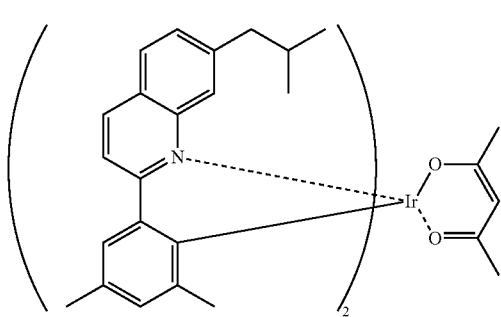
B-5
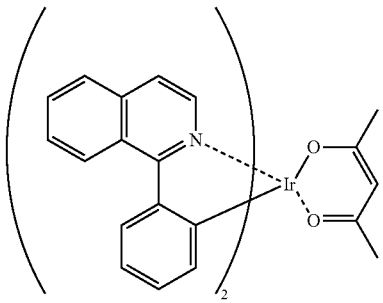
B-6
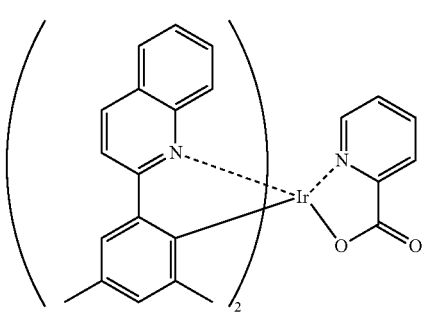
B-7
B-8
B-9
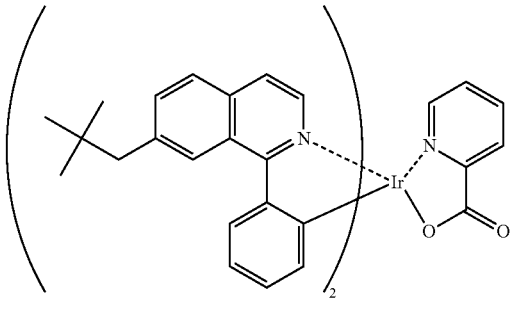

An organic EL device in Comparative Example 2-1 was manufactured in the same manner as in Comparative Example 1-1, except that vapor deposition was performed by changing a composition ratio of the film of the light emitting layer from 9:91 (mass ratio) of A-1 to C-1 in Comparative Example 1-1 to 5:95 (mass ratio) of B-1 to C-1 (film thickness: 30 nm). A direct current constant voltage was applied to the organic EL device to emit light by means of a source measure unit Model 2400 manufactured by Toyo Technica, and as a result, light emission derived from B-1 could be obtained.

Examples 2-1 to 2-249 and Comparative Examples 2-2 to 2-15

Devices in Examples 2-1 to 2-249 and Comparative Examples 2-2 to 2-15 were manufactured in the same manner as in Comparative Example 2-1, except that the materials used in Comparative Example 2-1 were changed into the materials described in Table 2. A direct current constant voltage was applied to the organic EL device to emit light by means of a source measure unit Model 2400 manufactured by Toyo Technica, and as a result, a light emission of color derived from each light emitting material could be obtained.

The devices thus-obtained above were evaluated in the same manner as in Example 1.

TABLE 2

|  | Light emitting layer | | Driving voltage (V) at 1000 cd/m$^2$ | External quantum efficiency (%) at 1000 cd/m$^2$ | Half-luminance intensity time (relative value) at an ambient air temperature of 70° C. and 1000 cd/m$^2$ |
|---|---|---|---|---|---|
|  | Light emitting material | Host material | | | |
| Comparative example 2-1 | B-1 | C-1 | 11.1 | 5.3 | 100 |
| Comparative example 2-2 | B-1 | C-3 | 11.3 | 5.4 | 104 |
| Comparative example 2-3 | B-1 | C-6 | 11.2 | 5.3 | 110 |
| Comparative example 2-4 | B-1 | C-9 | 11.4 | 5.1 | 108 |
| Comparative example 2-5 | B-1 | H-1 | 10.8 | 5.6 | 96 |
| Comparative example 2-6 | B-3 | H-1 | 10.6 | 5.8 | 185 |
| Comparative example 2-7 | B-6 | H-1 | 10.5 | 5.7 | 176 |
| Comparative example 2-8 | B-8 | H-1 | 10.4 | 5.5 | 153 |
| Example 2-1 | B-2 | C-1 | 10.3 | 6.1 | 239 |
| Example 2-2 | B-2 | C-3 | 10.5 | 6.3 | 243 |
| Example 2-3 | B-2 | C-6 | 10.3 | 6.2 | 266 |
| Example 2-4 | B-2 | C-9 | 10.5 | 6.1 | 233 |
| Example 2-5 | B-3 | C-1 | 10.7 | 6.3 | 253 |
| Example 2-6 | B-3 | C-3 | 10.8 | 6.4 | 264 |
| Example 2-7 | B-3 | C-4 | 10.7 | 6.6 | 275 |
| Example 2-8 | B-3 | C-6 | 10.5 | 6.4 | 271 |
| Example 2-9 | B-3 | C-7 | 10.6 | 6.5 | 264 |
| Example 2-10 | B-3 | C-8 | 10.9 | 6.2 | 234 |
| Example 2-11 | B-4 | C-2 | 10.6 | 6.5 | 265 |
| Example 2-12 | B-4 | C-3 | 10.7 | 6.4 | 276 |
| Example 2-13 | B-4 | C-5 | 10.1 | 6.9 | 253 |
| Example 2-14 | B-4 | C-6 | 10.6 | 6.4 | 294 |
| Example 2-15 | B-4 | C-7 | 10.5 | 6.5 | 301 |
| Example 2-16 | B-4 | C-9 | 10.8 | 6.3 | 278 |
| Example 2-17 | B-5 | C-1 | 10.3 | 6.1 | 223 |
| Example 2-18 | B-5 | C-2 | 10.4 | 6.3 | 235 |
| Example 2-19 | B-5 | C-3 | 10.3 | 6.5 | 253 |
| Example 2-20 | B-5 | C-6 | 10.5 | 6.2 | 272 |
| Example 2-21 | B-5 | C-8 | 10.7 | 6.1 | 211 |
| Example 2-22 | B-6 | C-1 | 10.1 | 6.3 | 288 |
| Example 2-23 | B-6 | C-3 | 10 | 6.4 | 273 |
| Example 2-24 | B-6 | C-4 | 10.3 | 6.5 | 298 |
| Example 2-25 | B-6 | C-6 | 10.2 | 6.2 | 285 |
| Example 2-27 | B-6 | C-7 | 10.3 | 6.2 | 301 |
| Example 2-28 | B-7 | C-1 | 10.4 | 6.2 | 242 |
| Example 2-29 | B-7 | C-3 | 10.4 | 6.3 | 261 |
| Example 2-30 | B-7 | C-4 | 10.4 | 6.4 | 279 |
| Example 2-31 | B-7 | C-6 | 10.2 | 6.3 | 280 |
| Example 2-32 | B-7 | C-8 | 10.4 | 6.2 | 251 |
| Example 2-33 | B-8 | C-1 | 10.2 | 6.1 | 241 |
| Example 2-34 | B-8 | C-2 | 10.3 | 6.2 | 235 |
| Example 2-35 | B-8 | C-6 | 10.1 | 6.4 | 253 |
| Example 2-36 | B-8 | C-8 | 10.1 | 6.3 | 278 |
| Example 2-37 | B-8 | C-9 | 10.4 | 6.1 | 239 |
| Example 2-38 | B-9 | C-1 | 10.6 | 6.3 | 234 |
| Example 2-39 | B-9 | C-2 | 10.4 | 6.3 | 237 |

TABLE 2-continued

| | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
| | Light emitting material | Host material | | | |
| Example 2-40 | B-9 | C-4 | 10.4 | 6.3 | 251 |
| Example 2-41 | B-9 | C-7 | 10.5 | 6.2 | 263 |
| Comparative example 2-9 | B-1 | C-11 | 10.9 | 5.4 | 118 |
| Comparative example 2-10 | B-1 | C-14 | 10.6 | 5.7 | 87 |
| Comparative example 2-11 | B-1 | C-18 | 11.0 | 5.4 | 86 |
| Comparative example 2-12 | B-1 | C-19 | 10.3 | 5.8 | 92 |
| Comparative example 2-13 | B-1 | C-20 | 10.2 | 5.8 | 109 |
| Comparative example 2-14 | B-1 | C-21 | 10.9 | 5.4 | 93 |
| Comparative example 2-15 | B-1 | C-22 | 10.8 | 5.5 | 81 |
| Example 2-42 | B-2 | C-11 | 10.1 | 6.3 | 262 |
| Example 2-43 | B-2 | C-12 | 9.8 | 6.4 | 213 |
| Example 2-44 | B-2 | C-14 | 9.3 | 6.8 | 228 |
| Example 2-45 | B-2 | C-15 | 9.6 | 6.5 | 221 |
| Example 2-46 | B-2 | C-19 | 9.4 | 6.6 | 252 |
| Example 2-47 | B-2 | C-20 | 9.2 | 7.2 | 286 |
| Example 2-48 | B-2 | C-22 | 9.7 | 6.5 | 205 |
| Example 2-49 | B-2 | C-23 | 10.4 | 6.0 | 234 |
| Example 2-50 | B-3 | C-11 | 10.5 | 6.5 | 281 |
| Example 2-51 | B-3 | C-13 | 10.0 | 6.8 | 219 |
| Example 2-52 | B-3 | C-14 | 9.8 | 7.1 | 236 |
| Example 2-53 | B-3 | C-15 | 9.9 | 6.7 | 201 |
| Example 2-54 | B-3 | C-16 | 10.3 | 6.5 | 208 |
| Example 2-55 | B-3 | C-19 | 9.8 | 7.1 | 233 |
| Example 2-56 | B-3 | C-20 | 9.6 | 7.4 | 297 |
| Example 2-57 | B-3 | C-21 | 10.5 | 6.4 | 240 |
| Example 2-58 | B-3 | C-23 | 10.9 | 6.2 | 249 |
| Example 2-59 | B-4 | C-11 | 10.3 | 6.8 | 296 |
| Example 2-60 | B-4 | C-13 | 9.7 | 7.2 | 230 |
| Example 2-61 | B-4 | C-14 | 9.4 | 7.5 | 244 |
| Example 2-62 | B-4 | C-18 | 10.0 | 7.1 | 216 |
| Example 2-63 | B-4 | C-19 | 9.5 | 7.1 | 241 |
| Example 2-64 | B-4 | C-20 | 9.4 | 7.6 | 309 |
| Example 2-65 | B-4 | C-21 | 10.5 | 6.5 | 249 |
| Example 2-66 | B-4 | C-22 | 9.7 | 7.1 | 215 |
| Example 2-67 | B-5 | C-11 | 10.0 | 6.4 | 255 |
| Example 2-68 | B-5 | C-14 | 9.3 | 7.5 | 219 |
| Example 2-69 | B-5 | C-17 | 10.8 | 5.8 | 217 |
| Example 2-70 | B-5 | C-19 | 9.4 | 7.4 | 210 |
| Example 2-71 | B-5 | C-20 | 9.2 | 7.7 | 268 |
| Example 2-72 | B-5 | C-22 | 9.7 | 6.7 | 199 |
| Example 2-73 | B-5 | C-23 | 10.4 | 6.0 | 217 |
| Example 2-74 | B-6 | C-11 | 9.8 | 6.4 | 313 |
| Example 2-75 | B-6 | C-12 | 9.9 | 6.5 | 258 |
| Example 2-76 | B-6 | C-14 | 9.2 | 7.5 | 264 |
| Example 2-77 | B-6 | C-15 | 9.7 | 6.8 | 238 |
| Example 2-78 | B-6 | C-19 | 9.3 | 7.5 | 256 |
| Example 2-79 | B-6 | C-20 | 9.1 | 7.4 | 281 |
| Example 2-80 | B-6 | C-21 | 10.0 | 6.2 | 281 |
| Example 2-81 | B-6 | C-23 | 10.3 | 6.2 | 282 |
| Example 2-82 | B-7 | C-11 | 10.3 | 6.4 | 266 |
| Example 2-83 | B-7 | C-13 | 9.8 | 7.2 | 203 |
| Example 2-84 | B-7 | C-14 | 9.5 | 7.5 | 229 |
| Example 2-85 | B-7 | C-16 | 10.0 | 6.9 | 191 |
| Example 2-86 | B-7 | C-19 | 9.6 | 7.3 | 224 |
| Example 2-87 | B-7 | C-20 | 9.5 | 7.3 | 275 |
| Example 2-88 | B-7 | C-21 | 10.2 | 6.2 | 230 |
| Example 2-89 | B-7 | C-22 | 9.8 | 7.1 | 195 |
| Example 2-90 | B-8 | C-11 | 10.0 | 6.2 | 266 |
| Example 2-91 | B-8 | C-14 | 9.3 | 7.5 | 228 |
| Example 2-92 | B-8 | C-17 | 10.9 | 5.7 | 236 |
| Example 2-93 | B-8 | C-19 | 9.4 | 7.3 | 219 |
| Example 2-94 | B-8 | C-20 | 9.2 | 7.6 | 273 |
| Example 2-95 | B-8 | C-22 | 9.9 | 6.7 | 199 |
| Example 2-96 | B-8 | C-23 | 10.3 | 6.2 | 232 |
| Example 2-97 | B-9 | C-11 | 10.4 | 6.5 | 266 |

TABLE 2-continued

|  | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
|  | Light emitting material | Host material | | | |
| Example 2-98 | B-9 | C-12 | 10.2 | 6.7 | 197 |
| Example 2-99 | B-9 | C-14 | 9.3 | 7.7 | 219 |
| Example 2-100 | B-9 | C-18 | 10.2 | 6.5 | 189 |
| Example 2-101 | B-9 | C-19 | 9.4 | 7.5 | 214 |
| Example 2-102 | B-9 | C-20 | 9.3 | 7.6 | 281 |
| Example 2-103 | B-9 | C-21 | 10.3 | 6.4 | 222 |
| Example 2-104 | B-9 | C-23 | 10.6 | 6.1 | 228 |
| Example 2-105 | B-2 | C-24 | 9.8 | 6.2 | 211 |
| Example 2-106 | B-3 | C-25 | 9.6 | 7.3 | 243 |
| Example 2-107 | B-4 | C-26 | 10.1 | 6.7 | 227 |
| Example 2-108 | B-5 | C-24 | 10.0 | 6.6 | 221 |
| Example 2-109 | B-6 | C-25 | 9.7 | 7.0 | 250 |
| Example 2-110 | B-7 | C-26 | 10.0 | 6.2 | 229 |
| Example 2-111 | B-8 | C-25 | 9.8 | 6.8 | 196 |
| Example 2-112 | B-9 | C-24 | 10.3 | 6.5 | 212 |
| Example 2-113 | B-2 | C-29 | 9.7 | 6.5 | 198 |
| Example 2-114 | B-3 | C-28 | 10.0 | 6.7 | 208 |
| Example 2-115 | B-4 | C-27 | 10.7 | 6.4 | 246 |
| Example 2-116 | B-5 | C-29 | 9.9 | 6.7 | 188 |
| Example 2-117 | B-6 | C-28 | 10.1 | 6.4 | 241 |
| Example 2-118 | B-7 | C-27 | 10.2 | 6.1 | 222 |
| Example 2-119 | B-8 | C-29 | 10.1 | 6.7 | 183 |
| Example 2-120 | B-9 | C-27 | 10.6 | 6.1 | 226 |
| Example 2-121 | B-2 | C-30 | 10.5 | 6.3 | 251 |
| Example 2-122 | B-2 | C-32 | 10.3 | 6.4 | 225 |
| Example 2-123 | B-2 | C-34 | 10.6 | 6.2 | 223 |
| Example 2-124 | B-2 | C-36 | 9.8 | 6.9 | 201 |
| Example 2-125 | B-2 | C-38 | 9.8 | 6.8 | 208 |
| Example 2-126 | B-2 | C-39 | 10.0 | 7.3 | 196 |
| Example 2-127 | B-2 | C-40 | 10.6 | 6.3 | 238 |
| Example 2-128 | B-2 | C-42 | 9.9 | 6.9 | 210 |
| Example 2-129 | B-3 | C-30 | 10.8 | 6.5 | 262 |
| Example 2-130 | B-3 | C-31 | 10.3 | 6.9 | 236 |
| Example 2-131 | B-3 | C-33 | 10.6 | 6.6 | 229 |
| Example 2-132 | B-3 | C-34 | 10.9 | 6.3 | 241 |
| Example 2-133 | B-3 | C-35 | 10.5 | 6.7 | 230 |
| Example 2-134 | B-3 | C-37 | 9.7 | 7.6 | 202 |
| Example 2-135 | B-3 | C-39 | 10.0 | 7.9 | 197 |
| Example 2-136 | B-3 | C-41 | 10.1 | 7.3 | 208 |
| Example 2-137 | B-4 | C-30 | 10.8 | 6.3 | 291 |
| Example 2-138 | B-4 | C-31 | 10.2 | 6.7 | 265 |
| Example 2-139 | B-4 | C-32 | 10.7 | 6.4 | 258 |
| Example 2-140 | B-4 | C-33 | 10.7 | 6.3 | 244 |
| Example 2-141 | B-4 | C-34 | 10.9 | 6.2 | 267 |
| Example 2-142 | B-4 | C-35 | 10.6 | 6.5 | 253 |
| Example 2-143 | B-4 | C-36 | 10.1 | 6.9 | 229 |
| Example 2-144 | B-4 | C-37 | 9.8 | 7.3 | 217 |
| Example 2-145 | B-4 | C-38 | 9.9 | 7.2 | 225 |
| Example 2-146 | B-4 | C-39 | 10.0 | 7.5 | 210 |
| Example 2-147 | B-4 | C-40 | 10.9 | 6.3 | 270 |
| Example 2-148 | B-4 | C-41 | 10.3 | 6.9 | 213 |
| Example 2-149 | B-4 | C-42 | 10.0 | 7.3 | 234 |
| Example 2-150 | B-5 | C-30 | 10.8 | 6.4 | 266 |
| Example 2-151 | B-5 | C-31 | 10.3 | 6.7 | 243 |
| Example 2-152 | B-5 | C-34 | 10.9 | 6.2 | 245 |
| Example 2-153 | B-5 | C-35 | 10.3 | 6.6 | 232 |
| Example 2-154 | B-5 | C-38 | 9.9 | 6.9 | 230 |
| Example 2-155 | B-5 | C-39 | 9.9 | 7.4 | 203 |
| Example 2-156 | B-6 | C-30 | 10.4 | 6.3 | 286 |
| Example 2-157 | B-6 | C-31 | 9.9 | 6.6 | 266 |
| Example 2-158 | B-6 | C-32 | 10.3 | 6.4 | 254 |
| Example 2-159 | B-6 | C-33 | 10.4 | 6.3 | 245 |
| Example 2-160 | B-6 | C-34 | 10.5 | 6.2 | 260 |
| Example 2-161 | B-6 | C-35 | 10.0 | 6.6 | 245 |
| Example 2-162 | B-6 | C-36 | 9.7 | 6.8 | 222 |
| Example 2-163 | B-6 | C-37 | 9.4 | 7.4 | 214 |
| Example 2-164 | B-6 | C-38 | 9.6 | 7.0 | 233 |
| Example 2-165 | B-6 | C-39 | 9.7 | 7.6 | 208 |
| Example 2-166 | B-6 | C-40 | 10.4 | 6.2 | 271 |

TABLE 2-continued

|  | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
|  | Light emitting material | Host material | | | |
| Example 2-167 | B-6 | C-41 | 10.0 | 6.5 | 224 |
| Example 2-168 | B-6 | C-42 | 9.8 | 7.0 | 229 |
| Example 2-169 | B-7 | C-30 | 10.5 | 6.3 | 273 |
| Example 2-170 | B-7 | C-32 | 10.3 | 6.4 | 248 |
| Example 2-171 | B-7 | C-33 | 10.4 | 6.4 | 236 |
| Example 2-172 | B-7 | C-36 | 9.8 | 6.9 | 211 |
| Example 2-173 | B-7 | C-37 | 9.5 | 7.5 | 213 |
| Example 2-174 | B-7 | C-40 | 10.5 | 6.2 | 260 |
| Example 2-175 | B-7 | C-41 | 10.2 | 6.5 | 223 |
| Example 2-176 | B-8 | C-30 | 10.3 | 6.1 | 239 |
| Example 2-177 | B-8 | C-33 | 10.3 | 6.2 | 210 |
| Example 2-178 | B-8 | C-34 | 10.4 | 6.0 | 219 |
| Example 2-179 | B-8 | C-37 | 9.3 | 7.2 | 188 |
| Example 2-180 | B-8 | C-38 | 9.6 | 6.9 | 204 |
| Example 2-181 | B-8 | C-41 | 10.2 | 6.4 | 197 |
| Example 2-182 | B-8 | C-42 | 10.0 | 6.7 | 207 |
| Example 2-183 | B-9 | C-30 | 10.5 | 6.2 | 243 |
| Example 2-184 | B-9 | C-31 | 10.2 | 6.4 | 224 |
| Example 2-185 | B-9 | C-32 | 10.4 | 6.3 | 218 |
| Example 2-186 | B-9 | C-33 | 10.5 | 6.1 | 212 |
| Example 2-187 | B-9 | C-37 | 9.6 | 7.3 | 185 |
| Example 2-188 | B-9 | C-38 | 9.9 | 7.0 | 201 |
| Example 2-189 | B-9 | C-39 | 9.9 | 7.5 | 181 |
| Example 2-190 | B-2 | C-46 | 9.8 | 6.5 | 241 |
| Example 2-191 | B-2 | C-48 | 9.5 | 6.7 | 237 |
| Example 2-192 | B-2 | C-50 | 9.2 | 6.9 | 277 |
| Example 2-193 | B-2 | C-52 | 10.5 | 6.0 | 239 |
| Example 2-194 | B-2 | C-54 | 9.8 | 6.6 | 211 |
| Example 2-195 | B-2 | C-56 | 9.3 | 6.7 | 200 |
| Example 2-196 | B-3 | C-46 | 9.9 | 6.7 | 244 |
| Example 2-197 | B-3 | C-47 | 10.1 | 6.5 | 233 |
| Example 2-198 | B-3 | C-49 | 9.8 | 6.8 | 223 |
| Example 2-199 | B-3 | C-51 | 10.6 | 6.3 | 245 |
| Example 2-200 | B-3 | C-53 | 10.3 | 6.4 | 251 |
| Example 2-201 | B-3 | C-55 | 10.3 | 6.6 | 250 |
| Example 2-202 | B-4 | C-46 | 9.7 | 6.7 | 273 |
| Example 2-203 | B-4 | C-47 | 10.1 | 6.3 | 250 |
| Example 2-204 | B-4 | C-48 | 9.4 | 6.9 | 261 |
| Example 2-205 | B-4 | C-49 | 9.3 | 6.8 | 238 |
| Example 2-206 | B-4 | C-50 | 9.3 | 7.3 | 295 |
| Example 2-207 | B-4 | C-51 | 10.7 | 6.2 | 275 |
| Example 2-208 | B-4 | C-52 | 10.6 | 6.4 | 273 |
| Example 2-209 | B-4 | C-53 | 10.5 | 6.4 | 279 |
| Example 2-210 | B-4 | C-54 | 9.9 | 6.5 | 238 |
| Example 2-211 | B-4 | C-55 | 10.3 | 6.4 | 262 |
| Example 2-212 | B-4 | C-56 | 9.5 | 6.7 | 222 |
| Example 2-213 | B-5 | C-46 | 10.1 | 6.8 | 251 |
| Example 2-214 | B-5 | C-47 | 10.3 | 6.4 | 229 |
| Example 2-215 | B-5 | C-50 | 9.6 | 7.1 | 233 |
| Example 2-216 | B-5 | C-51 | 10.6 | 6.0 | 248 |
| Example 2-217 | B-5 | C-54 | 10.1 | 6.5 | 223 |
| Example 2-218 | B-5 | C-55 | 10.4 | 6.2 | 244 |
| Example 2-219 | B-6 | C-46 | 9.8 | 6.8 | 266 |
| Example 2-220 | B-6 | C-47 | 10.0 | 6.4 | 245 |
| Example 2-221 | B-6 | C-48 | 9.5 | 7.1 | 260 |
| Example 2-222 | B-6 | C-49 | 9.5 | 7.1 | 233 |
| Example 2-223 | B-6 | C-50 | 9.4 | 7.5 | 288 |
| Example 2-224 | B-6 | C-51 | 10.3 | 6.0 | 262 |
| Example 2-225 | B-6 | C-52 | 10.2 | 6.1 | 266 |
| Example 2-226 | B-6 | C-53 | 10.2 | 6.3 | 272 |
| Example 2-227 | B-6 | C-54 | 10.0 | 6.7 | 232 |
| Example 2-228 | B-6 | C-55 | 10.1 | 6.4 | 258 |
| Example 2-229 | B-6 | C-56 | 9.8 | 7.0 | 210 |
| Example 2-230 | B-7 | C-46 | 9.9 | 6.8 | 255 |
| Example 2-231 | B-7 | C-48 | 9.7 | 7.1 | 244 |
| Example 2-232 | B-7 | C-49 | 9.8 | 7.1 | 221 |
| Example 2-233 | B-7 | C-50 | 9.6 | 7.5 | 280 |
| Example 2-234 | B-7 | C-52 | 10.2 | 6.1 | 257 |
| Example 2-235 | B-7 | C-53 | 10.0 | 6.5 | 261 |

TABLE 2-continued

|  | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
| --- | --- | --- | --- | --- | --- |
|  | Light emitting material | Host material |  |  |  |
| Example 2-236 | B-7 | C-56 | 9.8 | 6.9 | 209 |
| Example 2-237 | B-8 | C-46 | 9.8 | 6.8 | 235 |
| Example 2-238 | B-8 | C-47 | 10.0 | 6.5 | 219 |
| Example 2-239 | B-8 | C-48 | 9.5 | 7.1 | 227 |
| Example 2-240 | B-8 | C-52 | 10.2 | 6.2 | 238 |
| Example 2-241 | B-8 | C-53 | 10.2 | 6.3 | 234 |
| Example 2-242 | B-8 | C-54 | 9.9 | 6.6 | 205 |
| Example 2-243 | B-9 | C-46 | 9.9 | 6.8 | 240 |
| Example 2-244 | B-9 | C-48 | 9.6 | 7.3 | 241 |
| Example 2-245 | B-9 | C-49 | 9.4 | 7.5 | 223 |
| Example 2-246 | B-9 | C-50 | 9.5 | 7.7 | 280 |
| Example 2-247 | B-9 | C-54 | 10.1 | 6.7 | 222 |
| Example 2-248 | B-9 | C-55 | 10.5 | 6.4 | 229 |
| Example 2-249 | B-9 | C-56 | 9.6 | 6.7 | 207 |

As apparent from the above results, the device of the present invention had higher external quantum efficiency and lower driving voltage than the comparative devices. In particular, high durability was shown when driving at a high temperature (70° C.).

Example 3

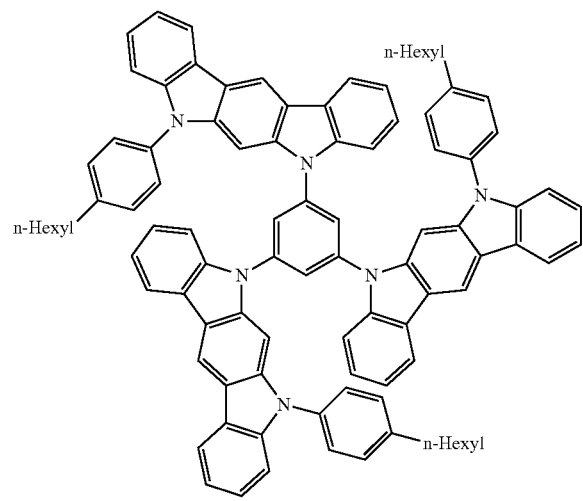

C-10

Comparative Example 3-1

A glass substrate having an ITO film having a thickness of 0.5 mm and each side of 2.5 cm in square (manufactured by Geomatec Co., Ltd., and surface resistance 10Ω/□) was put into a washing container, ultrasonically washed in 2-propanol, followed by UV-ozone treatment for 30 min. A solution of poly(3,4-ethylenedioxythiophene)-polystyrene-sulfonate (PEDOT/PSS) diluted with pure water in an amount of 70% by mass was coated on this by using a spin coater to provide a hole transporting layer having a thickness of 50 nm. A methylene chloride solution in which A-1 and C-1 were dissolved in a ratio of 4:96 (mass ratio) was coated by using a spin coater to obtain a light emitting layer having a thickness of 30 nm. Thereon, BAlq [bis-(2-methyl-8-quinolinolate)-4-(phenylphenolate)aluminum] was vapor-deposited to a thickness of 40 nm. Thereon, lithium chloride as a cathode buffer layer and aluminum as a cathode were vapor-deposited to thicknesses of 0.5 nm and 150 nm, respectively, in a vapor deposition apparatus. This was placed in a glove box substituted with argon gas so as not to be exposed to the atmosphere and sealed using a stainless steel-made sealing tube and a UV-curable adhesive (XNR5516HV, manufactured by Nagase-CHIBA Ltd.) to manufacture an organic EL device in Comparative Example 3-1. A direct current constant voltage was applied to the organic EL device to emit light by means of a source measure unit Model 2400 manufactured by Toyo Technica, and as a result, light emission derived from A-1 could be obtained.

Examples 3-1 to 3-133 and Comparative Examples 3-2 to 3-7

Devices in Examples 3-1 to 3-133 and Comparative Examples 3-2 to 3-7 were manufactured in the same manner as in Comparative Example 3-1, except that the materials used in Comparative Example 3-1 were changed into the materials described in Table 3. A direct current constant voltage was applied to the organic EL device to emit light by means of a source measure unit Model 2400 manufactured by Toyo Technica, and as a result, a light emission of color derived from each light emitting material could be obtained.

The devices thus-obtained above were evaluated in the same manner as in Example 1.

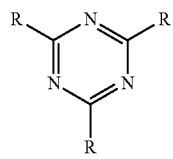 R = 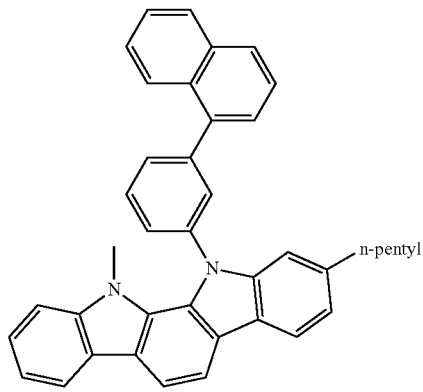 C-43
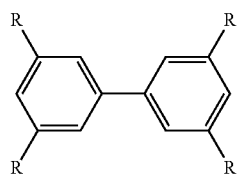 R = 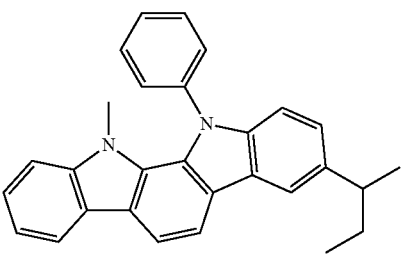 C-44
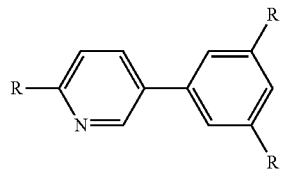 R = 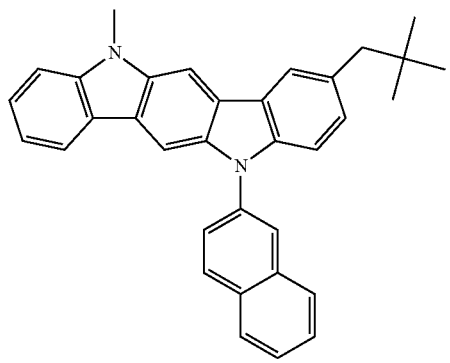 C-45
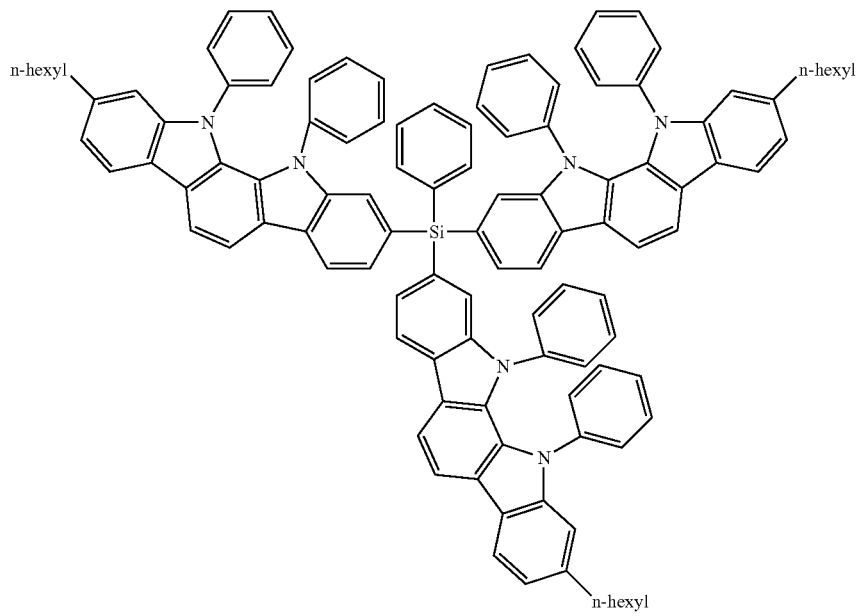 C-57

-continued
C-58
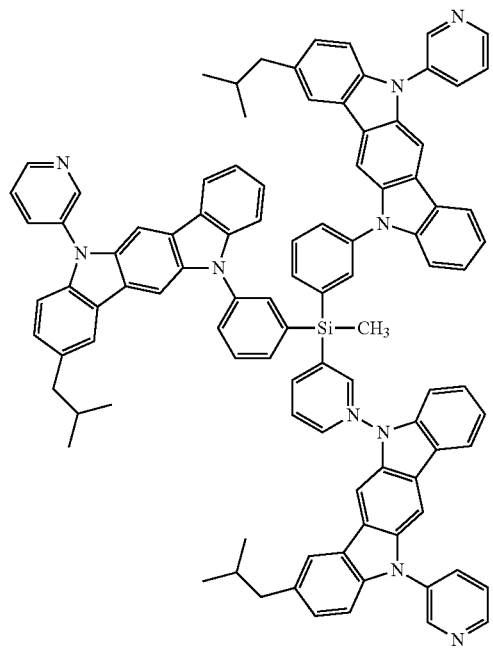
C-59
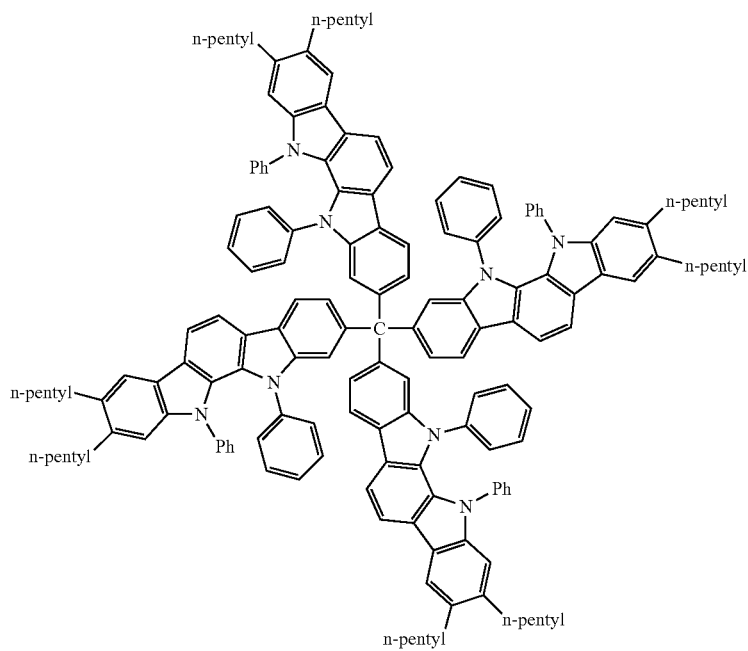
TABLE 3
| | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
| | Light emitting material | Host material | | | |
| Comparative example 3-1 | A-1 | C-1 | 14.3 | 3.2 | 100 |
| Comparative example 3-2 | A-1 | C-3 | 14.9 | 2.9 | 92 |
| Comparative example 3-3 | A-1 | C-10 | 15.6 | 2.8 | 83 |

TABLE 3-continued

| | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
| | Light emitting material | Host material | | | |
| Comparative example 3-4 | A-1 | H-1 | 14.5 | 2.8 | 131 |
| Comparative example 3-5 | A-5 | H-1 | 13.8 | 3.8 | 183 |
| Example 3-1 | A-2 | C-1 | 13.6 | 5.1 | 215 |
| Example 3-2 | A-2 | C-3 | 13.7 | 4.9 | 242 |
| Example 3-3 | A-2 | C-6 | 13.6 | 4.9 | 259 |
| Example 3-4 | A-2 | C-10 | 14.0 | 4.7 | 208 |
| Example 3-5 | A-3 | C-1 | 13.6 | 5.3 | 239 |
| Example 3-6 | A-3 | C-2 | 13.7 | 5.4 | 247 |
| Example 3-7 | A-3 | C-9 | 13.5 | 5.3 | 232 |
| Example 3-8 | A-3 | C-10 | 13.9 | 5.1 | 209 |
| Example 3-9 | A-4 | C-2 | 13.4 | 5.8 | 258 |
| Example 3-10 | A-4 | C-3 | 13.6 | 5.7 | 261 |
| Example 3-11 | A-4 | C-6 | 13.4 | 5.7 | 283 |
| Example 3-12 | A-4 | C-8 | 13.7 | 5.6 | 239 |
| Example 3-13 | A-5 | C-1 | 13.3 | 5.6 | 259 |
| Example 3-14 | A-5 | C-6 | 13.8 | 5.3 | 366 |
| Example 3-15 | A-5 | C-9 | 13.5 | 5.5 | 261 |
| Example 3-16 | A-5 | C-10 | 14.1 | 5.1 | 223 |
| Example 3-130 | A-6 | C-1 | 13.3 | 5.7 | 249 |
| Example 3-131 | A-6 | C-4 | 13.5 | 5.5 | 276 |
| Example 3-132 | A-6 | C-9 | 13.4 | 5.6 | 281 |
| Example 3-133 | A-6 | C-10 | 14.2 | 5.0 | 209 |
| Comparative example 3-6 | A-1 | C-14 | 13.5 | 3.7 | 94 |
| Comparative example 3-7 | A-1 | C-21 | 14.3 | 3.3 | 91 |
| Example 3-17 | A-2 | C-11 | 13.4 | 5.3 | 239 |
| Example 3-18 | A-2 | C-14 | 12.2 | 6.0 | 201 |
| Example 3-19 | A-2 | C-15 | 12.4 | 5.8 | 188 |
| Example 3-20 | A-2 | C-22 | 13.3 | 5.4 | 179 |
| Example 3-21 | A-3 | C-11 | 13.4 | 5.5 | 261 |
| Example 3-22 | A-3 | C-12 | 13.1 | 5.7 | 197 |
| Example 3-23 | A-3 | C-14 | 12.3 | 6.5 | 220 |
| Example 3-24 | A-3 | C-16 | 13.3 | 5.7 | 193 |
| Example 3-25 | A-3 | C-18 | 13.2 | 5.6 | 188 |
| Example 3-26 | A-3 | C-21 | 13.0 | 5.8 | 192 |
| Example 3-27 | A-4 | C-11 | 13.2 | 6.0 | 275 |
| Example 3-28 | A-4 | C-13 | 12.5 | 6.6 | 231 |
| Example 3-29 | A-4 | C-14 | 12.2 | 6.9 | 244 |
| Example 3-30 | A-4 | C-17 | 13.6 | 5.7 | 260 |
| Example 3-31 | A-4 | C-23 | 13.6 | 5.6 | 239 |
| Example 3-32 | A-5 | C-11 | 13.1 | 5.8 | 283 |
| Example 3-33 | A-5 | C-12 | 12.9 | 5.8 | 217 |
| Example 3-34 | A-5 | C-14 | 12.1 | 6.7 | 243 |
| Example 3-35 | A-5 | C-18 | 13.0 | 5.7 | 208 |
| Example 3-36 | A-5 | C-21 | 13.0 | 5.8 | 245 |
| Example 3-37 | A-6 | C-11 | 13.0 | 5.9 | 277 |
| Example 3-38 | A-6 | C-13 | 12.3 | 6.5 | 216 |
| Example 3-39 | A-6 | C-14 | 12.0 | 6.9 | 232 |
| Example 3-40 | A-6 | C-15 | 12.2 | 6.7 | 218 |
| Example 3-41 | A-6 | C-18 | 12.7 | 6.1 | 208 |
| Example 3-42 | A-6 | C-22 | 12.4 | 6.5 | 203 |
| Example 3-43 | A-4 | C-24 | 13.0 | 6.2 | 240 |
| Example 3-44 | A-5 | C-25 | 12.5 | 6.3 | 208 |
| Example 3-45 | A-6 | C-26 | 12.7 | 6.1 | 233 |
| Example 3-46 | A-2 | C-27 | 13.7 | 5.2 | 207 |
| Example 3-47 | A-3 | C-28 | 13.3 | 5.6 | 186 |
| Example 3-48 | A-4 | C-27 | 13.5 | 5.7 | 244 |
| Example 3-49 | A-4 | C-29 | 12.5 | 6.2 | 210 |
| Example 3-50 | A-5 | C-28 | 12.8 | 6.0 | 209 |
| Example 3-51 | A-6 | C-27 | 13.5 | 5.5 | 233 |
| Example 3-52 | A-2 | C-30 | 13.8 | 5.0 | 238 |
| Example 3-53 | A-2 | C-32 | 13.6 | 5.1 | 218 |
| Example 3-54 | A-2 | C-34 | 13.7 | 5.1 | 221 |
| Example 3-55 | A-2 | C-36 | 13.1 | 5.4 | 187 |
| Example 3-56 | A-2 | C-38 | 13.0 | 5.5 | 193 |
| Example 3-57 | A-2 | C-43 | 12.8 | 5.6 | 180 |
| Example 3-58 | A-2 | C-44 | 13.9 | 5.2 | 212 |
| Example 3-59 | A-3 | C-30 | 13.6 | 5.3 | 237 |

TABLE 3-continued

| | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
| | Light emitting material | Host material | | | |
| Example 3-60 | A-3 | C-31 | 13.2 | 5.6 | 215 |
| Example 3-61 | A-3 | C-33 | 13.5 | 5.3 | 204 |
| Example 3-62 | A-3 | C-34 | 13.5 | 5.2 | 219 |
| Example 3-63 | A-3 | C-35 | 13.2 | 5.5 | 210 |
| Example 3-64 | A-3 | C-37 | 12.5 | 6.2 | 197 |
| Example 3-65 | A-3 | C-39 | 12.2 | 6.6 | 192 |
| Example 3-66 | A-3 | C-45 | 13.2 | 5.8 | 211 |
| Example 3-67 | A-4 | C-30 | 13.5 | 5.7 | 263 |
| Example 3-68 | A-4 | C-32 | 13.4 | 5.8 | 237 |
| Example 3-69 | A-4 | C-33 | 13.4 | 5.7 | 228 |
| Example 3-70 | A-4 | C-36 | 12.9 | 6.2 | 213 |
| Example 3-71 | A-4 | C-40 | 13.6 | 5.6 | 255 |
| Example 3-72 | A-4 | C-41 | 13.2 | 5.9 | 224 |
| Example 3-73 | A-4 | C-43 | 12.7 | 6.3 | 217 |
| Example 3-74 | A-4 | C-45 | 13.1 | 6.1 | 219 |
| Example 3-75 | A-5 | C-30 | 13.6 | 5.5 | 288 |
| Example 3-76 | A-5 | C-34 | 13.5 | 5.5 | 273 |
| Example 3-77 | A-5 | C-35 | 13.2 | 5.8 | 265 |
| Example 3-78 | A-5 | C-38 | 12.9 | 6.0 | 244 |
| Example 3-79 | A-5 | C-39 | 12.8 | 6.6 | 229 |
| Example 3-80 | A-5 | C-42 | 13.2 | 5.9 | 240 |
| Example 3-81 | A-5 | C-44 | 13.7 | 5.7 | 261 |
| Example 3-82 | A-5 | C-45 | 13.2 | 5.9 | 259 |
| Example 3-83 | A-6 | C-30 | 13.4 | 5.5 | 265 |
| Example 3-84 | A-6 | C-31 | 12.9 | 5.8 | 240 |
| Example 3-85 | A-6 | C-32 | 13.2 | 5.6 | 233 |
| Example 3-86 | A-6 | C-37 | 12.3 | 6.5 | 214 |
| Example 3-87 | A-6 | C-40 | 13.4 | 5.6 | 256 |
| Example 3-88 | A-6 | C-41 | 12.5 | 5.8 | 228 |
| Example 3-89 | A-6 | C-42 | 12.2 | 6.2 | 233 |
| Example 3-90 | A-6 | C-43 | 12.3 | 6.1 | 213 |
| Example 3-91 | A-6 | C-45 | 12.6 | 5.8 | 221 |
| Example 3-92 | A-2 | C-46 | 13.2 | 5.3 | 235 |
| Example 3-93 | A-2 | C-48 | 12.8 | 5.7 | 228 |
| Example 3-94 | A-2 | C-49 | 12.7 | 5.8 | 209 |
| Example 3-95 | A-2 | C-52 | 13.6 | 4.8 | 232 |
| Example 3-96 | A-2 | C-54 | 13.3 | 5.2 | 224 |
| Example 3-97 | A-2 | C-57 | 13.4 | 5.0 | 246 |
| Example 3-98 | A-2 | C-58 | 13.0 | 5.4 | 221 |
| Example 3-99 | A-3 | C-46 | 13.3 | 5.5 | 247 |
| Example 3-100 | A-3 | C-47 | 13.5 | 5.2 | 224 |
| Example 3-101 | A-3 | C-49 | 13.0 | 5.8 | 209 |
| Example 3-102 | A-3 | C-51 | 13.7 | 5.1 | 243 |
| Example 3-103 | A-3 | C-53 | 13.6 | 5.2 | 229 |
| Example 3-104 | A-3 | C-55 | 13.6 | 5.4 | 233 |
| Example 3-105 | A-3 | C-57 | 13.5 | 5.2 | 255 |
| Example 3-106 | A-3 | C-59 | 13.5 | 5.4 | 228 |
| Example 3-107 | A-4 | C-46 | 12.8 | 6.1 | 266 |
| Example 3-108 | A-4 | C-48 | 12.4 | 6.5 | 254 |
| Example 3-109 | A-4 | C-49 | 12.5 | 6.5 | 236 |
| Example 3-110 | A-4 | C-52 | 13.6 | 5.5 | 261 |
| Example 3-111 | A-4 | C-53 | 13.4 | 5.6 | 268 |
| Example 3-112 | A-4 | C-56 | 12.6 | 6.3 | 213 |
| Example 3-113 | A-4 | C-58 | 13.3 | 6.2 | 255 |
| Example 3-114 | A-4 | C-59 | 13.5 | 5.7 | 262 |
| Example 3-115 | A-5 | C-46 | 13.0 | 6.1 | 313 |
| Example 3-116 | A-5 | C-48 | 12.7 | 6.4 | 307 |
| Example 3-117 | A-5 | C-49 | 12.5 | 6.5 | 261 |
| Example 3-118 | A-5 | C-51 | 13.9 | 5.2 | 312 |
| Example 3-119 | A-5 | C-54 | 13.1 | 6.0 | 259 |
| Example 3-120 | A-5 | C-57 | 13.5 | 5.5 | 341 |
| Example 3-121 | A-5 | C-58 | 12.9 | 6.2 | 288 |
| Example 3-122 | A-6 | C-46 | 13.1 | 5.9 | 270 |
| Example 3-123 | A-6 | C-48 | 12.6 | 6.3 | 256 |
| Example 3-124 | A-6 | C-49 | 12.5 | 6.3 | 231 |
| Example 3-125 | A-6 | C-52 | 13.5 | 5.4 | 267 |
| Example 3-126 | A-6 | C-53 | 13.3 | 5.5 | 269 |
| Example 3-127 | A-6 | C-54 | 13.1 | 5.9 | 242 |
| Example 3-128 | A-6 | C-58 | 13.0 | 6.0 | 258 |
| Example 3-129 | A-6 | C-59 | 13.3 | 5.6 | 271 |

As apparent from the above results, the device of the present invention had higher external quantum efficiency and lower driving voltage than comparative devices. In particular, high durability was shown when driving at a high temperature (70° C.). Example 3 exemplifies the manufacture of a light emitting layer by coating, and is excellent in terms of manufacturing costs.

Example 4

Comparative Example 4-1

An organic EL device in Comparative Example 4-1 was manufactured in the same manner as in Comparative Example 3-1, except that vapor deposition was performed by changing a composition of the film of the light emitting layer from 4:96 (mass ratio) of A-1 to C-1 in Comparative Example 3-1 to 4:96 (mass ratio) of B-1 to C-1 (film thickness: 30 nm).

A direct current constant voltage was applied to the organic EL device to emit light by means of a source measure unit Model 2400 manufactured by Toyo Technica, and as a result, light emission derived from B-1 could be obtained.

Examples 4-1 to 4-184 and Comparative Examples 4-2 to 4-9

Devices in Examples 4-1 to 4-184 and Comparative Examples 4-2 to 4-9 were manufactured in the same manner as in Comparative Example 4-1, except that the materials used in Comparative Example 4-1 were changed into the materials described in Table 4. A direct current constant voltage was applied to the organic EL device to emit light by means of a source measure unit Model 2400 manufactured by Toyo Technica, and as a result, a light emission of color derived from each light emitting material could be obtained.

The devices thus-obtained above were evaluated in the same manner as in Example 1.

TABLE 4

| | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
| | Light emitting material | Host material | | | |
| Comparative example 4-1 | B-1 | C-1 | 15.4 | 2.2 | 100 |
| Comparative example 4-2 | B-1 | C-6 | 15.6 | 2.4 | 117 |
| Comparative example 4-3 | B-1 | C-9 | 15.5 | 2.4 | 94 |
| Comparative example 4-4 | B-1 | C-10 | 16.4 | 1.9 | 79 |
| Comparative example 4-5 | B-1 | H-1 | 15.1 | 2.4 | 98 |
| Comparative example 4-6 | B-6 | H-1 | 14.8 | 2.5 | 165 |
| Example 4-1 | B-2 | C-1 | 14.6 | 3.0 | 251 |
| Example 4-2 | B-2 | C-3 | 14.8 | 3.1 | 258 |
| Example 4-3 | B-2 | C-7 | 14.7 | 3.0 | 289 |
| Example 4-4 | B-2 | C-10 | 15.4 | 2.8 | 219 |
| Example 4-5 | B-3 | C-1 | 15.1 | 3.1 | 267 |
| Example 4-6 | B-3 | C-6 | 14.9 | 3.2 | 278 |
| Example 4-5 | B-3 | C-8 | 15.1 | 3.0 | 241 |
| Example 4-6 | B-3 | C-9 | 15.1 | 3.1 | 273 |
| Example 4-7 | B-4 | C-2 | 14.9 | 3.3 | 273 |
| Example 4-8 | B-4 | C-6 | 15.0 | 3.4 | 302 |
| Example 4-9 | B-4 | C-7 | 15.1 | 3.4 | 313 |
| Example 4-10 | B-4 | C-10 | 15.6 | 3.0 | 238 |
| Example 4-11 | B-5 | C-1 | 15.0 | 3.3 | 246 |
| Example 4-12 | B-5 | C-6 | 15.2 | 3.1 | 281 |
| Example 4-13 | B-5 | C-7 | 15.3 | 3.2 | 279 |
| Example 4-14 | B-5 | C-10 | 16.0 | 2.9 | 222 |
| Example 4-15 | B-6 | C-1 | 14.7 | 3.1 | 302 |
| Example 4-16 | B-6 | C-6 | 14.9 | 3.1 | 297 |
| Example 4-17 | B-6 | C-9 | 14.7 | 3.0 | 281 |
| Example 4-18 | B-6 | C-10 | 15.8 | 2.7 | 231 |
| Example 4-19 | B-7 | C-1 | 15.0 | 3.3 | 259 |
| Example 4-20 | B-7 | C-6 | 15.2 | 3.1 | 287 |
| Example 4-21 | B-7 | C-9 | 15.1 | 3.2 | 245 |
| Example 4-22 | B-7 | C-10 | 15.8 | 2.8 | 211 |
| Example 4-23 | B-9 | C-1 | 15.2 | 3.0 | 248 |
| Example 4-24 | B-9 | C-7 | 15.2 | 3.1 | 271 |
| Example 4-25 | B-9 | C-10 | 15.8 | 2.8 | 222 |
| Comparative example 4-7 | B-1 | C-11 | 15.2 | 2.3 | 112 |
| Comparative example 4-8 | B-1 | C-14 | 14.8 | 2.8 | 85 |
| Comparative example 4-9 | B-1 | C-20 | 14.7 | 2.9 | 119 |
| Example 4-26 | B-2 | C-11 | 14.3 | 3.3 | 272 |
| Example 4-27 | B-2 | C-12 | 13.9 | 3.4 | 211 |
| Example 4-28 | B-2 | C-14 | 12.8 | 4.4 | 231 |
| Example 4-29 | B-2 | C-15 | 13.0 | 4.2 | 219 |

TABLE 4-continued

|  | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
|  | Light emitting material | Host material | | | |
| Example 4-30 | B-2 | C-18 | 14.0 | 3.4 | 205 |
| Example 4-31 | B-2 | C-20 | 12.6 | 4.6 | 283 |
| Example 4-32 | B-2 | C-21 | 14.3 | 3.2 | 237 |
| Example 4-33 | B-3 | C-11 | 14.7 | 3.4 | 282 |
| Example 4-34 | B-3 | C-13 | 13.9 | 4.1 | 239 |
| Example 4-35 | B-3 | C-14 | 13.7 | 4.5 | 250 |
| Example 4-36 | B-3 | C-16 | 14.0 | 4.0 | 225 |
| Example 4-37 | B-3 | C-19 | 13.6 | 4.5 | 233 |
| Example 4-38 | B-3 | C-20 | 13.5 | 4.6 | 298 |
| Example 4-39 | B-3 | C-22 | 13.8 | 4.1 | 213 |
| Example 4-40 | B-4 | C-11 | 14.7 | 3.6 | 291 |
| Example 4-41 | B-4 | C-12 | 14.7 | 3.8 | 240 |
| Example 4-42 | B-4 | C-14 | 13.2 | 4.8 | 261 |
| Example 4-43 | B-4 | C-17 | 15.0 | 3.2 | 255 |
| Example 4-44 | B-4 | C-20 | 13.1 | 5.0 | 319 |
| Example 4-45 | B-4 | C-23 | 15.0 | 3.3 | 259 |
| Example 4-46 | B-5 | C-11 | 14.8 | 3.5 | 263 |
| Example 4-47 | B-5 | C-13 | 13.8 | 4.5 | 219 |
| Example 4-48 | B-5 | C-14 | 13.5 | 4.9 | 231 |
| Example 4-49 | B-5 | C-18 | 14.3 | 4.0 | 207 |
| Example 4-50 | B-5 | C-19 | 13.4 | 4.8 | 227 |
| Example 4-51 | B-5 | C-20 | 13.2 | 5.1 | 275 |
| Example 4-52 | B-5 | C-21 | 14.7 | 3.5 | 229 |
| Example 4-53 | B-6 | C-2 | 14.7 | 3.0 | 298 |
| Example 4-54 | B-6 | C-11 | 14.4 | 3.4 | 322 |
| Example 4-55 | B-6 | C-12 | 14.3 | 3.7 | 267 |
| Example 4-56 | B-6 | C-14 | 13.3 | 4.5 | 291 |
| Example 4-57 | B-6 | C-16 | 13.8 | 4.1 | 271 |
| Example 4-58 | B-6 | C-20 | 13.2 | 4.8 | 333 |
| Example 4-59 | B-6 | C-23 | 14.8 | 3.0 | 297 |
| Example 4-60 | B-7 | C-11 | 14.6 | 3.6 | 286 |
| Example 4-61 | B-7 | C-13 | 13.5 | 4.0 | 227 |
| Example 4-62 | B-7 | C-14 | 13.1 | 4.5 | 240 |
| Example 4-63 | B-7 | C-15 | 13.3 | 4.2 | 229 |
| Example 4-64 | B-7 | C-19 | 13.2 | 4.6 | 243 |
| Example 4-65 | B-7 | C-20 | 12.9 | 4.7 | 302 |
| Example 4-66 | B-7 | C-22 | 13.5 | 3.9 | 204 |
| Example 4-67 | B-9 | C-11 | 14.8 | 3.3 | 271 |
| Example 4-68 | B-9 | C-12 | 14.5 | 3.7 | 208 |
| Example 4-69 | B-9 | C-14 | 13.3 | 4.4 | 235 |
| Example 4-70 | B-9 | C-17 | 15.3 | 2.9 | 255 |
| Example 4-71 | B-9 | C-18 | 14.7 | 3.3 | 197 |
| Example 4-72 | B-9 | C-20 | 13.1 | 4.8 | 277 |
| Example 4-73 | B-9 | C-23 | 15.4 | 3.0 | 262 |
| Example 4-74 | B-2 | C-26 | 14.0 | 3.7 | 227 |
| Example 4-75 | B-3 | C-25 | 13.6 | 4.3 | 209 |
| Example 4-76 | B-4 | C-24 | 14.5 | 3.7 | 263 |
| Example 4-77 | B-5 | C-26 | 14.5 | 3.8 | 220 |
| Example 4-78 | B-6 | C-25 | 14.0 | 4.0 | 245 |
| Example 4-79 | B-7 | C-24 | 14.4 | 3.8 | 238 |
| Example 4-80 | B-9 | C-25 | 14.2 | 3.9 | 197 |
| Example 4-81 | B-2 | C-29 | 13.2 | 3.8 | 209 |
| Example 4-82 | B-3 | C-28 | 13.6 | 4.3 | 229 |
| Example 4-83 | B-4 | C-27 | 14.9 | 3.4 | 266 |
| Example 4-84 | B-5 | C-29 | 14.0 | 4.4 | 211 |
| Example 4-85 | B-6 | C-27 | 14.8 | 3.1 | 293 |
| Example 4-86 | B-7 | C-28 | 14.0 | 3.8 | 232 |
| Example 4-88 | B-9 | C-27 | 15.2 | 2.9 | 240 |
| Example 4-89 | B-2 | C-30 | 14.7 | 3.0 | 255 |
| Example 4-90 | B-2 | C-32 | 14.6 | 3.0 | 228 |
| Example 4-91 | B-2 | C-34 | 14.7 | 3.1 | 241 |
| Example 4-92 | B-2 | C-38 | 13.3 | 4.0 | 212 |
| Example 4-93 | B-2 | C-43 | 13.0 | 4.0 | 210 |
| Example 4-94 | B-2 | C-44 | 14.6 | 3.2 | 242 |
| Example 4-95 | B-3 | C-30 | 14.9 | 3.1 | 277 |
| Example 4-96 | B-3 | C-33 | 14.6 | 3.2 | 240 |
| Example 4-97 | B-3 | C-34 | 14.8 | 3.1 | 262 |
| Example 4-98 | B-3 | C-35 | 14.5 | 3.5 | 238 |
| Example 4-99 | B-3 | C-37 | 13.6 | 4.3 | 228 |
| Example 4-100 | B-3 | C-39 | 13.7 | 4.6 | 223 |
| Example 4-101 | B-3 | C-45 | 14.0 | 4.3 | 239 |
| Example 4-102 | B-4 | C-30 | 14.9 | 3.4 | 299 |
| Example 4-103 | B-4 | C-32 | 14.6 | 3.5 | 264 |

TABLE 4-continued

|  | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
|  | Light emitting material | Host material | | | |
| Example 4-104 | B-4 | C-33 | 14.7 | 3.4 | 258 |
| Example 4-105 | B-4 | C-40 | 14.8 | 3.3 | 281 |
| Example 4-106 | B-4 | C-41 | 14.3 | 3.9 | 242 |
| Example 4-107 | B-4 | C-43 | 13.3 | 4.6 | 255 |
| Example 4-108 | B-4 | C-45 | 14.2 | 3.9 | 263 |
| Example 4-109 | B-5 | C-30 | 14.9 | 3.1 | 273 |
| Example 4-110 | B-5 | C-34 | 14.8 | 3.1 | 259 |
| Example 4-111 | B-5 | C-35 | 14.4 | 3.6 | 234 |
| Example 4-112 | B-5 | C-39 | 13.8 | 4.2 | 230 |
| Example 4-113 | B-5 | C-42 | 13.8 | 4.3 | 222 |
| Example 4-114 | B-5 | C-44 | 15.0 | 3.3 | 255 |
| Example 4-115 | B-5 | C-45 | 14.5 | 3.7 | 238 |
| Example 4-116 | B-6 | C-30 | 14.7 | 3.1 | 293 |
| Example 4-117 | B-6 | C-31 | 14.2 | 3.5 | 272 |
| Example 4-118 | B-6 | C-32 | 14.5 | 3.3 | 266 |
| Example 4-119 | B-6 | C-34 | 14.8 | 3.1 | 284 |
| Example 4-120 | B-6 | C-42 | 13.6 | 3.8 | 259 |
| Example 4-121 | B-6 | C-43 | 13.3 | 4.3 | 266 |
| Example 4-122 | B-6 | C-45 | 14.2 | 3.8 | 278 |
| Example 4-123 | B-7 | C-30 | 14.9 | 3.1 | 280 |
| Example 4-124 | B-7 | C-31 | 14.4 | 3.6 | 262 |
| Example 4-125 | B-7 | C-35 | 14.3 | 3.6 | 249 |
| Example 4-126 | B-7 | C-36 | 13.7 | 4.2 | 222 |
| Example 4-127 | B-7 | C-37 | 13.4 | 4.5 | 228 |
| Example 4-128 | B-7 | C-43 | 13.3 | 4.4 | 233 |
| Example 4-129 | B-7 | C-45 | 14.1 | 4.0 | 266 |
| Example 4-130 | B-9 | C-30 | 15.1 | 3.0 | 284 |
| Example 4-131 | B-9 | C-34 | 15.0 | 3.0 | 271 |
| Example 4-132 | B-9 | C-35 | 14.3 | 3.9 | 247 |
| Example 4-133 | B-9 | C-36 | 14.0 | 4.1 | 225 |
| Example 4-134 | B-9 | C-37 | 13.3 | 4.6 | 235 |
| Example 4-135 | B-9 | C-43 | 13.1 | 4.8 | 259 |
| Example 4-136 | B-9 | C-45 | 14.2 | 4.0 | 270 |
| Example 4-137 | B-2 | C-46 | 14.2 | 3.4 | 256 |
| Example 4-138 | B-2 | C-48 | 13.7 | 3.8 | 240 |
| Example 4-139 | B-2 | C-50 | 12.7 | 4.5 | 292 |
| Example 4-140 | B-2 | C-52 | 14.8 | 3.0 | 255 |
| Example 4-141 | B-2 | C-57 | 14.6 | 3.2 | 269 |
| Example 4-142 | B-2 | C-58 | 14.0 | 3.5 | 243 |
| Example 4-143 | B-3 | C-46 | 14.2 | 3.7 | 251 |
| Example 4-144 | B-3 | C-49 | 13.8 | 4.1 | 226 |
| Example 4-145 | B-3 | C-50 | 13.5 | 4.6 | 288 |
| Example 4-146 | B-3 | C-51 | 15.0 | 3.1 | 252 |
| Example 4-147 | B-3 | C-53 | 14.8 | 3.2 | 259 |
| Example 4-148 | B-3 | C-55 | 14.8 | 3.3 | 247 |
| Example 4-149 | B-3 | C-59 | 14.6 | 3.4 | 233 |
| Example 4-150 | B-4 | C-46 | 14.4 | 3.8 | 271 |
| Example 4-151 | B-4 | C-48 | 13.8 | 4.4 | 257 |
| Example 4-152 | B-4 | C-50 | 13.3 | 4.9 | 306 |
| Example 4-153 | B-4 | C-52 | 15.0 | 3.3 | 268 |
| Example 4-154 | B-4 | C-54 | 14.5 | 3.7 | 235 |
| Example 4-155 | B-4 | C-57 | 14.9 | 3.6 | 288 |
| Example 4-156 | B-4 | C-59 | 14.8 | 3.5 | 256 |
| Example 4-157 | B-5 | C-46 | 14.5 | 3.7 | 257 |
| Example 4-158 | B-5 | C-50 | 13.5 | 4.9 | 280 |
| Example 4-159 | B-5 | C-52 | 15.1 | 3.0 | 253 |
| Example 4-160 | B-5 | C-54 | 14.4 | 3.8 | 229 |
| Example 4-161 | B-5 | C-56 | 14.0 | 4.3 | 202 |
| Example 4-162 | B-5 | C-58 | 14.1 | 3.9 | 243 |
| Example 4-163 | B-5 | C-59 | 14.8 | 3.2 | 235 |
| Example 4-164 | B-6 | C-46 | 14.3 | 3.8 | 297 |
| Example 4-165 | B-6 | C-47 | 14.6 | 3.4 | 267 |
| Example 4-166 | B-6 | C-49 | 13.7 | 4.2 | 255 |
| Example 4-167 | B-6 | C-50 | 13.2 | 4.7 | 324 |
| Example 4-168 | B-6 | C-52 | 15.0 | 3.1 | 271 |
| Example 4-169 | B-6 | C-54 | 14.0 | 4.0 | 249 |
| Example 4-170 | B-6 | C-59 | 14.7 | 3.3 | 259 |
| Example 4-171 | B-7 | C-46 | 14.3 | 3.8 | 262 |
| Example 4-172 | B-7 | C-47 | 14.7 | 3.4 | 248 |
| Example 4-173 | B-7 | C-51 | 15.0 | 3.1 | 264 |
| Example 4-174 | B-7 | C-53 | 14.8 | 3.3 | 272 |
| Example 4-175 | B-7 | C-55 | 14.7 | 3.4 | 260 |
| Example 4-176 | B-7 | C-57 | 14.9 | 3.3 | 273 |

TABLE 4-continued

|  | Light emitting layer | | Driving voltage (V) at 1000 cd/m² | External quantum efficiency (%) at 1000 cd/m² | Half-luminance intensity time (relative value) at an ambient air temperature of 70° C. and 1000 cd/m² |
|---|---|---|---|---|---|
|  | Light emitting material | Host material | | | |
| Example 4-177 | B-7 | C-58 | 14.0 | 4.0 | 248 |
| Example 4-178 | B-9 | C-46 | 14.6 | 3.7 | 252 |
| Example 4-179 | B-9 | C-50 | 13.1 | 4.7 | 299 |
| Example 4-180 | B-9 | C-51 | 15.0 | 3.0 | 254 |
| Example 4-181 | B-9 | C-52 | 14.8 | 3.2 | 255 |
| Example 4-182 | B-9 | C-53 | 14.6 | 3.3 | 243 |
| Example 4-183 | B-9 | C-57 | 14.9 | 3.3 | 261 |
| Example 4-184 | B-9 | C-59 | 14.5 | 3.5 | 239 |

As apparent from the above results, the device of the present invention had higher external quantum efficiency and lower driving voltage than the comparative devices. In particular, high durability was shown when driving at a high temperature (70° C.). Example 4 exemplifies the manufacture of a light emitting layer by coating, and is excellent in terms of manufacturing costs.

Industrial Applicability

According to the present invention, an organic electroluminescence device having excellent light emission efficiency and durability (in particular, durability when driving at high temperature) may be provided.

Although the present invention has been described with reference to detailed and specific embodiments thereof, it is obvious to those skilled in the art that various changes or modifications may be made without departing from the spirit and scope of the present invention.

This application claims priority from Japanese Patent Application (Japanese Patent Application No. 2009-201153) filed on Aug. 31, 2009, Japanese Patent Application (Japanese Patent Application No. 2009-223456) filed on Sep. 28, 2009, and Japanese Patent Application (Japanese Patent Application No. 2010-076449) filed on Mar. 29, 2010, the disclosures of which are incorporated herein by reference in its entirety.

Explanation of Reference Numerals and Symbols

- 2: Substrate
- 3: Anode
- 4: Hole injection layer
- 5: Hole transporting layer
- 6: Light emitting layer
- 7: Hole blocking layer
- 8: Electron transporting layer
- 9: Cathode
- 10: Organic electroluminescence device (Organic EL device)
- 11: Organic layer
- 12: Protective layer
- 14: Adhesive layer
- 16: Sealing vessel
- 20: Light emission apparatus
- 30: Light scattering member
- 30A: Light incident surface
- 30B: Light reflecting surface
- 31: Transparent substrate
- 32: Microparticulate
- 40: Illumination apparatus

The invention claimed is:

1. An organic electroluminescence device, comprising on a substrate: a pair of electrodes; at least one layer of an organic layer including a light emitting layer containing a light emitting material disposed between the electrodes, wherein the light emitting layer contains at least each one of a compound represented by the following Formula (3) and a compound represented by the following Formula (D-5):

$$Z^3-(Y^3)_{n_3} \quad (3)$$

wherein $Z^3$ represents benzene, or biphenyl and may be further substituted by at least one group selected from the group consisting of an alkyl group, an aryl group, a silyl group, a cyano group, a fluorine atom and a combination thereof; $Y^3$ represents a group represented by the following Formula (15a); and $n^3$ represents an integer of 2:

(15a)

wherein $R_{155}$ represents a hydrogen atom; each of $R_{154}$ and $R_{156}$ independently represents a hydrogen atom, an alkyl group, a silyl group, a fluorine atom, a cyano group or a trifluoromethyl group, and these groups may be further substituted with at least one of an alkyl group having 1 to 6 carbon atoms and a phenyl group; $R_{157}$ represents a benzene ring, a naphthalene ring, a pyridine ring, a triazine ring or a pyrimidine ring, and these rings may be further substituted with at least one group selected from a methyl group, an isobutyl group, a t-butyl group, a neopentyl group, a phenyl group, a naphthyl group, a cyano group and a fluorine atom; and * represents a bond for linking to $Z^3$:

(D-5)

wherein each of $R_3$ to $R_{10}$ independently represents a hydrogen atom, an alkyl group or an aryl group; each of $R_3'$ to $R_6'$ represents a hydrogen atom, an alkyl group or an aryl group; and each of $R_y$ independently represents a hydrogen atom, an alkyl group, a perfluoroalkyl group, a halogen atom or an aryl group;

wherein the compound of formula (D-5) is selected from the group consisting of:

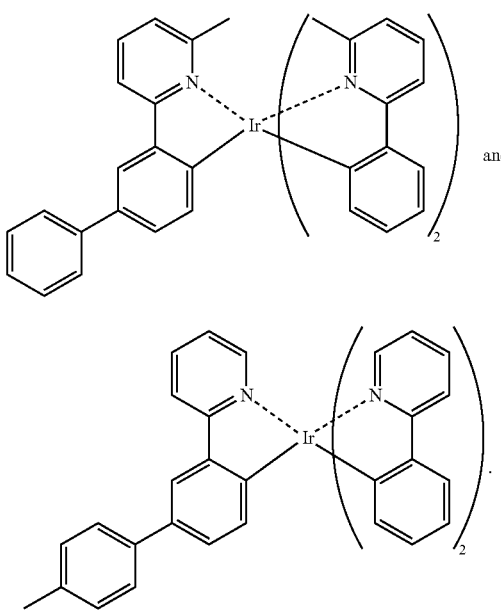

2. The organic electroluminescence device according to claim 1, wherein the compound represented by Formula (3) is represented by the following Formula (5):

(5)

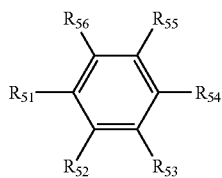

wherein each of $R_{51}$ to $R_{56}$ independently represents a hydrogen atom, a methyl group, an isobutyl group, a t-butyl group, a neopentyl group, a phenyl group, a naphthyl group, a cyano group, a fluorine atom or a group represented by the following Formula (10):

(10)

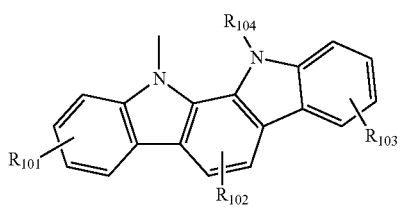

wherein $R_{102}$ represents a hydrogen atom; each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and $R_{104}$ represents a benzene ring, a naphthalene ring, a pyridine ring, a triazine ring or a pyrimidine ring, and these rings may be further substituted by at least one group selected from the group consisting of a methyl group, an isobutyl group, a t-butyl group, a neopentyl group, a phenyl group, a naphthyl group, a cyano group and a fluorine atom.

3. The organic electroluminescence device according to claim 1, wherein the compound represented by Formula (3) is represented by the following Formula (6):

(6)

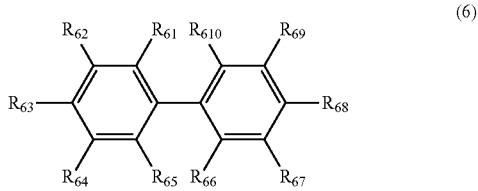

wherein each of $R_{61}$ to $R_{610}$ independently represents a hydrogen atom, a methyl group, an isobutyl group, a t-butyl group, a neopentyl group, a phenyl group, a naphthyl group, a cyano group, a fluorine atom or a group represented by the following Formula (10), provided that each of at least two of $R_{61}$ to $R_{610}$ is independently a group represented by the following Formula (10):

(10)

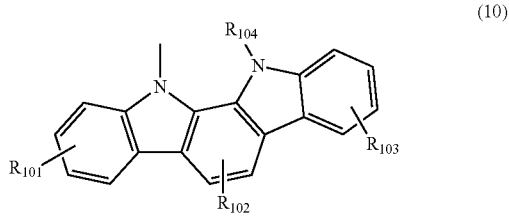

wherein $R_{102}$ represents a hydrogen atom; each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6 carbon atoms and a phenyl group; and $R_{104}$ represents a benzene ring, a naphthalene ring, a pyridine ring, a triazine ring or a pyrimidine ring, and these rings may be further substituted by at least one group selected from the group consisting of a methyl group, an isobutyl group, a t-butyl group, a neopentyl group, a phenyl group, a naphthyl group, a cyano group and a fluorine atom.

4. The organic electroluminescence device according to claim 3, wherein the compound represented by Formula (6) is represented by the following Formula (7):

(7)

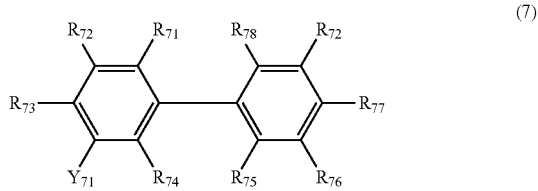

wherein each of $R_{71}$ to $R_{78}$ independently represents a hydrogen atom, a methyl group, an isobutyl group, a t-butyl group, a neopentyl group, a phenyl group, a naphthyl group, a cyano group, or a fluorine atom; and each of $Y_{71}$ and $Y_{72}$ is independently a group represented by the following Formula (10):

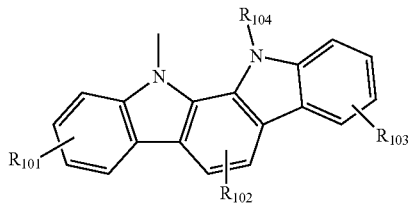
(10)

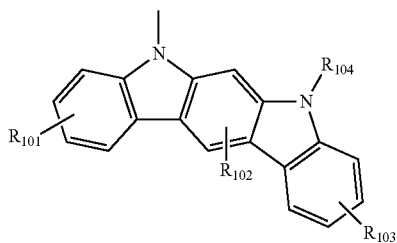
(10-2)

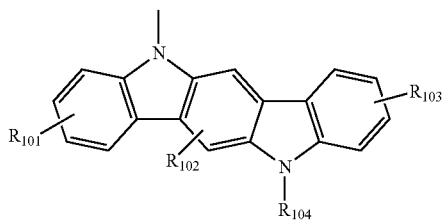
(10-3)

wherein $R_{102}$ represents a hydrogen atom; each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6carbon atoms and a phenyl group; and $R_{104}$ represents a benzene ring, a naphthalene ring, a pyridine ring, a triazine ring or a pyrimidine ring, and these rings may be further substituted by at least one group selected from the group consisting of a methyl group, an isobutyl group, a t-butyl group, a neopentyl group, a phenyl group, a naphthyl group, a cyano group and a fluorine atom.

5. The organic electroluminescence device according to claim 3, wherein the compound represented by Formula (6) is represented by the following Formula (8):

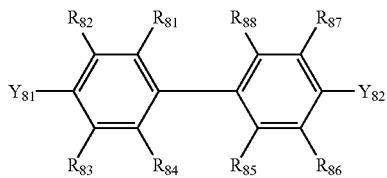
(8)

wherein each of $R_{81}$ to $R_{88}$ independently represents a hydrogen atom, a methyl group, an isobutyl group, a t-butyl group, a neopentyl group, a phenyl group, a naphthyl group, a cyano group, or a fluorine atom; and each of $Y_{81}$ and $Y_{82}$ is independently a group represented by the following Formula (10):

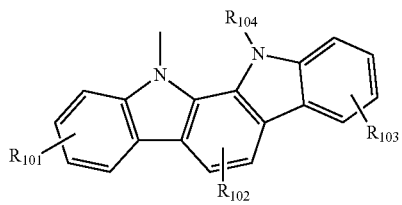
(10)

wherein $R_{102}$ represents a hydrogen atom; each of $R_{101}$ and $R_{103}$ independently represents a hydrogen atom, an alkyl group, a silyl group, a fluorine atom, a cyano group or a trifluoromethyl group, and these groups may be further substituted by at least one of an alkyl group having 1 to 6carbon atoms and a phenyl group; and $R_{104}$ represents a benzene ring, a naphthalene ring, a pyridine ring, a triazine ring or a pyrimidine ring, and these rings may be further substituted by at least one group selected from the group consisting of a methyl group, an isobutyl group, a t-butyl group, a neopentyl group, a phenyl group, a naphthyl group, a cyano group and a fluorine atom.

6. The organic electroluminescence device according to claim 1, wherein the light emitting layer containing at least each one of the compound represented by Formula (3) and the compound represented by Formula (D-5) is formed by a wet process.

7. A light emission apparatus including the organic electroluminescence device according to claim 1.

8. A display apparatus including the organic electroluminescence device according to claim 1.

9. An illumination apparatus including the organic electroluminescence device according to claim 1.

10. The organic electroluminescence device of claim 1, wherein the compound of Formula (15a) is selected from the group consisting of:

162

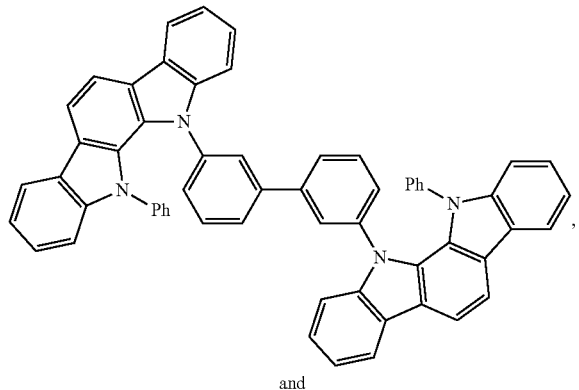

and

C-34

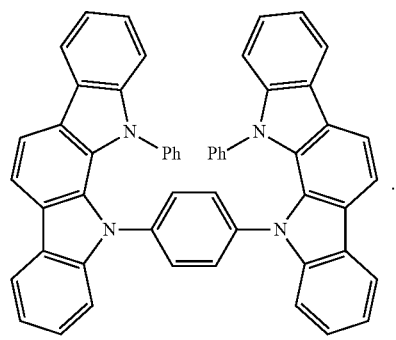

11. A composition, comprising: at least each one of a compound represented by the following Formula (3) and a compound represented by the following Formula (D-5):

$$Z^3—(Y^3)_{n3} \quad (3)$$

wherein $Z^3$ represents benzene, or biphenyl, and may be further substituted by at least one group selected from the group consisting of an alkyl group, an aryl group, a silyl group, a cyano group, a fluorine atom and a combination thereof; $Y^3$ represents a group represented by the following Formula (15a); and $n^3$ represents an integer of 2:

(15a)

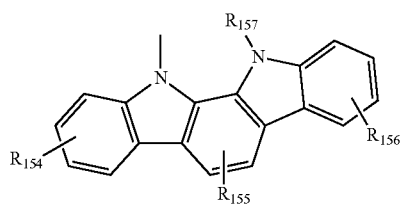

wherein $R_{155}$ represents a hydrogen atom; each of $R_{154}$ and $R_{156}$ independently represents a hydrogen atom, an alkyl group, a silyl group, a fluorine atom, a cyano group or a trifluoromethyl group, and these groups may be further substituted with at least one of an alkyl group having 1 to 6 carbon atoms and a phenyl group; $R_{157}$ represents a benzene ring, a naphthalene ring, a pyridine ring, a triazine ring or a pyrimidine ring, and these rings may be further substituted with at least one group selected from a methyl group, an isobutyl group, a t-butyl group, a neopentyl group, a phenyl group, a naphthyl group, a cyano group and a fluorine atom; and * represents a bond for linking to $Z^3$:

(D-5)

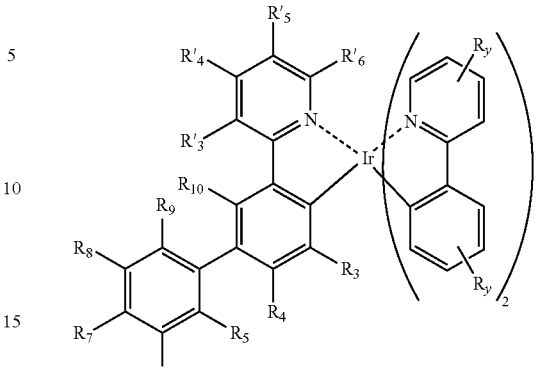

wherein each of $R_3$ to $R_{10}$ independently represents a hydrogen atom, an alkyl group or an aryl group; each of $R_3'$ to $R_6'$ represents a hydrogen atom, an alkyl group or an aryl group; wherein each of $R_y$ independently represents a hydrogen atom, an alkyl group, a perfluoroalkyl group, a halogen atom or an aryl group;

wherein the compound of formula (D-5) is selected from the group consisting of:

A-3

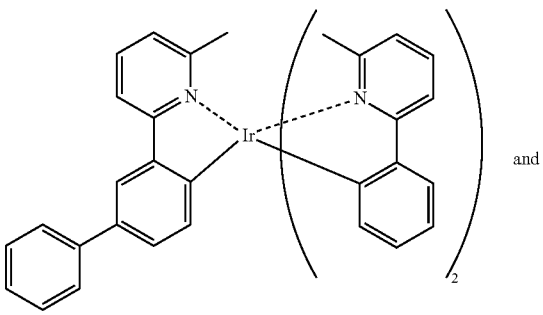

and

A-5

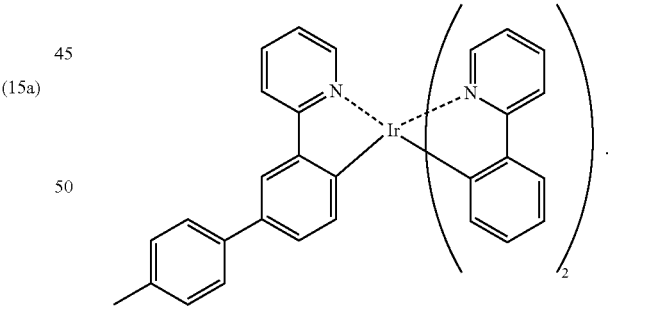

12. A light emitting layer, comprising: at least each one of a compound represented by the following Formula (3) and a compound represented by the following Formula (D-5):

$$Z^3—(Y^3)_{n3} \quad (3)$$

wherein $Z^3$ represents benzene, or biphenyl and may be further substituted by at least one group selected from the group consisting of an alkyl group, an aryl group, a silyl group, a cyano group, a fluorine atom and a combination thereof; $Y^3$ represents a group represented by the following Formula (15a); and $n^3$ represents an integer of 2:

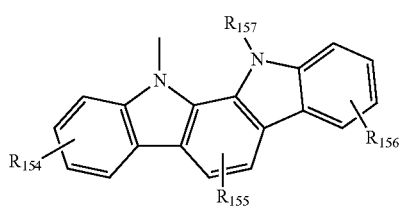

(15a)

wherein $R_{155}$ represents a hydrogen atom; each of $R_{154}$ and $R_{156}$ independently represents a hydrogen atom, an alkyl group, a silyl group, a fluorine atom, a cyano group or a trifluoromethyl group, and these groups may be further substituted with at least one of an alkyl group having 1 to 6 carbon atoms and a phenyl group; $R_{157}$ represents a benzene ring, a naphthalene ring, a pyridine ring, a triazine ring or a pyrimidine ring, and these rings may be further substituted with at least one group selected from a methyl group, an isobutyl group, a t-butyl group, a neopentyl group, a phenyl group, a naphthyl group, a cyano group and a fluorine atom; and represents a bond for linking to $Z^3$:

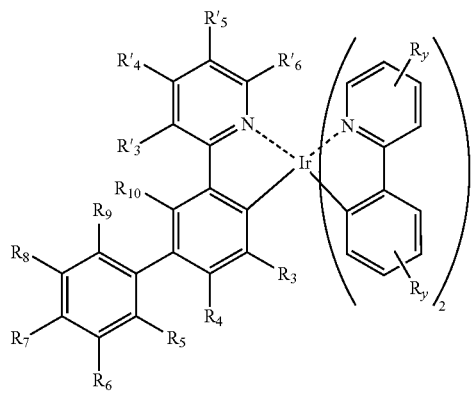

(D-5)

wherein each of $R_3$ to $R_{10}$ independently represents a hydrogen atom, an alkyl group or an aryl group; $R_3'$ to $R_6'$ represents a hydrogen atom, an alkyl group or an aryl group; wherein each of $R_y$ independently represents a hydrogen atom, an alkyl group, a perfluoroalkyl group, a halogen atom or an aryl group wherein the compound of formula (D-5) is selected from the group consisting of:

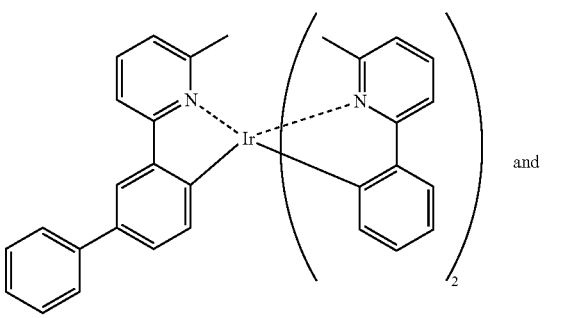

A-3 and

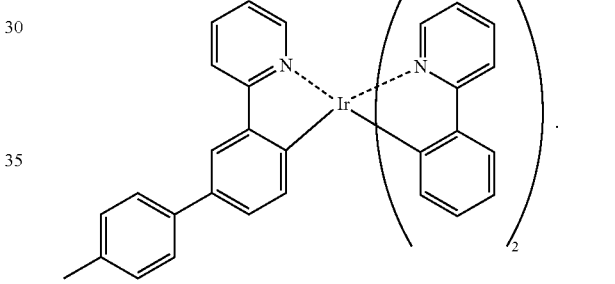

A-5

* * * * *